US012662518B2

(12) United States Patent
Altieri et al.

(10) Patent No.: US 12,662,518 B2
(45) Date of Patent: Jun. 23, 2026

(54) ENGINEERED PEPTIDE AND PEPTIDE MIMETIC COMPOSITIONS AND METHODS

(71) Applicant: The Wistar Institute of Anatomy and Biology, Philadelphia, PA (US)

(72) Inventors: Dario Altieri, Philadelphia, PA (US); Young Chan Chae, Philadelphia, PA (US); Jae Ho Seo, Philadelphia, PA (US)

(73) Assignee: The Wistar Institute of Anatomy and Biology, Philadelphia, PA (US)

(*) Notice: Subject to any disclaimer, the term of this patent is extended or adjusted under 35 U.S.C. 154(b) by 1128 days.

(21) Appl. No.: 17/641,346

(22) PCT Filed: Sep. 9, 2020

(86) PCT No.: PCT/US2020/049888
§ 371 (c)(1),
(2) Date: Mar. 8, 2022

(87) PCT Pub. No.: WO2021/050510
PCT Pub. Date: Mar. 18, 2021

(65) Prior Publication Data

US 2022/0348620 A1 Nov. 3, 2022

Related U.S. Application Data

(60) Provisional application No. 62/908,207, filed on Sep. 30, 2019, provisional application No. 62/897,971, filed on Sep. 9, 2019.

(51) Int. Cl.

| | |
|---|---|
| ***C07K 14/00*** | (2006.01) |
| ***A61K 35/00*** | (2006.01) |
| ***A61K 38/17*** | (2006.01) |
| ***C07K 14/47*** | (2006.01) |

(52) U.S. Cl.
CPC .......... *C07K 14/4747* (2013.01); *A61K 35/00* (2013.01); *A61K 38/1761* (2013.01)

(58) Field of Classification Search
CPC ........... C07K 14/4747; C07K 2319/10; A61K 35/00; A61K 38/1761; A61K 38/00; A61P 35/00
See application file for complete search history.

(56) References Cited

U.S. PATENT DOCUMENTS

2006/0141528 A1 6/2006 Aebersold et al.
2007/0099251 A1 5/2007 Zhang et al.
2009/0030178 A1* 1/2009 Chang .................. C07K 14/005 530/324
2012/0087862 A1 4/2012 Hood et al.
2018/0141977 A1 5/2018 Otterlei et al.
2018/0188260 A1* 7/2018 Kritzer ..................... C12Q 1/32
2019/0192691 A1 6/2019 Barrett et al.

OTHER PUBLICATIONS

Gandre-Babbe et al. Molecular Biology of the Cell. vol. 19, 2402-2412, Jun. 2008.*
International Search Report and Written Opinion, PCT/US2020/049888, dated Jan. 12, 2021.
Baines, et al., "Loss of cyclophilin D reveals a critical role for mitochondrial permeability transition in cell death", Nature 434, 658-662 (2005).
Blaszczyk, et al., "Modeling of protein-peptide interactions using the CABS-dock web server for binding site search and flexible docking", Methods 93 (2016) 72-83.
De La Fuente-Nunez, et al., "D-enantiomeric peptides that eradicate wild-type and multi-drug resistant biofilms and protect against lethal Pseudomonas aeruginosa infections", Chem Biol., Feb. 19, 2015; 22(2): 196-205.
Kurcinski, et al., "CABS-dock web server for the flexible docking of peptides to proteins without prior knowledge of the binding site", Nucleic Acids Research, 2015, vol. 43, 6 pages.
Mazure, "VDAC in Cancer", BBA—Bioenergetics 1858 (2017) 665-673.
Osellame, et al., "Cooperative and independent roles of the Drp1 adaptors Mff, MiD49 and MiD51 in mitochondrial fission", J Cell Sci., Jun. 1, 2016; 129(11): 2170-2181.
Otera, et al., "Mff is an essential factor for mitochondrial recruitment of Drp1 during mitochondrial fission in mammalian cells", J. Cell Biol., vol. 191, No. 6, 1141-1158.
Seo, et al., "MFF Regulation of Mitochondrial Cell Death Is a Therapeutic Target in Cancer", Cancer Res; 79(24) Dec. 15, 2019, pp. 6215-6226.
Seo, et al., "Mitochondrial fission factor is a novel Myc-dependent regulator of mitochondrial permeability in cancer", EBioMedicine 48 (2019) 353-363.
Youle, et al., "Mitochondrial Fission, Fusion, and Stress", Science (2012) 337: 1062-1065.

* cited by examiner

*Primary Examiner* — Jeanette M Lieb
(74) *Attorney, Agent, or Firm* — Saul Ewing LLP; Kathryn Doyle; Alireza Behrooz

(57) ABSTRACT

The present invention relates to Mitochondrial Fission Factor (MFF)-derived peptides or peptide mimetics and to methods of making MFF-derived peptides or peptide mimetics. Also provided are methods of treating a disease in a subject in need thereof, comprising administering to the subject an effective amount of a MFF-derived peptide or peptide mimetic.

31 Claims, 94 Drawing Sheets

Specification includes a Sequence Listing.

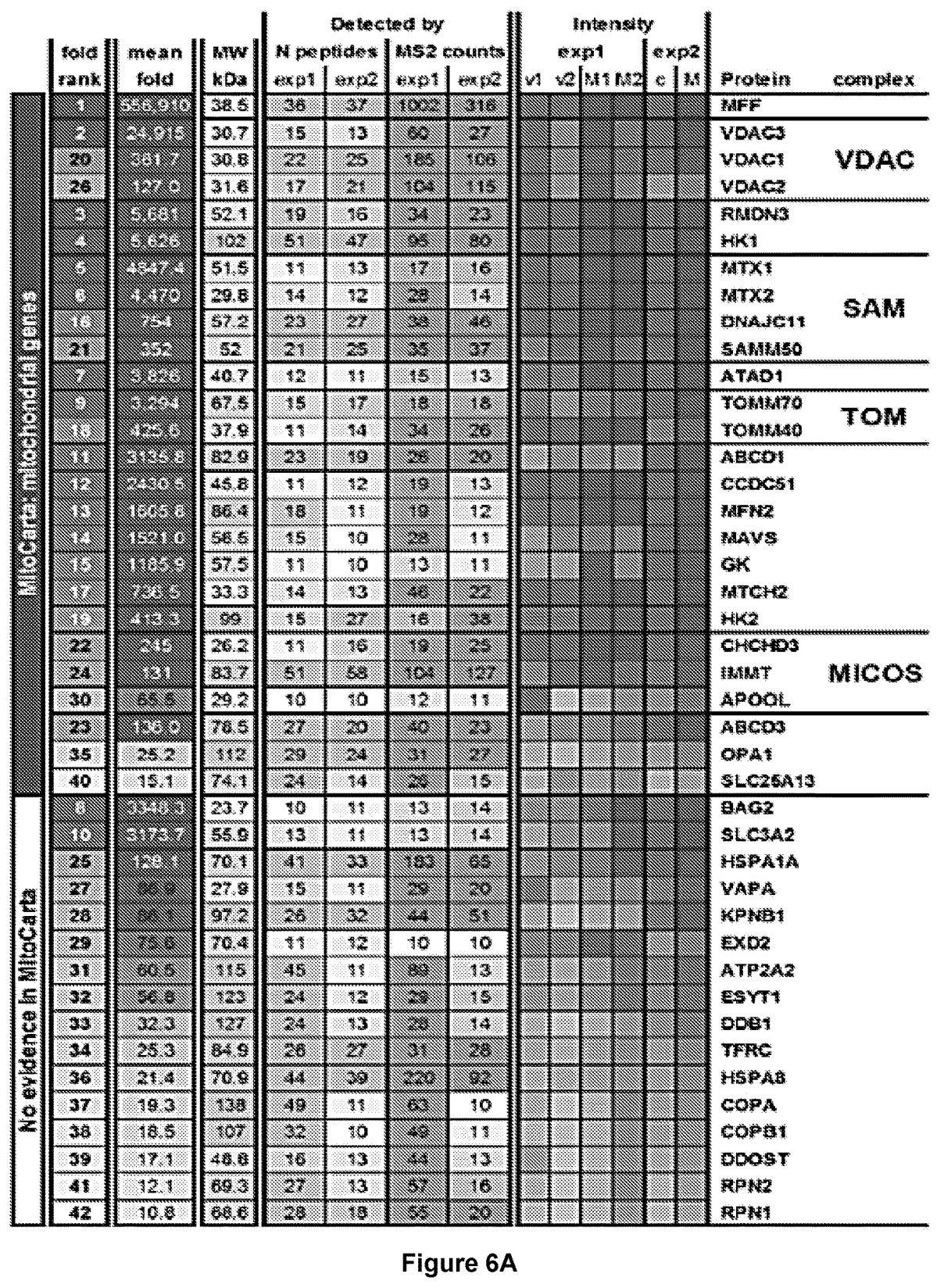

| | fold | mean | MW | Detected by | | | | Intensity | | | | | | | |
|---|---|---|---|---|---|---|---|---|---|---|---|---|---|---|---|
| | | | | N peptides | | MS2 counts | | exp1 | | | | exp2 | | | |
| | rank | fold | kDa | exp1 | exp2 | exp1 | exp2 | v1 | v2 | M1 | M2 | c | M | Protein | complex |
| MitoCarta: mitochondrial genes | 1 | 556,910 | 38.5 | 36 | 37 | 1002 | 318 | | | | | | | MFF | |
| | 2 | 24,915 | 30.7 | 15 | 13 | 60 | 27 | | | | | | | VDAC3 | VDAC |
| | 20 | 381.7 | 30.8 | 22 | 25 | 185 | 108 | | | | | | | VDAC1 | |
| | 26 | 127.0 | 31.6 | 17 | 21 | 104 | 115 | | | | | | | VDAC2 | |
| | 3 | 5,681 | 52.1 | 19 | 16 | 34 | 23 | | | | | | | RMDN3 | |
| | 4 | 5,626 | 102 | 51 | 47 | 95 | 80 | | | | | | | HK1 | |
| | 5 | 4847.4 | 51.5 | 11 | 13 | 17 | 16 | | | | | | | MTX1 | SAM |
| | 6 | 4,470 | 29.8 | 14 | 12 | 28 | 14 | | | | | | | MTX2 | |
| | 16 | 754 | 57.2 | 23 | 27 | 38 | 46 | | | | | | | DNAJC11 | |
| | 21 | 352 | 52 | 21 | 25 | 35 | 37 | | | | | | | SAMM50 | |
| | 7 | 3,826 | 40.7 | 12 | 11 | 15 | 13 | | | | | | | ATAD1 | |
| | 9 | 3,294 | 67.5 | 15 | 17 | 18 | 18 | | | | | | | TOMM70 | TOM |
| | 18 | 425.6 | 37.9 | 11 | 14 | 34 | 26 | | | | | | | TOMM40 | |
| | 11 | 3134.8 | 82.9 | 23 | 19 | 28 | 20 | | | | | | | ABCD1 | |
| | 12 | 2430.5 | 45.8 | 11 | 12 | 19 | 13 | | | | | | | CCDC51 | |
| | 13 | 1605.8 | 86.4 | 18 | 11 | 19 | 12 | | | | | | | MFN2 | |
| | 14 | 1521.0 | 56.5 | 15 | 10 | 28 | 11 | | | | | | | MAVS | |
| | 15 | 1185.9 | 57.5 | 11 | 10 | 13 | 11 | | | | | | | GK | |
| | 17 | 736.5 | 33.3 | 14 | 13 | 46 | 22 | | | | | | | MTCH2 | |
| | 19 | 413.3 | 99 | 15 | 27 | 16 | 38 | | | | | | | HK2 | |
| | 22 | 249 | 26.2 | 11 | 16 | 19 | 25 | | | | | | | CHCHD3 | MICOS |
| | 24 | 131 | 83.7 | 51 | 58 | 104 | 127 | | | | | | | IMMT | |
| | 30 | 65.5 | 29.2 | 10 | 10 | 12 | 11 | | | | | | | APOOL | |
| | 23 | 136.0 | 78.5 | 27 | 20 | 40 | 23 | | | | | | | ABCD3 | |
| | 35 | 25.2 | 112 | 29 | 24 | 31 | 27 | | | | | | | OPA1 | |
| | 40 | 15.1 | 74.1 | 24 | 14 | 26 | 15 | | | | | | | SLC25A13 | |
| No evidence in MitoCarta | 8 | 3348.3 | 23.7 | 10 | 11 | 13 | 14 | | | | | | | BAG2 | |
| | 10 | 3173.7 | 55.9 | 13 | 11 | 13 | 14 | | | | | | | SLC3A2 | |
| | 25 | 149.1 | 70.1 | 41 | 33 | 183 | 65 | | | | | | | HSPA1A | |
| | 27 | 96.9 | 27.8 | 15 | 11 | 29 | 20 | | | | | | | VAPA | |
| | 28 | 86.1 | 97.2 | 26 | 32 | 44 | 51 | | | | | | | KPNB1 | |
| | 29 | 75.8 | 70.4 | 11 | 12 | 10 | 10 | | | | | | | EXD2 | |
| | 31 | 60.5 | 115 | 45 | 11 | 89 | 13 | | | | | | | ATP2A2 | |
| | 32 | 56.8 | 123 | 24 | 12 | 29 | 15 | | | | | | | ESYT1 | |
| | 33 | 32.3 | 127 | 24 | 13 | 28 | 14 | | | | | | | DDB1 | |
| | 34 | 25.3 | 84.9 | 26 | 27 | 31 | 28 | | | | | | | TFRC | |
| | 36 | 21.4 | 70.9 | 44 | 39 | 220 | 92 | | | | | | | HSPA8 | |
| | 37 | 19.3 | 138 | 49 | 11 | 63 | 10 | | | | | | | COPA | |
| | 38 | 18.5 | 107 | 32 | 10 | 49 | 11 | | | | | | | COPB1 | |
| | 39 | 17.1 | 48.8 | 16 | 13 | 44 | 13 | | | | | | | DDOST | |
| | 41 | 12.1 | 69.3 | 27 | 13 | 57 | 16 | | | | | | | RPN2 | |
| | 42 | 10.8 | 68.6 | 28 | 18 | 55 | 20 | | | | | | | RPN1 | |

Figure 6A

| | | |
|---|---|---|
| DGANLSSARGILSLIQSSTRRAYQQILDVL | MFF #8 | SEQ ID NO: 8 |
| NLSSARGILSLIQSSTRRAYQQILDVL | MFF #8-1 | SEQ ID NO: 11 |
| SARGILSLIQSSTRRAYQQILDVL | MFF #8-2 | SEQ ID NO: 12 |
| GILSLIQSSTRRAYQQILDVL | MFF #8-3 | SEQ ID NO: 13 |
| SLIQSSTRRAYQQILDVL | MFF #8-4 | SEQ ID NO: 14 |
| QSSTRRAYQQILDVL | MFF #8-5 | SEQ ID NO: 15 |
| DGANLSSARGILSLIQSSTRRAYQQIL | MFF #8-6 | SEQ ID NO: 16 |
| DGANLSSARGILSLIQSSTRRAYQ | MFF #8-7 | SEQ ID NO: 17 |
| DGANLSSARGILSLIQSSTRR | MFF #8-8 | SEQ ID NO: 18 |
| DGANLSSARGILSLIQSS | MFF #8-9 | SEQ ID NO: 19 |
| DGANLSSARGILSLI | MFF #8-10 | SEQ ID NO: 20 |

Figure 10C

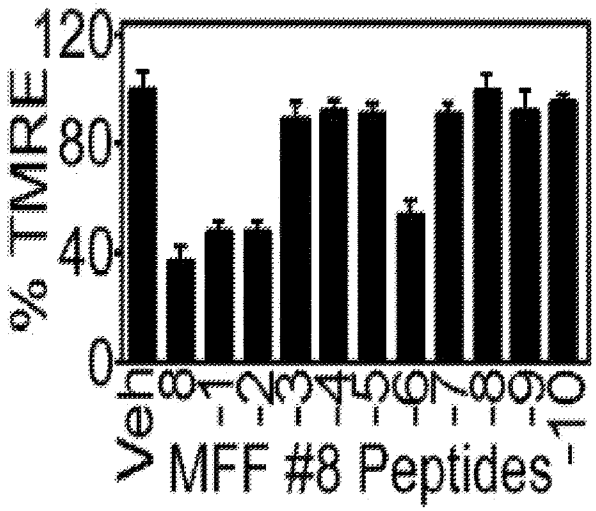

Figure 10D

ENGINEERED PEPTIDE AND PEPTIDE MIMETIC COMPOSITIONS AND METHODS

CROSS REFERENCE TO RELATED APPLICATIONS

The present application is a 35 U.S.C. § 371 national phase application from, and claiming priority to, International Application No. PCT/US2020/049888 filed Sep. 9, 2020, which is entitled to priority under 35 U.S.C. § 119(e) to U.S. Provisional Patent Application No. 62/897,971 filed Sep. 9, 2019 and U.S. Provisional Patent Application No. 62/908,207 filed Sep. 30, 2019, all of which are incorporated herein by reference in their entireties.

STATEMENT REGARDING FEDERALLY SPONSORED RESEARCH OR DEVELOPMENT

This invention was made with government support under CA140043, CA220446 and CA010815 awarded by the National Institutes of Health. The government has certain rights in the invention.

BACKGROUND OF THE INVENTION

The regulators of mitochondrial cell death in cancer have remained elusive, hampering the development of new therapies. In the present disclosure, it is demonstrated that protein isoforms of Mitochondrial Fission Factor (MFF1 and MFF2), a molecule that controls mitochondrial size and shape, i.e. mitochondrial dynamics, are overexpressed in patients with non-small cell lung cancer and form homo- and heterodimeric complexes with the voltage-dependent anion channel-1 (VDAC1, also called VDAC), a key regulator of mitochondrial outer membrane permeability. By molecular modeling and mutagenesis studies, MFF was observed to insert into the interior hole of the VDAC1 ring using Arg225, Arg236 and Gln241 as key contact sites. Peptidyl mimicry of this binding interface is demonstrated, and a cell-permeable MFF Ser223-Leu243 D-enantiomeric peptidomimetic disrupts the MFF-VDAC1 complex, in vivo, acutely depolarizing mitochondria and triggering cell death in heterogeneous tumor types, including drug-resistant melanoma, but not cultures of normal cells. In preclinical models, treatment with the MFF peptidomimetic was well tolerated and delivers anticancer activity in patient-derived xenografts, primary breast and lung adenocarcinoma 3D organoids and glioblastoma neurospheres. These data identify the MFF-VDAC1 complex as a novel regulator of mitochondrial cell death and actionable therapeutic target in cancer.

There is a need in the art for recombinant optimized peptide and peptide mimetics that target mitochondrial permeability, for methods of making the recombinant optimized peptide, and for peptide mimetics and methods of their use in the treatment of cancer. The invention of the present disclosure addresses these needs.

SUMMARY OF THE INVENTION

The current disclosure is based on the discovery that peptides and peptide mimetics derived from mitochondrial fission factor (MFF) can be used to target the protein of the mitochondrial voltage-dependent anion channel-1 or VDAC1 (also called VDAC) gene preferably in cancer cells. As a result of this targeting, mitochondrial depolarization occurs leading to cell death and inhibition of tumor cell growth.

Thus, in some aspects, the current invention includes a Mitochondrial Fission Factor (MFF)-derived peptide comprising an amino acid sequence that is at least 85%, 90%, 91%, 92%, 93%, 94%, 95%, 96%, 97%, 98%, 99%, 99.5% or 100% identical to at least a 10 amino acid consecutive sequence of any one of SEQ ID NO: 1-23.

In certain embodiments, the peptide comprises the amino acid sequence of any one of SEQ ID NO: 1-23.

In certain embodiments, the peptide consists of the amino acid sequence of any one of SEQ ID NO: 1-23.

In certain embodiments, the amino acid sequence of any one of SEQ ID NO: 11, 12, 18 or 21.

In certain embodiments, the peptide is conjugated to a cell-penetrating amino acid sequence.

In certain embodiments, the cell-penetrating amino acid sequence is selected from the group consisting of an HIV-Tat cell-penetrating sequence, penetratin (also known as antennapedia), cR10 and Pep-1.

In certain preferred embodiments, the cell-penetrating amino acid sequence comprises SEQ ID NO: 24.

In some aspects, the current invention includes a polynucleotide encoding the peptide of any one of the above embodiments and aspects and any other embodiment or aspect of the current invention.

In some aspects, the current invention includes a pharmaceutical composition comprising the polynucleotide of any of the above embodiments and aspects and any other embodiment or aspect of the current invention and a pharmaceutically acceptable carrier, diluent or excipient.

In some aspects, the current invention includes a pharmaceutical composition comprising at least one of the peptides of any one of above embodiments and aspects and any other embodiment or aspect of the current invention and a pharmaceutically acceptable carrier, diluent or excipient.

In some aspects, the current invention includes a method of treating a disease in a subject in need thereof, comprising administering to the subject an effective amount of the peptide or polynucleotide or the pharmaceutical composition of any one of above embodiments and aspects or any other embodiment or aspect of the current invention.

In certain embodiments, the disease is cancer.

In certain embodiments, the cancer is prostate cancer (e.g., androgen independent), glioblastoma, breast cancer, breast adenocarcinoma, lung cancer, non-small cell lung cancer, melanoma, ovarian cancer, hematological B-cell cancer, hematological T-cell cancer, metastatic cancer, treatment-resistant tumor (e.g., Braf/Medi resistant melanoma) or myc+ cancer.

In certain embodiments of the above aspects of the invention or any other aspect described herein, the invention further comprises administering a second agent to the subject.

In certain embodiments, the second agent is a molecularly targeted therapy, a vaccine, a chemotherapeutic agent (e.g., etoposide or doxorubicin), radiation, or combinations thereof.

In some aspects, the current invention includes a method of targeting MFF in a subject in need thereof, comprising administering to the subject an effective amount of the peptide of any of the above embodiments and aspects or any other embodiment or aspect of the current invention.

In some aspects, the current invention includes a kit comprising the pharmaceutical composition of any of the above aspects and embodiments or any other aspect or embodiment disclosed herein and a delivery agent.

In certain embodiments, the delivery agent is for oral, intranasal, transbuccal, transdermal, intraperitoneal, intramuscular, intravenous, or other injectable form of delivery.

In some aspects, the current invention includes a peptide mimetic comprising a retro-Inver so D-enantiomer of the MFF-derived peptide of any of the above aspects and embodiments or any aspect or embodiment of the current invention.

In certain preferred embodiments, the peptide mimetic is a retro-inverso D-enantiomer of the MFF-derived peptide of SEQ ID NO: 21.

In certain embodiments, the peptide mimetic is conjugated to a cell-penetrating amino acid sequence.

In certain embodiments, the cell-penetrating amino acid sequence is an HIV-Tat cell-penetrating sequence, penetratin, cR10 or Pep-1.

In certain preferred embodiments, the cell-penetrating amino acid sequence is SEQ ID NO: 24.

In some aspects, the invention includes a pharmaceutical composition comprising the peptide mimetic of any one of the above aspects and embodiments or any other aspect and embodiment of the current invention and a pharmaceutically acceptable carrier, diluent or excipient.

In some aspects, the invention includes a method of treating a disease in a subject in need thereof, comprising administering to the subject an effective amount of the peptide mimetic or the pharmaceutical composition of any of the above aspects and embodiments or any other aspect and embodiment of the current invention.

In certain embodiments, the disease is cancer.

In certain embodiments, the cancer is prostate cancer (e.g., androgen independent), glioblastoma, breast cancer, breast adenocarcinoma, lung cancer, non-small cell lung cancer, melanoma, ovarian cancer, hematological B-cell cancer, hematological T-cell cancer, metastatic cancer, treatment-resistant tumor (e.g., Braf/Medi resistant melanoma) or myc+ cancer.

In certain embodiments of the above aspects and embodiments or any other aspect and embodiment of the current invention, the method further comprises administering a second agent to the subject.

In certain embodiments, the second agent is a molecularly targeted therapy, a vaccine, a chemotherapeutic agent (e.g., etoposide or doxorubicin), radiation, or combinations thereof.

In some aspects, the invention includes a method of targeting MFF in a subject in need thereof, comprising administering to the subject an effective amount of the peptide mimetic of any one of the above aspects and embodiments or any aspect and embodiment of the current invention.

In some aspects, the invention includes a kit comprising the pharmaceutical composition of claim 24 and a delivery agent.

In certain embodiments, the delivery agent is for oral, intranasal, transbuccal, transdermal, intraperitoneal, intramuscular, intravenous, or other injectable form of delivery.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 1A shows MIT expression by immunohistochemistry in localized and metastatic prostate cancer patients (n=192). N, normal; PIN, prostatic intraepithelial neoplasia; Ca, adenocarcinoma. Insets, image magnification of selected regions. MFF expression in prostate cancer metastases to bone or lungs are shown. Scale bars, 100 μm. FIG. 1**R shows that the indicated increasing concentrations of recombinant VDAC1 were mixed with affinity-purified Flag-MFF1 followed by pull-down and Western blotting.

FIG. 2A shows that prostate cancer DU145 or PC3 cells were transfected with vector or MFF1 cDNA and analyzed for mitochondrial morphology by fluorescence microscopy. Elong, elongated; Inter, intermediate; fragm, fragmented. Data are expressed as box and whiskers (min to max); +, mean. FIG. 2B shows that DU145 or PC3 cells were transfected with control non-targeting siRNA (Ctrl) or MFF-directed siRNA (MFF) and analyzed for mitochondrial membrane potential by TMRE staining and flow cytometry with or without the uncoupler, FCCP. Representative experiment (n=3). FIG. 2C shows that cells transfected as in FIG. 2B were analyzed for oxygen consumption rates (OCR) on a Seahorse XFe96 Bioenergetics Flux Analyzer. Mean±SD of replicates of a representative experiment (n=3). FIG. 2D illustrates that the conditions were as in FIG. 2C and ATP production was quantified. Mean±SD (n=3). FIG. 2E illustrates that PC3 cells transfected with the indicated siRNA were analyzed by Western blotting. p, phosphorylated. The position of LC3 (I) or lipidated LC3 (II) is indicated. FIG. 2F illustrates that PC3 cells expressing GFP-LC3 were transfected with the indicated siRNA and analyzed by fluorescence microscopy. FIG. 2G illustrates that siRNA-transfected PC3 cells were analyzed for Annexin V and propidium iodide (PI) staining by multiparametric flow cytometry. The percentage of cells in each quadrant is indicated. FIG. 2H illustrates that PC3 cells stably transduced with pLKO or MFF-directed shRNA (MFF) were analyzed for cell proliferation by direct cell counting at the indicated time intervals. Each tracing corresponds to an individual experiment (n=3). FIG. 2I illustrates that the indicated shRNA-transduced cells were analyzed for colony formation after 14 d by crystal violet staining. Representative experiment out of at least two independent determinations. FIG. 2J illustrates that siRNA-transfected cells (100-200 nM) were analyzed for cell viability by an MTT assay. Mean±SD (n=3). FIG. 2K illustrates that shRNA-transduced PC3 cells were injected s.c. in immunocompromised athymic nude mice and tumor growth was measured at the indicated time intervals. Each symbol corresponds to an individual tumor. Lines correspond to means.

FIG. 3A shows a schematic diagram of high-throughput screening of MFF-derived peptides for inhibition of mitochondrial membrane potential. MTE, mitochondrial extracts. FIG. 3B illustrates, for conditions as in FIG. 3A, that MFF peptides (20 μM for 40 min) were screened for modulation of mitochondrial membrane potential by TMRE staining. Mean±SD of replicates from a representative experiment (n=2). FIG. 3C illustrates that the indicated cell types transfected with vector (Vect) or Flag-MFF1 were immunoprecipitated (IP) with an antibody to Flag, treated with MFF peptide #1 or #8 as in FIG. 3B, and analyzed by Western blotting (left and middle Western blots). $Ig_L$, Ig light chain. PC3 cell extracts were fractionated on beads-coupled MFF peptide #8 by affinity chromatography and bound proteins were identified by Western blotting (right Western blot). FIG. 3D illustrates isothermal titration calorimetry binding data of WT MFF peptide #8-11 (left) or MFF scrambled peptide (Scramb, right) to human recombinant VDAC. Representative experiment (n=4). FIG. 3E illustrates a structural model of VDAC-MFF peptide #8-11 complex generated with the CABS-Dock server. The MFF peptide (green stick) binds the interior cavity of VDAC (blue carton/stick) in an extensive network of interactions blocking access to solutes. FIG. 3F illustrates predicted contact sites of MFF residues R225, R236 or Q241 with the VDAC structure. FIG. 3G illustrates that PC3 cells transfected with WT Flag-MFF or mutant Flag-MFF R225D, R236D or Q241A were immunoprecipitated (IP) with an antibody to Flag and immune complexes were analyzed by Western blotting (left panel) and quantified by densitometry (right panel). AU, arbitrary units. FIG. 3H illustrates that PC3 cells transduced with pLKO or MFF-directed shRNA were reconstituted with WT MFF or MFF deleted in the VDAC binding domain (DN) or MFF carrying the double mutation R225D/R236D (DD) and analyzed for cell proliferation by direct cell count. Data are the mean±SD (n=3)a.

FIG. 4A illustrates that PC3 cells treated with cell-permeable scrambled peptide or MFF peptide #8-11 (10 μM) were analyzed for single-cell TMRE labeling, by time-lapse videomicroscopy. FIG. 4B illustrates that PC3 cells were treated with the indicated MFF peptides or $CaCl_2$ and supernatants (Sup) or mitochondrial (Mito) extracts were analyzed by Western blotting. FIG. 4C illustrates that tumor (LNCaP, C4-2B, PC3, DU145, PC3) or normal (BPH-1, HFF) cell types were treated with the indicated concentrations (μM) of cell-permeable scrambled peptide or MFF peptide #8-11 (MFF) and analyzed for cell death after 2 h. Mean±SD of replicates (n=3). FIG. 4D illustrates that PC3 cells were treated (0-50 μM) with cell-permeable scrambled peptide, WT MFF peptide #8-11 or MFF peptide #8-11 containing the double mutation R225D/R236D (DD) and analyzed for cell death at the indicated time intervals. Mean±SD (n=3). FIGS. 4E and 4F illustrate that patient-derived human glioblastoma (GBM) neurospheres in culture were treated with cell-permeable scrambled peptide (50 μM) or the indicated increasing concentrations of MFF (D) 8-11 peptidomimetic (μM) for 1, 3, or 24 h (FIG. 4E, representative GBM neurospheres after 24-h treatment are shown), stained with calcein (live cells) or To-Pro (dead cells), and normalized fluorescence units (FU) were quantified (FIG. 4F). BF, bright field. Mean±SD, two individual patients analyzed. *, p=0.01-0.03 compared to scrambled peptide (Scr). FIG. 4G illustrates that PC3 cells ($5\times10^6$ cells in 50% Matrigel) were engrafted on the flanks of immunocompromised athymic mice, and animals randomized in two groups (8-10 tumors per group) received cell-permeable scrambled peptide or MFF (D) 8-11 peptidomimetic (50 mg/kg, daily i.p.) with quantification of tumor growth. Symbols correspond to individual tumors. Trend lines are shown. FIG. 4H illustrates that, for conditions that were as in FIG. 4G, average (mean±SEM) tumor volume was measured on day 13 of treatment. **, p=0.008. FIG. 4I illustrates that patient-derived organoids of non-small-cell lung cancer (NSCLC) were treated with cell-permeable scrambled peptide (Scramb, 100 μM) or MFF (D) 8-11 peptidomimetic (100 μM), and analyzed after 24 h by hematoxylin-eosin (H&E) staining and immunohistochemistry for Ki-67 or cleaved caspase-3 (Cl. Casp.3). Scale bar, 100 μm. FIG. 4J illustrates, for conditions that were as in FIG. 4I, that the percentage of cells stained for Ki-67 or cleaved caspase-3 was quantified. Mean±SD (average of 2-3 independent fields). *, p=0.02; ***, p=0.0004 for 100 μM MFF (D) 8-11 peptidomimetic compared to scrambled peptide.

FIG. 5A illustrates Amplification of MFF and Drp1 in prostate cancer (77 patients, 107 samples). CRPC, castration-resistant prostate cancer; NEPC, neuroendocrine prostate cancer. FIG. 5B illustrates TCGA correlation (n=380) between MFF expression and prostate cancer progression. NR, no recurrence at 5 years; R, recurrence at 5 years. FIG. 5C illustrates TCGA correlation (n=380) of MFF expression (log MFF copy number) and prostate cancer survival. A, alive at 5 years; ND, alive without disease at 5 years; D, dead with disease at 5 years. FIG. 5D illustrates that prostate tissue samples harvested from Transgenic Adenocarcinoma of the Mouse Prostate (TRAMP) mice and containing neuroendocrine (NE) tumors or adenocarcinoma (AdCa) were examined for expression of Drp1 or MFF, by immunohistochemistry. Scale bar, 20 μm. FIGS. 5E-5F show that cases of metastatic (met) human prostate cancer to lymph nodes (LN, FIG. 5E) or bone or lungs (FIG. 5F) were stained by immunohistochemistry for expression of MFF, prostate-specific antigen (PSA) or hematoxylin/eosin (H&E). FIG. 5G shows the correlation between MFF expression in a cohort of prostate cancer patients (n=192) and Gleason grade.*, p=0.01; **, p=0.002. ns, not significant. FIG. 5H shows the correlation between MFF expression in a cohort of prostate cancer patients (n=192) and tumor size.*, p=0.01; **, p=0.002. ns, not significant. Figure SI shows MFF mRNA expression and copy number in the Cancer Cell Line Encyclopedia. Inset, MFF mRNA expression in prostate cancer cell lines. FIG. 5J shows that the indicated prostate cancer lines were analyzed by Western blotting. CRPC, castration-resistant prostate cancer, AR, androgen receptor. Bar graph, densitometric quantification of MFF protein bands.

FIGS. 6A-6F illustrate MFF-associated proteins in prostate cancer. FIG. 6A shows a heat map of MFF-associated proteins identified by a 1D proteomics screening in prostate adenocarcinoma PC3 cells. The mean fold, number of peptides and MS counts in two independent experiments are shown. The four main categories of MFF-associated proteins by pathway analysis (VDAC, SAM, TOM, MICOS) are shown on the right. FIG. 6B shows a schematic diagram of predicted human MFF isoforms generated by alternative splicing of a single MFF locus. TM, transmembrane domain. FIG. 6C shows total extracts from PC3 cells were analyzed by Western blotting (top panel). The position of individual MFF isoforms is indicated. The bottom panels illustrate that total extracts from DU145 or PC3 cells were analyzed by Western blotting. The position of individual MFF isoforms is indicated. FIGS. 6D-6F show PC3 cells transfected with vector or the indicated HA-, Myc-, or Flag-tagged MFF constructs were immunoprecipitated (IP) with an antibody to Flag and analyzed by Western blotting. TCE, total cell extracts; Sup, supernatant.

FIG. 7A shows that PC3 cells transfected with MFF1 were analyzed for changes in mitochondrial morphology by MitoTracker and MFF staining and fluorescence microscopy. Representative images are shown. FIG. 7B shows that DU145 or PC3 cells were transfected with control non-targeting siRNA (Ctrl) or MFF-directed siRNA, labeled as in FIG. 7A, and analyzed for mitochondrial morphology by fluorescence microscopy. FIG. 7C shows that siRNA-transfected DU145 or PC3 cells as in FIG. 7B were analyzed for changes in mitochondrial morphology by fluorescence microscopy. Elong, elongated; Fragm, fragmented; Inter, intermediate. Data are expressed as box and whiskers (min to max); +, mean (n=3). FIG. 7D shows that siRNA-transfected DU145 or PC3 cells as in FIG. 7B were analyzed for mitochondrial mass by MitoTracker (MT) staining and flow cytometry.

FIG. 8A shows DU145 or PC3 cells were transfected with control non-targeting siRNA (Ctrl) or MFF-directed siRNA and analyzed for changes in mitochondrial membrane potential by TMRE staining and flow cytometry, with or without the uncoupler, FCCP. Mean±SD of replicates (n=2). FIG. 8B shows normal prostate epithelial BPH-1 and RWPE1 cells were transfected as in FIG. 8A, and analyzed for TMRE fluorescence, by flow cytometry. Representative experiment (n=2). FIG. 8C shows that siRNA-transfected DU145 or PC3 cells as in FIG. 8A were quantified for oxygen consumption rates (OCR) using a Seahorse XFe96 Bioenergetics Flux Analyzer. Mean±SD of replicates (n=3). FIG. 8D shows that, for conditions that were as in FIG. 8A, siRNA-transfected cells were analyzed for production of mitochondrial superoxide (mitoSox), by fluorescence microscopy. Data are expressed as box and whiskers (min to max); +, mean (n=4). *, p<0.0001. FIG. 8E shows that DU145 cells stably transduced with pLKO or MFF-directed shRNA (MFF) were analyzed for glucose consumption. Mean±SD of replicates (n=3). , p=0.001-0.002. FIG. 8F shows that DU145 cells stably transduced with pLKO or MFF-directed shRNA (MFF) were analyzed for lactate production. Mean±SD of replicates (n=3). , p=0.001-0.002. FIG. 8G shows that PC3 cells expressing GFP-LC3 were transfected with the indicated siRNA and cells with punctate LC3 staining were quantified by fluorescence microscopy. Mean±SD of replicates (n=3). *, p=0.0006.

FIG. 9A is a Western blot. DU145 or PC3 cells stably transduced with pLKO or MFF-directed shRNA (MFF) were analyzed by Western blotting. FIG. 9B shows DU145 cells were transfected with control siRNA (Ctrl) or MFF-directed siRNA (MFF) and analyzed for Annexin V and propidium iodide (PI) staining by multiparametric flow cytometry. The percentage of cells in each quadrant is indicated. FIG. 9C shows two independent clones of DU145 or PC3 cells stably expressing MFF-directed shRNA (clones #1 and #2) or control pLKO were analyzed by Western blotting. Cl., cleaved. FIG. 9D shows PC3 cells transfected with control non-targeting siRNA (Ctrl) or two independent MFF-directed siRNA (#A, #C) were analyzed by Western blotting. Cl., cleaved. FIG. 9E shows siRNA-transfected PC3 cells as in FIG. 9E were incubated with stress stimuli, doxorubicin (0.5 μM), etoposide (10 μM), hydrogen peroxide ($H_2O_2$, 300 μM) or serum- and glucose-deprivation (Starv) and analyzed by Western blotting. Cl., cleaved. FIG. 9F shows, for conditions that were as in FIG. 9D, that siRNA-transfected cells were analyzed for cell proliferation by direct cell counting at the indicated time intervals. Each line corresponds to an individual experiment (n=3). FIG. 9G shows that shRNA-transduced cells expressing pLKO or MFF-directed shRNA (clones #1 and #2) were analyzed for colony formation after 14 d by crystal violet staining. Mean±SD of replicates (n=3).

FIGS. 10A-10G illustrate requirements of MFF-VDAC recognition. FIG. 10A shows Mitochondrial extracts from PC3 or BPH-1 cells were incubated with MFF peptide #1 (30 μM) or MFF peptide #8 (10-30 μM) and analyzed for changes in mitochondrial membrane potential by TMRE staining. Mean±SD of replicates (n=2). FIG. 10B shows a schematic diagram of MFF isoforms (MFF1-MFF5) and position of a VDAC binding site (PTP) in MFF1 and MFF2. The minimal MFF-VDAC interacting region (peptide #8-11) as determined by peptide mutagenesis is indicated. PTP, permeability transition pore; TM, transmembrane domain. FIG. 10C shows a sequence of partially overlapping MFF synthetic peptides derived from MFF peptide #8 used in this study. FIG. 10D shows mitochondrial extracts from PC3 cells were incubated with MFF peptide #8 variants as in FIG. 10C and analyzed for changes in TMRE fluorescence. Mean±SD of replicates (n=2). FIG. 10E shows PC3 cells transfected with WT Flag-MFF or mutant Flag-MFF R225D, R236D or Q241A were immunoprecipitated with an antibody to Flag and immune complexes were analyzed by Western blotting. Bars corresponding to densitometric quantification of protein bands for VDAC, HK-II and MFF in supernatants (Sup) or immunoprecipitates (IP). FIG. 10F shows a Western Blot. PC3 cells stably transduced with MFF-directed shRNA were reconstituted with vector, WT MFF or mutant MFF lacking the VDAC-interacting domain (DN, as in FIG. 10B) and analyzed by Western blotting. FIG. 10G shows a Western Blot. Conditions were as in FIG. 10F, except that shRNA-transduced PC3 cells were reconstituted with WT MFF, MFF-DN or MFF containing the double mutation R225D/R236D (DD), and analyzed by Western blotting.

FIG. 11A illustrates that PC3 cells were incubated with vehicle, cell-permeable scrambled peptide or cell-permeable MFF peptide #8-11, stained with MitoTracker (MT, total mitochondria) and TMRE (mitochondrial membrane potential) and imaged at the indicated time intervals, by time-lapse videomicroscopy. Representative images at t=0 min or t=120 min are shown. FIG. 11B illustrates that, for conditions as in FIG. 11A, changes in TMRE and MitoTracker staining were quantified in PC3 cells incubated with vehicle at the indicated time intervals. FIG. 11C illustrates flow cytometry results. The conditions were as in FIG. 11A, and changes in TMRE staining were analyzed in the whole cell population by flow cytometry. FIG. 11D illustrates that the results were quantified. Mean±SD of replicates (n=2). FIG. 11E illustrates that BPH-1 cells were incubated with vehicle, cell-permeable MFF #8-11 peptide or $CaCl_2$ and mitochondrial extracts (Mito) or supernatants (Sup) were analyzed by Western blotting. FIG. 11F: Isogenic pairs of drug-sensitive (WM983B S, WM35 S) or drug-resistant (WM983B_R, WM35_R) melanoma cell lines were incubated with the indicated increasing concentrations of the cell-permeable MFF peptide #8-11 or cell-permeable scrambled peptide (50 μM) and analyzed for cell death by CellTox reactivity at various time intervals. Mean±SD (n=2).

FIG. 12A illustrates that PC3 cells were incubated with the indicated increasing concentrations (μM) of cell-permeable scrambled peptide or cell-permeable MFF peptide #8-11 and analyzed for cell death at the indicated time intervals. Mean±SD of replicates (n=2). FIG. 12B illustrates that glioblastoma LN229 cells or normal human foreskin fibroblasts (HFF) were treated with cell-permeable scrambled peptide or cell-permeable MFF peptide #8-11 (μM) and analyzed for cell death at the indicated time intervals. Mean±SD of replicates (n=3). FIGS. 12C and 12D illustrate that DU145 or PC3 cells were incubated with cell-permeable scrambled peptide or cell-permeable MFF peptide #8-11 (0-50 μM), mixed with the indicated concentrations of Z-VAD-fmk (Z-VAD, 0-50 μM for 75 min) or cyclosporine A (CsA, 0-10 μM for 75 min), and analyzed for cell death at the indicated time intervals. Mean±SD of replicates (n=2). FIG. 12E illustrates that DU145 or PC3 cells were incubated with the indicated cell permeable peptides as in FIG. 12C, and total cell extracts were analyzed by Western blotting. Veh, vehicle; Scr, scrambled; MFF, MFF peptide #8-11. FIG. 12F illustrates that PC3 cells were incubated with cell-permeable scrambled peptide, MFF peptide #8-11 or MFF peptide #8-11 containing the double mutation R225D/R236D (DD) and total cell extracts were analyzed by Western blotting. FIG. 12G illustrates that WT or $CypD^{-/-}$ mouse embryonic fibroblasts (MEFs) were incubated with cell-permeable scrambled peptide (Scr) or MFF peptide #8-11 (25 μM) and analyzed for cell death at the indicated time intervals. Mean±SD or replicates (n=2).

FIG. 13A illustrates the predicted structure of MFF peptide #8-11 with L-amino acids (top) or retro-inverso D-enantiomer (bottom). FIG. 13B shows PC3 cells were treated with biotin-labeled MFF (D) 8-11 peptidomimetic (10 μM), incubated with streptavidin-FITC (TRITC) and intracellular peptidomimetic accumulation was analyzed after 20 min by fluorescence microscopy. Nuclei were stained with DAPI. Representative experiment. FIG. 13C shows PC3 cells were incubated with the indicated concentrations (10-25 μM) of cell-permeable scrambled peptide (Scr), MFF peptide #8-11 (L) or MFF (D) 8-11 peptidomimetic and analyzed for changes in mitochondrial membrane potential by TMRE labeling and flow cytometry. Mean±SD of replicates (n=2). FIG. 13D shows, for conditions as in FIG. 13C, that treated PC3 cells were analyzed for cell death at the indicated time intervals. Mean±SD of replicates (n=2). FIG. 13E shows PC3 cells were treated with cell-permeable scrambled peptide (top) or MFF (D) peptidomimetic (bottom, both at 10 μM) and imaged continuously by time-lapse video microscopy. Representative still images of t=0 min (left) or t=15 min (right) are shown. Scale bar, 100 μm. FIG. 13F shows PC3 cells ($5\times10^6$ cells in 50% Matrigel) were engrafted on the flanks of immunocompromised athymic mice, and animals randomized in two groups (2 tumors/mouse; 8-10 tumors per group) received cell-permeable scrambled peptide or MFF (D) 8-11 peptidomimetic (10 mg/kg, daily i.p.) with quantification of tumor growth. Symbols correspond to individual tumors. Trend lines are shown. FIG. 13G shows patient-derived human glioblastoma (GBM) neurospheres in culture were treated with cell-permeable scrambled peptide (50 μM) or the indicated increasing concentrations of MFF (D) 8-11 peptidomimetic (μM) for 1, 3, or 24 h (1-h treatment is shown), stained with calcein (live cells) or To-Pro (dead cells), and analyzed by fluorescence microscopy.

FIG. 14A-14B show primary, patient-derived organoids established ex vivo from cases of non-small cell lung cancer (NSCLC, FIG. 14A) or breast adenocarcinoma (FIG. 14B) were treated with MFF (D) 8-11 peptidomimetic (50 μM, FIG. 14A) or cell permeable scrambled peptide or MFF (D) 8-11 peptidomimetic (50-100 μM, FIG. 14B) for 24 h before staining for hematoxylin-eosin (H&E), Ki-67 or cleaved caspase-3 (Cl.Clasp.3). Scale bar, 100 μm. FIG. 14C shows, for conditions as in FIG. 14B, that the percentage of cells positive for Ki-67 or cleaved caspase-3 in treated breast adenocarcinoma organoids was quantified. Mean±SD (average of 2-3 independent fields). *, p=0.02 for 100 μM MFF (D) 8-11 peptidomimetic compared to scrambled peptide. FIG. 14D shows the indicated NSCLC (A549, H460) or breast adenocarcinoma (MDA-231, MCF-7) cell lines were analyzed by Western blotting. The position of the various MFF isoforms is indicated. FIG. 14E shows that the indicated cell lines as in FIG. 14D were incubated with the indicated concentrations (10-25 μM) of cell-permeable scrambled peptide (Scr) or MFF (D) 8-11 peptidomimetic and analyzed for changes in mitochondrial membrane potential by TMRE staining and flow cytometry (top) or cell death by CellTox reactivity (bottom) at the indicated time intervals. Mean±SD of replicates (n=2). FIG. 14F shows that tumor-bearing, immunocompromised mice were treated with vehicle (Veh) or MFF (D) 8-11 peptidomimetic and animal weight was measured at the indicated time intervals. Mean±SD (n=5).

FIG. 15A shows ChIP-Seq tracks of time-dependent Myc accumulation at the MFF promoter in Burkitt's lymphoma P493 cells at three different time points (t=0, 1 and 24 h) after removal of doxycycline (Dox) or neuroblastoma BE2C, Kelly or NGP cell lines. FIG. 15B shows ChIP of Myc accumulation at the MFF promoter in PC3 cells transfected with control non-targeting siRNA (siCtrl) or Myc-directed siRNA (siMyc). IgG, non-binding IgG. Mean±SD. , p=0.004; ns, not significant. FIGS. 15C-15D show PC3 cells were transfected with siCtrl or siMyc and analyzed for MFF expression by quantitative PCR (FIG. 15C) or Western blotting (FIG. 15D). Mean±SD. , p=0.002. FIG. 15E shows Neuroblastoma Shep21 cells stably transfected with a Dox-regulated conditional Myc-directed shRNA were analyzed for changes in Myc mRNA expression in the presence or absence of Dox, by quantitative PCR. Mean±SD. FIGS. 15F-15G: The conditions are as in FIG. 15E and Shep21 cells were analyzed for MFF expression with or without Dox by quantitative PCR (FIG. 15F) or Western blotting (FIG. 15G). Mean±SD. *p<0.0001. FIGS. 15H-15I: Shep ER neuroblastoma cells stably transfected with a 4OHT-inducible N-Myc transgene were analyzed for changes in Myc (FIG. 15H) or MFF (FIG. 15I) mRNA expression with or without 4OHT by quantitative PCR. Mean±SD. *p<0.0001.

FIGS. 16A-16C: PC3 cells were transfected with vector, Flag-MFF1 (FIG. 16A), Flag-MFF2 (FIG. 16B) or Flag-MIFFS (FIG. 16C), immunoprecipitated (IP) with an antibody to Flag and analyzed by Western blotting. Sup, supernatant; Unb, unbound. FIG. 16D: PC3 cells transfected with siCtrl or siMFF (top) or treated with $H_2O_2$ (bottom) were labeled with calcein in the presence of $CoCl_2$ and analyzed by flow cytometry. Numbers indicate fluorescence units per each condition. None, untreated. FIG. 16E: DU145 (top) or PC3 (bottom) cells were transfected with siCtrl or MFF-directed siRNA (siMFF) and analyzed for mitochondrial inner membrane potential by TMRE staining and flow cytometry with or without suboptimal concentrations of the uncoupler, FCCP. Representative experiment (n=3). FIG. 16F: The conditions are as in FIG. 16E, and TMRE staining was quantified in siRNA-transfected PC3 cells. Mean±SD.

FIG. 17A: DU145 (top) or PC3 (bottom) cells were transfected with siCtrl or siMFF and analyzed for oxygen consumption rates (OCR) on a Seahorse XFe96 Bioenergetics Flux Analyzer. Mean±SD (n=3). FIG. 17B: The conditions are as in FIG. 17A, and siRNA-transfected DU145 or PC3 cells were quantified for basal (top) and maximal (bottom) respiratory capacity. Mean±SD (n=3). *, p=0.0009-<0.0001. FIG. 17C: The conditions are as in FIG. 17A, and the rate of ATP production was quantified in siRNA-transfected cells. Mean±SD. *, p<0.0001; , p=0.001. FIG. 17D: siRNA-transfected DU145 (top) or PC3 (bottom) cells as in (FIG. 17A) were analyzed for mitochondrial superoxide (mitoSox) production by fluorescence microscopy. Mean±SD. *, p<0.0001. FIG. 17E: DU145 or PC3 cells transfected with increasing concentrations of siMFF (10-20 nM) were analyzed by Western blotting. p, phosphorylated. FIGS. 17F-17G: PC3 cells expressing LC3-GFP and transfected with siCtrl or siMFF were analyzed by confocal fluorescence microscopy (FIG. 17F) and the percentage of cells with punctate LC3-GFP staining was quantified (FIG. 17G). Mean±SD (n=3). ***, p<0.0001.

FIGS. 18A-18B: DU145 (top) or PC3 (bottom) cells transfected with siCtrl or increasing concentrations of siMFF (100-200 nM) were analyzed by Western blotting (FIG. 18A) and mitochondrial-dependent cell viability was determined by an MTT assay (FIG. 18B). Mean±SD (n=3). *, p<0.0001. FIG. 18C: PC3 cells were transfected with siCtrl or siMFF and analyzed for cellular morphology by light contrast microscopy. Arrows, cells with membrane blebbing and chromatin condensation. Scale bars, 50 μm. FIG. 18D: Two independent clones of DU145 or PC3 cells stably expressing shMFF (MFF #1 and MFF #2) or pLKO were analyzed by Western blotting. Cl., cleaved. Bar graph, densitometric quantification of total PARP (t-PARP) bands. FIG. 18E: DU145 (left) or PC3 (right) cells were transfected with siCtrl or siMFF and analyzed for Annexin V and propidium iodide (PI) staining by multiparametric flow cytometry. The percentage of cells in each quadrant is indicated. FIGS. 18F-18G: WT, $VDAC1^{-/-}$ or $CypD^{-/-}$ MEF were transfected with siCtrl or siMFF and analyzed for cell viability by Trypan blue exclusion and direct cell counting after 48 h (FIG. 18F) or an MTT assay (FIG. 18G). Mean±SD. *, p<0.0001; **, p=0.001; ns, not significant.

FIG. 19A: PC3 cells were transfected with siCtrl or two independent MFF-directed siRNA (siMFF #A and siMFF #C) and analyzed for cell proliferation by direct cell counting during a 3-day interval. Each tracing corresponds to an individual experiment (n=3). *, p=0.0002-0.0003. FIG. 19B: DU145 (left) or PC3 (right) cells stably transduced with pLKO or MFF-directed shRNA (shMFF) were analyzed for cell proliferation by direct cell counting at the indicated time intervals. Each tracing corresponds to an individual experiment (n=3). *, p<0.0001. FIGS. 19C-19D: PC3 cells transfected with siCtrl or siMFF were analyzed for DNA content by PI staining and flow cytometry (FIG. 19C, representative experiment; number corresponds to the percentage of cells in each peak) and the percentage of cells in the indicated cell cycle phase was quantified (FIG. 19D). Mean±SD (n=2). FIGS. 19E-19F: PC3 cells transduced with pLKO or shMFF were reconstituted with MFF2 cDNA and analyzed by Western blotting (FIG. 19E) or cell proliferation by direct cell counting after 72 h (FIG. 19F). Mean±SD (n=8). *, p<0.0001; ns, not significant. FIGS. 19G-19H: PC3 or DU145 cells stably transduced with two independent MFF-directed shRNA (clones #1 and #2) or pLKO were analyzed for colony formation after 14 d by crystal violet staining (FIG. 19G, representative experiment) and quantified (FIG. 19H). Mean±SD (n=4). *, p=<0.0001-0.003. FIG. 19I: PC3 cells stably transduced with pLKO (top) or shMFF (bottom) were injected s.c. on the flanks of immunocompromised athymic nude mice and tumor growth was measured at the indicated time intervals with a caliper. Each symbol corresponds to an individual tumor. Tumor measurements ($mm^3$) at day 30 are as follows: pLKO, 292.3±40.1 (n=9); MFF shRNA, 124.4±35.4 (n=9). **, p=0.006.

FIGS. 20A-20B: Representative cases of metastatic (met) human prostate cancer to lymph nodes (FIG. 20A, LN) or bone or lungs (FIG. 20B) were stained by immunohistochemistry for expression of MFF, prostate-specific antigen (PSA) or hematoxylin/eosin (H&E). FIGS. 20C-20D: Correlation between MFF expression in a cohort of prostate cancer patients and Gleason grade (FIG. 20C) or tumor size (FIG. 20D). The patient groups for FIG. 20C are as follows: <7 (n=62); 3-4 (n=68); >7 (n=29). *, p=0.01; , p=0.002. The patient groups for FIG. 20**D are as follows: T1-2 (n=124); T3-4 (n=68). ns, not significant.

FIG. 21A: Prostate tissue samples harvested from Transgenic Adenocarcinoma of the Mouse Prostate (TRAMP) mice (n=13) and containing neuroendocrine tumors (NE, n=6), well-differentiated prostatic adenocarcinomas (AdCa, n=2) or phyllodes-type prostate cancer (Phyllodes, n=6) were examined for expression of Drp1 or MFF, by immunohistochemistry (IHC). Representative images. Mouse #7036 had both phylloides-type tumors and well-differentiated AdCa. An IHC score is indicated per each representative field. Scale bars, 20 μm (NE and AdCa) or 200 μm (phyllodes). FIG. 21B: Normal prostatic epithelial cells BPH-1 or RWPE1 or prostate cancer cells LAPC1, LNCaP, C4-2, C4-2B, DU145 or PC3 were analyzed by Western blotting. CRPC, castration-resistant, AR, androgen receptor. Bar graph, densitometric quantification of MFF protein bands.

FIG. 22A: Schematic diagram of predicted human MFF isoforms generated by alternative splicing of a single MFF locus. TM, transmembrane domain. The nomenclature of MFF isoforms by numbers or letters is indicated. FIG. 22B: PC3 cells were transfected with vector or Flag-MFF1 cDNA and analyzed by Western blotting. The position of endogenous MFF isoforms or Flag-MFF1 is indicated. FIG. 22C: PC3 (left) or DU145 (right) cells transfected with MFF1 cDNA were analyzed for changes in mitochondrial morphology by MitoTracker and MFF staining and fluorescence microscopy. Representative images. Nuclei were stained with DAPI. Merge, image merging. FIG. 22D: DU145 (top) or PC3 (bottom) cells transfected as in FIG. 22C were quantified for differential mitochondrial morphology by fluorescence microscopy. Elong, elongated; Inter, intermediate; fragm, fragmented. Data are expressed as box and whiskers (min to max); +, mean. ***, p<0.0001.

FIGS. 23A-23B: PC3 cells transfected with control non-targeting siRNA (siCtrl) or two independent MFF-directed siRNA (siMFF #A and siMFF #C) (FIG. 23A) or DU145 or PC3 cells stably transduced with pLKO or MFF-directed shRNA (shMFF) (FIG. 23B) were analyzed by Western blotting. The molecular weight range of MFF isoforms is indicated. FIG. 23C: PC3 cells were transfected with siCtrl or siMFF and analyzed for changes in mitochondrial morphology by MitoTracker and MFF staining and fluorescence microscopy. Representative images. FIG. 23D: The siRNA silencing conditions are as in FIG. 23C and DU145 (left) or PC3 (right) cells were quantified for changes in mitochondrial morphology by fluorescence microscopy. Elong, elongated; Fragm, fragmented; Inter, intermediate. Data are expressed as box and whiskers (min to max); +, mean (n=3). FIG. 23E: siRNA-transfected DU145 or PC3 cells as in FIG. 23C were analyzed for mitochondrial mass by MitoTracker (MT) staining and flow cytometry.

FIG. 24A: PC3 cells transfected with siCtrl or siMFF were treated with $H_2O_2$ and analyzed for changes in calcein-$CoCl_2$ fluorescence by flow cytometry. Numbers correspond to fluorescence units. FIG. 24B: Normal prostatic epithelial BPH-1 or RWPE1 cells were transfected with siCtrl or siMFF and analyzed by TMRE staining and flow cytometry. Representative experiment (n=2). FIG. 24C: DU145 or PC3 cells were transfected with siCtrl or siMFF and analyzed for Extracellular Acidification Rates (ECAR) on a Seahorse XFe96 Bioenergetics Flux Analyzer. Mean±SD (n=3). FIG. 24D: DU145 or PC3 cells transfected as in FIG. 24C were analyzed for changes in glycolysis (left) and glycolytic capacity (right) using a Seahorse XFe96 Bioenergetics Flux Analyzer. Mean±SD (n=3). , p=0.003-0.006; *, p<0.0001.

FIG. 25A: PC3 cells transfected with siCtrl or siMFF were incubated with doxorubicin (0.5 μM), etoposide (10 μM), hydrogen peroxide ($H_2O_2$, 300 μM) or serum- and glucose-deprivation and analyzed by Western blotting. Cl., cleaved. FIG. 25B: Wild type (WT) or VDAC1$^{-/-}$ mouse embryonic fibroblasts (MEF) were analyzed by Western blotting. FIG. 25C: DU145 cells were transfected with siCtrl or two independent MFF-directed siRNA (siMFF #A and siMFF #C) and analyzed for cell proliferation by direct cell counting during a 3-day interval. Each tracing corresponds to an individual experiment (n=3). , p=0.001 (siMFF #C); *, p=0.0005 (siMFF #A). FIG. 25D: Glioblastoma LN229 or neuroblastoma SK-N-SH cells were transfected with siCtrl or siMFF and analyzed for cell proliferation by direct cell counting after 72 h. Mean±SD. , p=0.007-0.008. FIG. 25**E: PC3 cells transfected with siCtrl or siMFF were analyzed for DNA content by propidium iodide (PI) staining and flow cytometry. The percentage of cells in each cell cycle phase is indicated. Exp., experiment.

FIGS. 26A-26B: MFF expression quantified in a cohort of non-small cell lung cancer (NSLC) patients by immunohistochemistry was correlated to lymph node status (FIG. 26A) or tumor size (FIG. 26B). FIG. 26C: MFF mRNA expression and copy number in the Cancer Cell Line Encyclopedia. Inset, MFF mRNA expression in prostate cancer cell lines.

FIG. 27A: Glioblastoma (GBM) LN229 cells or normal HFF were treated with the indicated increasing concentrations of cell-permeable scrambled peptide or cell-permeable MFF peptide #8-11 (0-40 μM) and analyzed for cell death at the indicated time intervals. Mean±SD (n=3). FIG. 27B: Primary, patient-derived human GBM neurospheres were treated with cell-permeable scrambled peptide (50 μM) or the indicated increasing concentrations of MFF (D) 8-11 peptidomimetic (10-50 μM) for 1 h, stained with calcein (live cells) or To-Pro (dead cells) and analyzed for fluorescence expression. FU, fluorescence units; BF, bright field.

FIG. 28A: PC3 cells were incubated with vehicle, cell-permeable scrambled peptide (scrambled) or cell-permeable MFF peptide #8-11 (10 μM), stained with MitoTracker (MT) and TMRE and imaged continuously by time-lapse videomicroscopy. Representative images at t=0 min and t=120 min. FIG. 28B: The conditions are as in (FIG. 28A) and changes in TMRE and MitoTracker labeling were quantified at the indicated time intervals. The decrease in MT signal after MFF peptide #8-11 treatment may reflect activation of mitophagy in these settings. FIG. 28C and FIG. 28D: PC3 (FIG. 28C) or normal BPH-1 (FIG. 28D) cells were treated with the indicated MFF peptides or $CaCl_2$ and supernatants (Sup) or mitochondrial extracts (Mito) were analyzed by Western blotting. FIG. 28E: The indicated tumor (LNCaP, C4-2B, PC3, DU145, PC3) or normal (BPH-1, HFF) cell types were treated with increasing concentrations (0-40 μM) of cell-permeable scrambled peptide (Scr) or MFF peptide #8-11 (MFF) and analyzed for cell death after 2 h by CellTox reactivity. Mean±SD (n=3). FIG. 28F: An isogenic pair of drug-sensitive (2058_S) or drug-resistant (2058_R) melanoma cell lines were incubated with increasing concentrations of cell-permeable MFF peptide #8-11 or cell-permeable scrambled peptide (50 μM) and analyzed for cell death by CellTox reactivity at the indicated time intervals. Mean±SD (n=2). FIG. 28G: PC3 cells were treated (0-50 μM) with cell-permeable scrambled peptide, WT MFF peptide #8-11 or MFF peptide #8-11 containing the double mutation Arg225Asp/Arg236Asp (DD) and analyzed for cell death at the indicated time intervals. Mean±SD (n=3). FIG. 28H: PC3 cells were incubated with cell-permeable scrambled peptide or cell-permeable MFF peptide #8-11 (0-50 μM), mixed with the indicated concentrations of cyclosporine A (CsA, 0-10 μM for 75 min), and analyzed for cell death at the indicated time intervals. Mean±SD (n=2). FIG. 28I: Immortalized wild type (WT) mouse embryonic fibroblasts (MEF) or $CypD^{-/-}$ MEF were incubated with cell-permeable scrambled peptide (Scr) or MFF peptide #8-11 (25 μM) and analyzed for cell death. Mean±SD (n=2). FIG. 28J: Immortalized WT or $VDAC1^{-/-}$ MEF were incubated with the indicated increasing concentrations of cell permeable MFF peptide #8-11 (10-50 μM) or scrambled peptide (50 μM) and analyzed for cell death at the indicated time intervals. Mean±SD (n=2).

FIG. 29A: Predicted structure of MFF peptide #8-11 with L-amino acids (top panel) or retro-inverso D-enantiomer (bottom panel). FIG. 29B: PC3 cells were treated with biotin-labeled MFF (D) 8-11 peptidomimetic (10 μM), incubated with streptavidin-FITC (TRITC) and intracellular peptidomimetic accumulation was analyzed after 20 min by fluorescence microscopy. Nuclei were stained with DAPI. Representative images (n=2). FIGS. 29C and 29D: PC3 cells were incubated with the indicated concentrations (10-25 μM) of cell-permeable scrambled peptide (Scr), MFF peptide #8-11 (L) or MFF (D) 8-11 peptidomimetic and analyzed for mitochondrial membrane potential by TMRE labeling and flow cytometry (C) or cell death (D) at the indicated time intervals. Mean±SD (n=2). FIG. 29E: PC3 cells ($5\times10^6$ in 50% Matrigel) were engrafted on the flanks of immunocompromised athymic mice, and animals randomized in two groups were treated with cell-permeable scrambled peptide or MFF (D) 8-11 peptidomimetic (50 mg/kg, daily i.p.) with quantification of tumor growth. Mean±SD (n=8-10). , p=0.008 (d. 13 measurements). FIG. 29F: Patient-derived xenograft (PDX) melanomas resistant to the combination therapy Dabrafenib (Deb) plus Trametinib (Tra) and growing in immunocompromised mice were treated with vehicle (Veh) or MFF (D) 8-11 peptidomimetic (50 mg/kg) and tumor growth was quantified at the indicated time intervals. Mean±SD (n=5). FIG. 29G: Primary, patient-derived organoids of non-small-cell lung cancer (NSCLC) were treated with cell-permeable scrambled peptide (Scramb, 100 μM) or MFF (D) 8-11 peptidomimetic (100 μM) and analyzed after 24 h by hematoxylin-eosin (H&E) staining or immunohistochemistry for Ki-67 or cleaved caspase-3 (Cl.Casp.3) expression. Scale bar, 100 μm. FIGS. 29H and 29I: The conditions are as in (FIG. 29G) and the percentage of cells stained for Ki-67 or cleaved caspase-3 in patient-derived NSCLC (FIG. 29H) or breast adenocarcinoma (FIG. 29**I) organoids was quantified. Mean±SD (average of 2-3 independent fields). *, p=0.02; ***, p=0.0004 for 100 μM MFF (D) 8-11 peptidomimetic compared to scrambled peptide.

FIGS. 29J and 29K: Patient-derived human glioblastoma (GBM) neurospheres in culture were treated with cell-permeable scrambled peptide (50 μM) or the indicated increasing concentrations of MFF (D) 8-11 peptidomimetic (μM) for 1, 3, or 24 h (FIG. 29J, representative GBM neurospheres after 24-h treatment are shown), stained with calcein (live cells) or To-Pro (dead cells), and normalized fluorescence units (FU) were quantified (FIG. 29K). BF, bright field. Mean±SD, two individual patients analyzed. The statistical analysis for each time point is as follows: 1-h, Scrambled peptide (Scr) vs. MFF 10, p=0.002; Scr vs. MFF 25, p=0.03; Scr vs. MFF 50, ns; 3-h, Scr vs. MFF 10, p=0.001; Scr vs. MFF 25, p=0.01; Scr vs. MFF 50, p=0.01; 24-h, Scr vs. MFF 10, p=0.03; Scr vs. MFF 25, p=0.02; Scr vs. MFF 50, p=0.01.

DETAILED DESCRIPTION

Definitions

Figure 1A:
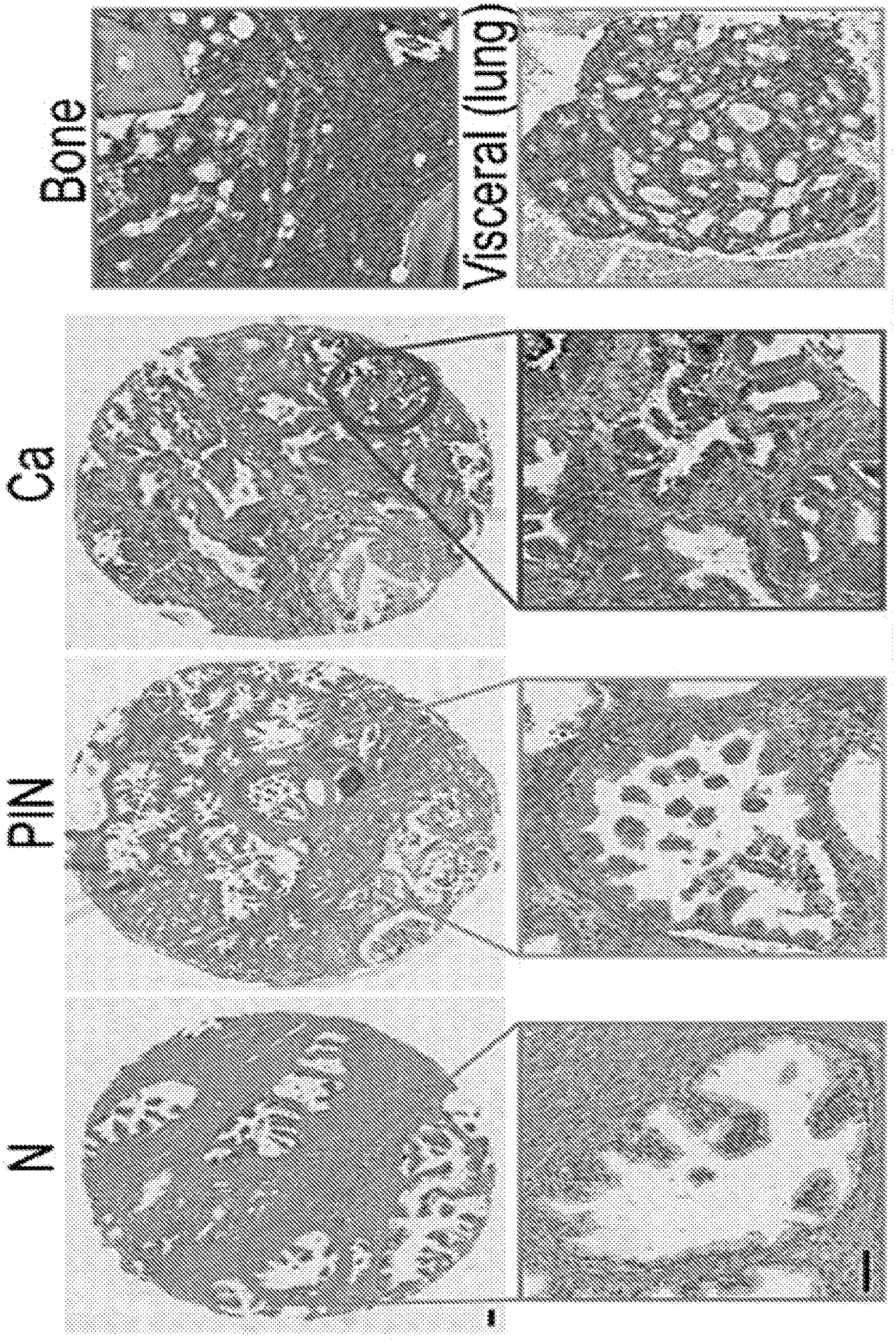
FIGS. 1A-1R illustrate Mitochondrial Fission Factor (MFF) in prostate cancer and non-small cell lung cancer (NSCLC)

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody can be replaced with other amino acid residues from the same side chain family and the altered antibody can be tested for the ability to bind antigens using the functional assays described herein.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

"Effective amount" or "therapeutically effective amount" are used interchangeably herein, and refer to an amount of a compound, formulation, material, or composition, as described herein effective to achieve a particular biological result or provides a therapeutic or prophylactic benefit. Such results may include, but are not limited to, anti-tumor activity as determined by any means suitable in the art.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein "endogenous" refers to any material from or produced inside an organism, cell, tissue or system.

As used herein, the term "exogenous" refers to any material introduced from or produced outside an organism, cell, tissue or system.

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., sendai viruses, lentiviruses, retroviruses, adenoviruses, and adeno-associated viruses) that incorporate the recombinant polynucleotide.

"Homologous" as used herein, refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous.

"Identity" as used herein refers to the subunit sequence identity between two polymeric molecules particularly between two amino acid molecules, such as, between two polypeptide molecules. When two amino acid sequences have the same residues at the same positions; e.g., if a position in each of two polypeptide molecules is occupied by an Arginine, then they are identical at that position. The identity or extent to which two amino acid sequences have the same residues at the same positions in an alignment is often expressed as a percentage. The identity between two amino acid sequences is a direct function of the number of matching or identical positions; e.g., if half (e.g., five positions in a polymer ten amino acids in length) of the positions in two sequences are identical, the two sequences are 50% identical; if 90% of the positions (e.g., 9 of 10), are matched or identical, the two amino acids sequences are 90% identical.

As used herein, an "instructional material" includes a publication, a recording, a diagram, or any other medium of expression which can be used to communicate the usefulness of the compositions and methods of the invention. The instructional material of the kit of the invention may, for example, be affixed to a container which contains the nucleic acid, peptide, and/or composition of the invention or be shipped together with a container which contains the nucleic acid, peptide, and/or composition. Alternatively, the instructional material may be shipped separately from the container with the intention that the instructional material and the compound be used cooperatively by the recipient.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

A "lentivirus" as used herein refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses. Vectors derived from lentiviruses offer the means to achieve significant levels of gene transfer in vivo.

By the term "modified" as used herein, is meant a changed state or structure of a molecule or cell of the invention. Molecules may be modified in many ways, including chemically, structurally, and functionally. Cells may be modified through the introduction of nucleic acids.

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

The term "overexpressed" tumor antigen or "overexpression" of a tumor antigen is intended to indicate an abnormal level of expression of a tumor antigen in a cell from a disease area like a solid tumor within a specific tissue or organ of the patient relative to the level of expression in a normal cell from that tissue or organ. Patients having solid tumors or a hematological malignancy characterized by overexpression of the tumor antigen can be determined by standard assays known in the art.

"Parenteral" administration of an immunogenic composition includes, e.g., subcutaneous (s.c.), intravenous (i.v.), intramuscular (i.m.), or intrasternal injection, or infusion techniques.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide encodes or specified by a gene, causes the gene product to be produced in a cell substantially only if the cell is a cell of the tissue type corresponding to the promoter.

A "signal transduction pathway" refers to the biochemical relationship between a variety of signal transduction molecules that play a role in the transmission of a signal from one portion of a cell to another portion of a cell. The phrase "cell surface receptor" includes molecules and complexes of molecules capable of receiving a signal and transmitting signal across the plasma membrane of a cell.

"Single chain antibodies" refer to antibodies formed by recombinant DNA techniques in which immunoglobulin heavy and light chain fragments are linked to the Fv region via an engineered span of amino acids. Various methods of generating single chain antibodies are known, including those described in U.S. Pat. No. 4,694,778; Bird (1988) Science 242:423-442; Huston et al. (1988) Proc. Natl. Acad. Sci. USA 85:5879-5883; Ward et al. (1989) Nature 334: 54454; Skerra et al. (1988) Science 242:1038-1041.

The term "subject" is intended to include living organisms in which an immune response can be elicited (e.g., mammals). A "subject" or "patient," as used therein, may be a human or non-human mammal. Non-human mammals include, for example, livestock and pets, such as ovine, bovine, porcine, canine, feline and murine mammals. Preferably, the subject is human.

As used herein, a "substantially purified" cell is a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some embodiments, the cells are cultured in vitro. In other embodiments, the cells are not cultured in vitro.

The term "therapeutic" as used herein means a treatment and/or prophylaxis. A therapeutic effect is obtained by suppression, remission, or eradication of a disease state.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

To "treat" a disease as the term is used herein, means to reduce the frequency or severity of at least one sign or symptom of a disease or disorder experienced by a subject.

The phrase "under transcriptional control" or "operatively linked" as used herein means that the promoter is in the correct location and orientation in relation to a polynucleotide to control the initiation of transcription by RNA polymerase and expression of the polynucleotide.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, Sendai viral vectors, adenoviral vectors, adeno-associated virus vectors, retroviral vectors, lentiviral vectors, and the like.

As used herein, the term "genetic construct" refers to the DNA or RNA molecules that comprise a nucleotide sequence which encodes protein. The coding sequence includes initiation and termination signals operably linked to regulatory elements including a promoter and polyadenylation signal capable of directing expression in the cells of the individual to whom the nucleic acid molecule is administered.

As used herein, the phrase "stringent hybridization conditions" or "stringent conditions" refers to conditions under which a nucleic acid molecule will hybridize another a nucleic acid molecule, but to no other sequences. Stringent conditions are sequence-dependent and will be different in different circumstances. Longer sequences hybridize specifically at higher temperatures. Generally, stringent conditions are selected to be about 5 C lower than the thermal melting point (Tm) for the specific sequence at a defined ionic strength and pH. The Tm is the temperature (under defined ionic strength, pH and nucleic acid concentration) at which 50% of the probes complementary to the target sequence hybridize to the target sequence at equilibrium. Since the target sequences are generally present in excess, at Tm, 50% of the probes are occupied at equilibrium. Typically, stringent conditions will be those in which the salt concentration is less than about 1.0 M sodium ion, typically about 0.01 to 1.0 M sodium ion (or other salts) at pH 7.0 to 8.3 and the temperature is at least about 30 C. for short probes, primers or oligonucleotides (e.g. 10 to 50 nucleotides) and at least about 60 C. for longer probes, primers or oligonucleotides. Stringent conditions may also be achieved with the addition of destabilizing agents, such as formamide.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

Peptides and Peptide Mimetics

Provided is a Mitochondrial Fission Factor (MFF)-derived peptide comprising the amino acid sequence of any one of SEQ ID NO: 1-23.

MFF-derived peptides of the invention comprise the peptides listed below:

Peptide #1: (SEQ ID NO: 1)
$^{25}$AEMAEISRIQYEMEYTEGISQRMRVP$^{50}$

Peptide #2: (SEQ ID NO: 2)
$^{49}$VPEKLKVAPPNADLEQGFQEGVPNASVIMQ$^{78}$

Peptide #3: (SEQ ID NO: 3)
$^{77}$MQVPERIVVAGNNEDVSFSRPADLDLIQST$^{106}$

Peptide #4: (SEQ ID NO: 4)
$^{105}$STPFKPLALKTPPRVLTLSERPLDFLDLER$^{134}$

Peptide #5: (SEQ ID NO: 5)
$^{133}$ERPPTTPQNEEIRAVGRLKRERSMSENAVR$^{162}$

Peptide #6: (SEQ ID NO: 6)
$^{161}$VRQNGQLVRNDSLWHRSDSAPRNKISRFQA$^{190}$

Peptide #7: (SEQ ID NO: 7)
$^{189}$QAPISAPEYTVTPSPQQARVCPPHMLPEDG$^{218}$

Peptide #8: (SEQ ID NO: 8)
$^{217}$DGANLSSARGILSLIQSSTRRAYQQILDVL$^{246}$

Peptide #9: (SEQ ID NO: 9)
$^{245}$VLDENRRPVLRGGSAAATSNPHHDNVRYGI$^{274}$

Peptide #10: (SEQ ID NO: 10)
$^{273}$GISNIDTTIEGTSDDLTV$^{290}$

Peptide #11: (SEQ ID NO: 23)
$^{290}$VVDAASLRRQIIKLNRRLQLLEEENKERAKREM$^{322}$

MFF, peptide 8#1, (SEQ ID NO: 11)
NLSSARGILSLIQSSTRRAYQQILDVL

MFF, peptide 8#2, (SEQ ID NO: 12)
SARGILSLIQSSTRRAYQQILDVL

MFF, peptide 8#3, (SEQ ID NO: 13)
GILSLIQSSTRRAYQQILDVL

MFF, peptide 8#4, (SEQ ID NO: 14)
SLIQSSTRRAYQQILDVL

MFF, peptide 8#5, (SEQ ID NO: 15)
QSSTRRAYQQILDVL

MFF, peptide 8 #6, (SEQ ID NO: 16)
DGANLSSARGILSLIQSSTRRAYQQIL

-continued

```
MFF, peptide 8#7,
                                    (SEQ ID NO: 17)
DGANLSSARGILSLIQSSTRRAYQ

MFF, peptide 8#8,
                                    (SEQ ID NO: 18)
DGANLSSARGILSLIQSSTRR

MFF, peptide 8#9,
                                    (SEQ ID NO: 19)
DGANLSSARGILSLIQSS

MFF, peptide 8#10,
                                    (SEQ ID NO: 20)
DGANLSSARGILSLI

MFF, peptide 8#11,
                                    (SEQ ID NO: 21)
SARGILSLIQSSTRRAYQQIL
and its corresponding scrambled version,

                                    (SEQ ID NO: 22)
SSQLRYLARSQRITIQLIAGS.
```

Also provided is a MFF-derived peptide comprising an amino acid sequence that is at least 85%, 90%, 91%, 92%, 93%, 94%, 95%, 96%, 97%, 98%, 99%, 99.5% or 100% identical to at least a 10 amino acid consecutive sequence of any one of SEQ ID NOs: 1-22. In some embodiments, the MFF-derived peptide is engineered and/or is not naturally occurring.

In some embodiments, the MFF-derived peptide binds to mitochondrial voltage-dependent anion channel-1 or VDAC or VDAC1. In some embodiments, binding of the MFF-derived peptide to VDAC results in mitochondrial depolarization in a cancer or tumor cell.

Also provided are MFF-derived peptides, wherein the peptide is conjugated to a cell-penetrating amino acid sequence. In some embodiments, the peptide is conjugated to the cell-penetrating amino acid sequence via a linker. In some embodiments, the linker is a peptide linker or a covalent chemical linker. In some embodiments, the cell-penetrating amino sequence is an HIV-Tat cell-penetrating sequence, penetratin (also known as antennapedia), cR10 and Pep-1. In further embodiments, the cell-penetrating amino acid sequence is RQIKIWFQNRRMK (SEQ ID NO: 24).

In some embodiments, the MFF-derived peptide that is conjugated to a cell-penetrating amino acid sequence binds to VDAC. In some embodiments, binding of the MFF-derived peptide, that is conjugated to a cell-penetrating amino acid sequence, to VDAC results in mitochondrial depolarization in a cancer or tumor cell.

A cell-permeable control scrambled peptide #8-11 (SEQ ID NO: 22) and two MFF peptide #8-11 mutants, lacking the entire VDAC interacting-sequence sequence $Ser^{223}$-$Leu^{243}$ (DN) or containing the double mutation R225D/R236D (DD) were also synthesized.

Provided is a peptide mimetic comprising a retro-inverso D-enantiomer of MFF peptide #8-11 containing all D-amino acids in the reverse orientation. In some embodiments, the peptide mimetic consists of the retro-inverso D-enantiomer of MFF peptide #8-11 containing all D-amino acids in the reverse orientation.

Without wishing to be bound by theory, protein isoforms of MFF are expressed at high levels in patients with primary and metastatic prostate cancer, compared to expression in normal tissues. MFF binds the mitochondrial permeability transition pore (PTP) components, voltage-dependent anion channel (VDAC) and hexokinase II (HK-II). Genetic silencing or peptidyl mimicry of the MFF-PTP complex induces acute mitochondrial dysfunction and tumor cell death, without affecting normal cells.

Without wishing to be bound by theory, MFF peptides that contain a minimal binding site for VDAC depolarize mitochondria in prostate cancer cells. Competitive peptidyl mimicry of MFF-VDAC complex results in cytotoxic activity in patient-derived glioblastoma neurospheres and xenograft tumor models.

In some embodiments, an MFF-derived peptide or peptide mimetic of the invention binds to VDAC. In some embodiments, binding of the MFF-derived peptide or peptide mimetic to VDAC results in mitochondrial depolarization in a cancer or tumor cell.

Nucleic Acids

Provided is a polynucleotide encoding the peptide of any one of the preceding embodiments. In some embodiments, the polynucleotide encodes a peptide comprising the amino acid sequence of any one of SEQ ID NO: 1-22. In some embodiments, the polynucleotide encodes a peptide that is conjugated to a cell-penetrating amino acid sequence. In some embodiments, the cell-penetrating amino sequence is an HIV-Tat cell-penetrating sequence, penetratin (also known as antennapedia), cR10 and Pep-1. In further embodiments, the cell-penetrating amino acid sequence is RQIKIWFQNRRMK (SEQ ID NO: 24).

Regulatory Elements and Nucleic Acid Components

Initiation codons and stop codon are generally considered to be part of a nucleotide sequence that encodes the desired protein. However, it is necessary that these elements are functional in the individual to whom the gene construct is administered. The initiation and termination codons must be in frame with the coding sequence.

Promoters and polyadenylation signals used must be functional within the cells of the individual.

Examples of promoters useful to practice the present invention, especially in the production of a genetic vaccine for humans, include but are not limited to promoters from Simian Virus 40 (SV40), Mouse Mammary Tumor Virus (MMTV) promoter, Human Immunodeficiency Virus (MV) such as the BIV Long Terminal Repeat (LTR) promoter, Moloney virus, ALV, Cytomegalovirus (CMV) such as the CMV immediate early promoter, Epstein Barr Virus (EBV), Rous Sarcoma Virus (RSV) as well as promoters from human genes such as human Actin, human Myosin, human Hemoglobin, human muscle creatine and human metalothionein.

Examples of polyadenylation signals useful to practice the present invention, especially in the production of a genetic vaccine for humans, include but are not limited to SV40 polyadenylation signals and LTR polyadenylation signals. In particular, the SV40 polyadenylation signal that is in pCEP4 plasmid (Invitrogen, San Diego Calif.), referred to as the SV40 polyadenylation signal, is used.

In addition to the regulatory elements required for DNA expression, other elements may also be included in the DNA molecule. Such additional elements include enhancers. The enhancer may be selected from the group including but not limited to: human Actin, human Myosin, human Hemoglobin, human muscle creatine and viral enhancers such as those from CMV, RSV and EBV.

Genetic constructs can be provided with mammalian origin of replication in order to maintain the construct extrachromosomally and produce multiple copies of the construct in the cell. Plasmids pVAX1, pCEP4 and pREP4 from Invitrogen (San Diego, Calif.) contain the Epstein Barr virus origin of replication and nuclear antigen EBNA-1 coding region which produces high copy episomal replication without integration. In order to maximize peptide production, regulatory sequences may be selected which are well suited for gene expression in the cells the construct is administered into. Moreover, codons may be selected which are most efficiently transcribed in the cell. One having ordinary skill in the art can produce DNA constructs that are functional in the cells. In some embodiments for which protein is used, i.e., the engineered peptides of the invention, for example, one having ordinary skill in the art can, using well known techniques, produce and isolate proteins of the invention using well known techniques. In some embodiments for which protein is used, for example, one having ordinary skill in the art can, using well known techniques, inserts DNA molecules that encode a protein of the invention into a commercially available expression vector for use in well-known expression systems. For example, the commercially available plasmid pSE420 (Invitrogen, San Diego, Calif.) may be used for production of protein in *E. coli*. The commercially available plasmid pYES2 (Invitrogen, San Diego, Calif.) may, for example, be used for production in *S. cerevisiae* strains of yeast. The commercially available MAXBAC™ complete baculovirus expression system (Invitrogen, San Diego, Calif.) may, for example, be used for production in insect cells. The commercially available plasmid pcDNA I or pcDNA3 (Invitrogen, San Diego, Calif.) may, for example, be used for production in mammalian cells such as Chinese Hamster Ovary cells. One having ordinary skill in the art can use these commercial expression vectors and systems or others to produce protein by routine techniques and readily available starting materials. (See e.g., Sambrook et al., Molecular Cloning, Third Ed. Cold Spring Harbor Press (2001) which is incorporated herein by reference.) Thus, the desired proteins can be prepared in both prokaryotic and eukaryotic systems, resulting in a spectrum of processed forms of the protein.

One having ordinary skill in the art may use other commercially available expression vectors and systems or produce vectors using well known methods and readily available starting materials. Expression systems containing the requisite control sequences, such as promoters and polyadenylation signals, and preferably enhancers are readily available and known in the art for a variety of hosts. See e.g., Sambrook et al., Molecular Cloning Third Ed. Cold Spring Harbor Press (2001). Genetic constructs include the protein coding sequence operably linked to a promoter that is functional in the cell line into which the constructs are transfected. Examples of constitutive promoters include promoters from cytomegalovirus or SV40. Examples of inducible promoters include mouse mammary leukemia virus or metallothionein promoters. Those having ordinary skill in the art can readily produce genetic constructs useful for transfecting with cells with DNA that encodes protein of the invention from readily available starting materials. The expression vector including the DNA that encodes the protein is used to transform the compatible host which is then cultured and maintained under conditions wherein expression of the foreign DNA takes place.

The protein produced is recovered from the culture, either by lysing the cells or from the culture medium as appropriate and known to those in the art. One having ordinary skill in the art can, using well known techniques, isolate protein that is produced using such expression systems. The methods of purifying protein from natural sources using antibodies which specifically bind to a specific protein as described above may be equally applied to purifying protein produced by recombinant DNA methodology.

In addition to producing proteins by recombinant techniques, automated peptide synthesizers may also be employed to produce isolated, essentially pure protein. Such techniques are well known to those having ordinary skill in the art and are useful if derivatives which have substitutions not provided for in DNA-encoded protein production.

Pharmaceutical Compositions

The pharmaceutical compositions according to the present invention are formulated according to the mode of administration to be used. In cases where pharmaceutical compositions are injectable pharmaceutical compositions, they are sterile, pyrogen free and particulate free. An isotonic formulation is preferably used. Generally, additives for isotonicity can include sodium chloride, dextrose, mannitol, sorbitol and lactose. In some cases, isotonic solutions such as phosphate buffered saline are preferred. Stabilizers include gelatin and albumin. In some embodiments, a vasoconstriction agent is added to the formulation.

It will be appreciated by a person skilled in the art that the peptide or peptide mimetic may be administered in admixture with a suitable pharmaceutical excipient diluent or carrier selected with regard to the intended route of administration and standard pharmaceutical practice. For example, see Remington: The Science and Practice of Pharmacy, 19th edition, 1995, Ed. Alfonso Gennaro, Mack Publishing Company, Pennsylvania, USA.

Delivery or Administration of Peptides and Peptide Mimetics

In some embodiments, the peptide or peptide mimetic may be administered orally, bucally or sublingually in the form of tablets, capsules, ovules, elixirs, solutions or suspensions, which may contain flavoring or coloring agents, for immediate, delayed or controlled-release applications. The peptide or peptide mimetic may also be administered via intracavernosal injection.

The peptide or peptide mimetic may also be administered parenterally. In some embodiments, the peptide or peptide mimetic may be administered intravenously, intra-articularly, intraperitoneally, intrathecally, intraventricularly, intrasternally, intracranially, intramuscularly or subcutaneously. In some embodiments, the peptide or peptide mimetic is administered by infusion techniques.

In some embodiments, the peptide or peptide mimetic is used in the form of a sterile aqueous solution that may contain other substances, for example, sufficient salts or glucose (or other sugars) to make the solution isotonic with blood. The aqueous solution should be suitably buffered (preferably to a pH of from 3 to 9), if necessary. The preparation of suitable parenteral formulations under sterile conditions is readily accomplished by standard pharmaceutical techniques well known to a person of skill in the art.

Formulations suitable for parenteral administration include aqueous and non-aqueous sterile injection solutions which may contain anti-oxidants, buffers, bacteriostats and solutes which render the formulation isotonic with blood. Suitable formulations for parenteral administration also include aqueous and non-aqueous suspensions which may include suspending agents and thickening agents. The formulations may be presented in unit-dose or multi-dose containers.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

Pharmaceutical compositions of the present invention may be administered in solid or liquid form such as tablets, capsules, powders, solutions, suspensions, emulsions and the like. Pharmaceutical compositions of the present invention may be administered orally, parenterally, subcutaneously, intravenously, intramuscularly, intraperitoneally, by nasal instillation, by implantation, by intracavitary or intravesical instillation, intraocularly, intraarterially, intralesionally, transdermally, or by the application to mucous membranes. In some embodiments, the peptide or peptide mimetic is administered intranasally or by inhalation. The peptide or peptide mimetic may be delivered in the form of a dry powder inhaler or an aerosol spray from a pressurized container, pump, spray or nebulizer with the use of a propellant. In some embodiments, the composition may be applied to the nose, throat or bronchial tubes, for example by inhalation.

The dosage of the above treatments to be administered to a patient will vary with the precise nature of the condition being treated and the recipient of the treatment and can be determined by physical and physiological factors such as body weight, severity of condition, previous or concurrent therapeutic interventions, and on the route of administration. The scaling of dosages for human administration can be performed according to art-accepted practices. For example, for oral, parenteral or other routes of administration to human patients, the daily dosage level of the peptide or peptide mimetic will usually be from 1 to 1000 mg per adult (i.e., from about 0.015 to 15 mg/kg), administered in single or multiple or divided doses. In some embodiments, the dosage level may be from about 0.5 mg/kg to about 10 mg/kg.

Human dosage amounts can initially be determined by extrapolating from the amount of compound used in mice or a similar animal model, as a skilled artisan recognizes it is routine in the art to modify the dosage for humans compared to animal models. In certain embodiments it is envisioned that the dosage may include an effective amount from between about 1 microgram/kg/body weight, from 5 microgram/kg/body weight, 10 microgram/kg/body weight, 50 microgram/kg/body weight, 100 microgram/kg/body weight, 200 microgram/kg/body weight, 350 microgram/kg/body weight, 500 microgram/kg/body weight, 1 milligram/kg/body weight, 5 milligram/kg/body weight, 10 milligram/kg/body weight, 50 milligram/kg/body weight, 100 milligram/kg/body weight, 200 milligram/kg/body weight, 350 milligram/kg/body weight, or 500 milligram/kg/body weight, to 1000 mg/kg/body weight or more per administration, and any range derivable therein. In other embodiments, the effective amount may be about 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 15, 20, 25, 30, 35, 40, 45, 50, 55, 60, 65, 70, 75, 80, 85, 90, 95, or about 100 mg/Kg body weight. In other embodiments, it is envisaged that effective amounts may be in the range of about 1 micrograms compound to about 100 mg compound. In other embodiments, the effective amount may be about 1, 2, 3, 4, 5, 6, 7, 8, 9, 10, 11, 12, 13, 14, 15, 16, 17, 18, 19, or 20 mg per single dose. In another embodiment, the effective amount comprises less than about 2, 3, 4, 5, 6, 7, 8, 9, 10, 15, 20, 25, 30, 35, 40, 45, 50, 55, 60, 65, 70, 75, 80, 85, 90, 95 mg daily. Of course, the single dosage amount or daily dosage amount may be adjusted upward or downward, as is routinely done in such treatment protocols, depending on the results of the initial clinical trials and the needs of a particular subject. Those of skill in the art would recognize the conditions and situations warranting modified dosing.

The precise determination of what would be considered an effective dose is based on factors individual to each subject, including their size, age, sex, weight, and condition of the particular subject. Dosages can be readily ascertained by those skilled in the art from this disclosure and the knowledge in the art.

Delivery or Administration of Nucleic Acids

In some embodiments, a nucleic acid encoding an engineered peptide or peptide mimetic of the invention is delivered to a subject or to a cell, tissue or organ of the subject. Introduction of a nucleic acid encoding any of the engineered peptides of the invention into a mammal can be accomplished using technology available in the art, disclosed, for example, in U.S. Pat. Nos. 5,593,972, 5,739,118, 5,817,637, 5,830,876, 5,962,428, 5,981,505, 5,580,859, 5,703,055, 5,676,594, and the priority applications cited therein, which are each incorporated herein by reference. In addition to the delivery protocols described in those applications, alternative methods of delivering DNA are described in U.S. Pat. Nos. 4,945,050 and 5,036,006, which are also incorporated herein by reference.

When taken up by a cell, the genetic construct(s) may remain present in the cell as a functioning extrachromosomal molecule and/or integrate into the cell's chromosomal DNA. DNA may be introduced into cells where it remains as separate genetic material in the form of a plasmid or plasmids. Alternatively, linear DNA that can integrate into the chromosome may be introduced into the cell. When introducing DNA into the cell, reagents that promote DNA integration into chromosomes may be added. DNA sequences that are useful to promote integration may also be included in the DNA molecule. Alternatively, RNA may be administered to the cell. It is also contemplated to provide the genetic construct as a linear minichromosome including a centromere, telomeres and an origin of replication. Gene constructs may remain part of the genetic material in attenuated live microorganisms or recombinant microbial vectors which live in cells. Gene constructs may be part of genomes of recombinant viral vaccines where the genetic material either integrates into the chromosome of the cell or remains extrachromosomal. Genetic constructs include regulatory elements necessary for gene expression of a nucleic acid molecule. The elements include: a promoter, an initiation codon, a stop codon, and a polyadenylation signal. In addition, enhancers are often required for gene expression of the sequence that encodes the peptide. It is necessary that these elements be operable linked to the sequence that encodes the desired peptide and that the regulatory elements are operably in the individual to whom they are administered.

The polynucleotides encoding the engineered peptides of the invention may be delivered using any of several well-known technologies including DNA injection (also referred to as DNA vaccination), recombinant vectors such as recombinant adenovirus, recombinant adenovirus associated virus and recombinant vaccinia virus.

Routes of administration include, but are not limited to, intramuscular, intranasal, intraperitoneal, intradermal, subcutaneous, intravenous, intra-arterial, intraocular and oral as well as topical, transdermal, by inhalation or suppository or to mucosal tissue such as by lavage to vaginal, rectal, urethral, buccal and sublingual tissue. Preferred routes of administration include intramuscular, intraperitoneal, intradermal and subcutaneous injection. Genetic constructs may be administered by means including, but not limited to, electroporation methods and devices, traditional syringes, needleless injection devices, or "microprojectile bombardment gone guns".

Examples of electroporation devices and electroporation methods preferred for facilitating delivery of the DNA vaccines, include those described in U.S. Pat. No. 7,245,963 by Draghia-Akli, et al., U.S. Patent Pub. 2005/0052630 submitted by Smith, et al., the contents of which are hereby incorporated by reference in their entirety. Also preferred, are electroporation devices and electroporation methods for facilitating delivery of the DNA vaccines provided in co-pending and co-owned U.S. patent application Ser. No. 11/874,072, filed Oct. 17, 2007, which claims the benefit under 35 USC 119(e) to U.S. Provisional Application Ser. No. 60/852,149, filed Oct. 17, 2006, and 60/978,982, filed Oct. 10, 2007, all of which are hereby incorporated in their entirety.

The following is an example of an embodiment using electroporation technology, and is discussed in more detail in the patent references discussed above: electroporation devices can be configured to deliver to a desired tissue of a mammal a pulse of energy producing a constant current similar to a preset current input by a user. The electroporation device comprises an electroporation component and an electrode assembly or handle assembly. The electroporation component can include and incorporate one or more of the various elements of the electroporation devices, including: controller, current waveform generator, impedance tester, waveform logger, input element, status reporting element, communication port, memory component, power source, and power switch. The electroporation component can function as one element of the electroporation devices, and the other elements are separate elements (or components) in communication with the electroporation component. In some embodiments, the electroporation component can function as more than one element of the electroporation devices, which can be in communication with still other elements of the electroporation devices separate from the electroporation component. The use of electroporation technology to deliver the improved HCV vaccine is not limited by the elements of the electroporation devices existing as parts of one electromechanical or mechanical device, as the elements can function as one device or as separate elements in communication with one another. The electroporation component is capable of delivering the pulse of energy that produces the constant current in the desired tissue, and includes a feedback mechanism. The electrode assembly includes an electrode array having a plurality of electrodes in a spatial arrangement, wherein the electrode assembly receives the pulse of energy from the electroporation component and delivers same to the desired tissue through the electrodes. At least one of the plurality of electrodes is neutral during delivery of the pulse of energy and measures impedance in the desired tissue and communicates the impedance to the electroporation component. The feedback mechanism can receive the measured impedance and can adjust the pulse of energy delivered by the electroporation component to maintain the constant current.

In some embodiments, the plurality of electrodes can deliver the pulse of energy in a decentralized pattern. In some embodiments, the plurality of electrodes can deliver the pulse of energy in the decentralized pattern through the control of the electrodes under a programmed sequence, and the programmed sequence is input by a user to the electroporation component. In some embodiments, the programmed sequence comprises a plurality of pulses delivered in sequence, wherein each pulse of the plurality of pulses is delivered by at least two active electrodes with one neutral electrode that measures impedance, and wherein a subsequent pulse of the plurality of pulses is delivered by a different one of at least two active electrodes with one neutral electrode that measures impedance.

In some embodiments, the feedback mechanism is performed by either hardware or software. Preferably, the feedback mechanism is performed by an analog closed-loop circuit. Preferably, this feedback occurs every 50 .mu.s, 20 .mu.s, 10 .mu.s or 1 .mu.s, but is preferably a real-time feedback or instantaneous (i.e., substantially instantaneous as determined by available techniques for determining response time). In some embodiments, the neutral electrode measures the impedance in the desired tissue and communicates the impedance to the feedback mechanism, and the feedback mechanism responds to the impedance and adjusts the pulse of energy to maintain the constant current at a value similar to the preset current. In some embodiments, the feedback mechanism maintains the constant current continuously and instantaneously during the delivery of the pulse of energy.

In some embodiments, the nucleic acid molecule is delivered to the cells in conjunction with administration of a polynucleotide function enhancer or a genetic vaccine facilitator agent. Polynucleotide function enhancers are described in U.S. Pat. Nos. 5,593,972, 5,962,428 and International Application Serial Number PCT/US94/00899 filed Jan. 26, 1994, which are each incorporated herein by reference. Genetic vaccine facilitator agents are described in U.S. Ser. No. 021,579 filed Apr. 1, 1994, which is incorporated herein by reference. The co-agents that are administered in conjunction with nucleic acid molecules may be administered as a mixture with the nucleic acid molecule or administered separately simultaneously, before or after administration of nucleic acid molecules.

In some embodiments, the pharmaceutical compositions according to the present invention comprise about 1 nanogram to about 2000 micrograms of DNA. In some preferred embodiments, pharmaceutical compositions according to the present invention comprise about 5 nanogram to about 1000 micrograms of DNA. In some preferred embodiments, the pharmaceutical compositions contain about 10 nanograms to about 800 micrograms of DNA. In some preferred embodiments, the pharmaceutical compositions contain about 0.1 to about 500 micrograms of DNA. In some preferred embodiments, the pharmaceutical compositions contain about 1 to about 350 micrograms of DNA. In some preferred embodiments, the pharmaceutical compositions contain about 25 to about 250 micrograms of DNA. In some preferred embodiments, the pharmaceutical compositions contain about 100 to about 200 microgram DNA.

Methods of Treatment

Provided is a method of treating a disease in a subject in need thereof, comprising administering to the subject an effective amount of any one of the peptide or peptide mimetics described herein. In some embodiments, the subject is human. In some embodiments, the peptide or peptide mimetic is provided in a pharmaceutical composition.

In some embodiments, the pharmaceutical composition may be delivered orally, parenterally, for example as a parenteral injection, intravenously, for example as an intravenous infusion, or by inhalation.

In some embodiments, a sample is a tissue or a bodily fluid sample. In some embodiments, the sample is a tumor sample, a blood sample, a blood plasma sample, a peritoneal fluid sample, an exudate or an effusion.

In some embodiments, a second agent is administered to the subject. In some embodiments, the second agent is an alkylating agent, antimetabolite, antibiotic, a plant-derived agent, platinum complex, campthotecin derivative, tyrosine kinase inhibitor, monoclonal antibody, interferon, biological response modifier, hormonal anti-tumor agent, anti-tumor viral agent, angiogenesis inhibitor, differentiating agent, PI3K/mTOR/AKT inhibitor, cell cycle inhibitor, apoptosis inhibitor, hsp 90 inhibitor, tubulin inhibitor, DNA repair inhibitor, anti-angiogenic agent, receptor tyrosine kinase inhibitor, topoisomerase inhibitor, taxane, agent targeting Her-2, hormone antagonist, agent targeting a growth factor receptor, or a pharmaceutically acceptable salt thereof. In some embodiments, the anti-tumor agent is citabine, capecitabine, valopicitabine or gemcitabine. In some embodiments, the anti-tumor agent is Avastin, Sutent, Nexavar, Recentin, ABT-869, Axitinib, Irinotecan, topotecan, paclitaxel, docetaxel, lapatinib, Herceptin, tamoxifen, progesterone, a steroidal aromatase inhibitor, a non-steroidal aromatase inhibitor, Fulvestrant, an inhibitor of epidermal growth factor receptor (EGFR), Cetuximab, Panitumimab, an inhibitor of insulin-like growth factor 1 receptor (IGF1R), or CP-751871.

In some embodiments, the disease is cancer. In some embodiments, the cancer is prostate cancer (e.g., androgen independent), glioblastoma, breast cancer, breast adenocarcinoma, lung cancer, non-small cell lung cancer, melanoma, ovarian cancer, hematological B-cell cancer, hematological T-cell cancer, metastatic cancer, treatment-resistant tumor (e.g., Braf/Medi resistant melanoma) or myc+ cancer. In some embodiments, the myc+ cancer is a solid tumor. In some embodiments, the myc+ solid tumor is androgen independent prostate, metastatic, ovarian, lung, breast or brain cancer.

In some embodiments, the cancer is a solid tumor. In some embodiments, the cancer is metastatic. In further embodiments, the cancer is ovarian cancer or prostate cancer.

In some embodiments, the ovarian cancer is metastatic ovarian cancer. In further embodiments, the ovarian cancer is deficient in homologous recombination DNA repair. In some embodiments, the ovarian cancer is hormone-dependent. In some embodiments, the ovarian cancer is BRCA deficient. In some embodiments, the BRCA-deficiency is in BRCA-1 or BRCA-2. In further embodiments, the BRCA-deficiency is in both BRCA-1 and BRCA-2.

In some embodiments, the prostate cancer is metastatic prostate cancer. In further embodiments, the prostate cancer is deficient in homologous recombination DNA repair.

In some embodiments, the prostate cancer is androgen dependent. In some embodiments, the method optionally results in an increased prostate specific antigen (PSA) index in the subject.

In some embodiments, the hematological B-cell cancer or the hematological T-cell cancer is a lymphoma or a leukemia. In some embodiments, the hematological B-cell cancer is diffuse large B-cell lymphoma.

Methods of Targeting MFF

Provided are methods of targeting MFF in a subject in need thereof, comprising administering to the subject an effective amount of the peptide mimetic of any one of the preceding embodiments.

Kits

Provided are kits comprising any one of the pharmaceutical compositions described above comprising a MFF-derived peptide or peptide mimetic and a delivery agent. In some embodiments, the delivery agent is for oral, intranasal, transbuccal, transdermal, intraperitoneal, intramuscular, intravenous, or other injectable form of delivery. In further embodiments the kit is in a suitable container comprising a therapeutically effective amount of the pharmaceutical composition comprising the MFF-derived peptide or peptide mimetic and the delivery agent. In some embodiments, the kit further comprises a second agent. In further embodiments, the second agent comprises a molecularly targeted therapy, a vaccine, a chemotherapeutic agent (e.g., etoposide or doxorubicin), radiation, or combinations thereof. In yet further embodiments, the kit comprises instructional material for administering the pharmaceutical compositions described above comprising a MFF-derived peptide or peptide mimetic and a delivery agent.

Also provided are kits comprising any one of the pharmaceutical compositions described above comprising a polynucleotide encoding a MFF-derived peptide and a delivery agent. In some embodiments, the delivery agent is for oral, intranasal, transbuccal, transdermal, intraperitoneal, intramuscular, intravenous, or other injectable form of delivery. In further embodiments the kit is in a suitable container comprising a therapeutically effective amount of the pharmaceutical composition comprising the polynucleotide and the delivery agent. In some embodiments, the kit further comprises a second agent. In further embodiments, the second agent comprises a molecularly targeted therapy, a vaccine, a chemotherapeutic agent (e.g., etoposide or doxorubicin), radiation, or combinations thereof. In yet further embodiments, the kit comprises instructional material for administering the pharmaceutical compositions described above comprising a polynucleotide and a delivery agent.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Materials and Methods

The materials and methods of the experimental examples of the present disclosure are now described.

Patient samples. A clinically-annotated series of 192 patients with histologically confirmed diagnosis of primary prostate cancer was used in this study (Conrad, M., Angeli, J. P., Vandenabeele, P. & Stockwell, B. R. Regulated necrosis: disease relevance and therapeutic opportunities. *Nat Rev Drug Discov* 15, 348-366 (2016)) together with 17 prostate cancer metastases to different organs (Table 1). Archival tissues and clinical records were obtained from Fondazione IRCCS Ca' Granda Hospital in Milan (Italy) under a protocol approved by the Institutional Review Boards (IRB) of Fondazione IRCCS Ca' Granda-Ospedale Maggiore Policlinico (code 1381/11). Because of the retrospective nature of this study and the use of data anonymization practices, the need for written informed consent was waived. For patients with primary prostate cancer, epithelial tissue samples for normal prostate, prostatic intraepithelial neoplasia (PIN) and prostate adenocarcinoma (AdCa) were arranged in tissue microarrays (TMA) blocks for immunohistochemical evaluations whereas distant metastases were analyzed as full sections. For organotypic tissue cultures, one breast cancer and two non-small cell lung cancer (NSCLC) tissues (Table 1) were subjected to tissue slicing and ex-vivo culturing as described (Fuchs, Y. & Steller, H. Live to die another way: modes of programmed cell death and the signals emanating from dying cells. *Nat Rev Mol Cell Biol* 16, 329-344 (2015)). Cultures were treated with cell permeable (D) MFF peptidomimetic or cell permeable scrambled peptide (50-100 μM) for 2 or 24 h. At harvesting, tissues were formalin-fixed, paraffin-embedded and processed for immunohistochemical analyses.

Immunohistochemistry. Four μm-thick sections from each tissue block were stained with an antibody to MFF (Protein Tech #17090-1-AP), Ki67 (clone 30-9; Ventana Medical Systems, Roche Group, Tucson, Ariz., USA) or cleaved caspase-3 (9661; Cell Signaling Technologies) using diaminobenzidine (DAB) as a chromogen as described (Fuchs, Y. & Steller, H. Live to die another way: modes of programmed cell death and the signals emanating from dying cells. *Nat Rev Mol Cell Biol* 16, 329-344 (2015)). Immunohistochemistry was performed using Benchmark Ultra Roche Ventana immunostainer (Roche Group, Tucson, Ariz.). All slides were counterstained with hematoxylin. Two pathologists (V.V. and S.F.) blinded to clinical data evaluated and scored all slides. When discrepancies occurred, the case was further reviewed to reach an agreement score.

MFF mRNA expression in public databases. For the Cancer Cell Line Encyclopedia (CCLE) (Izzo, V., Bravo-San Pedro, J. M., Sica, V., Kroemer, G. & Galluzzi, L. Mitochondrial Permeability Transition: New Findings and Persisting Uncertainties. *Trends Cell Biol* 26, 655-667 (2016)), analysis of MFF mRNA expression was accessed via the cBioPortal for Cancer Genomics (www.cbioportal.org) (Karch, J. & Molkentin, J. D. Identifying the components of the elusive mitochondrial permeability transition pore. *Proc Natl Acad Sci USA* 111, 10396-10397 (2014)) and downloaded. Individual cancer cell lines were grouped by primary tissue of origin according to the CCLE classification and levels of MFF mRNA were plotted against the copy number of MFF using GraphPad Prism 6.0 software. The TCGA tumor expression data for MFF mRNA (RNA-seq values) were downloaded from the cBioPortal and plotted with GraphPad Prism 6.0 software.

Cells and cell culture. Human prostate adenocarcinoma (LNCaP, C4-2, C4-2B, PC3 and DU145), non-small cell lung cancer (A549, H460), breast adenocarcinoma (MDA-231, MCF-7), normal prostate epithelial (RWPE-1) and human glioblastoma (LN229) cells were obtained from the American Type Culture Collection (ATCC, Manassas, Va.), and maintained in culture according to the supplier's specifications. Benign prostate hyperplasia (BPH1) cells were a gift from Dr. Simon Hayward (Vanderbilt University, Nashville, Tenn.) and primary human foreskin fibroblasts (HFF) were a gift from Dr. Meenhard Herlyn (The Wistar Institute, Philadelphia, Pa.). Cell passaging was limited to <40 passages from receipt and cell lines were authenticated by STR profiling with AmpF1STR Identifiler PCR Amplification Kit (Life Technologies) at the Wistar Institute's Genomics facility. Mycoplasma free-cultures were confirmed at the beginning of the studies, and every 2 months afterwards, by direct polymerase chain reaction (PCR) of cultures using Bioo Scientific Mycoplasma Primer Sets (cat #375501) and Hot Start polymerase (QIAGEN).

Chromatin immunoprecipitation (ChIP). PC3 cells transfected with siCtrl or Myc-directed siRNA (siMyc) for 72 h were used for ChIP experiments. Cells were cross-linked with formaldehyde, and the fragmented chromatin was immunoprecipitated with non-binding rabbit IgG or a rabbit monoclonal antibody to Myc (Abcam #Ab32072). The total input was the supernatant of each incubation reaction without antibody treatment. Real-time PCR amplification of the precipitated chromatin fragments was performed using SYBR green master mix (Applied Biosystems) on an ABI7500 sequence detection system using the manufacturer's instructions.

Immunofluorescence and confocal microscopy. PC3 or DU145 cells transfected with control non-targeting siRNA (siCtrl) or MFF-directed siRNA (siMFF), or alternatively, expressing control plasmid or MFF cDNA were fixed in formalin/PBS (4% final concentration) for 15 min at 22° C., permeabilized with 0.1% Triton X-100/PBS for 5 min, washed, and incubated in 5% normal goat serum (NGS, Vector Labs) diluted in 0.3 M glycine/PBS for 60 min. Primary antibodies against MFF (1:100) or MTCO2 (mitochondrial marker, 1:500) were added in 5% NGS/0.3 M glycine/PBS and incubated for 18 h at 4° C. After three washes in PBS, secondary antibodies conjugated to Alexa488, TRITC or Alexa633 were diluted 1:500 in 5% NGS/0.3 M glycine/PBS and added to cells for 1 h at 22° C. Where indicated, F-actin was stained with phalloidin Alexa (1:200 dilution) for 30 min at 22° C. Slides were washed and mounted in 4,6-diamidino-2-phenylindole (DAPI)-containing Prolong Gold mounting medium (Life Technologies). Cells were visualized by Z-stack imaging and confocal microscopy (SPFS II, Leica). At least 70 cells per sample were analyzed and mitochondrial morphologies were classified as fragmented (individual round- or rod-shaped organelles, >80% displaying an axial length of <4 μm), intermediate (majority ~4 μm), or tubular (often interconnected in branched networks, >80% displaying a length of >4 μm).

Immunoprecipitation (IP). Cells were harvested and lysed with IP buffer (50 mM Tris-HCl, pH 7.5, 150 mM NaCl, 1 mM EDTA) containing 1% CHAPS, EDTA-free Protease Inhibitor Cocktail (Sigma-Aldrich) and Phosphatase Inhibitor Cocktail PhosSTOP (Roche). After sonication, lysates were centrifuged at 15,000×g for 30 min, and cell extracts were incubated with anti-Flag-conjugated beads (Sigma-Aldrich). The precipitates were washed five times, separated by SDS-polyacrylamide gel electrophoresis and processed for Western blotting together with samples representing unbound material and supernatant.

Mitochondrial outer membrane permeability. PC3 cells ($3\times10^5$) transfected with siCtrl or siMFF were stained with calcein (0.01 μM) and cobalt chloride (0.4 μM) (MitoProbe Transition Pore Assay, Molecular Probes, cat #M34153) for 15 min in HBSS (with calcium and without phenol red), washed in PBS, pH 7.4, and analyzed on a FACS Celesta flow cytometer at 488 nm excitation and emission filters. Intact cells were gated in the FSC/SSC plot to exclude small debris.

Mitochondrial membrane potential. Normal prostatic epithelial RWPE1 or BPH-1 cells or prostate cancer PC3 or DU145 cells were transfected with siCtrl or siMFF and analyzed on a FACS Calibur flow cytometer, with the TMRE signal as FL1. Intact cells were gated in the FSC/SSC plot to exclude small debris. The resulting FL1 data were plotted on a histogram.

Cell death. PC3 or DU145 cells ($1\times10^6$) were transfected with siCtrl or siMFF, labeled for Annexin V and propidium iodide (PI) (BD Biosciences) and analyzed by multiparametric flow cytometry. Alternatively, mitochondria-associated changes in cell viability were quantified by an MTT assay or Trypan blue dye exclusion assay and light microscopy. In some experiments, PC3 cells transfected with siCtrl or siMFF were analyzed for proteolytic processing of PARP with or without stress stimuli, $H_2O_2$, nutrient deprivation or chemotherapeutic drugs, doxorubicin or etoposide, by Western blotting.

Antibodies and reagents. The following antibodies to MFF (Protein Tech #17090-1-AP), Hexokinase-I (HK-I, Cell signaling #2024), Hexokinase-II (HK-II, Cell Signaling #2867), VDAC (Cell Signaling #4866), PARP (Cell Signaling #9532), $Asp^{214}$ Cleaved PARP (Cell Signaling #9541), Caspase-3 (Cell Signaling #9662), $Asp^{175}$ Cleaved Caspase-3 (Cell signaling #9661), Caspase-9 (Cell Signaling #9502), Cleaved Caspase-9 (Cell Signaling #9505), $Thr^{172}$-phosphorylated AMPKα (Cell Signaling #2535), AMPKα (Cell Signaling #2603), LC3B (Cell Signaling #3868), Drp1 (Cell Signaling #8570), MFN1 (Cell Signaling #14739), MFN2 (Cell Signaling #9482), OPA1 (BD Laboratories #612606), Cytochrome c (BD Laboratories #556432), $Ser^{555}$-phosphorylated ULK1 (Cell Signaling #5869), $Ser^{757}$-phosphorylated ULK1 (Cell Signaling #6888), ULK1 (Cell Signaling #8054), HMGB1 (Cell Signaling #6893), Cyclophilin A (Cell Signaling #2175), Flag (Sigma-Aldrich #F1804), β-tubulin (Sigma-Aldrich #T8328) or β-actin (Sigma-Aldrich #A5441) were used for Western blotting. An antibody to mitochondria MTCO2 (Abcam #ab3298) was used for immunofluorescence. An antibody to Drp1 (Sigma-Aldrich #HPA039324), was used for immunohistochemistry. Libraries of MFF peptides and their scrambled sequences utilized as control (purity >90%) were synthesized by Thermo Fisher Scientific or GenScript. Z-VAD-fmk and Cyclosporin A (CsA) were purchased from Selleckchem. Carbonyl cyanide 4-(trifluoromethoxy)phenylhydrazone (FCCP), Oligomycin, Antimycin and Rotenone were from Agilent. MitoTracker Green, phalloidin Alexa Fluor, TMRE, and secondary antibodies for immunofluorescence were from Molecular Probes.

Plasmids and gene silencing. cDNA clones encoding human MFF1, MFF5 or control vector were purchased from GeneCopoeia (Cat. n. EX-Z4766, EX-Z0675). An MFF2 cDNA was obtained from Addgene. An MFF4 cDNA was constructed by mutagenesis of the MFF5 cDNA using QuikChange II XL Site-Directed Mutagenesis kit (Agilent Technologies) and confirmed by DNA sequencing. Mutations in the MFF sequence were also generated using QuikChange II, and confirmed by DNA sequencing. An MFF2 cDNA deleted in the VDAC minimal interacting region $^{223}$SARGILSLIQSSTRRAYQQILDVL$^{246}$ (SEQ ID NO: 12) was generated by site-specific mutagenesis using QuickChange II and confirmed by DNA sequencing. pEGFP-LC3 was purchased from Addgene (Cat. n. 24290). Transfection of plasmid DNA (1 μg) was carried out using 2 μl X-Treme gene HP (Roche) for 24 h. For gene knockdown experiments, tumor cells were transfected with control, non-targeting small interfering RNA (siRNA) pool (D-001810, Dharmacon) or specific siRNA pools targeting MFF (Santa Cruz #sc-94736) or individual MFF-directed siRNA sequences (Santa Cruz #Sc-94736-A and C). A specific siRNA targeting MFF (SantaCruz #SC-94736-A: 5'-GAACAAAGAACGUGCUAAAUUUU-3') (SEQ ID NO: 25) was synthesized by Dharmacon. Cells were transfected with the various siRNA (30-60 nM) in the presence of Lipofectamine RNAiMAX (Invitrogen) at a 1:1 ratio (vol siRNA 20 μM:vol Lipofectamine RNAiMAX). After 48 h, transfected cells were validated for protein knockdown by Western blotting or qPCR and processed for subsequent experiments. Alternatively, two independent shRNA sequences were used for targeting human MFF: TRCN0000167581 and TRCN0000343573 (Sigma Aldrich). An empty pLKO-based lentivirus was used as control. Individual clones of PC3 and DU145 cells stably expressing shRNA targeting MFF were generated by infection with lentiviral particles, followed by a 2-week selection in the presence of puromycin at 2 μg/ml.

Identification of MFF-associated proteins using 1D proteomics. PC3 cells were transfected with MFF1 cDNA, solubilized in lysis buffer (20 mM Tris, pH 7.5, 150 mM NaCl, 1 mM EDTA, 1 mM EGTA, 1% CHAPS) in the presence of 1% CHAPS, EDTA-free Protease Inhibitor Cocktail (Sigma-Aldrich) and Phosphatase Inhibitor Cocktail PhosSTOP (Roche). After sonication, lysates were centrifuged at 15,000×g for 30 min, and cell extracts were incubated with anti-Flag-conjugated agarose bead (Sigma-Aldrich) for 4 h at 4° C. After five washes in lysis buffer, MFF-associated proteins were separated by SDS gel electrophoresis. The entire gel region was excised and digested with trypsin, as described (Galluzzi, L., Bravo-San Pedro, J. M. & Kroemer, G. Organelle-specific initiation of cell death. *Nat Cell Biol* 16, 728-736 (2014)). Tryptic peptides were analyzed by LC-MS/MS on a Q Exactive HF mass spectrometer (ThermoFisher Scientific) coupled with a NanoACQUITY UPLC system (Waters). Samples were injected onto a UPLC Symmetry trap column (180 μm i.d.×2 cm packed with 5 μm C18 resin; Waters), and tryptic peptides were separated by RP-HPLC on a BEH C18 nanocapillary analytical column (75 μm i.d.×25 cm, 1.7 μm particle size; Waters) using a 95-min gradient. Eluted peptides were analyzed by the mass spectrometer set to repetitively scan m/z from 400 to 2000 in positive ion mode. The full MS scan was collected at 60,000-resolution followed by data-dependent MS/MS scans at 15,000-resolution on the 20 most abundant ions exceeding a minimum threshold of 20,000. Peptide match was set as preferred, the exclude isotopes option and charge-state screening were enabled to reject singly and unassigned charged ions. Peptide sequences were identified using MaxQuant 1.5.2.8 (Vyas, S., Zaganjor, E. & Haigis, M. C. Mitochondria and Cancer. Cell 166, 555-566 (2016)). MS/MS spectra were searched against the UniProt human protein database using full tryptic specificity with up to two missed cleavages, static carboxamidomethylation of Cys, and variable oxidation of Met and protein N-terminal acetylation. Consensus identification lists were generated with false discovery rates of 1% at protein and peptide levels.

Figure 1B:
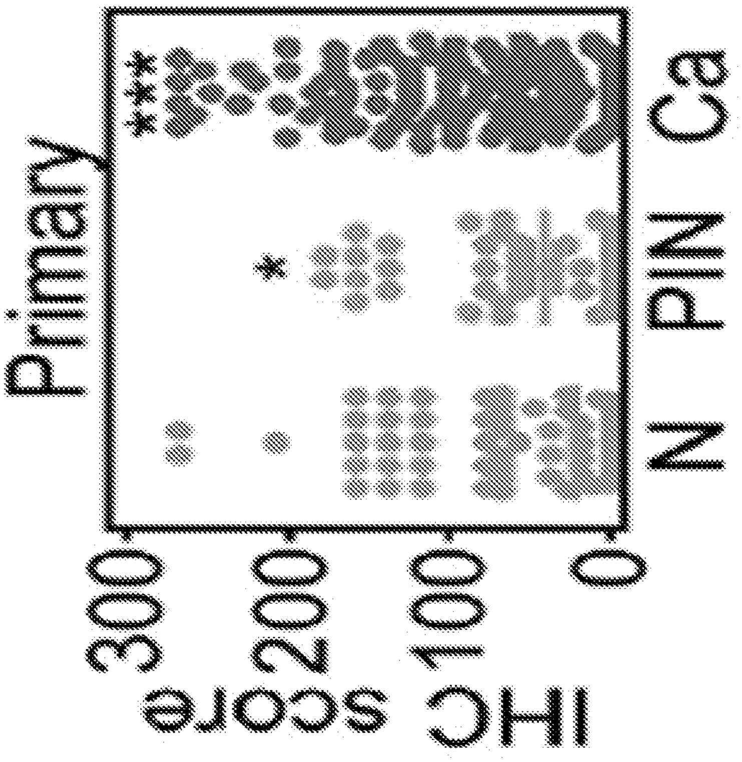
FIG. 1B shows quantification of MFF expression by immunohistochemistry (IHC) in primary prostate cancer. *, p=0.01; *, p<0.0001 (all compared to normal prostate).
Figure 1C:
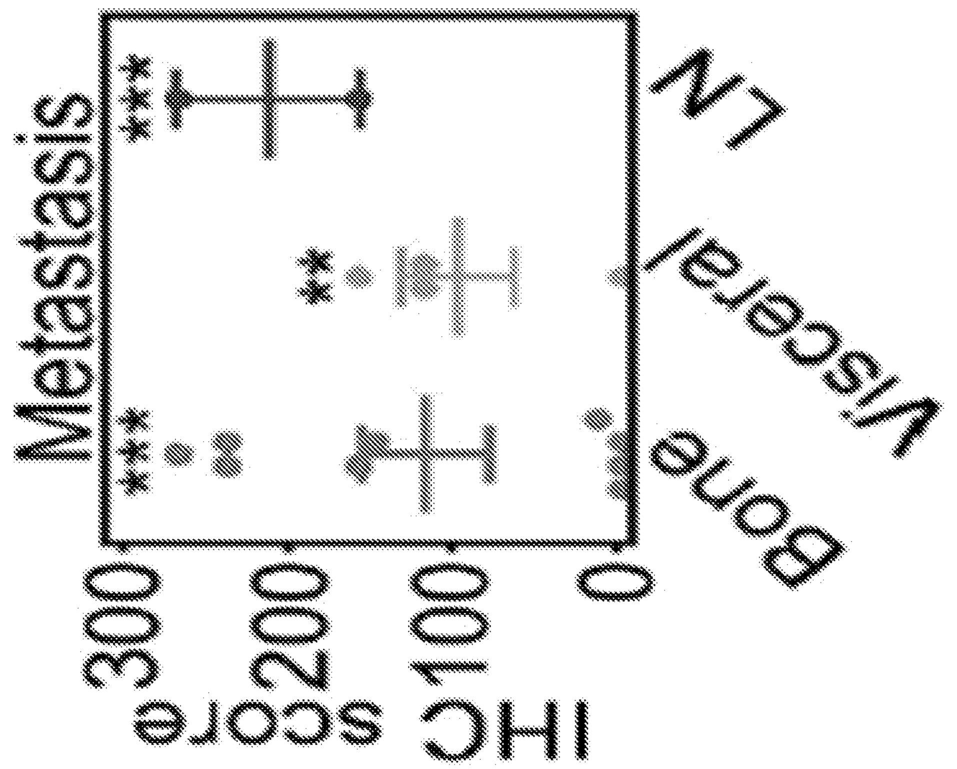
FIG. 1C shows quantification of MFF expression by immunohistochemistry (IHC) in metastatic prostate cancer. , p=0.003; *, p<0.0001 (all compared to normal prostate). LN, lymph nodes.
Figure 1D:
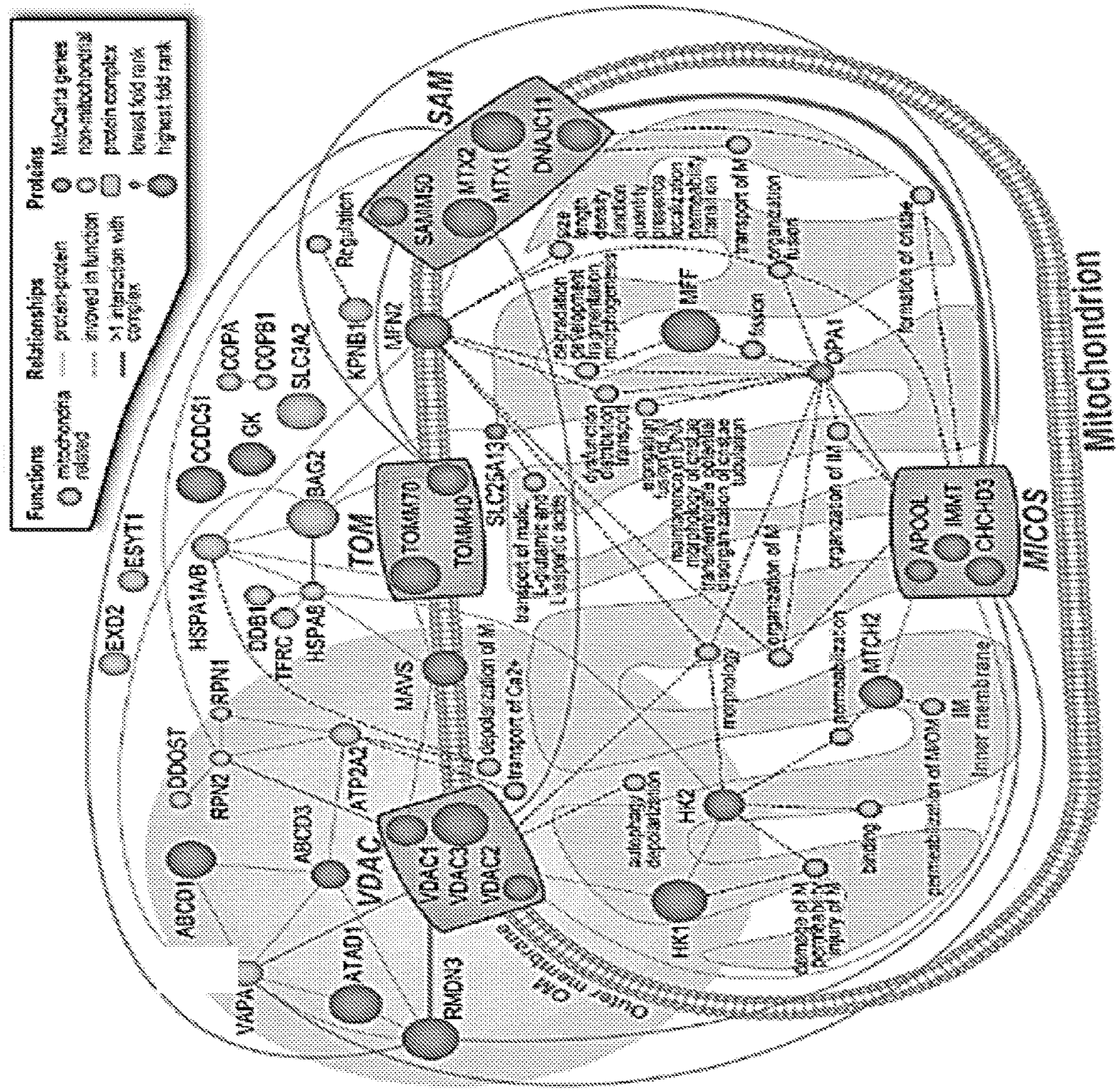
FIG. 1D shows an ingenuity pathway analysis of MFF-associated proteins identified by 1D proteomics.

Bioinformatics analysis. Proteomics intensity data were floored to the minimum detected signal (intensity of $10^5$) and log 2-scaled. Proteins were then annotated as mitochondrial-related using MitoCarta 2.0 database (Croce, C. M. & Reed, J. C. Finally, An Apoptosis-Targeting Therapeutic for Cancer. Cancer Res 76, 5914-5920 (2016)). Proteins detected in both MFF experiments with at least 10 peptides as well as at least 10 MS/MS spectra counts and at least 10-fold higher intensity than controls were reported as significant interacting proteins (Croce, C. M. & Reed, J. C. Finally, An Apoptosis-Targeting Therapeutic for Cancer. Cancer Res 76, 5914-5920 (2016)). Ingenuity Pathway Analysis (IPA®, QIAGEN Redwood City, www.qiagen.com/ingenuity) was used to identify all known protein-protein interactions between proteins in the list of candidates and their involvement in mitochondrial functions. All found interactions and functions were represented in a combined model (FIG. 1D).

Immunoprecipitation. Cells were harvested and lysed with PLD assay buffer (50 mM HEPES-NaOH, pH 7.3, 3 mM EGTA, 3 mM $CaCl_2$, 3 mM $MgCl_2$, 80 mM KCl) containing 1% CHAPS, EDTA-free Protease Inhibitor Cocktail (Sigma-Aldrich) and Phosphatase Inhibitor Cocktail PhosSTOP (Roche). After sonication, lysates were centrifuged at 15,000×g for 30 min, and cell extracts were incubated with anti-Flag-conjugated beads (Sigma-Aldrich). The precipitates were washed five times, separated by sodium dodecyl sulfate-polyacrylamide gel electrophoresis (SDS-PAGE) and processed for Western blotting.

Expression and purification of human VDAC1. A full length human VDAC1 cDNA (hVDAC1) was cloned into pET28b vector containing an N-terminal hexahistidine-SUMO fusion tag, with a flexible linker cleavable by tobacco etch virus (TEV) protease. The hVDAC1 was expressed in *E. coli* ScarabXpress T7 lac competent cells (Scarab genomics) for 16 h at 16° C. using 1 mM IPTG (Denville Scientific Inc.). The cells were harvested by centrifugation and lysed on ice via sonication in buffer containing 25 mM Tris-HCl (pH 7.5), 1 M Urea, 1 M KCl, 5% glycerol, 1 mM Benzamidine and 1 mM PMSF (Ni Buffer A). The lysate was centrifuged at 18,000 rpm for 20 min at 4° C. The cell pellet was first washed extensively in Ni Buffer A with 1% Triton X-100 and then solubilized in buffer containing 20 mM Tris-HCl (pH 7.9), 500 mM NaCl, 4 M guanidine-HCl and 10% glycerol for 45 min with gentle stirring. The supernatant was collected following centrifugation at 20,000 rpm for 10 min at 4° C. The protein was then purified over nickel-nitrilotriacetic acid (Ni-NTA—Qiagen) column and buffer-exchanged to 25 mM Tris-HCl (pH 7.5), 500 mM KCl, 5% glycerol, 1 mM benzamidine and 1 mM PMSF (Ni buffer C) with 2% n-Octylglucoside (Research Products International). The protein was then eluted with 300 mM imidazole and treated overnight with TEV at 4° C. to cleave the His-SUMO tag. The protein was then buffer exchanged to buffer C with 100 mM salt and loaded onto tandem HS(poros)-HQ(poros) column to remove the TEV and the His-SUMO fusion tag. The cleaved, full length hVDAC1 was collected from the HS-HQ flow through, concentrated using amicon ultra filter (10 kDa cut off) and used for further experiments.

Isothermal titration calorimetry (ITC). ITC experiments were performed using MIcroCal iTC200 (Malvern). Purified full-length hVDAC1 was buffer-exchanged into 25 mM HEPES-KOH (pH 7.5), 0.1 M KCl, 5% glycerol, 2% n-Octylglucoside, and 1 mM TCEP (ITC buffer). Wild type (WT) MFF peptide 8#11 corresponding to the minimal interacting sequence affecting mitochondrial membrane potential, SARGILSLIQSSTRRAYQQIL (SEQ ID NO: 21), and its control scrambled variant, SSQLRYLARSQRITIQLIAGS (SEQ ID NO: 22; see below) were also prepared in ITC buffer. The ITC binding experiments were carried out at 20° C. Peptides at a concentration of 100 μM were added by 2.47 μl injections to 10 μM hVDAC1. The data collected was processed in MicroCal Origin software (Malvern).

hVDAC1-MFF model generation. The hVDAc1-MFF model was generated using the CABS-dock server (Otera, H., et al. Mff is an essential factor for mitochondrial recruitment of Drp1 during mitochondrial fission in mammalian cells. J Cell Biol 191, 1141-1158 (2010); Youle, R. J. & van der Bliek, A. M. Mitochondrial fission, fusion, and stress. Science 337, 1062-1065 (2012)). The coordinates of hVDAC1 (PDB ID: 2JK4) (Mazure, N. M. VDAC in cancer. *Biochim Biophys Acta* 1858, 665-673 (2017)) and the WT MFF peptide sequence (SARGILSLIQSSTRRAYQQIL) (SEQ ID NO: 21) were provided for the modeling. The MFF peptide docking into hVDAC1 structure was carried out in three steps as described (Otera, H., et al. Mff is an essential factor for mitochondrial recruitment of Drp1 during mitochondrial fission in mammalian cells. *J Cell Biol* 191, 1141-1158 (2010); Youle, R. J. & van der Bliek, A. M. Mitochondrial fission, fusion, and stress. Science 337, 1062-1065 (2012)). In this study, the best binding mode of the peptide from the 10-top scored was used.

Peptidyl mimicry of MFF recognition.
A library of partially overlapping synthetic Peptides duplicating the entire MFF1 sequence was as follows:

Peptide #1:
(SEQ ID NO: 1)
$^{25}$AEMAEISRIQYEMEYTEGISQRMRVP$^{50}$

Peptide #2:
(SEQ ID NO: 2)
$^{49}$VPEKLKVAPPNADLEQGFQEGVPNASVIMQ$^{78}$

Peptide #3:
(SEQ ID NO: 3)
$^{77}$MQVPERIVVAGNNEDVSFSRPADLDLIQST$^{106}$

Peptide #4:
(SEQ ID NO: 4)
$^{105}$STPFKPLALKTPPRVLTLSERPLDFLDLER$^{134}$

Peptide #5:
(SEQ ID NO: 5)
$^{133}$ERPPTTPQNEEIRAVGRLKRERSMSENAVR$^{162}$

Peptide #6:
(SEQ ID NO: 6)
$^{161}$VRQNGQLVRNDSLWHRSDSAPRNKISRFQA$^{190}$

Peptide #7:
(SEQ ID NO: 7)
$^{189}$QAPISAPEYTVTPSPQQARVCPPHMLPEDG$^{218}$

Peptide #8:
(SEQ ID NO: 8)
$^{217}$DGANLSSARGILSLIQSSTRRAYQQILDV$^{L246}$

Peptide #9:
(SEQ ID NO: 9)
$^{245}$VLDENRRPVLRGGSAAATSNPHHDNVRYGI$^{274}$

Peptide #10:
(SEQ ID NO: 10)
$^{273}$GISNIDTTIEGTSDDLTV$^{290}$

Peptide #11:
(SEQ ID NO: 23)
$^{290}$VVDAASLRRQIIKLNRRLQLLEEENKERAKREM$^{322}$

A library of deletion peptides based on the MFF #8 sequence
(SEQ ID NO: 8)
$^{217}$DGANLSSARGILSLIQSSTRRAYQQILDVL$^{246}$
was synthesized as follows MFF, peptide 8#1,
(SEQ ID NO: 11)
NLSSARGILSLIQSSTRRAYQQILDVL MFF, peptide 8#2,
(SEQ ID NO: 12)
SARGILSLIQSSTRRAYQQILDVL MFF, peptide 8#3,
(SEQ ID NO: 13)
GILSLIQSSTRRAYQQILDVL -continued

```
MFF, peptide 8#4,
                                        (SEQ ID NO: 14)
SLIQSSTRRAYQQILDVL

MFF, peptide 8#5,
                                        (SEQ ID NO: 15)
QSSTRRAYQQILDVL

MFF, peptide 8#6,
                                        (SEQ ID NO: 16)
DGANLSSARGILSLIQSSTRRAYQQIL

MFF, peptide 8#7,
                                        (SEQ ID NO: 17)
DGANLSSARGILSLIQSSTRRAYQ

MFF, peptide 8#8,
                                        (SEQ ID NO: 18)
DGANLSSARGILSLIQSSTRR

MFF, peptide 8#9,
                                        (SEQ ID NO: 19)
DGANLSSARGILSLIQSS

MFF, peptide 8#10,
                                        (SEQ ID NO: 20)
DGANLSSARGILSLI
```

The minimal MFF interacting sequence with VDAC, designated peptide 8#11 with the sequence SARGILSLIQSSTRRAYQQIL (SEQ ID NO: 21) and its corresponding scrambled version, SSQLRYLARSQRITIQLIAGS (SEQ ID NO: 22) were also synthesized. For targeting experiments of the MFF-VDAC interaction in tumor cells, the MFF peptide 8#11 was made cell permeable with the addition of an $NH_2$-terminus biotin-Ahx linker and HIV Tat cell-penetrating sequence RQIKIWFQNRRMK (SEQ ID NO: 24). A cell-permeable control scrambled peptide #8-11 and two MFF peptide #8-11 mutants, lacking the entire VDAC interacting-sequence sequence $Ser^{223}$-$Leu^{243}$ (DN) or containing the double mutation R225D/R236D (DD) were also synthesized. To generate a clinical candidate peptidomimetic inhibitor of the MFF recognition in vivo, a retro-inverso D-enantiomer of MFF peptide #8-11 was synthesized containing all D-amino acid in the reverse orientation, as described (Eisner, V., Picard, M. & Hajnoczky, G. Mitochondrial dynamics in adaptive and maladaptive cellular stress responses. *Nat Cell Biol* 20, 755-765 (2018)). A scrambled D-enantiomer peptide was also synthesized as control for these experiments. All peptides were synthesized with >95% purity.

Analysis of bioenergetics. Glucose concentrations were determined in medium of PC3 cells using a glucose kit (Sigma-Aldrich). Briefly, $2\times10^6$ cells stably transfected with control pLKO or MFF-directed shRNA were seeded in 10 $cm^2$ tissue culture dishes for 48 h, and 200 μl aliquots of culture medium were incubated with 1 ml assay mixture, containing 1.5 mM NAD, 1 mM ATP, 1.0 U/ml hexokinase, and 1.0 U/ml G6PDH. Glucose concentrations were determined by measuring the amount of reduced NAD to NADH by G6PDH and quantified by absorbance at 340 nm. Extracellular lactate concentrations were measured in PC3 cells using a colorimetric assay (Abcam), with quantification of lactate-dependent conversion of NADP to NADPH in the presence of excess lactate dehydrogenase (LDH) by absorbance at 450 nm. Intracellular ATP concentrations were determined by a luciferin-luciferase method using a microplate luminometer (Beckman Coulter) against standard ATP solutions as reference.

Cellular respiration. PC3 or DU145 cells were transfected with control non-targeting siRNA or MFF-directed siRNA and analyzed after 48 h for oxygen consumption rates (OCR) using an Extracellular Flux System 24 Instrument (Seahorse Bioscience, Billerica, Md.). Briefly, $2.5\times10^4$ cells were plated in each well of a Seahorse XF24 cell culture plate (100 μl volume). After 4-h incubation to allow the cells to adhere to the plate, an additional volume (150 μl) of media was added to each well, and the cells were grown for 24 h at 37° C. in 5% $CO_2$. The media was then exchanged with unbuffered DMEM XF assay media (Seahorse Bioscience) supplemented with 2 mM glutaMAX, 1 mM sodium pyruvate and 5 mM glucose (pH 7.4 at 37° C.) and equilibrated for 30 min at 37° C. and ~0.04% $CO_2$ before the experiment. Cellular OCR was monitored in basal condition (before any addition) and after addition of oligomycin (1.25 μM), FCCP (0.4 μM), and antimycin plus rotenone (0.25 μM), all dissolved in DMSO. The three drugs were injected into the XF24 sequentially, and OCR was quantified after three cycles of mixing (150 seconds), waiting (120 seconds), and measuring (210 seconds). This cycle was repeated following each injection.

Mitochondrial ROS determination. PC3 cells transfected with control non-targeting siRNA or MFF-directed siRNA were incubated with 5 μM MitoSOX Red (Life Technology) for 10 min in complete culture medium, washed three times in warm PBS and counted. Ten thousand stained cells in 100 μl of PBS were analyzed on a microplate florescent reader (Ex/Em=510/580 nm, Molecular Devices). Unlabeled cells were used as basal control.

Analysis of mitochondrial membrane potential. PC3 or DU145 cells transfected with control non-targeting siRNA or MFF-directed siRNA were incubated with 100 nM tetramethylrhodamine, ethyl ester (TMRE, Abcam) for 30 min at 37° C. In some experiments, PC3 cells were treated with cell-permeable scrambled peptide or cell-permeable MFF #8-11 peptide, washed three times in PBS, pH 7.4, and analyzed on a FACSCalibur flow cytometer, with the TMRE signal as FL1. Intact cells were gated in the FSC/SSC plot to exclude small debris. Cells treated with 20 μM FCCP 10 min prior to TMRE staining were used as a negative control. The resulting FL1 data were plotted on a histogram. For quantification of membrane potential of purified mitochondria, mitochondria isolated from PC3 cells (50 μg) were suspended in 400 μl of SB buffer (0.2 M sucrose, 10 mM Tris-MOPS, pH 7.4, 5 mM succinate, 1 mM sodium phosphate, 10 μM EGTA-Tris, 2 μM rotenone). Samples were treated with control scrambled peptide or the various MFF peptides for 20 min at 22° C., and incubated with 100 nM TMRE for 30 min at 22° C. After two washes with SB buffer, mitochondria were recovered by centrifugation at 6000×g for 10 min, suspended in 100 μl of SB buffer and mitochondrial membrane potential was quantified on a florescence microplate reader (Ex/Em=535/595 nm, Beckman Coulter). Samples treated with 2 mM $CaCl_2$ were used as control for the lowest membrane potential (fully depolarized state).

Cell death and apoptosis. For determination of apoptosis, PC3 or DU145 cells ($1\times10^6$) were transfected with control non-targeting siRNA or MFF-directed siRNA, labeled for Annexin V and propidium iodide (PI) (BD Biosciences) and analyzed by multiparametric flow cytometry (BD). The various cell-permeable MFF peptides were examined for induction of cytotoxicity using a CellTOX Green cytotoxicity assay kit (Promega). Briefly, $10^4$ normal or tumor cells in 100 μl complete medium were plated on white opaque 96-well plate. After 24 h, the various WT or mutant cell-permeable MFF peptides were added in the presence of 100 μl of CellTOX Green reagent (2×), and cell death was quantified as changes in florescence intensity for 5 h at 10 min intervals using a plate reader (Ex/Em=485/535 nm, Beckman Coulter). Lysis Solution in the assay kit was used as cytotoxicity control (100% cell death) and treatment with PBS was used as a control for 100% cell viability.

Colony formation assay. Four hundred PC3 or DU145 cells stably expressing control pLKO or two independent MFF-targeting shRNA were plated in triplicate in 6-multi-well plates. Colonies were washed in PBS and fixed/stained for 30 min in 0.5% w/v crystal violet/methanol after two weeks. Plates were rinsed in tap water and dried before scoring. Macroscopically visible colonies were manually counted.

Autophagy. Cells expressing control non-targeting siRNA or MFF-directed siRNA were transfected after 24 h with GFP-LC3 cDNA. After 36 h, cells were fixed in 4% formaldehyde/PBS for 15 min at 22° C., washed, permeabilized with 0.1% Triton X-100/PBS for 5 min, washed, and blocked with 10% normal goat serum/PBS for 1 h. After washing, cells were incubated with phalloidin Alexa Fluor in 1% BSA/0.3 M glycine/PBS for 1 h at 22° C. Slides were washed and mounted in DAPI-containing Prolong Gold mounting medium (Invitrogen). At least 20 random fields from 2 independent experiments were analyzed by Z-stack imaging by confocal microscopy (SPFS II, Leica). A minimum of 200 cells were analyzed for punctate LC3 fluorescence staining to obtain mean values.

Immunofluorescence and confocal microscopy. PC3 or DU145 cells transfected with control non-targeting siRNA or MFF-directed siRNA, or alternatively, expressing control plasmid or MFF cDNA were fixed in formalin/PBS (4% final concentration) for 15 min at 22° C., permeabilized with 0.1% Triton X-100/PBS for 5 min, washed, and incubated in 5% normal goat serum (NGS, Vector Labs) diluted in 0.3 M glycine/PBS for 60 min. Primary antibodies against MFF (1:100) or MTCO2 (mitochondrial marker, 1:500) were added in 5% NGS/0.3 M glycine/PBS and incubated for 18 h at 4° C. After three washes in PBS, secondary antibodies conjugated to Alexa488, TRITC or Alexa633 were diluted 1:500 in 5% NGS/0.3 M glycine/PBS and added to cells for 1 h at 22° C. Where indicated, F-actin was stained with phalloidin Alexa (1:200 dilution) for 30 min at 22° C. Slides were washed and mounted in 4,6-diamidino-2-phenylindole (DAPI)-containing Prolong Gold mounting medium (Life Technologies). Cells were visualized by Z-stack imaging by confocal microscopy (SPFS II, Leica). At least 70 cells per sample were analyzed and mitochondrial morphologies were classified as fragmented (individual round- or rod-shaped organelles, >80% displaying an axial length of <4 μm), intermediate (majority ~4 μm), or tubular (often inter-connected in branched networks, >80% displaying a length of >4 μm).

For time-lapse videomicroscopy, PC3 cells ($2\times10^4$) growing in high optical-quality glass bottom chambered 8-well cell culture slides (MatTek Corporation) were stained with 100 nM TMRE (Abcam) and 50 nM MitoTracker Green FM (Life Technologies) for 20 min. After three washes in warm complete medium, cells were treated with cell-permeable scrambled peptide or cell-permeable MFF #8-11 peptide and imaged with a ×63 1.40 NA oil objective on a Leica TCS SP8 X inverted laser scanning confocal microscope. Short duration time-lapse sequences were carried out in a Tokai Hit incubation chamber equilibrated to 37° C. and 5% $CO_2$. Images were taken every 3 min for 2 h. At least 50 individual cells in five microscopy fields per treatment condition were collected. A minimum of 100 cells were analyzed from 2 independent experiments. For morphologic assessment of cell death induced by MFF targeting, PC3 cells were treated with 10 μM cell-permeable scrambled peptidomimetic or MFF (D) peptidomimetic and imaged continuously by time-lapse videomicroscopy between 0 and 30 min at 37° C.

Glioblastoma (GBM) neurospheres. Primary, patient-derived GBM neurospheres were isolated and maintained in culture essentially as described (Senft, D. & Ronai, Z. A. Regulators of mitochondrial dynamics in cancer. Curr Opin Cell Biol 39, 43-52 (2016)). Tissue samples were obtained from chemotherapy- or radiotherapy-naïve patients with confirmed histological diagnosis of WHO grade IV glioma (GBM) undergoing treatment at the Neurosurgery Division of Fondazione IRCCS Ca' Granda Ospedale Maggiore Policlinco (Milan, Italy). Written informed consent was obtained from all patients. Neurospheres were cyto-spinned on charged slides (Thermo Scientific, Waltham, Mass.) and treated with cell-permeable scrambled peptide (50 μM) or cell-permeable retro-inverso D-enantiomer MFF peptide (10-50 μM) for up to 24 h. Control-normalized changes in cell viability under the various conditions were determined by the ratio of Calcein (alive) and To-Pro (dead) staining and fluorescence microscopy (Eclipse Ti-E, Nikon Instruments, Florence, Italy).

Animal studies. Studies involving vertebrate animals (rodents) were carried out in accordance with the Guide for the Care and Use of Laboratory Animals of the National Institutes of Health (NIH). Protocols were approved by the Institutional Animal Care and Use Committee (IACUC) of The Wistar Institute (Protocol #112625). Groups of 4-6 weeks-old male athymic nude mice (Crl:NU(NCr)-Foxn1$^{nu}$, Charles River Laboratory) were injected s.c. with PC3 clones ($5\times10^6$ cells) stably transduced with pLKO or MFF-directed shRNA and tumor volume was quantified with a caliper over a two-week interval. For therapeutic experiments, PC3 xenograft tumors engrafted in athymic nude mice ($5\times10^6$ PC3 cells in 50% Matrigel) were allowed to grow to ~100 $mm^3$ volume. Tumor-bearing animals were randomized into two groups receiving cell-permeable scrambled peptide (50 mg/kg) or cell-permeable retro-inverso D-enantiomer MFF peptide (10-50 mg/kg) as daily i.p. injections in PBS, pH 7.2. Tumor growth under the various conditions was measured with a caliper during a two-week time interval and quantified.

Statistical analysis. Data were analyzed using the two-sided unpaired t, chi-square or Kruskal-Wallis (with p value correction for multiple testing) tests using a GraphPad software package (Prism 6.0) for Windows. Data are expressed as mean±SD of replicates from a representative experiment out of at least two or three independent determinations or as mean±SD of three individual experiments. A p value of <0.05 was considered as statistically significant.

The experimental examples of the present invention are now described.

TABLE 1

Clinico-pathological characteristics of patient-derived tissue samples used herein.

| Group | ID | Site | Notes[1] |
|---|---|---|---|
| PCa metastasis | Met 3 | Brain | PSA positive; NE differentiation |
| | Met 5 | Bone | PSA positive |
| | Met 1 | Lung | PSA positive |
| | Met 2 | Lung | PSA positive |
| | Met 6 | Bone | PSA positive |
| | Met 7 | Bone | PSA positive |

TABLE 1-continued

Clinico-pathological characteristics of patient-derived tissue samples used herein.

| Group | ID | Site | Notes[1] |
|---|---|---|---|
| | Met 8 | Liver | PSA positive |
| | Met 9 | Axillary lymph nodes | PSA positive |
| | Met 10 | Bone | PSA positive |
| | Met 11 | Bone | PSA positive |
| | Met 12 | Brain | PSA positive |
| | Met 13 | Bone | PSA positive |
| | Met 14 | Inguinal lymph nodes | PSA positive |
| | Met 15 | Bone | PSA positive |
| | Met 16 | Bone | PSA positive |
| | Met 17 | Bone | PSA positive |
| | Met 20 | Lung | PSA positive |
| Organ cultures | OC1 | Lung | NSCLC-SCC (pT2aN1) |
| | OC2 | Lung | NSCLC-SCC (pT1cN0) |
| | OC3 | Breast | DIC; Grade: G2 |
| GBM | NS91 | Brain | IDH1-WT; MGMT-UM |
| | NS92 | Brain | IDH1-WT; MGMT-M |

[1]PSA, prostate specific antigen;
NSCLC, Non-Small Cell Lung Cancer;
SCC, squamous cell carcinoma;
DIC, Ductal Infiltrating Carcinoma;
IDH1-WT, IDH1 wild-type;
MGMT-UM/M, MGMT methylated/unmethylated

Example 1—MFF Expression in Prostate Cancer and Non-Small Cell Lung Cancer (NSCLC)

Figure 5B:
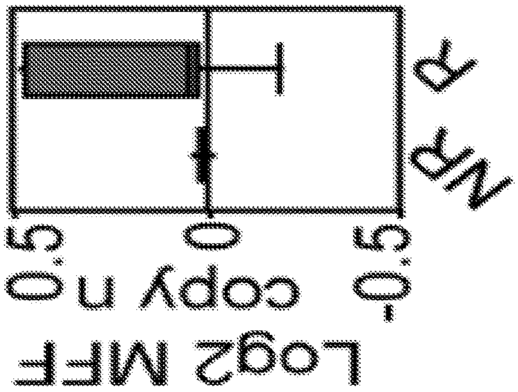
FIGS. 5A-5J illustrate MFF expression in prostate cancer.
Figure 5C:
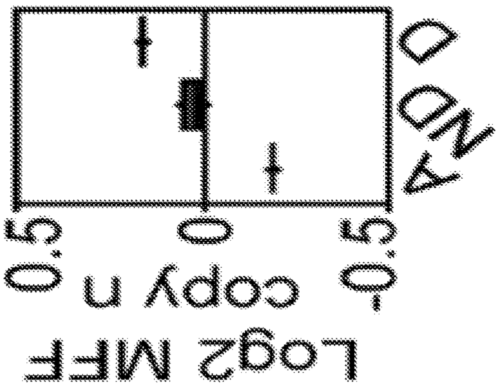
Figure 5A:
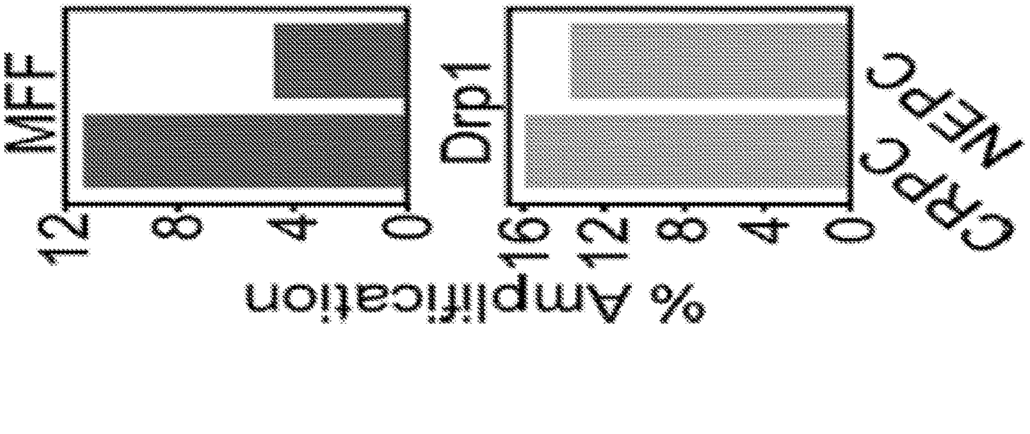
Figure 5D:
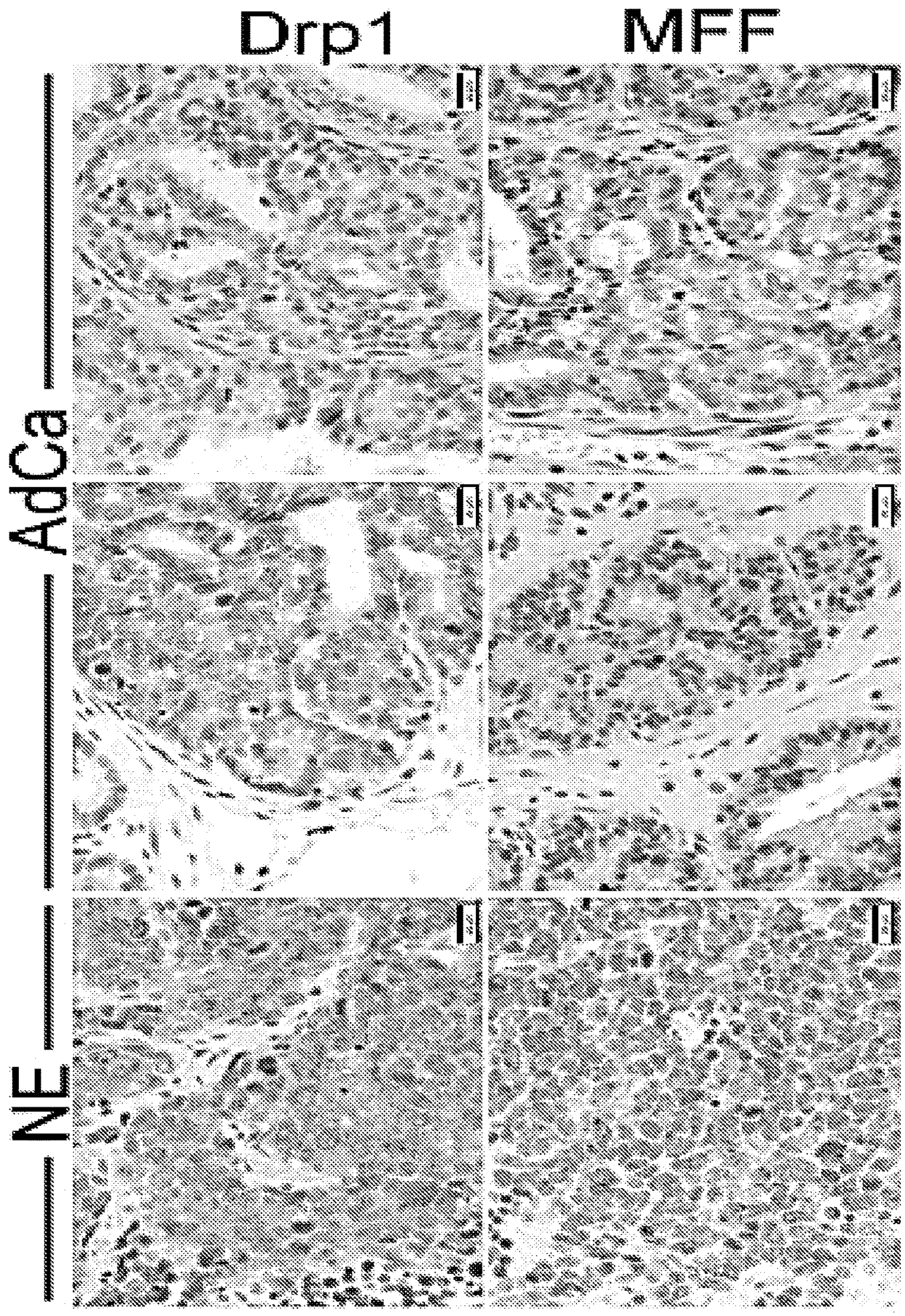

The expression of mitochondrial fission regulators, Dynamin-Related Protein-1 (Drp1) (Senft, D. & Ronai, Z. A. Regulators of mitochondrial dynamics in cancer. Curr Opin Cell Biol 39, 43-52 (2016)) and its cognate receptor on the mitochondrial outer membrane, Mitochondrial Fission Factor (MFF) (Otera, H., et al. Mff is an essential factor for mitochondrial recruitment of Drp1 during mitochondrial fission in mammalian cells. *J Cell Biol* 191, 1141-1158 (2010)) were studied herein, in prostate cancer. Analysis of public databases showed that MFF and Drp-1 were amplified in castration-resistant and neuroendocrine prostate cancer (FIG. 5A). In particular, increased MFF expression correlated with prostate cancer relapse (FIG. 5B) and abbreviated patient survival (FIG. 5C). Consistent with this, MFF was highly expressed in genetic models of prostate adenocarcinoma and neuroendocrine prostate cancer in Transgenic Adenocarcinoma of the Mouse Prostate (TRAMP) mice, whereas Drp-1 was undetectable (FIG. 5D).

Based on these data, the expression of MFF was next examined by immunohistochemistry in a cohort of 192 patients with localized and metastatic prostate cancer (Table 1). In this series, MFF levels increased from normal prostate to prostatic intraepithelial neoplasia (PIN) and were the highest in localized (FIGS. 1A-1B) as well as metastatic prostate cancer to lymph nodes, bones and visceral sites (FIGS. 1A and 1C).

Figure 5F:
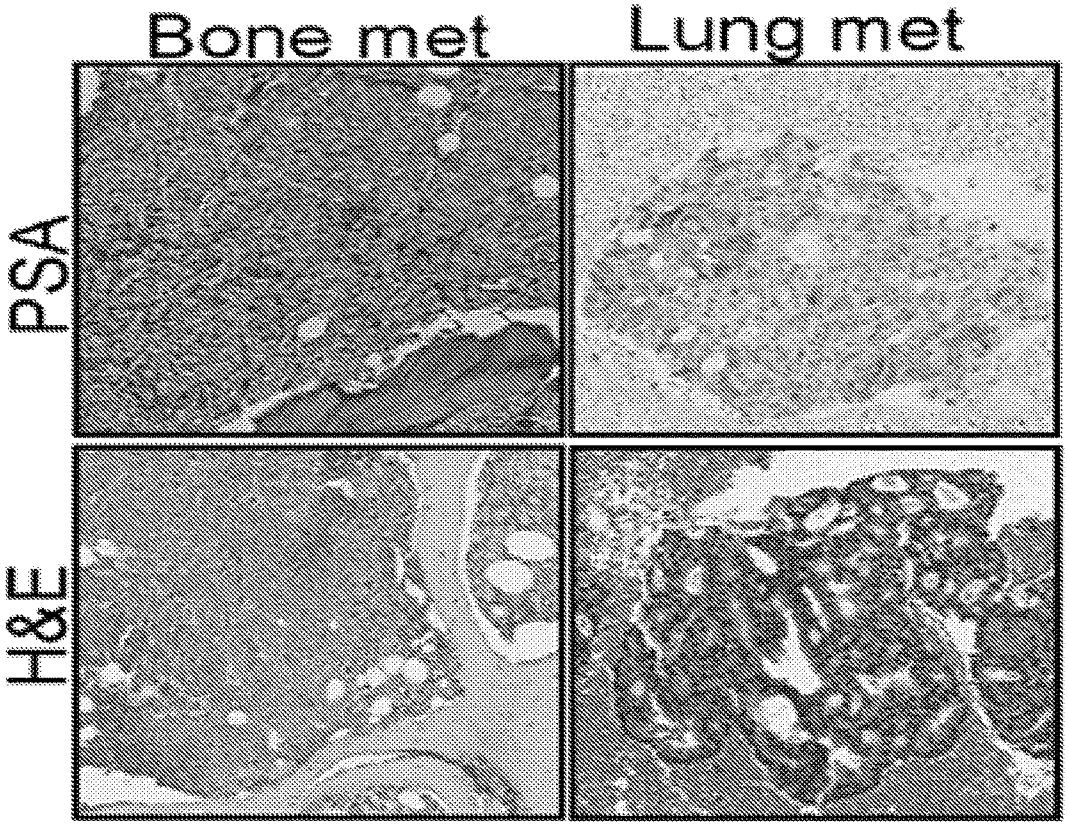
Figure 5E:
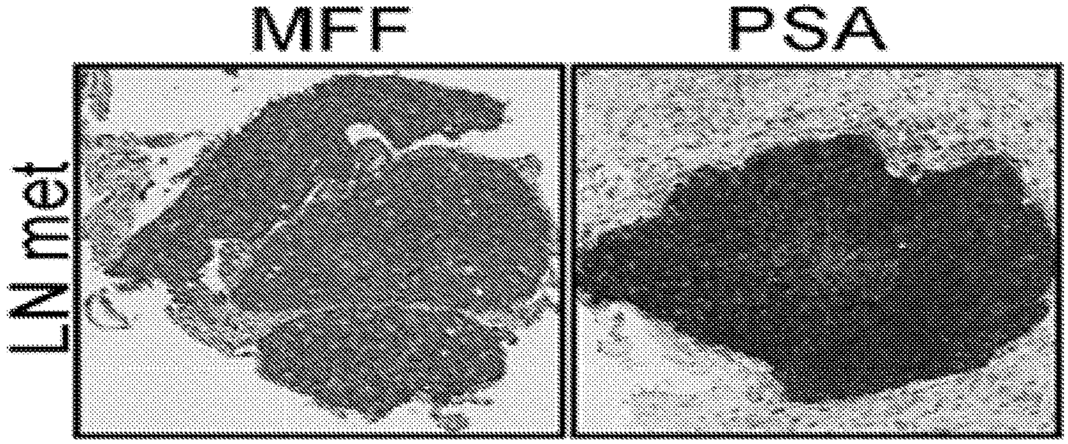
Figure 5H:
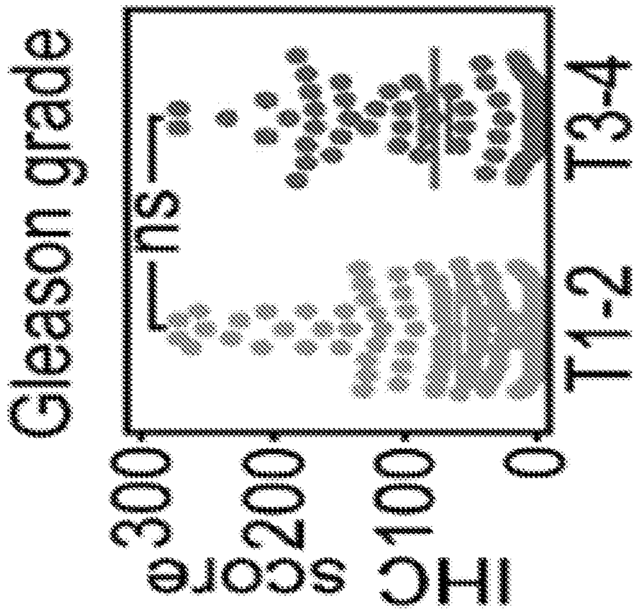
Figure 5G:
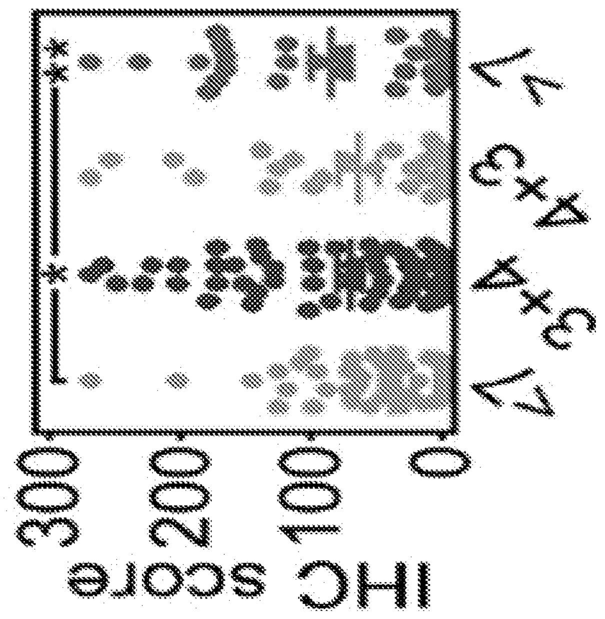
Figure 5J:
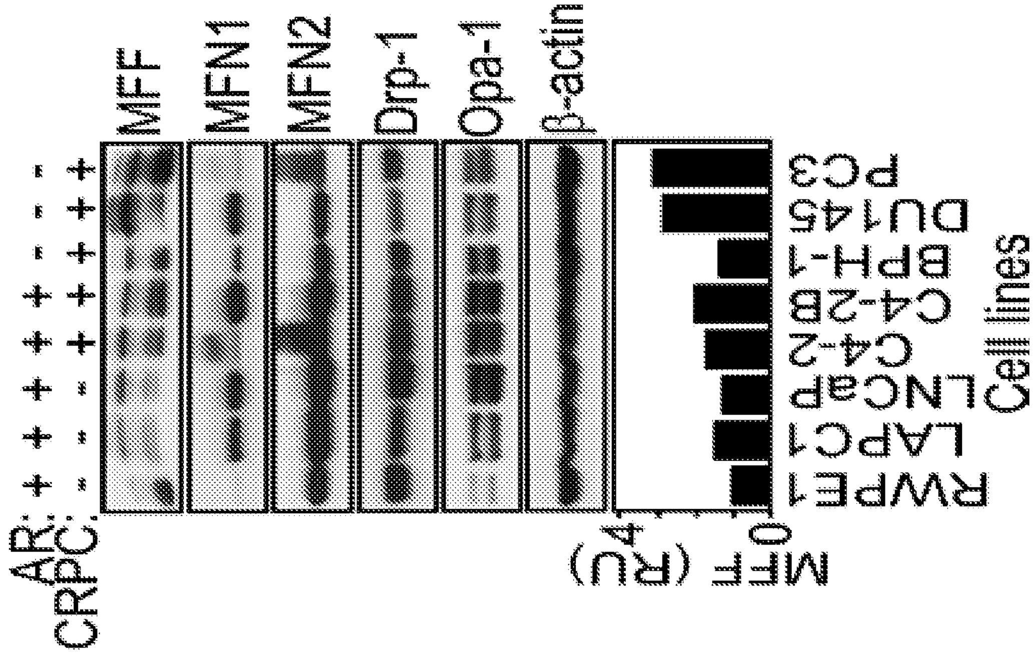
Figure 5I:
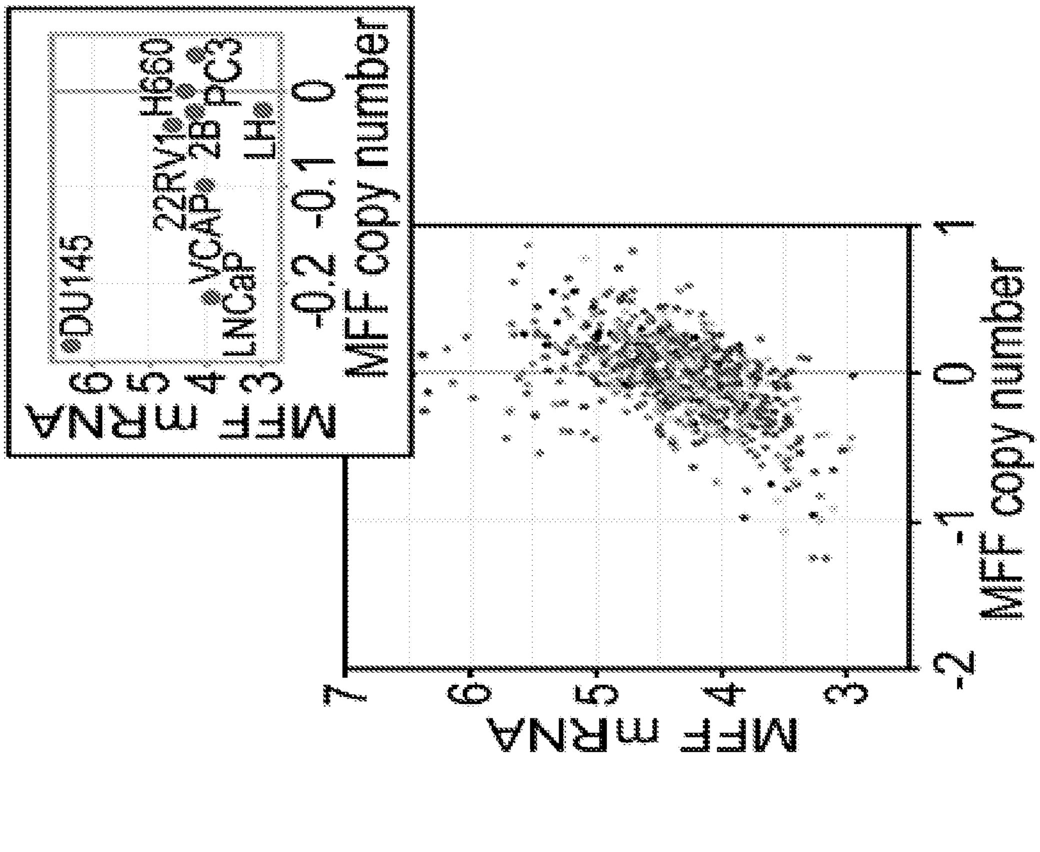

Confirming their prostatic origin, these metastatic sites stained positive for prostate-specific antigen (PSA) (FIGS. 5E and 5F). Increased MFF expression correlated with high Gleason grade (FIG. 5G), but not tumor size (FIG. 5H). Consistent with these results, most prostate cancer cell lines expressed MFF (FIG. 5I), with the highest levels observed in castration-resistant as opposed to androgen receptor (AR)-positive cell types (FIG. 5J). Other regulators of mitochondrial fusion (MFN1, MFN2, Opal) or fission (Drp1) did not show differential expression in prostate cancer cell lines (FIG. 5J).

The expression of MFF was also examined in a clinically-annotated cohort of non-small cell lung cancer (NSCLC) patients (Table 2):

Clinico-pathological characteristics of non-small cell lung cancer (NSCLC) patient series used in this study (n=72)*.

| | Feature | n |
|---|---|---|
| Histotype | Adenocarcinoma (AdCa) | 57 |
| | Squamous Cell Carcinoma (SCC) | 15 |
| pN | N0 | 45 |
| | N1, 2 | 26 |
| pT | pT1a, b | 24 |
| | pT2a, b | 30 |
| | pT3, 4 | 18 |
| Grade | na | 2 |
| | Grade 1 | 4 |
| | Grade 2 | 36 |
| | Grade 3 | 30 |
| | ALK-R** | 15 |

*67 out of 72 samples were evaluable for MFF expression by immunohistochemistry.
**ALK-R, ALK rearrangement.

Figure 1E:
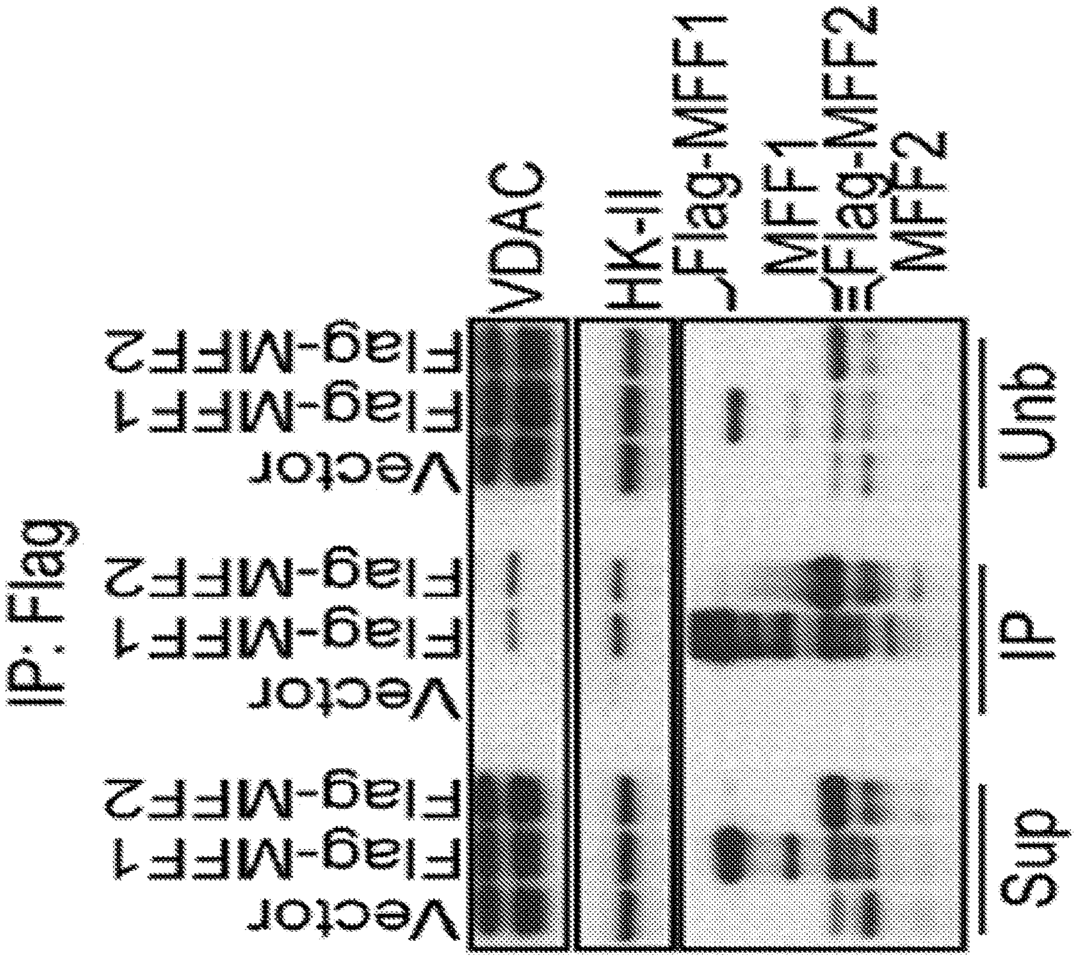
FIG. 1E shows a Western blot. PC3 cells were transfected with vector, Flag-MFF1, or Flag-MFF2 cDNA, immunoprecipitated (IP) with an antibody to Flag and analyzed by Western blotting. The position of endogenous or Flag-MFF isoforms is indicated. Sup, supernatant; Unb, unbound.
Figure 1H:
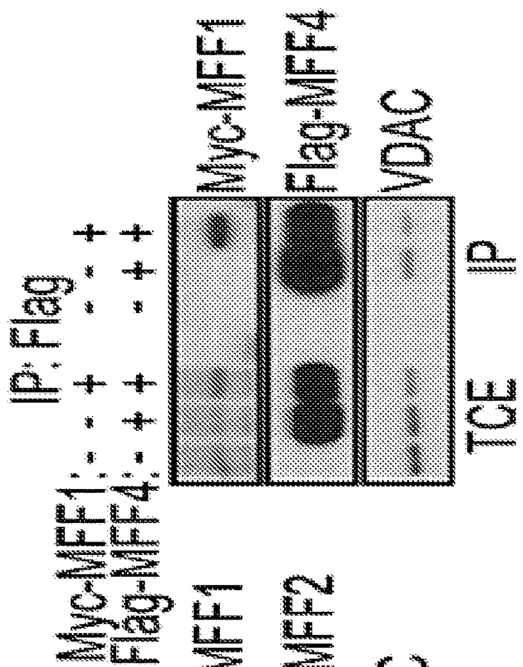
FIGS. 1F-1H show Western blots. PC3 cells were transfected with vector or the indicated Flag-tagged MFF isoforms, immunoprecipitated (IP) with an antibody to Flag and analyzed by Western blotting. TCE, total cell extracts.
Figure 1G:
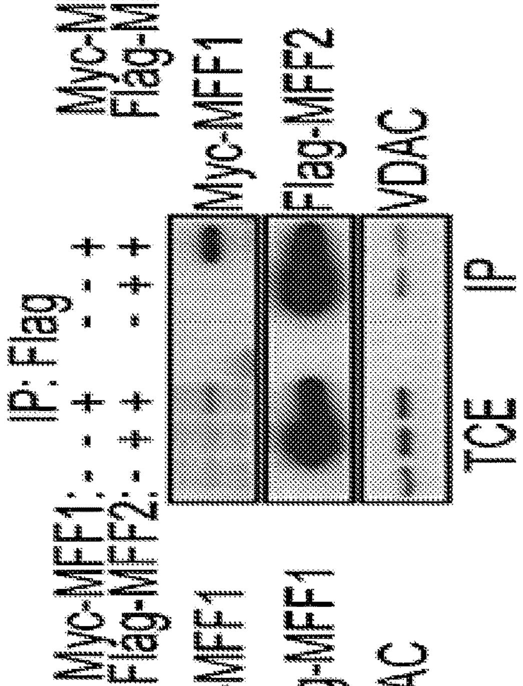
Figure 1F:
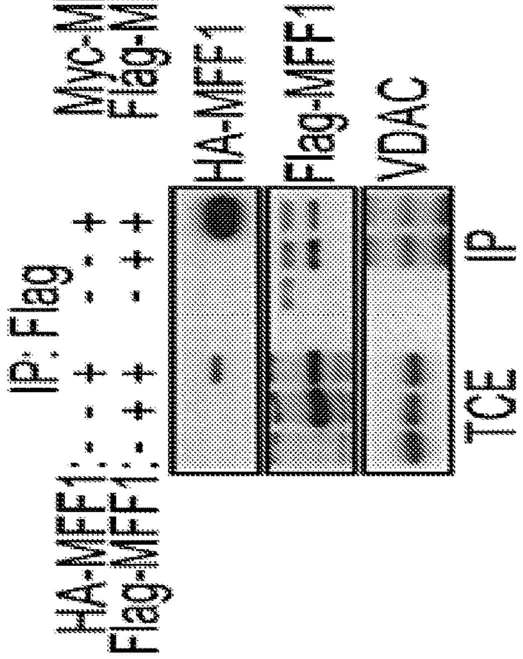
Figure 1I:
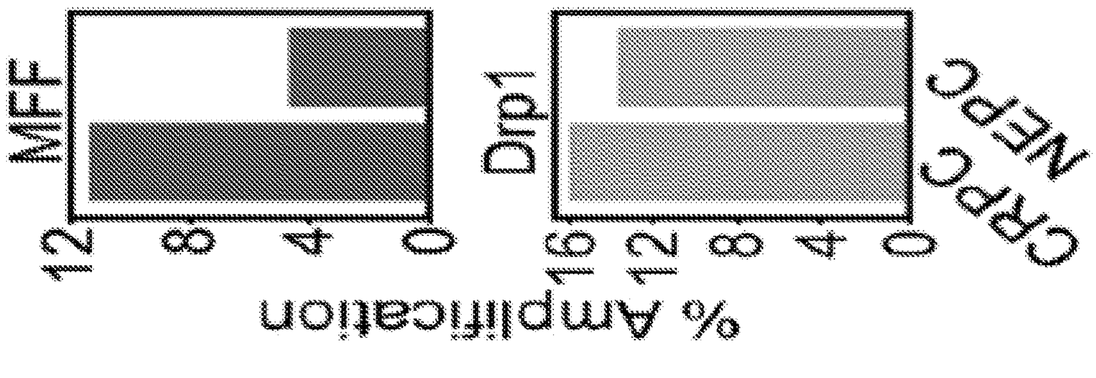
FIG. 1I shows amplification of MFF and Drp1 in prostate cancer (77 patients, 107 samples). CRPC, castration-resistant prostate cancer; NEPC, neuroendocrine prostate cancer.
Figure 1J:
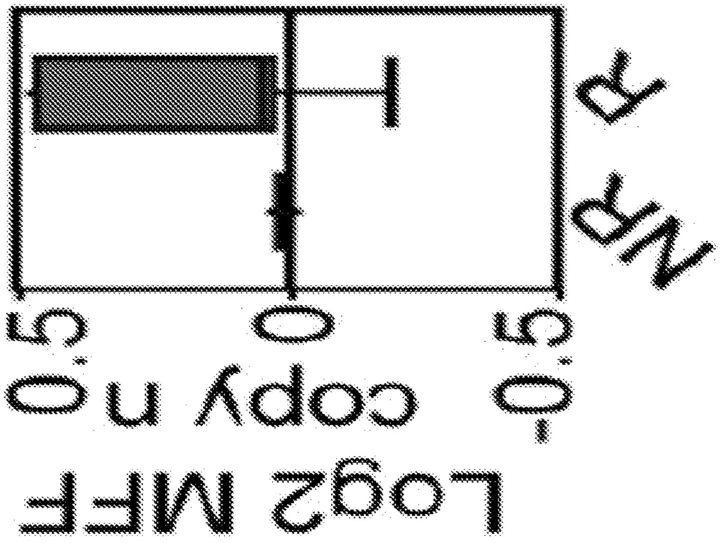
FIG. 1J shows TCGA correlation (n=380) between MFF expression and prostate cancer progression. NR, no recurrence at 5 years; R, recurrence at 5 years.
Figure 1K:
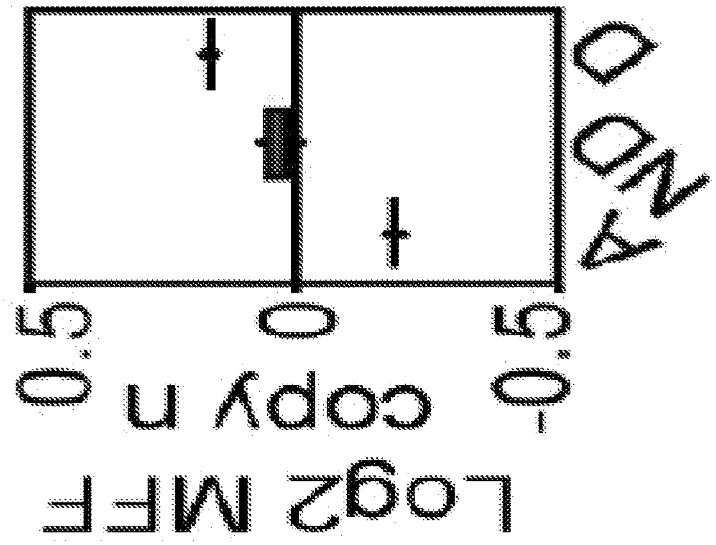
FIG. 1K shows TCGA correlation (n=380) of MFF expression (log MFF copy number) and prostate cancer survival. A, alive at 5 years; ND, alive with no evidence of disease at 5 years; D, dead with disease at 5 years.
Figure 1M:
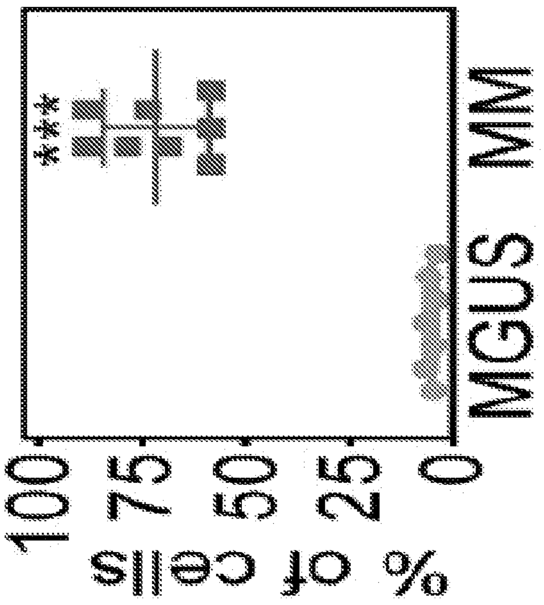
FIGS. 1L-1M show MFF expression in representative patient samples of Monoclonal Gammopathy of Uncertain Significance (MGUS, n=7) or Multiple Myeloma (MM, n=8) by immunohistochemistry (FIG. 1L) and quantification of IHC score (FIG. 1M). Scale bar, 50 μm. *, p<0.0001.
Figure 1L:
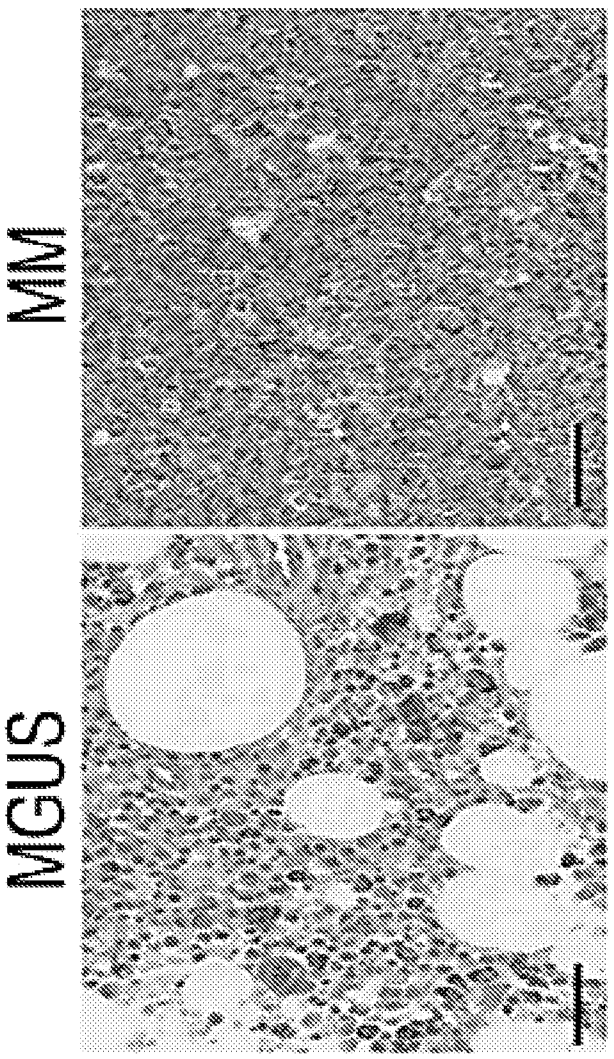
Figure 1O:
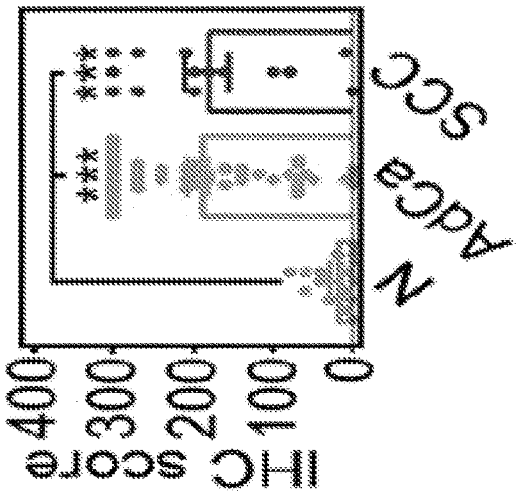
FIGS. 1O-1P show quantification of MFF expression in NSCLC by immunohistochemistry (IHC) compared to normal lung (FIG. 1O) or according to tumor grade (FIG. 1P). Mean±SD. *, p<0.0001; ns, not significant.
Figure 1N:
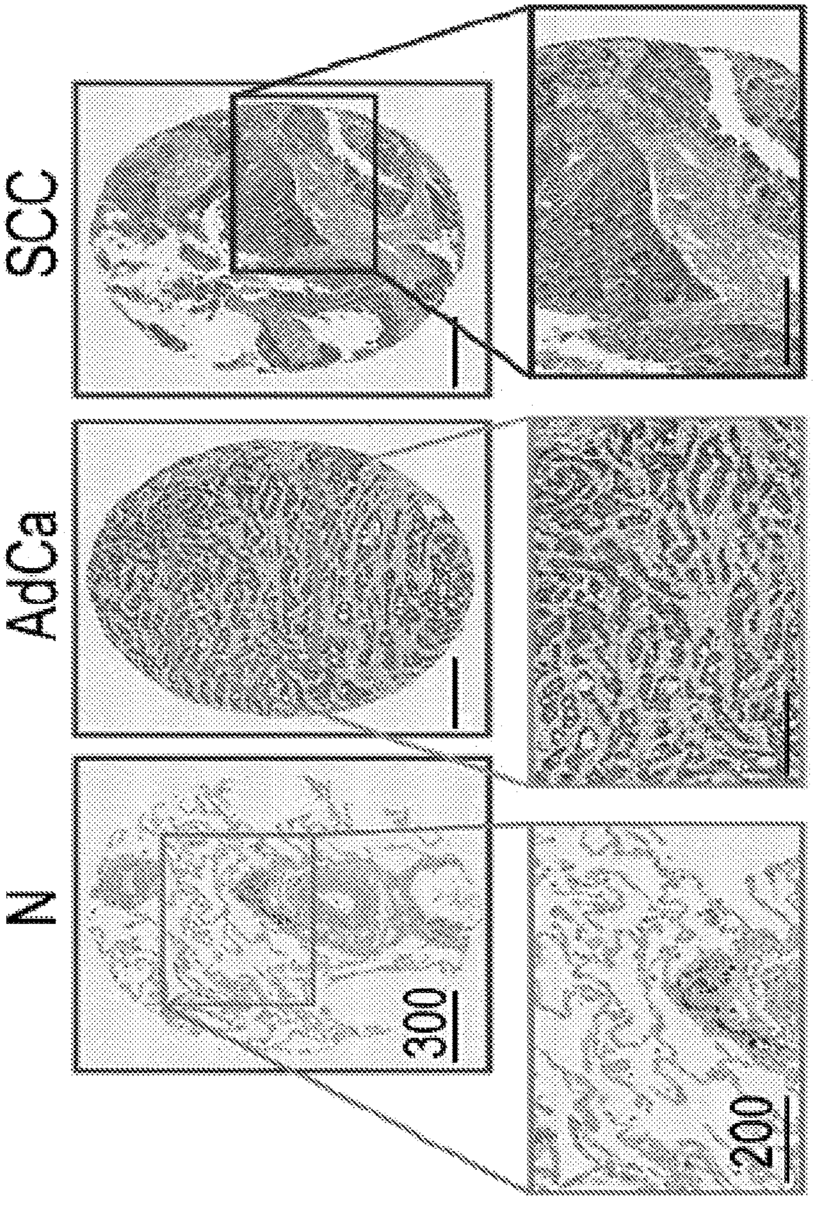
FIG. 1N shows MFF expression in a cohort of non-small cell lung cancer (NSLC) patients by immunohistochemistry. N, normal; AdCa, adenocarcinoma; SCC, squamous cell carcinoma. Insets, image magnification of indicated regions. Scale bars (top), 300 μm; (bottom), 200 μm.
Figure 26C:
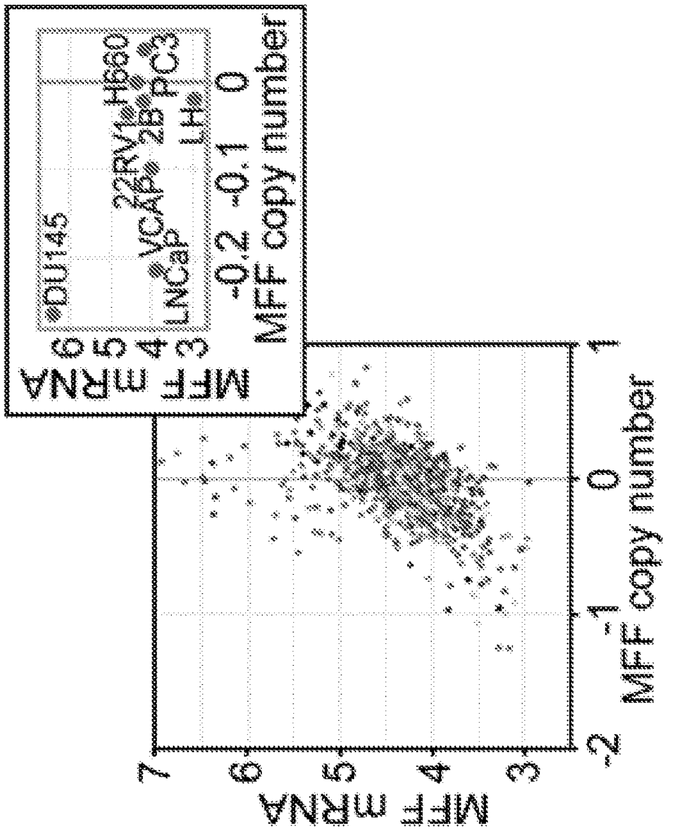
FIGS. 26A-26C illustrate MFF expression in cancer.
Figure 26A:
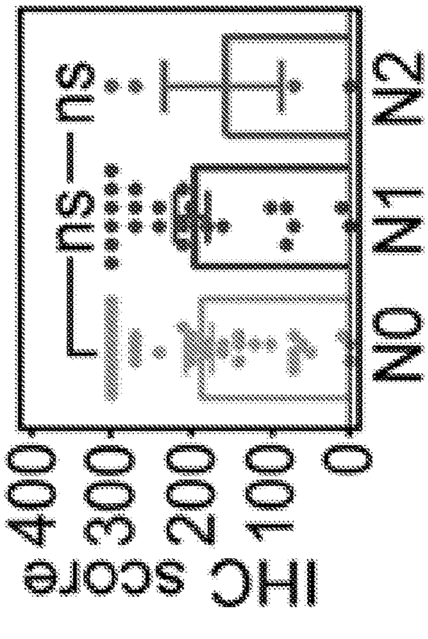
Figure 26B:
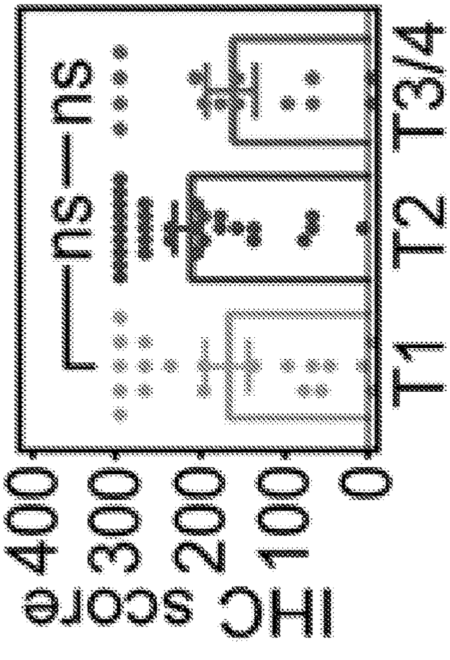

MFF was differentially overexpressed in NSCLC patients, including cases of adenocarcinoma (AdCa) and squamous cell carcinoma (SCC), compared to normal bronchus (FIGS. 1N and 1O). In this cohort, MFF expression did not correlate with tumor grade (FIG. 1P), nodal status (FIG. 26A) or tumor size (FIG. 26B). MFF was also differentially overexpressed in patient samples of prostatic adenocarcinoma, compared to normal prostate. Similarly, MFF was highly expressed in multiple tumor cell lines, including prostate cancer (FIG. 26C).

Figure 1P:
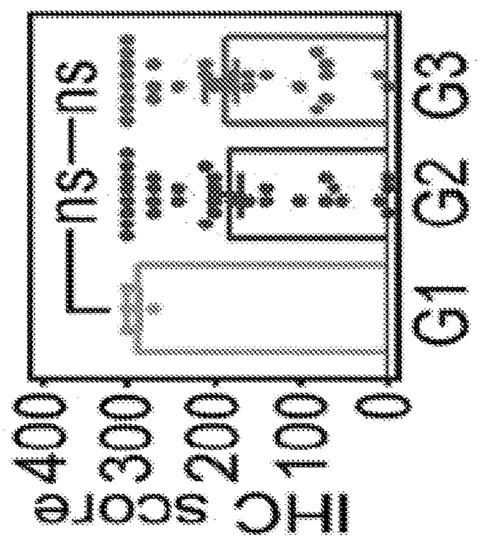

To uncover potential additional function(s) of MFF in cancer, a proteomics screen for MFF-associated proteins was conducted in prostate adenocarcinoma PC3 cells. 42 proteins were identified that associate with MFF (FIG. 6A), including regulators of mitochondrial cell death, such as VDAC1-3, metaxin-1 and -2 (MTX1, MTX2), and hexokinase-I and -II (HK-I, HK-II) (FIG. 6A, FIG. 1P). Other MFF-associated proteins comprised mitochondrial receptors for protein import (TOMM70, TOMM40), protein sorting (SAM50), and cristae remodeling (DNAJC11, APOOL-MIC27, CHCHD3) (FIG. 6A, FIG. 1P). Therefore, VDAC1 was focused on as the most abundant regulator of mitochondrial outer membrane permeability in cancer.

Figure 1Q:
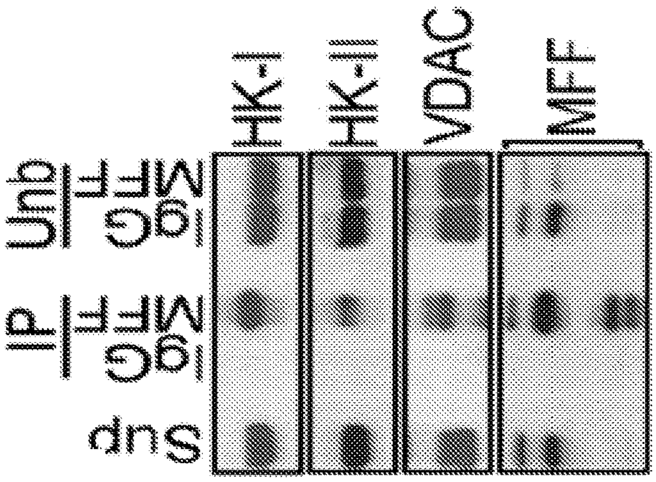
FIG. 1Q shows how PC3 extracts were immunoprecipitated with IgG or an antibody to MFF and endogenous co-associated proteins were identified by Western blotting.
Figure 1R:
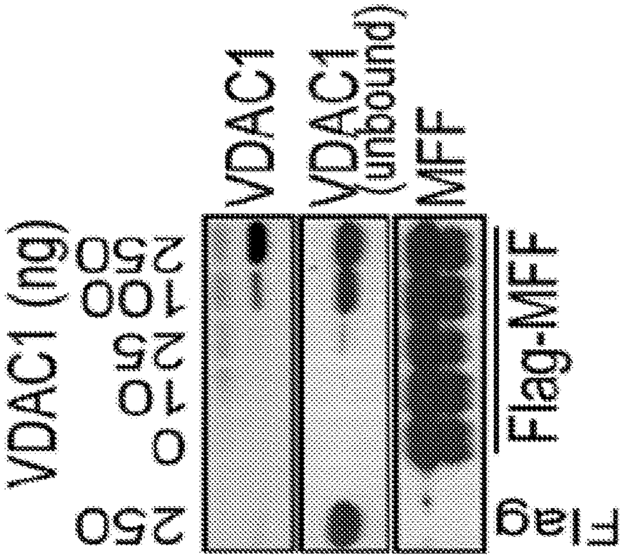
Figure 6C:
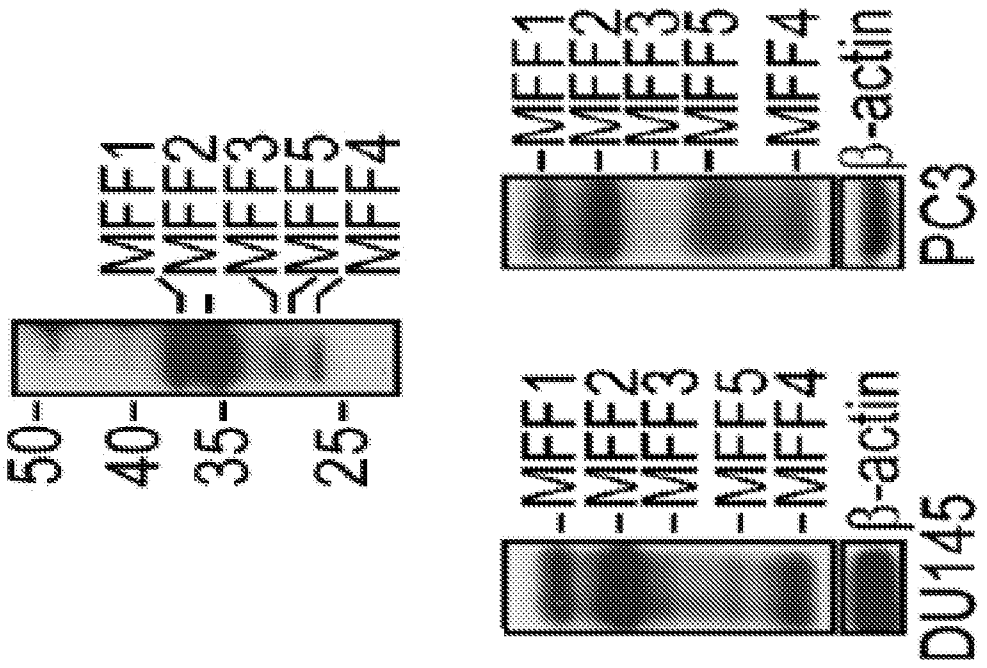
Figure 6B:
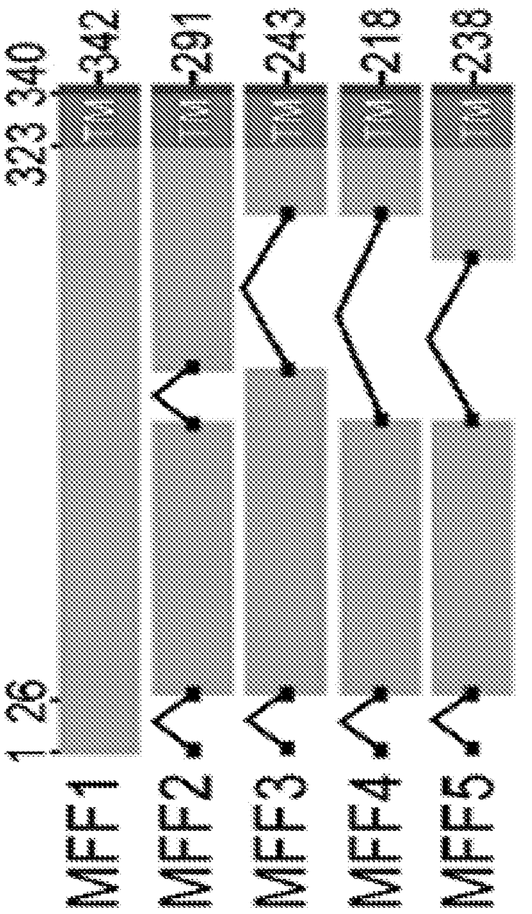
Figure 6D:
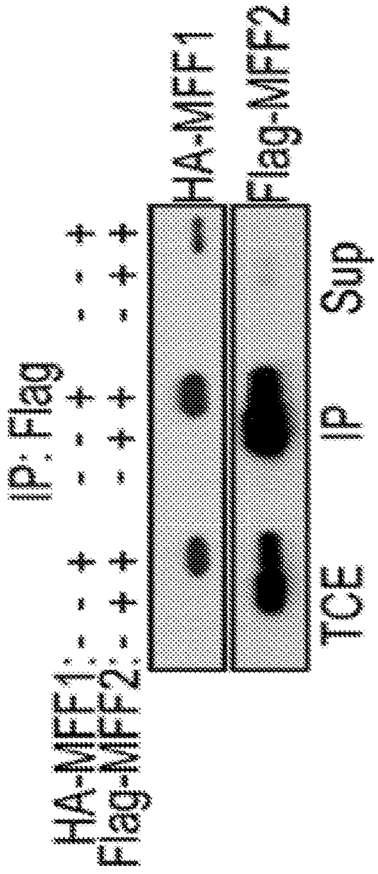
Figure 6E:
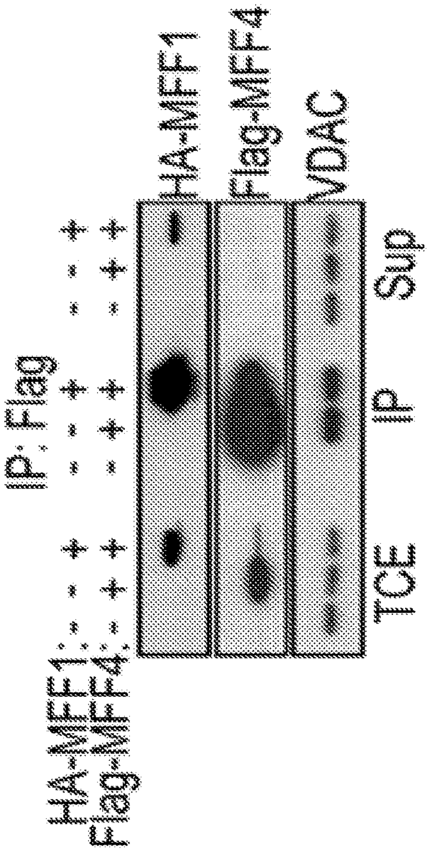
Figure 6F:
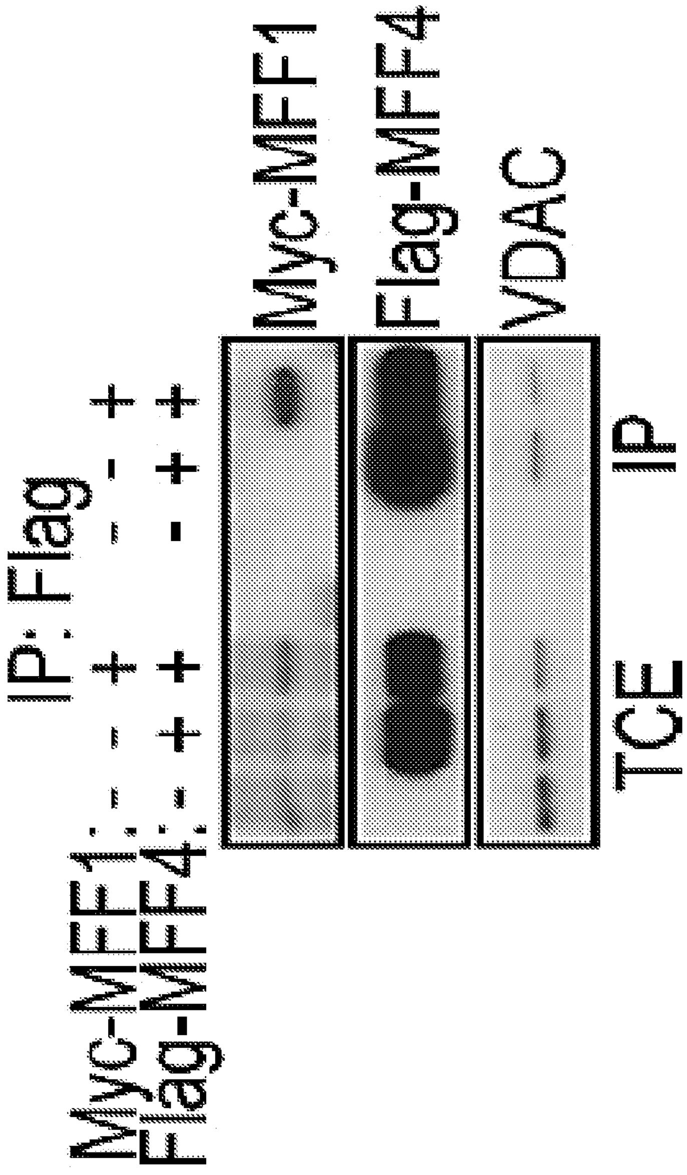

Processing of the human MFF locus is complex and predicted to generate at least five protein isoforms by alternative splicing (FIG. 6B). Of these, MFF1 and MFF2 were the most prominently expressed in PC3 and DU145 prostate cancer cells (FIG. 6C). Consistent with the results of the proteomics screen, Flag-MFF1 or Flag-MFF2 bound VDAC1 in co-immunoprecipitation experiments, in vivo (FIG. 1E). HK-II, which associates with VDAC at the mitochondrial outer membrane and is important for cell survival, was also present in MFF-VDAC1 complexes (FIG. 1E). Similar results were obtained in analysis of endogenous proteins, as endogenous MFF associated with endogenous HK-I, HK-II and VDAC1 in co-immunoprecipitation studies from PC3 cells (FIG. 1Q). To test whether MFF directly interacted with VDAC1, increasing concentrations of recombinant VDAC1 was next mixed with affinity-purified Flag-MFF1. In these experiments, Flag-MFF1 directly bound recombinant VDAC1 in a concentration-dependent manner, whereas uncoupled beads had no effect (FIG. 1R). Next, the role of other MFF isoforms (FIG. 6B) was assessed in the association with VDAC1. In co-immunoprecipitation experiments of differentially tagged recombinant proteins, it was found that MFF isoforms assembled in homodimers, such as MFF1-MFF1 (FIG. 1R), as well as heterodimers, including MFF1-MFF2 (FIG. 1H, FIG. 6D) and MFF1-MFF4 (FIGS. 6E and 6F) in the VDAC1 complex.

Example 2—MFF Regulation of Mitochondrial Functions

To understand the function of MFF in prostate cancer, a proteomics screening for MFF-associated proteins in castration-resistant prostate adenocarcinoma PC3 cells was carried out. 42 proteins that associate with MFF were identified (FIG. 6A), including many PTP components, such as VDAC (all three isoforms) (Mazure, N. M. VDAC in cancer. *Biochim Biophys Acta* 1858, 665-673 (2017)), metaxin-1 and -2 (MTX1, MTX2), and hexokinase-I and -II (HK-I, HK-II) (FIG. 6A, FIG. 1D). Other MFF-associated proteins comprised mitochondrial receptors for protein import (TOMM70, TOMM40), protein sorting (SAM50), and regulators of cristae (DNAJC11, APOOL-MIC27, CHCHD3) (FIG. 6A, FIG. 1D). As the control of mitochondrial permeability transition is critical for tumor cell survival, a potential association between MFF and the PTP was focused on herein. Processing of the human MFF locus is predicted to generate at least five protein isoforms by alternative splicing (FIG. 6B), and of these, MFF1 and MFF2 were the most abundantly represented in PC3 cells (FIG. 6C). Consistent with the results of the proteomics screen, MFF1 and MFF2 readily bound VDAC in co-immunoprecipitation experiments (FIG. 1E). HK-II, which associates with VDAC at the outer mitochondrial membrane (Izzo, V., Bravo-San Pedro, J. M., Sica, V., Kroemer, G. & Galluzzi, L. Mitochondrial Permeability Transition: New Findings and Persisting Uncertainties. *Trends Cell Biol* 26, 655-667 (2016)), was also present in MFF-VDAC complexes (FIG. 1E). The reciprocal relationship between MFF isoforms and VDAC binding was studied next. By co-immunoprecipitation of differentially-tagged proteins, MFF molecules were found to form homodimers, such as MFF1-MFF1 (FIG. 1F), as well as heterodimers, including MFF1-MFF2 (FIG. 1G, FIG. 6D) and MFF1-MFF4 (FIG. 1H, FIG. 6E) in binding to VDAC.

Figure 7B:
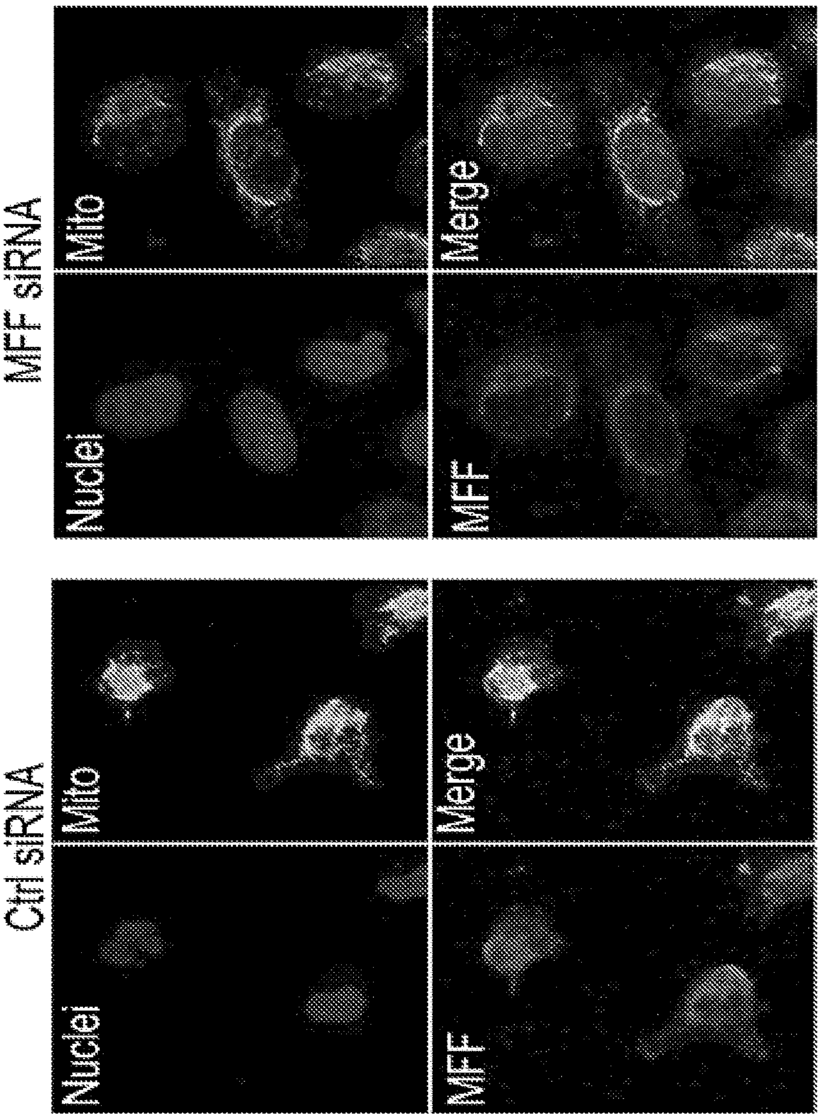
FIGS. 7A-7D illustrate MFF regulation of mitochondrial dynamics.
Figure 7A:
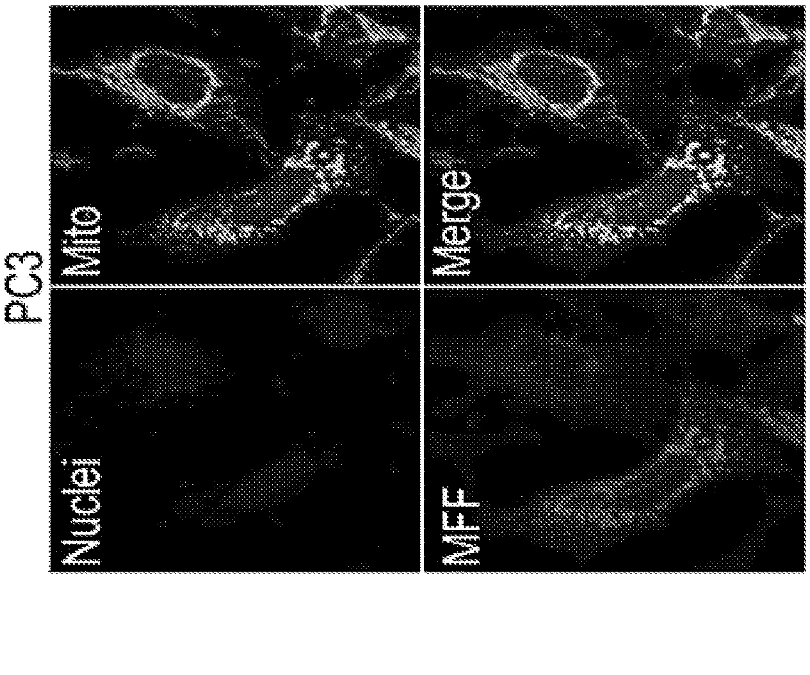
Figure 7D:
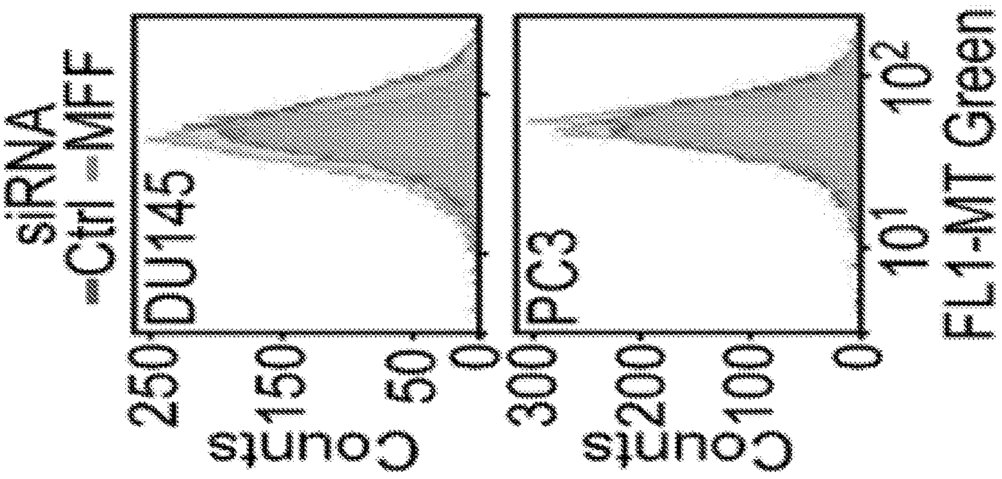
Figure 7C:
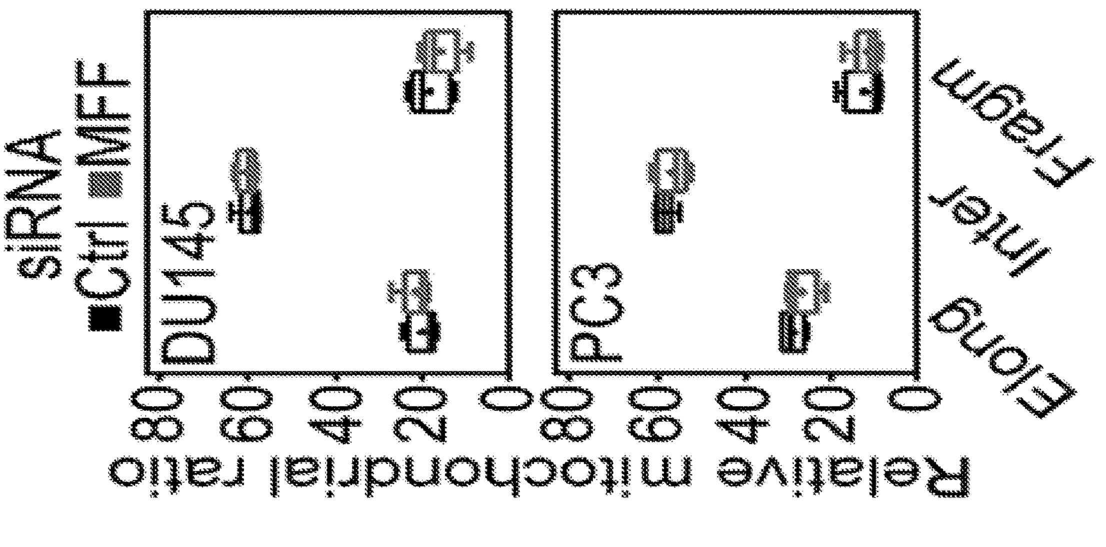

Whether MFF expression in cancer still functioned in mitochondrial dynamics (Otera, H., et al. Mff is an essential factor for mitochondrial recruitment of Drp1 during mitochondrial fission in mammalian cells. *J Cell Biol* 191, 1141-1158 (2010)) was studied next. Expression of MFF in PC3 cells caused extensive mitochondrial fragmentation, i.e. fission, and loss of mitochondrial elongation (FIG. 2A, FIG. 7A), consistent with previous results (Otera, H., et al. Mff is an essential factor for mitochondrial recruitment of Drp1 during mitochondrial fission in mammalian cells. *J Cell Biol* 191, 1141-1158 (2010)). Conversely, knockdown of MFF by small interfering RNA (siRNA) had no effect (FIGS. 7B and 7C), in line with the function of other mitochondrial receptors in Drp1 binding (Osellame, L. D., et al. Cooperative and independent roles of the Drp1 adaptors Mff, MiD49 and MiD51 in mitochondrial fission. *J Cell Sci* 129, 2170-2181 (2016)). Similarly, MFF depletion did not affect mitochondrial mass in PC3 cells (FIG. 7D).

Figures 2A, 2B, 2C, 2D:
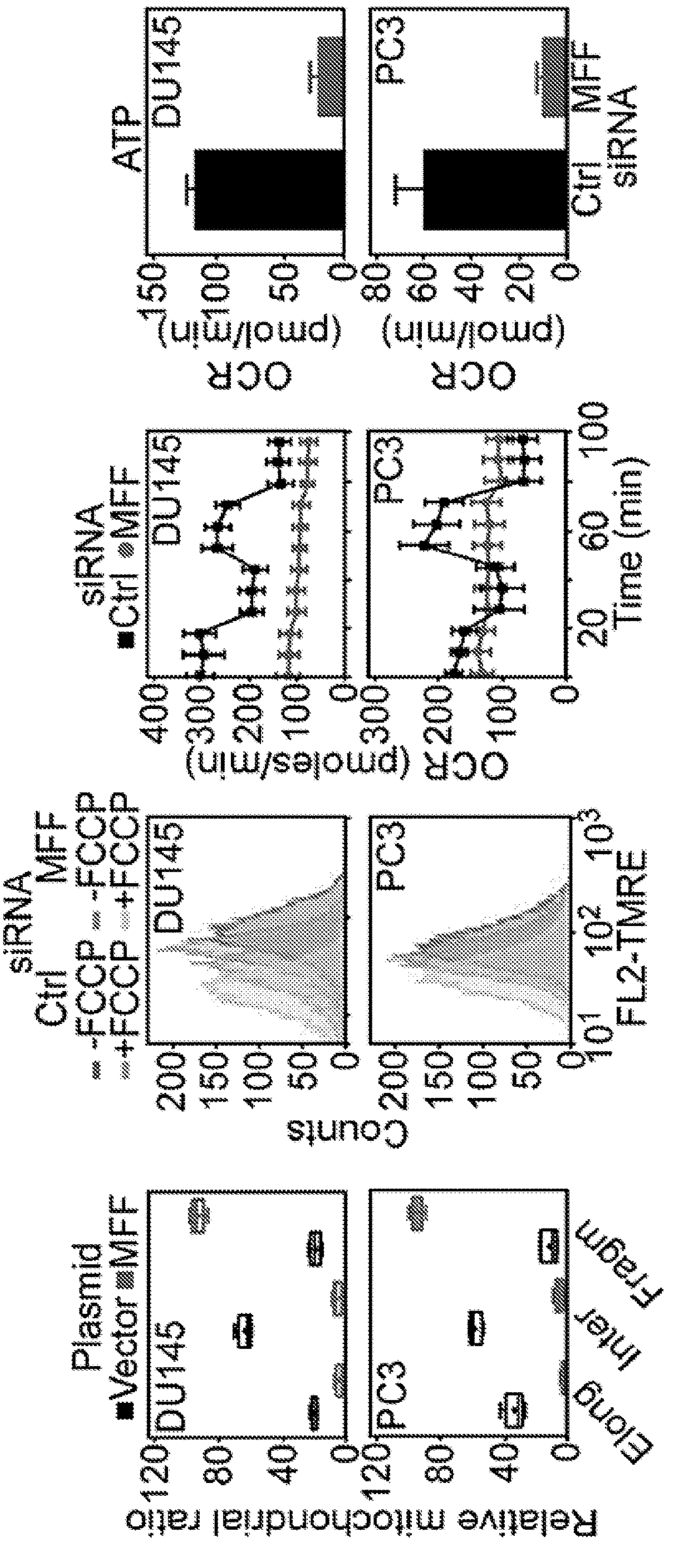
FIGS. 2A-2K illustrate MFF regulation of mitochondrial functions.
Figure 2E:
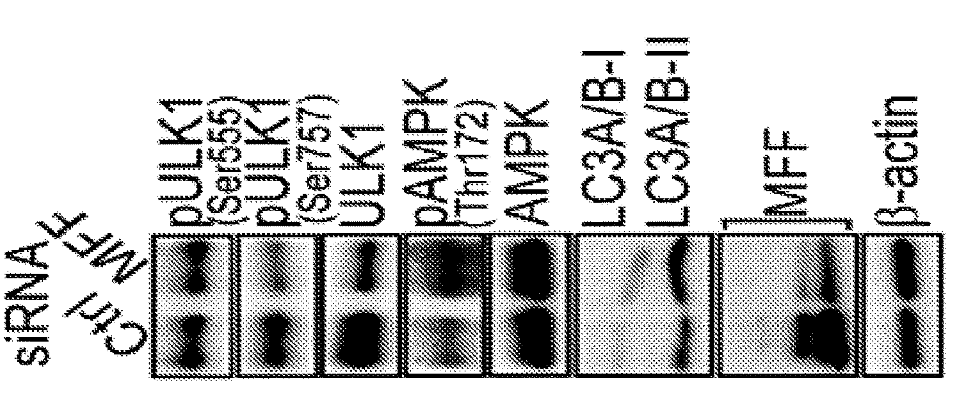
Figure 2F:
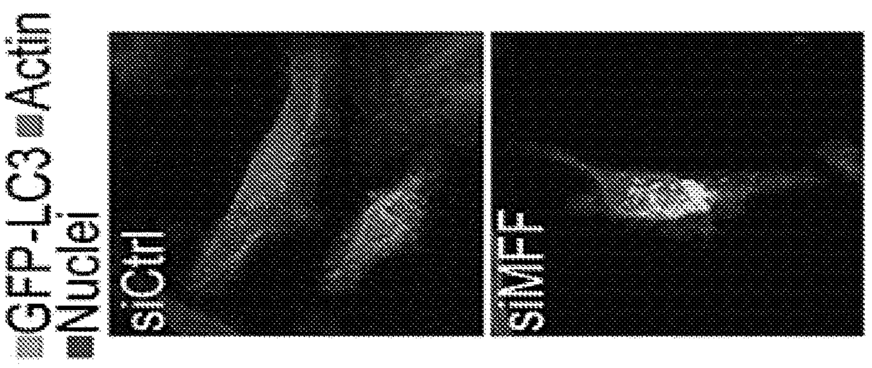
Figure 8A:
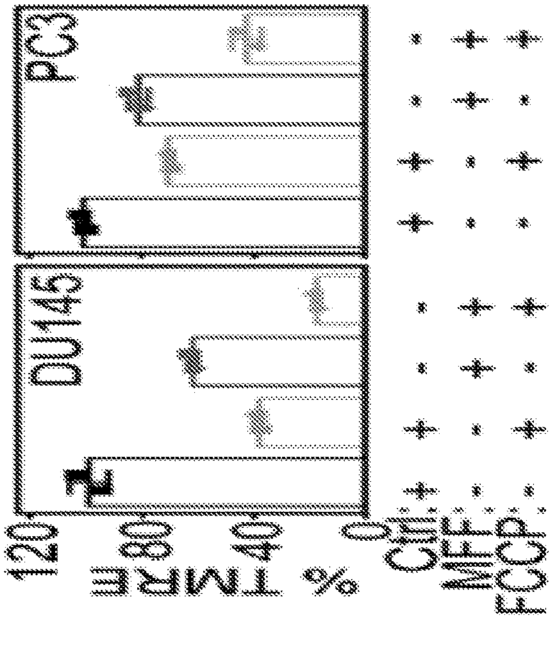
FIGS. 8A-8G illustrate MFF control of mitochondrial bioenergetics.
Figure 8B:
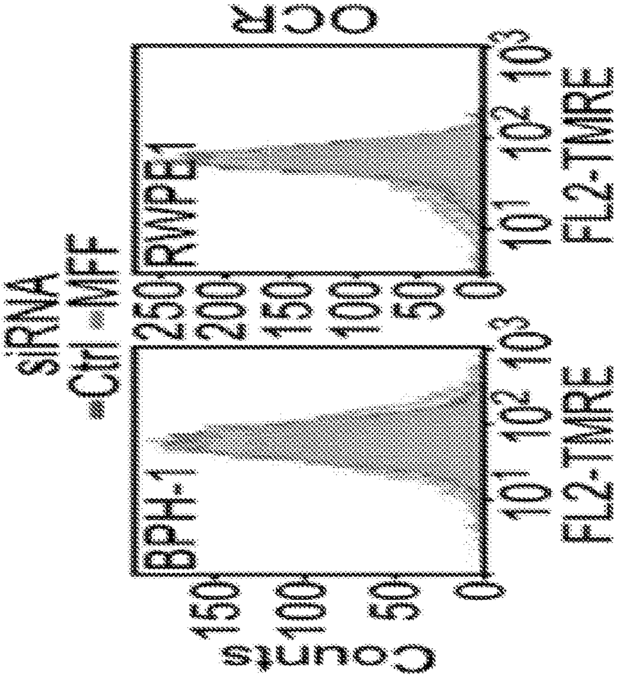
Figure 8C:
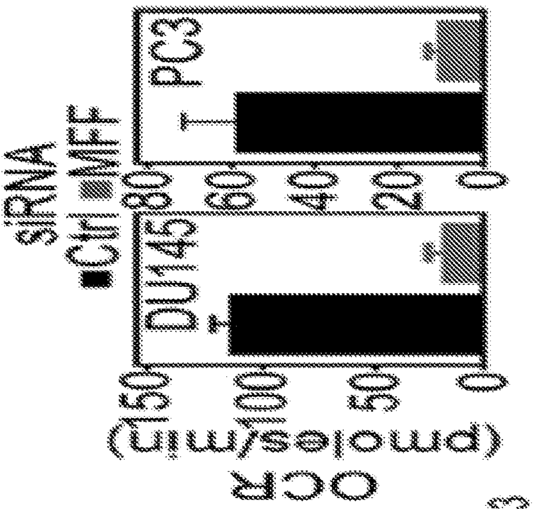
Figure 8G:
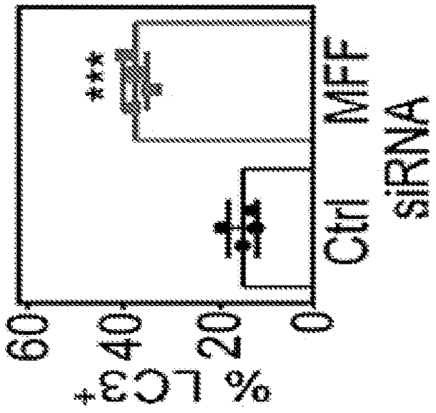
Figure 8F:
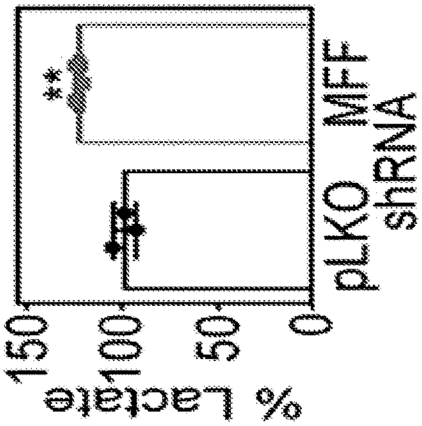
Figure 8E:
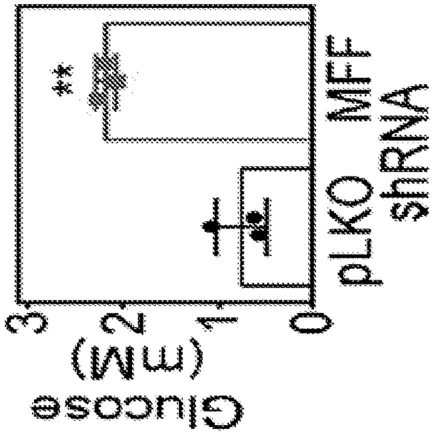
Figure 8D:
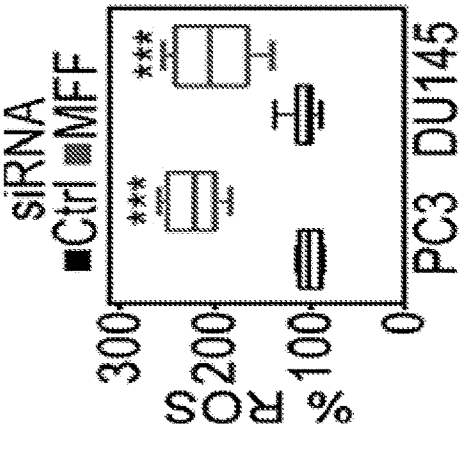

For its novel association with VDAC (Mazure, N. M. VDAC in cancer. *Biochim Biophys Acta* 1858, 665-673 (2017)), whether MFF influenced mitochondrial permeability transition was studied next. MFF knockdown in prostate cancer cells caused sudden dissipation of mitochondrial membrane potential, a hallmark of mitochondrial permeability transition (Izzo, V., Bravo-San Pedro, J. M., Sica, V., Kroemer, G. & Galluzzi, L. Mitochondrial Permeability Transition: New Findings and Persisting Uncertainties. *Trends Cell Biol* 26, 655-667 (2016)), in a reaction augmented by the uncoupler carbonyl cyanide p-trifluoromethoxyphenylhydrazone (FCCP) (FIG. 2B, FIG. 8A). Conversely, siRNA silencing of MFF in normal prostate epithelial BPH-1 or RWPE1 cells had no effect (FIG. 8B). Loss of mitochondrial inner membrane potential uncouples the organelle respiratory chain and, accordingly, MFF-depleted cells exhibited extensive bioenergetics defects. This included lower oxygen consumption rates (OCR, FIG. 2C, FIG. 8C), a marker of oxidative phosphorylation, decreased ATP production (FIG. 2D), and heightened generation of ROS (FIG. 8D). Despite an increase in glucose consumption (FIG. 8E) and lactate generation (FIG. 8F), MFF-targeted cells remained nutrient-starved. This was evidenced by increased phosphorylation ($Thr^{172}$) of the energy sensor, AMPK (FIG. 2E) and activation of autophagy, characterized by LC3 lipidation (FIG. 2E), differential phosphorylation of the autophagy activator, ULK1 on the AMPK ($Ser^{555}$) versus mTOR ($Ser^{757}$) site (FIG. 2E) and punctate LC3 fluorescence staining (FIG. 2F and FIG. 8G).

Figure 2G:
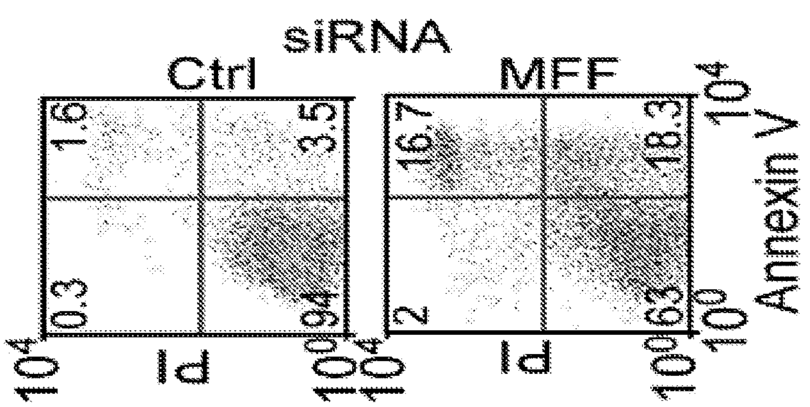
Figure 2H:
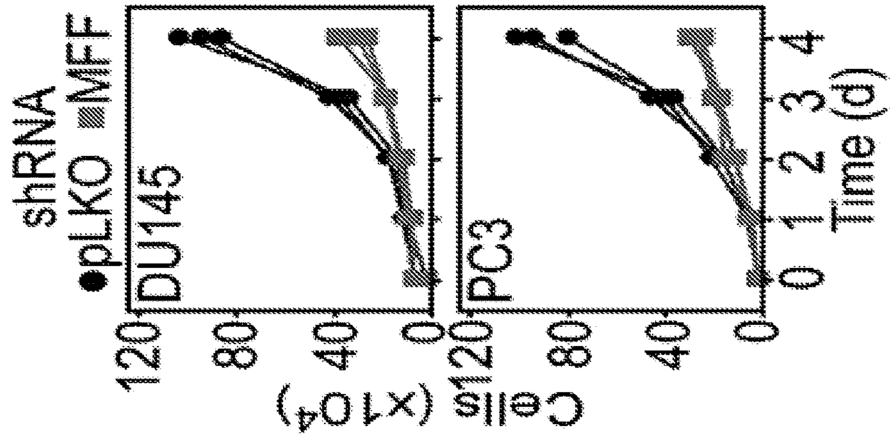
Figure 2I:
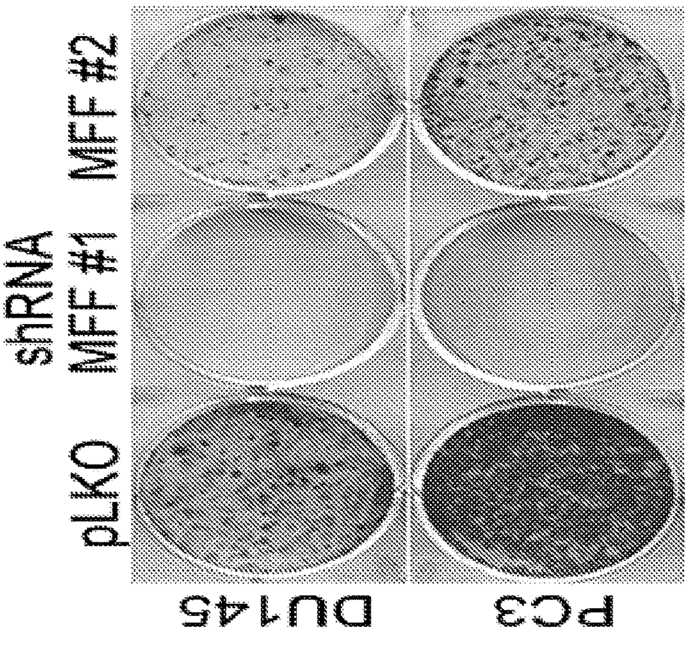
Figure 2J:
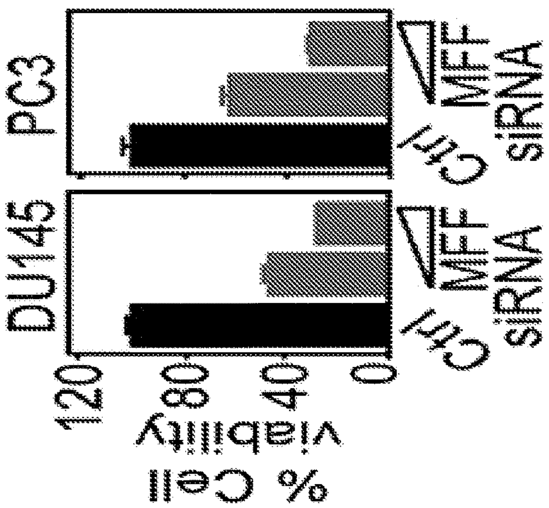
Figure 2K:
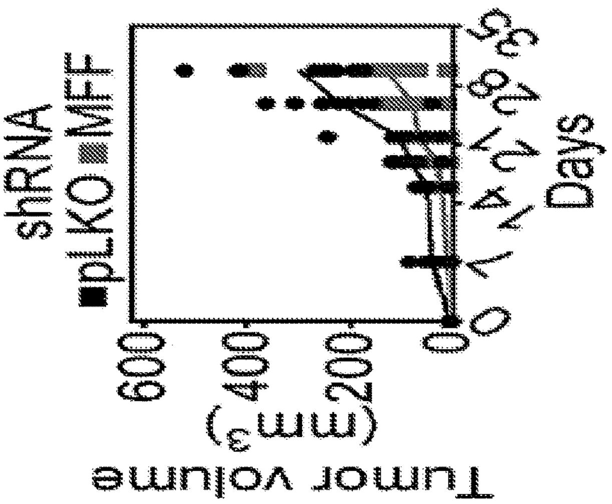
Figure 9C:
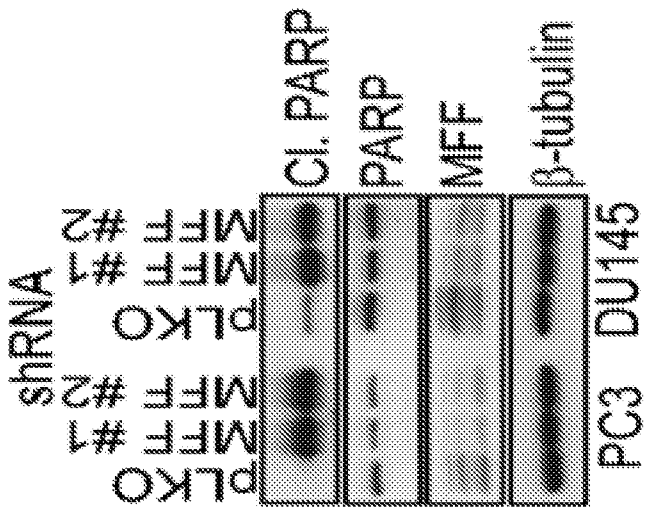
FIGS. 9A-9G illustrate MFF regulation of tumor cell death.
Figure 9B:
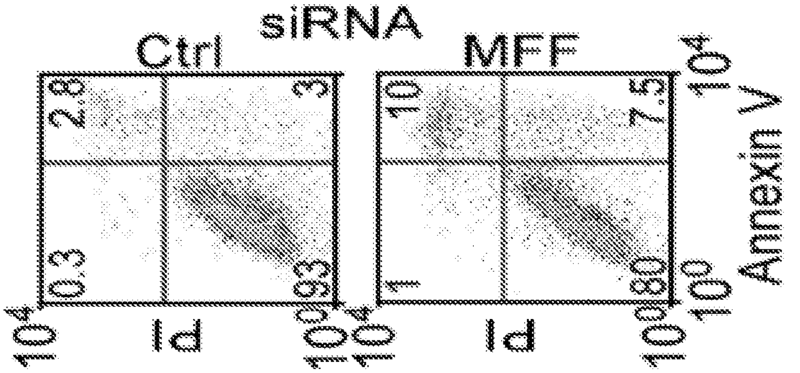
Figure 9A:
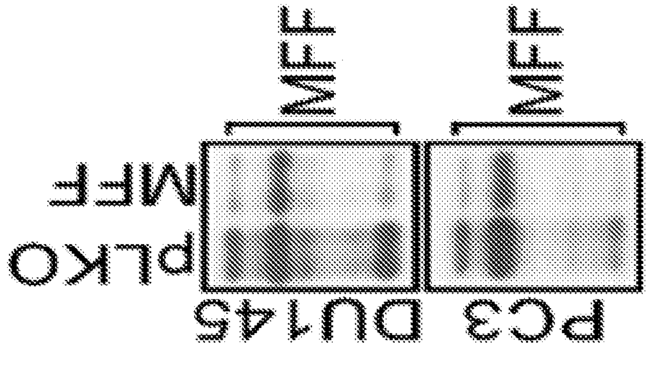
Figure 9E:
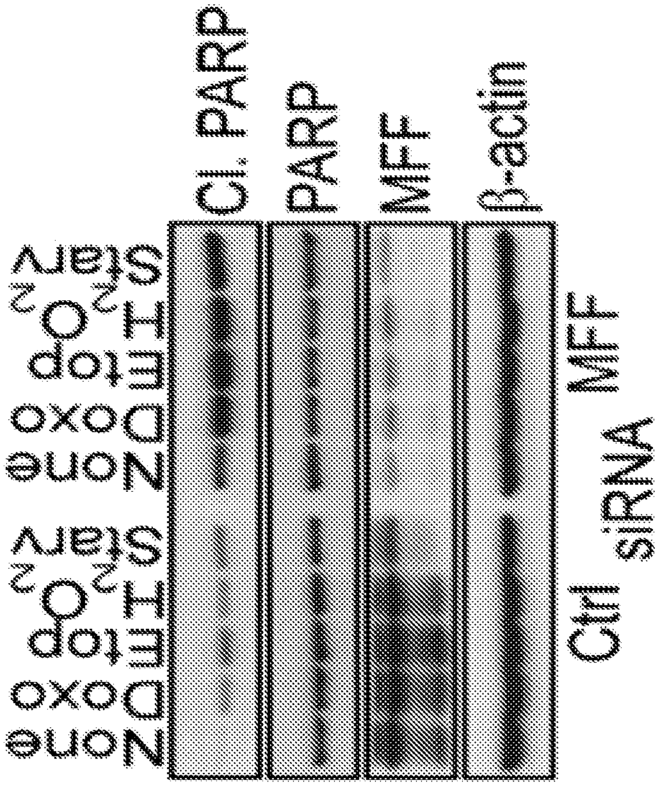
Figure 9D:
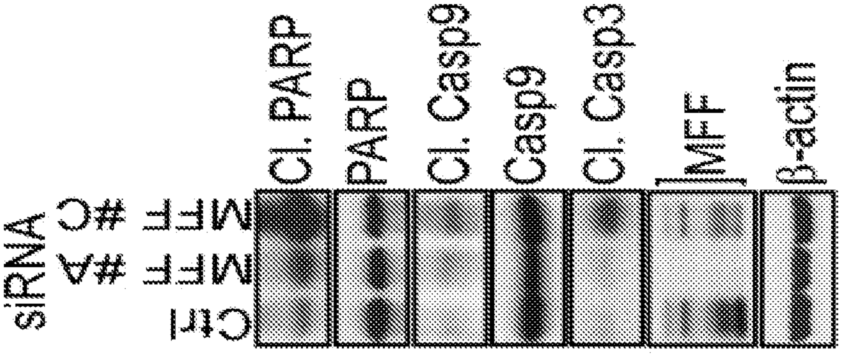
Figure 9G:
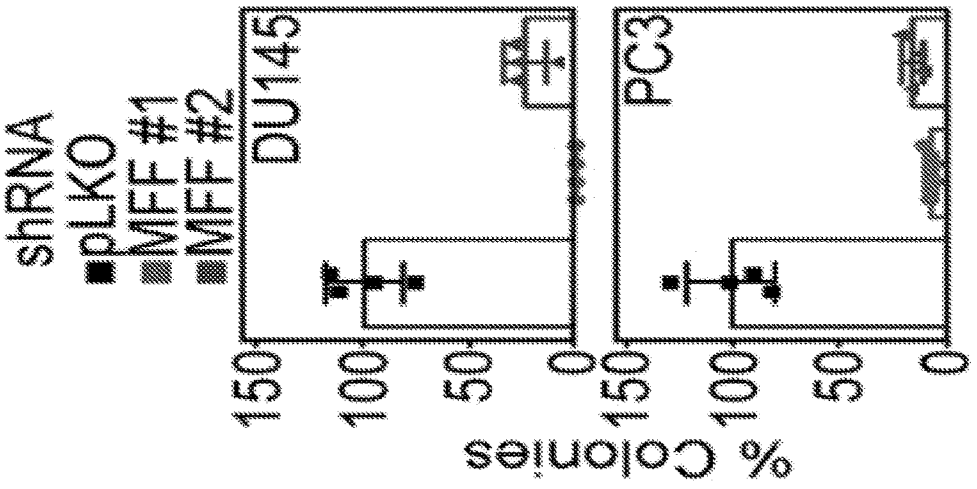
Figure 9F:
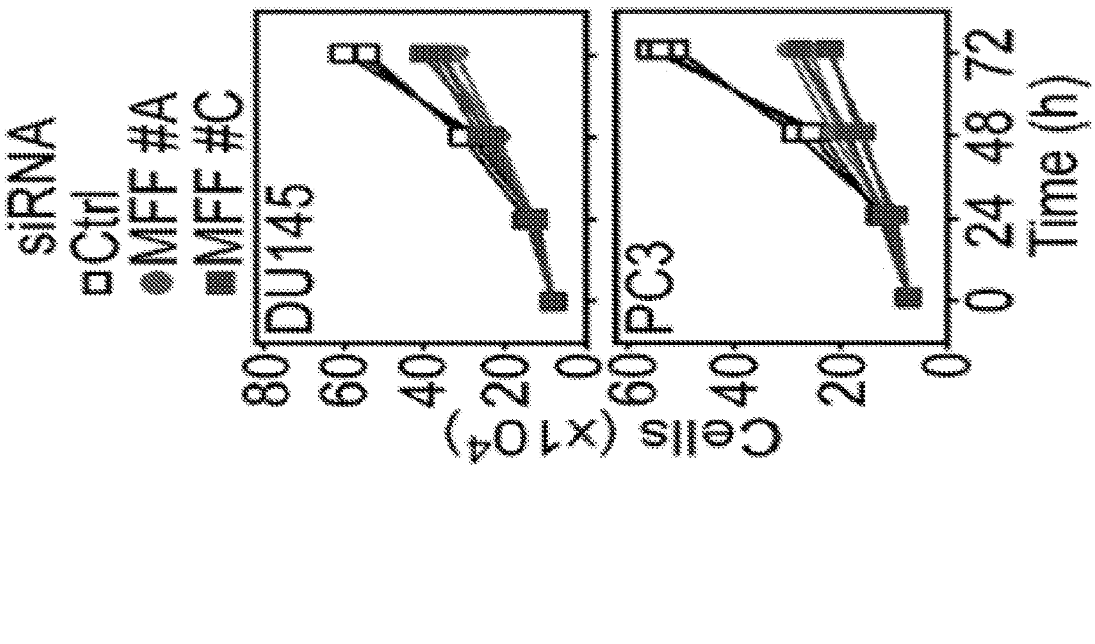

Aberrantly increased mitochondrial permeability precedes many forms of cell death (Izzo, V., Bravo-San Pedro, J. M., Sica, V., Kroemer, G. & Galluzzi, L. Mitochondrial Permeability Transition: New Findings and Persisting Uncertainties. *Trends Cell Biol* 26, 655-667 (2016)). Accordingly, MFF depletion by shRNA (FIG. 9A) or siRNA (FIG. 7B) induced hallmarks of apoptosis (Fuchs, Y. & Steller, H. Live to die another way: modes of programmed cell death and the signals emanating from dying cells. *Nat Rev Mol Cell Biol* 16, 329-344 (2015)) in tumor cells, with increased Annexin V labeling (FIG. 2G, FIG. 9B), proteolytic processing of PARP (FIGS. 9C and 9D) and generation of active caspase-9 and -3 (FIG. 9D). When combined with other stress stimuli, such as nutrient deprivation, oxidative stress or chemotherapeutic drugs, MFF knockdown potentiated PARP cleavage in prostate cancer cells (FIG. 9E). Because of mitochondrial damage, bioenergetics defects, and induction of apoptosis, MFF depletion suppressed prostate cancer proliferation (FIG. 2H, FIG. 9F), inhibited colony formation (FIG. 2I, FIG. 9G), and decreased tumor cell viability (FIG. 2J). Accordingly, PC3 cells silenced for MFF lost tumorigenic potential in vivo, and were unable to form xenograft tumors in engrafted immunocompromised mice, compared to pLKO transfectants (FIG. 2K).

Example 3—Peptidyl Mimicry of the MFF-VDAC Complex

Figure 3B:
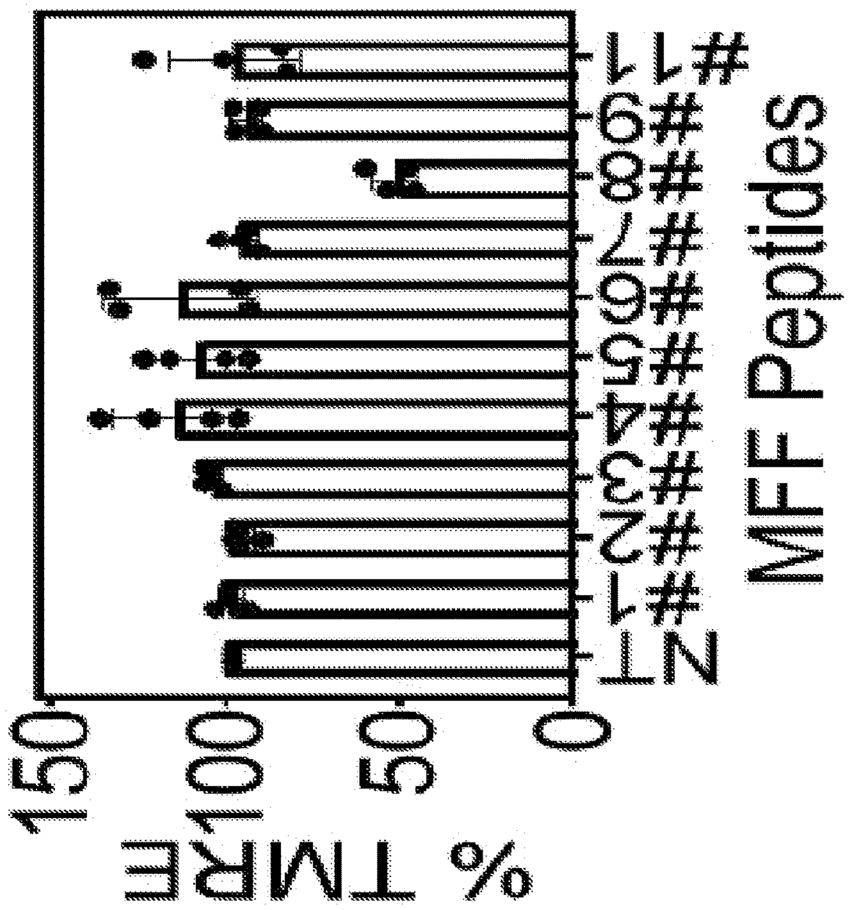
FIGS. 3A-3H illustrate peptidyl mimicry of the MFF-VDAC complex.
Figure 3A:
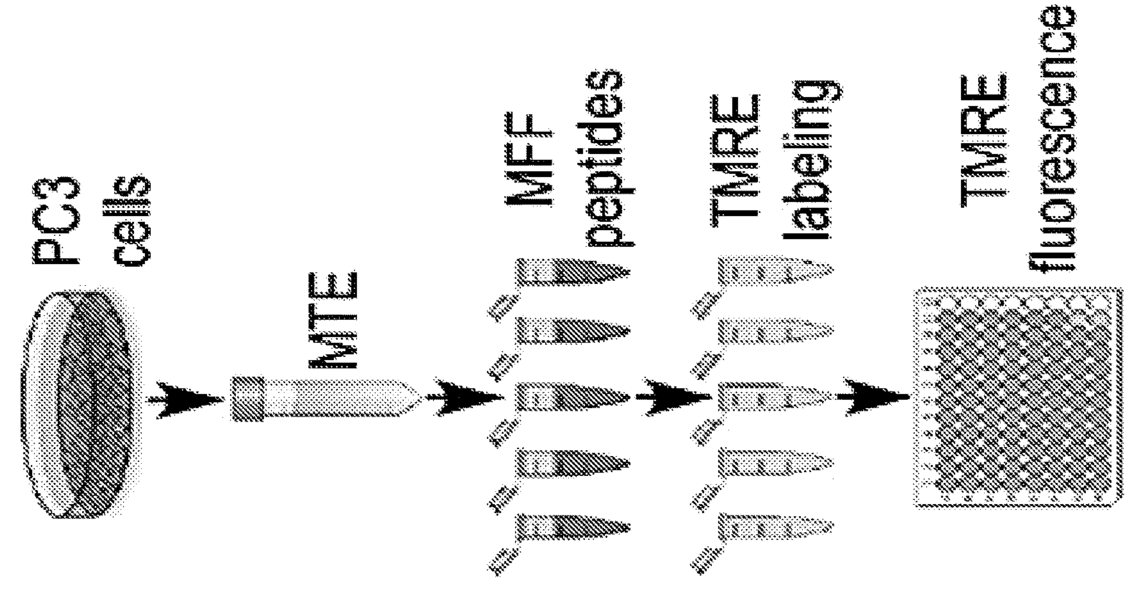

Together, these data suggest that MFF is a novel PTP regulator (Vyas, S., Zaganj or, E. & Haigis, M. C. Mitochondria and Cancer. *Cell* 166, 555-566 (2016)), and an important survival factor in cancer. To better understand this pathway, a library of partially overlapping synthetic peptides duplicating the entire MFF1 sequence (SEQ ID NOs: 1-10 and 23) was screened in a high-throughput assay for depolarization of isolated tumor (PC3) mitochondria (FIG. 3A). MFF peptide #8 corresponding to the sequence $Asp^{217}$-$Leu^{246}$ (SEQ ID NO: 8) depolarized tumor mitochondria, whereas none of the other MFF sequences was effective (FIG. 3B). Also, MFF peptide #8 did not depolarize mitochondria of normal BPH-1 cells (FIG. 10A), reinforcing the selectivity of the MFF-VDAC pathway in cancer. Among all MFF isoforms, only MFF1 and MFF2 contained the peptide

#8 sequence (FIG. 10B), consistent with the selective ability of these isoforms to bind VDAC, in vivo (FIGS. 1E and 1Q) and in vitro (FIG. 1R).

Figure 3C:
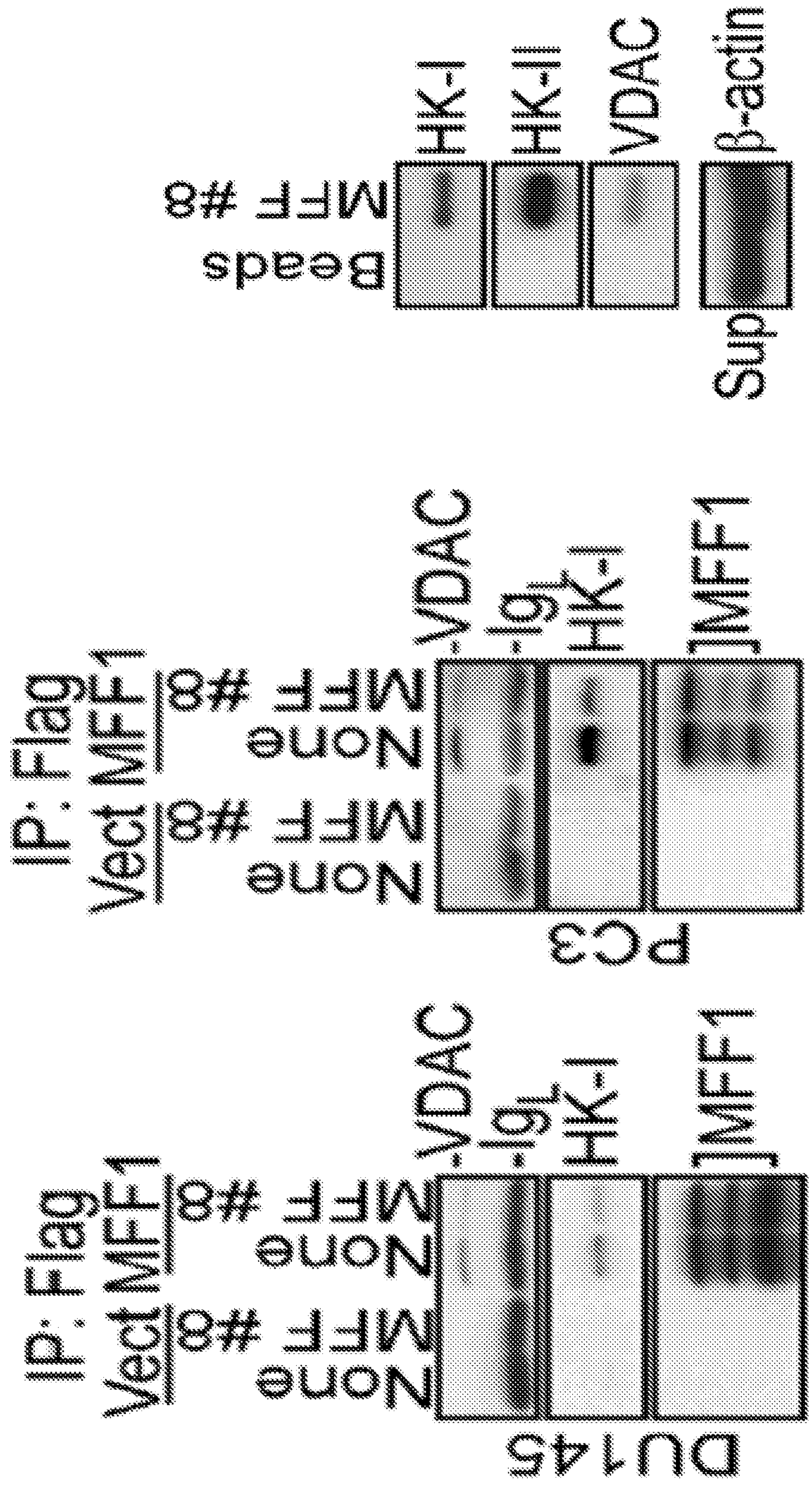
Figure 10B:
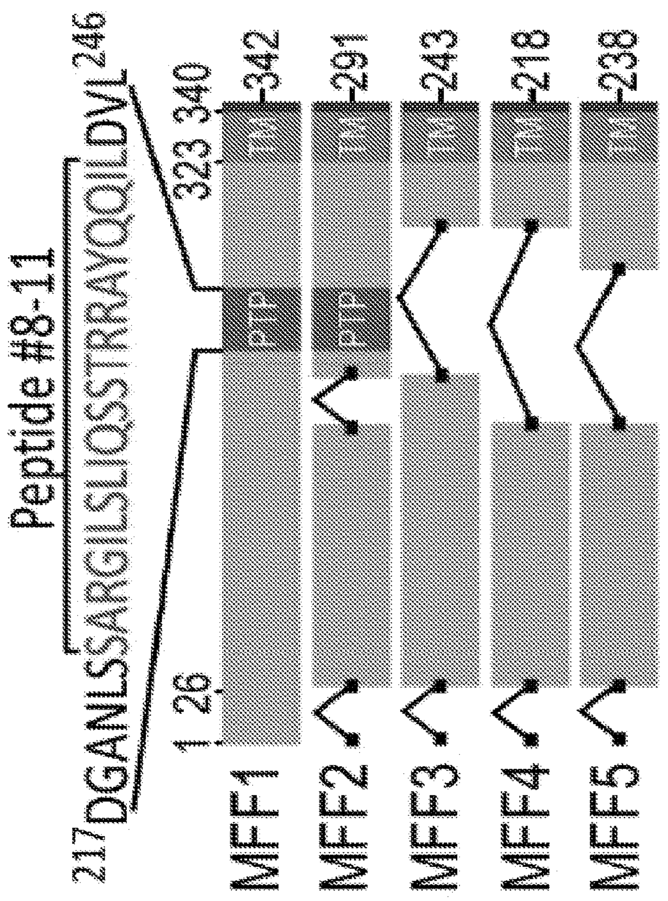
Figure 10A:
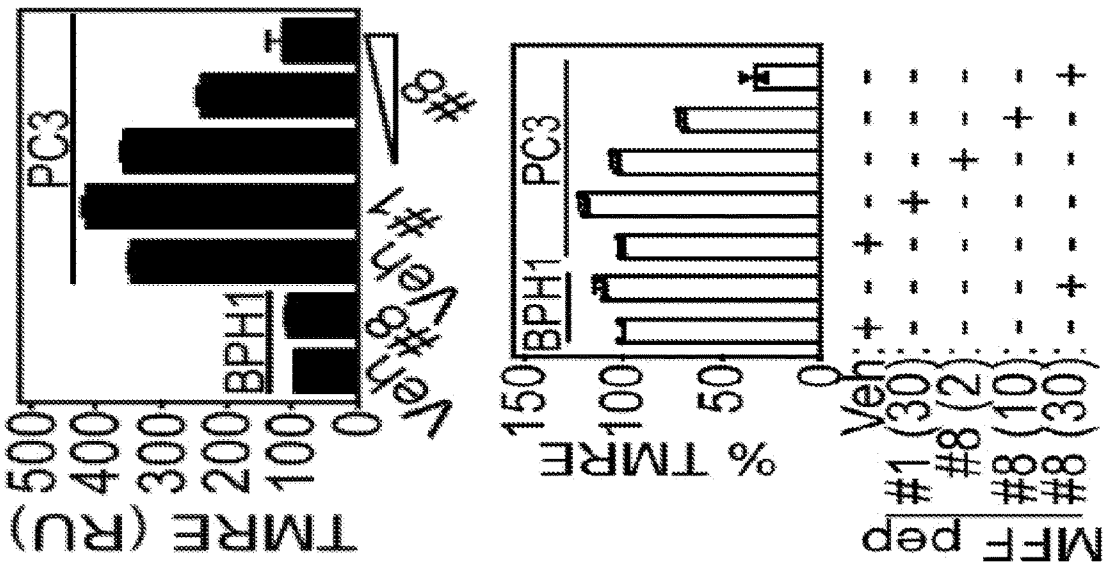

When added to isolated cell extracts, MFF peptide #8 was a competitive antagonist of the MFF-PTP complex, disrupting the interaction between MFF and VDAC or HK-I (FIG. 3C). To further narrow the MFF-PTP binding interface, variants of peptide #8 containing amino- or carboxy-terminus deletions were synthesized (FIG. 10C). In the high-throughput assay of mitochondrial permeability transition (FIG. 3A), it was found that peptide #8 variants #1, #2 and #6 (FIG. 10C) depolarized isolated tumor mitochondria, whereas none of the other sequences was effective (FIG. 10D). Based on these results, a new MFF peptide #8-11 was synthesized, containing the sequence $Ser^{223}$-$Leu^{243}$, which comprises a minimal binding site for VDAC (FIG. 10B).

Figure 3D:
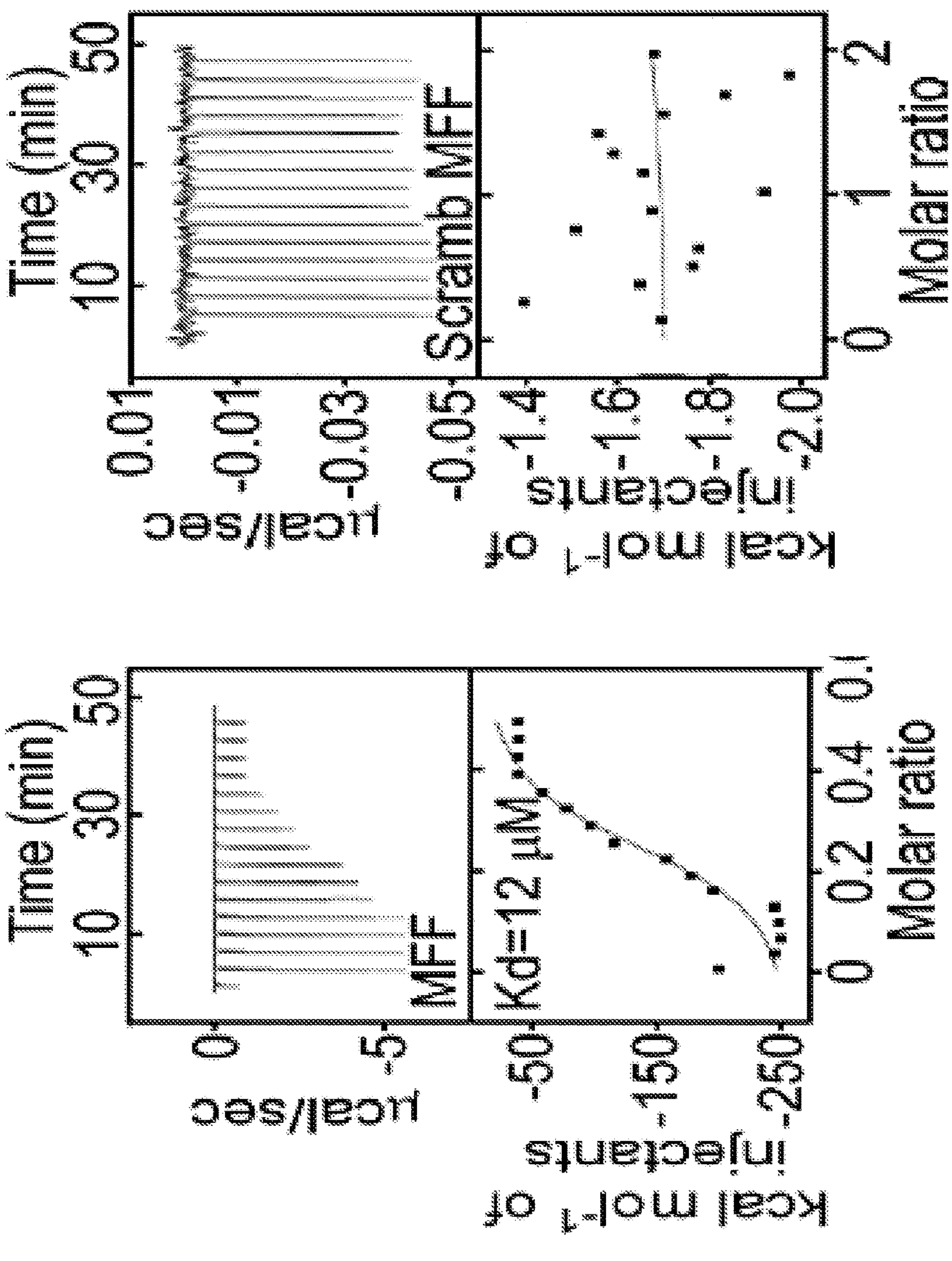
Figure 3E:
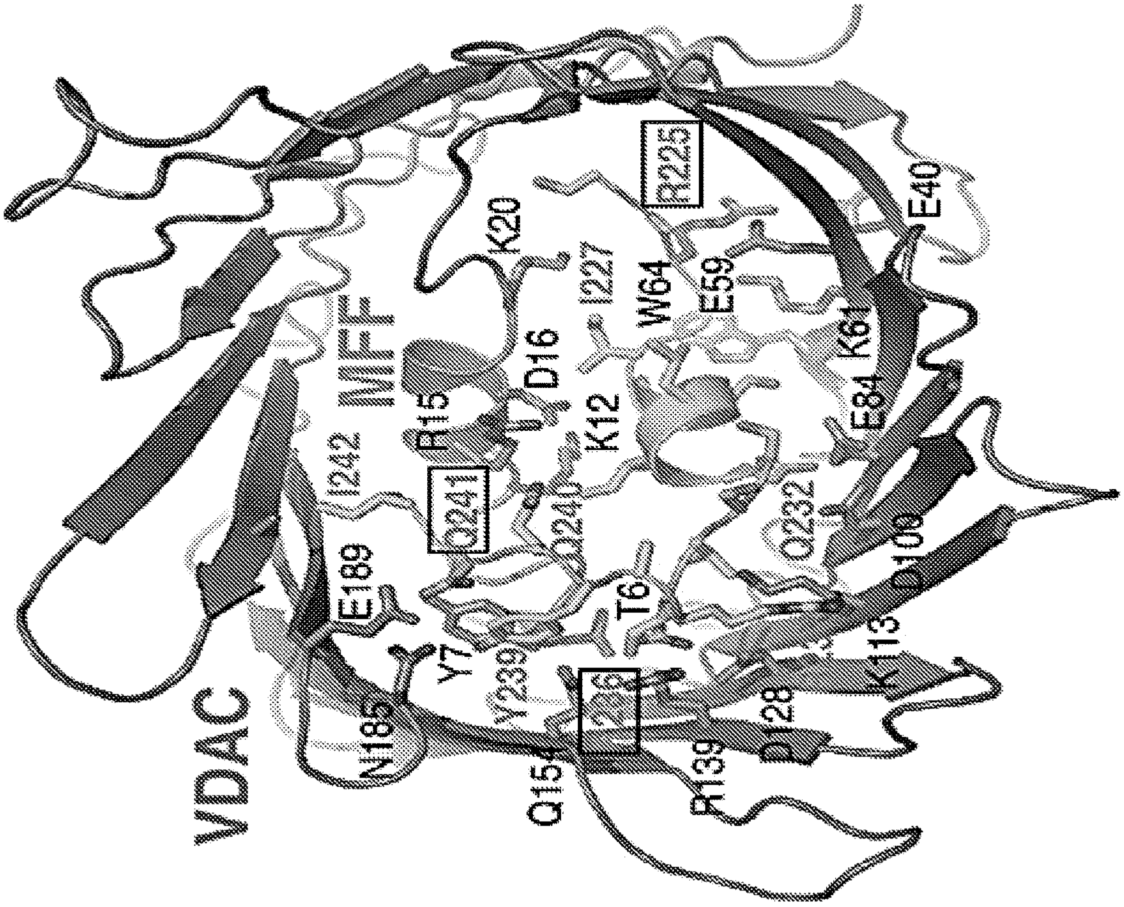
Figure 3F:
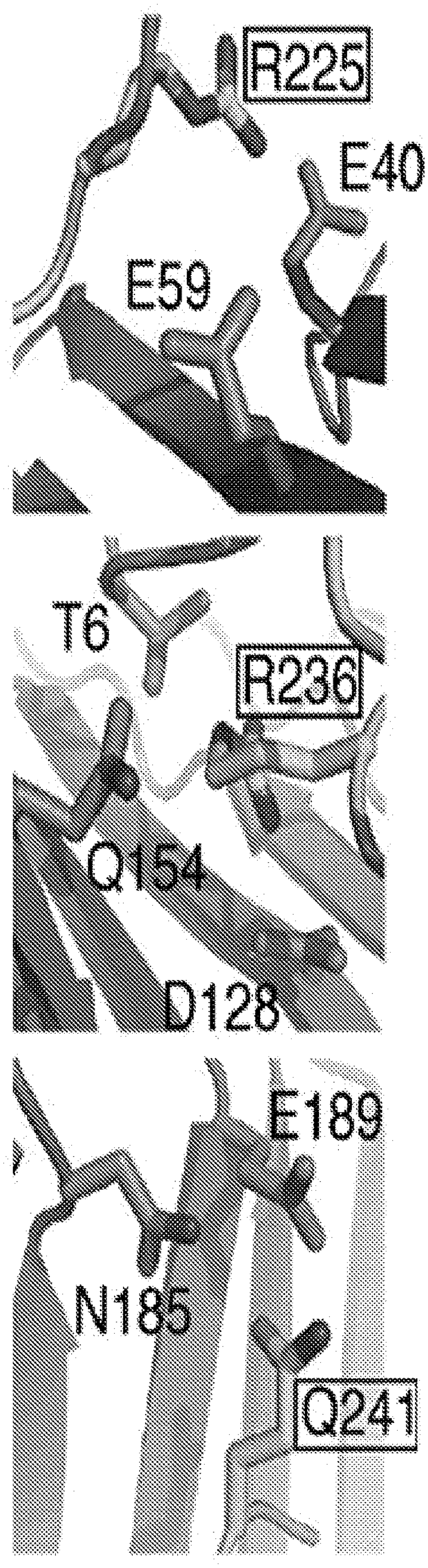
Figure 3G:
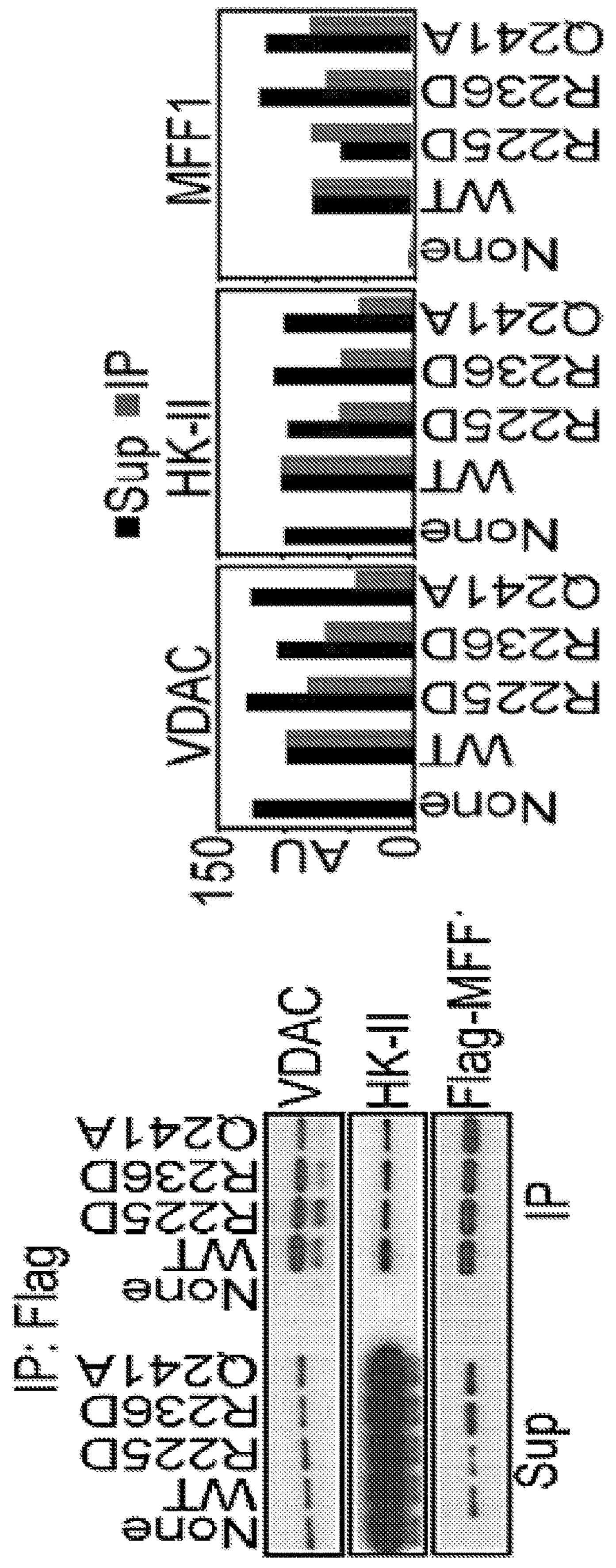
Figure 3H:
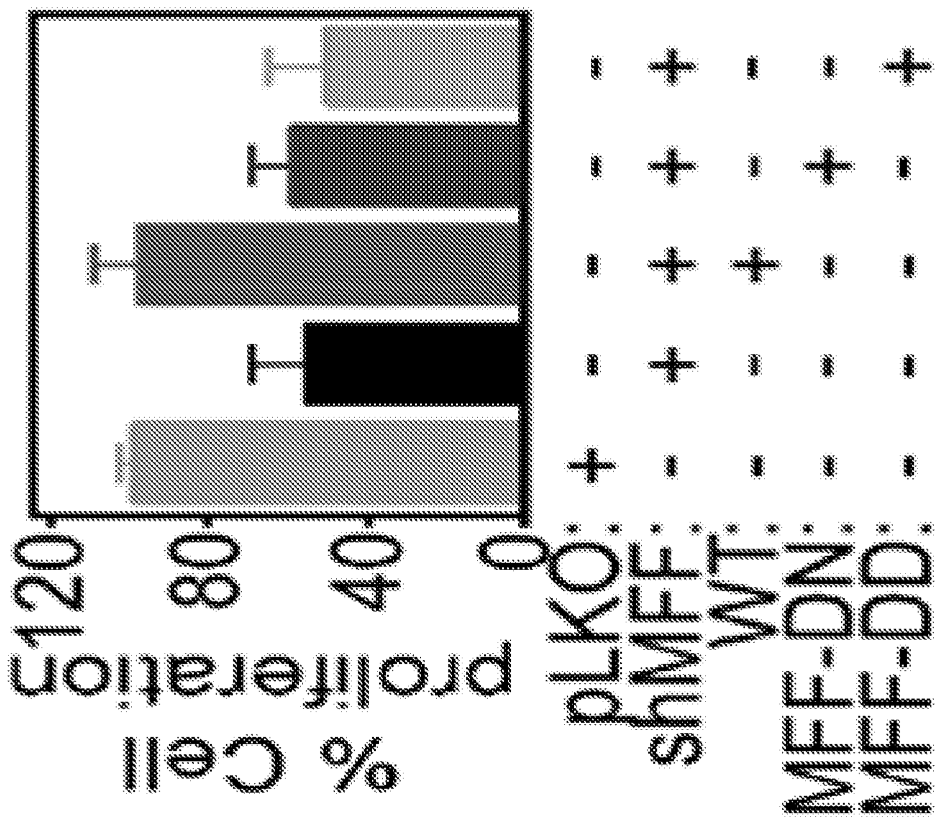
Figure 10E:
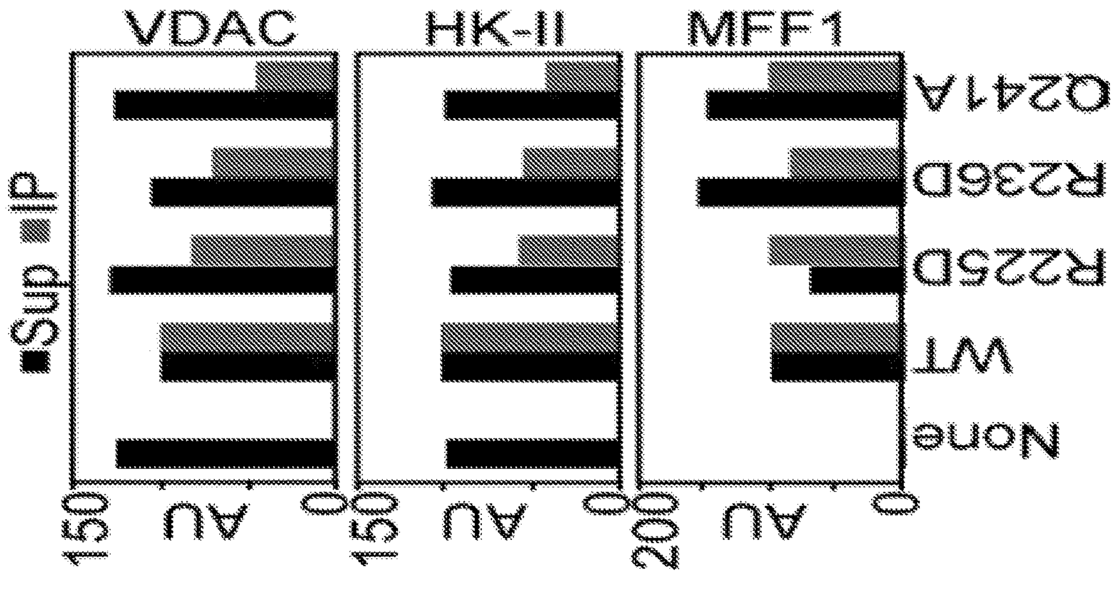
Figure 10F:
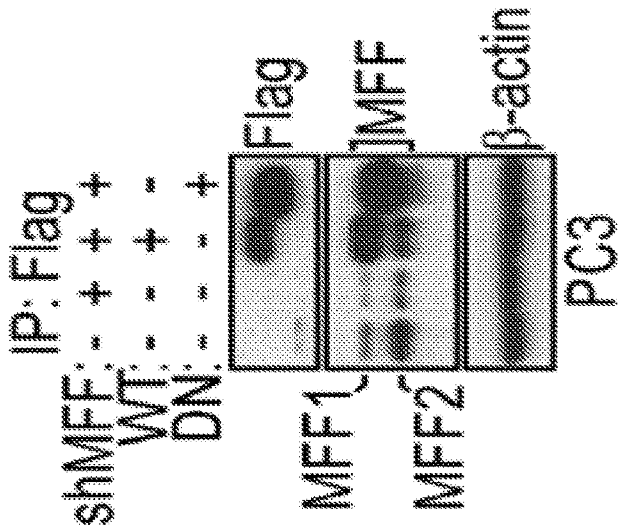
Figure 10G:
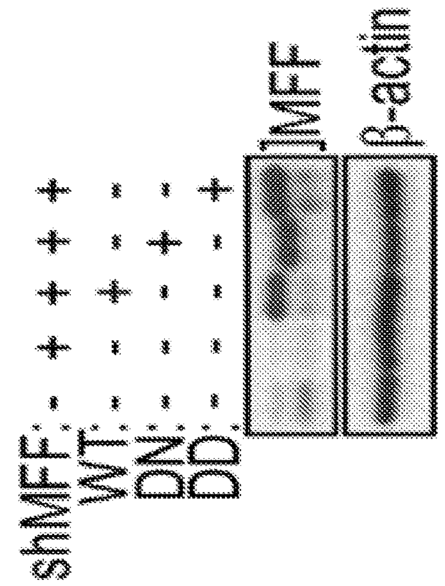

By isothermal titration calorimetry (ITC), the MFF peptide #8-11 bound human recombinant VDAC with a Kd of ~12 μM (FIG. 3D). A scrambled sequence was ineffective (FIG. 3D). Molecular modeling studies carried out with the CABS dock server (Blaszczyk, M., et al. Modeling of protein-peptide interactions using the CABS-dock web server for binding site search and flexible docking. Methods 93, 72-83 (2016); Kurcinski, M., Jamroz, M., Blaszczyk, M., Kolinski, A. & Kmiecik, S. CABS-dock web server for the flexible docking of peptides to proteins without prior knowledge of the binding site. *Nucleic Acids Res* 43, W419-424 (2015)) placed the MFF $Ser^{223}$-$Leu^{243}$ sequence in the interior hole of the VDAC ring (FIG. 3E), with an average RMSD of 4.1, cluster density of 36 and number of contact elements of 148 (FIG. 3E). In this model, three MFF residues appear to play a key role in the MFF-VDAC complex (FIG. 3F). MFF residue R225 is predicted to contact E40 and E59, R236 contacts the side chains of T6, Q154 and D128 and Q241 is within coordinating distance of N185 and E189 of VDAC (FIG. 3F). To test these predictions, MFF1 mutants were generated containing single amino acid substitutions, R225D, R236D or Q241A. Compared to wild type (WT) MFF1, each of the three MFF1 mutants showed reduced binding to VDAC and HK-II, by co-immunoprecipitation (FIG. 3G, FIG. 10E). As an independent approach, MFF-silenced PC3 cells were reconstituted using various non-siRNA inhibitable MFF constructs. Re-expression of WT MFF1 in knockdown cells restored cell proliferation, comparably to control cultures (FIG. 3H). Instead, expression of MFF1 deleted in the entire VDAC binding domain (DN) (FIG. 10F) or MFF1 containing the double mutation, R225D/R236D (DD) (FIG. 10G) did not rescue cell proliferation (FIG. 3H).

Next, to further narrow the MFF-VDAC1 binding interface, variants of peptide #8 were synthesized (SEQ ID NO: 11-20) with amino- or carboxy-terminus deletions (FIG. 10C). Using a high-throughput assay of mitochondrial depolarization (FIG. 3A), it was found that variants #1, #2 and #6 of peptide #8 (FIG. 10C) depolarized isolated tumor mitochondria (FIG. 10D). None of the other MFF peptide #8-derived sequences was effective (FIG. 10D). Therefore, a new MFF peptide #8-11 containing the sequence Ser223-Leu243, corresponding to a minimal binding site for VDAC1 was synthesized (FIG. 10B).

Example 4—Targeting of the MFF-VDAC Complex

Figure 4A:
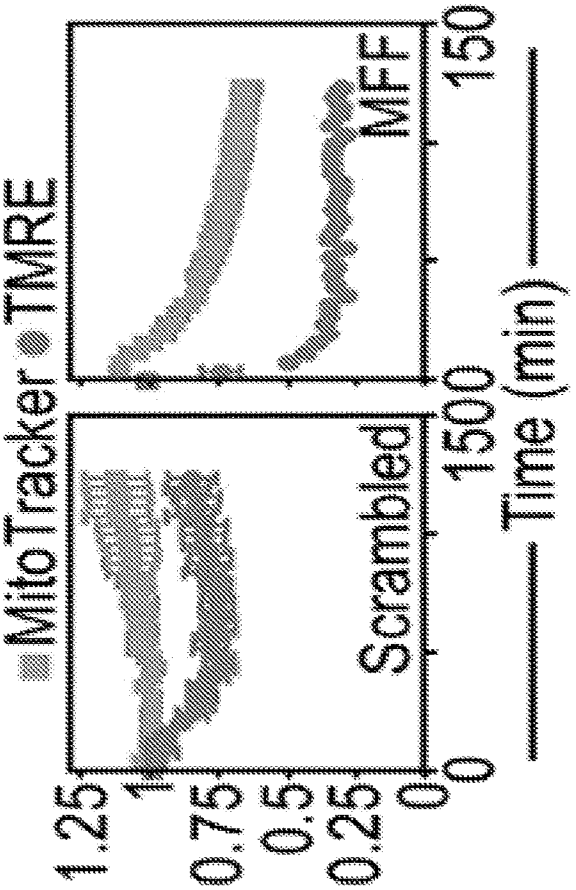
FIGS. 4A-4J illustrate preclinical targeting of the MFF-VDAC complex.
Figure 4B:
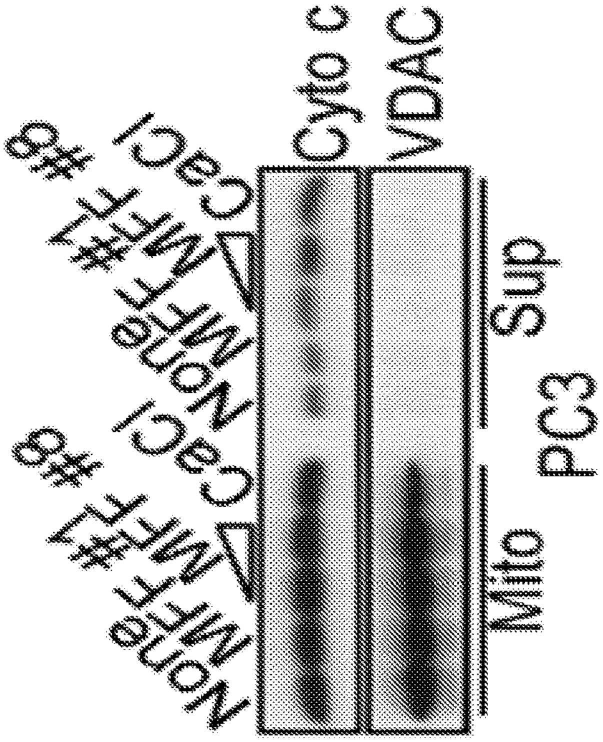
Figure 4D:
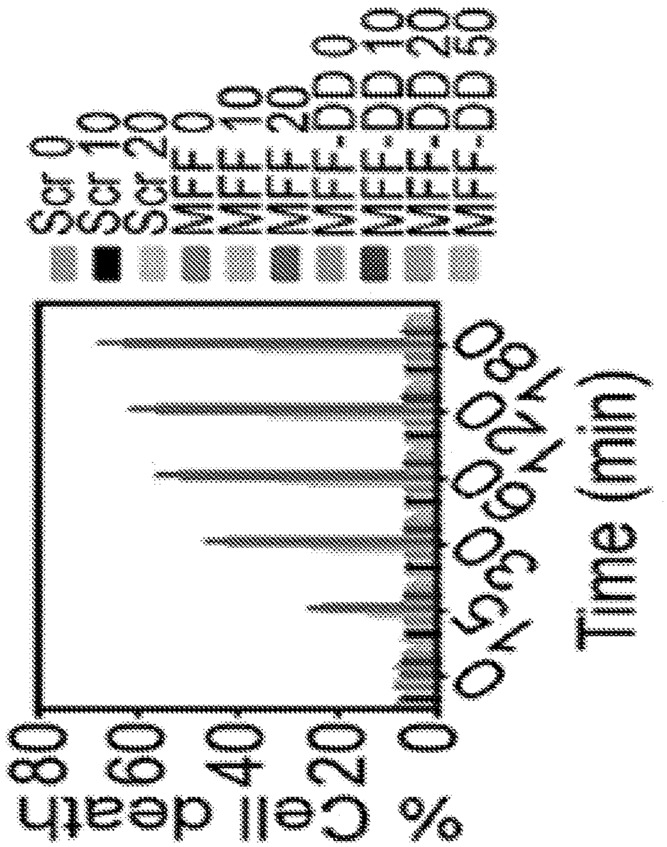
Figure 4C:
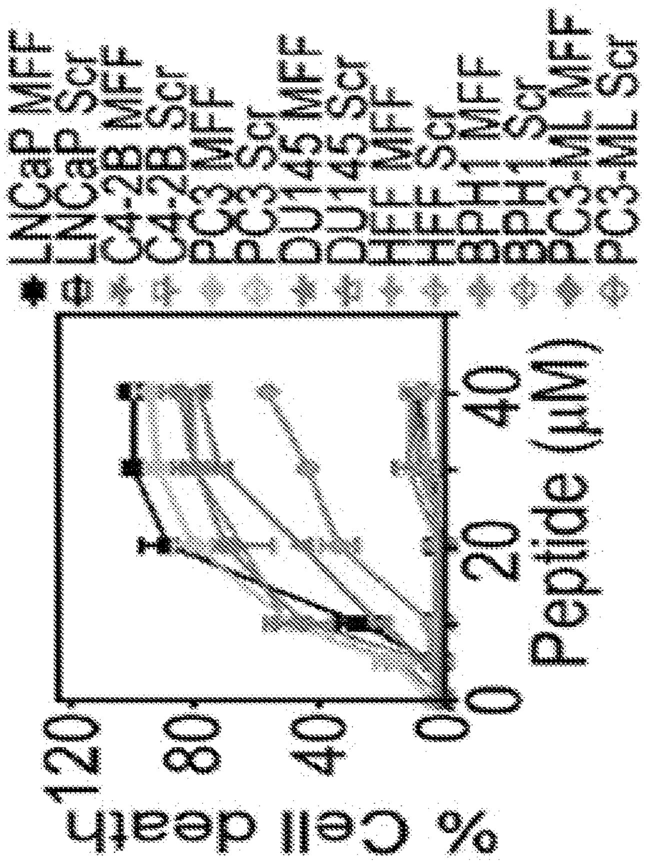
Figure 11A:
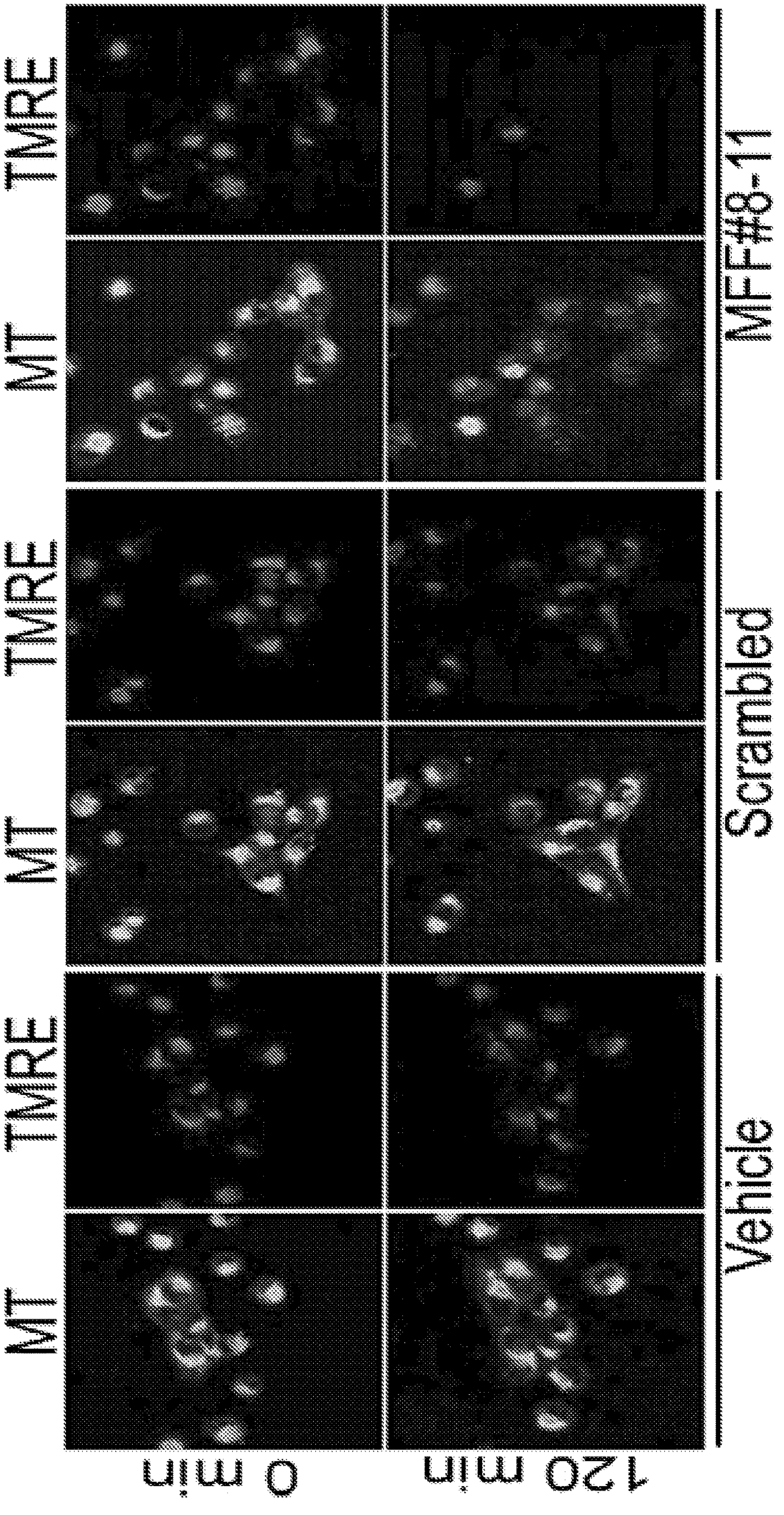
FIGS. 11A-11F illustrate MFF-VDAC peptidyl mimicry.
Figure 11B:
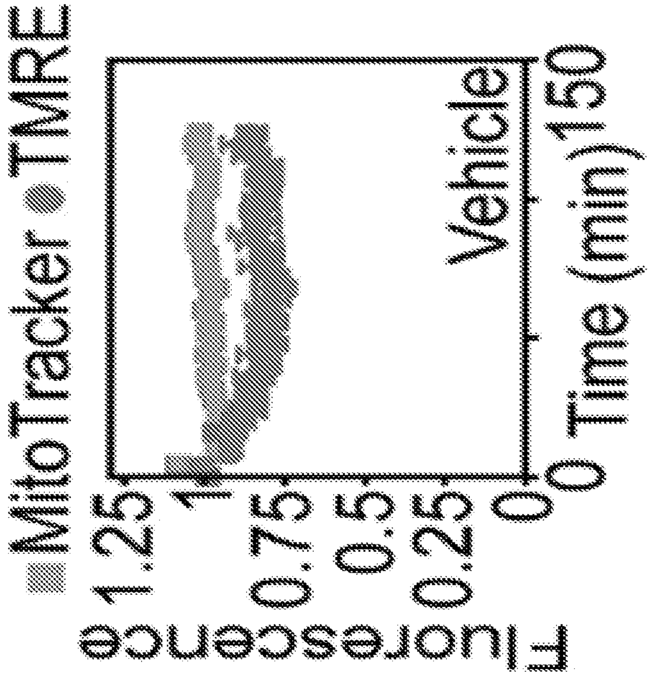
Figure 11C:
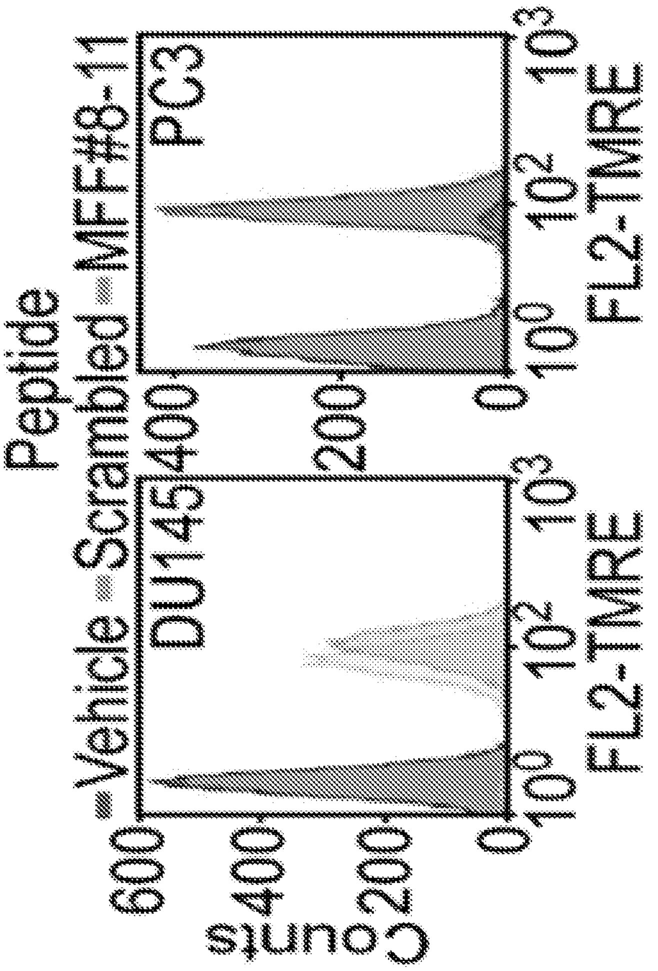
Figure 11D:
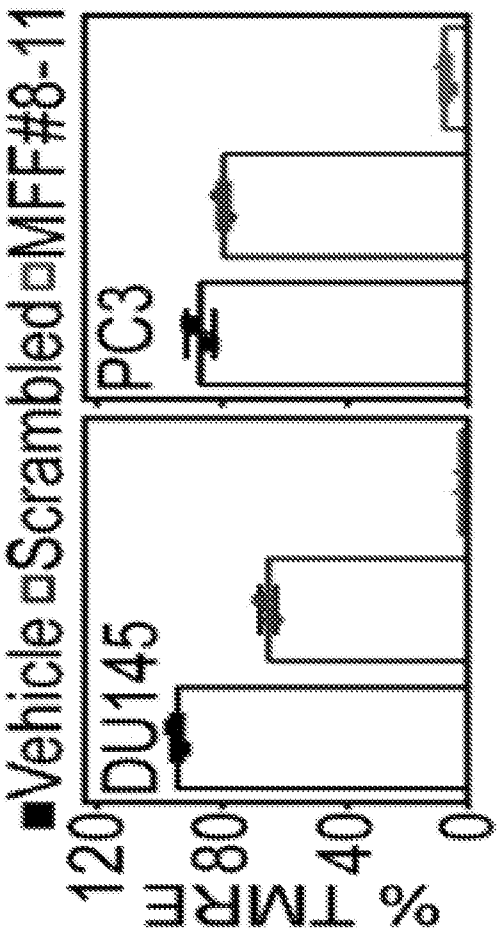
Figure 11E:
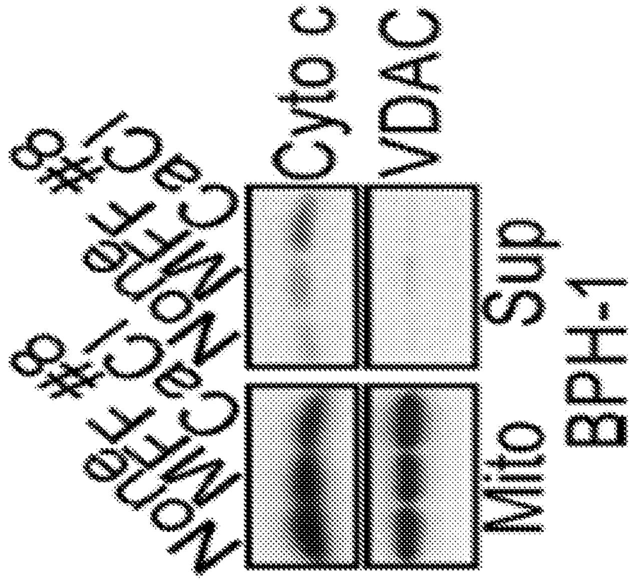
Figure 12B:
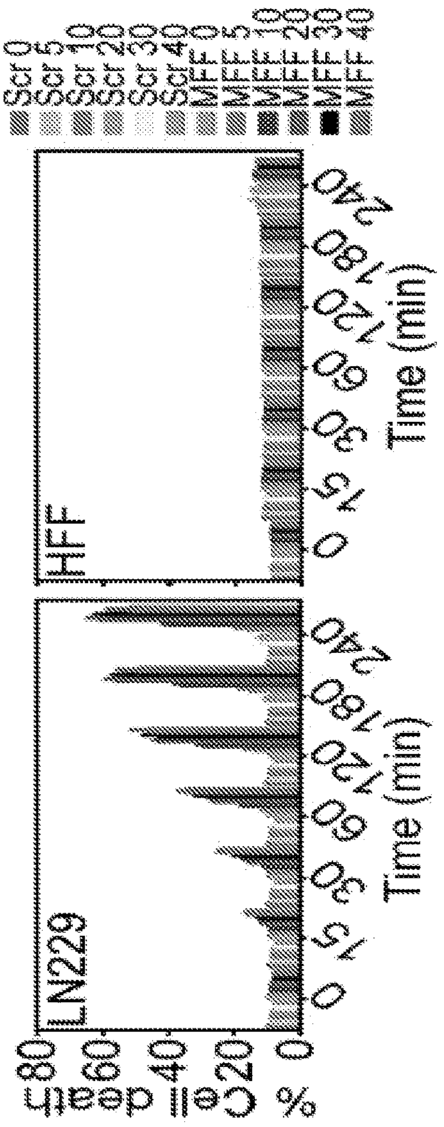
FIGS. 12A-12G illustrate the cell death requirements of MFF-VDAC peptidyl mimicry.
Figure 12A:
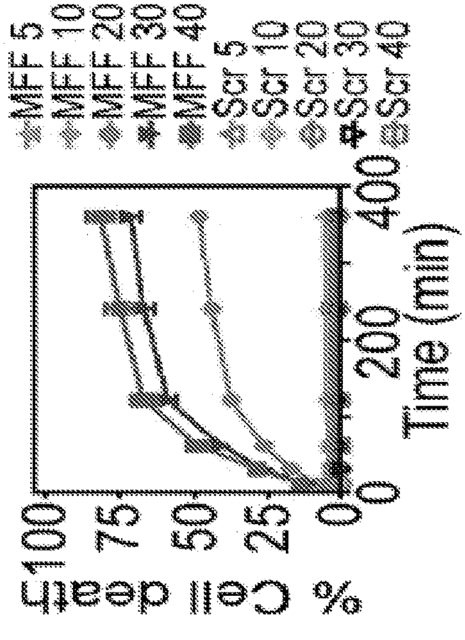

The feasibility of targeting MFF for cancer therapy was studied next, and the MFF peptide #8-11 was made cell-permeable via the addition of an $NH_2$-terminus RQIKIWFQNRRMK (SEQ ID NO: 24) HIV-Tat cell-penetrating sequence. The cell-permeable MFF peptide, but not a cell-permeable scrambled sequence, induced acute loss of mitochondrial membrane potential in single-cell analysis by time-lapse videomicroscopy (FIG. 4A, FIGS. 11A and 11B) or whole cell population (FIGS. 11C and 11D). Consistent with mitochondrial permeability transition (Izzo, V., Bravo-San Pedro, J. M., Sica, V., Kroemer, G. & Galluzzi, L. Mitochondrial Permeability Transition: New Findings and Persisting Uncertainties. *Trends Cell Biol* 26, 655-667 (2016)), treatment with the cell-permeable MFF peptide induced cytochrome c release from tumor (FIG. 4B), but normal BPH-1 cells (FIG. 11E). An unrelated MFF peptide (MFF #1) had no effect (FIG. 4B). In addition, the cell-permeable MFF peptide killed ($IC_{50}$~10 μM) prostate (FIG. 4C, FIG. 12A) and non-prostate cancer cell types, i.e. glioblastoma (FIG. 12B), in a concentration- and time-dependent manner. Normal prostatic epithelial cells (FIG. 4C) or fibroblasts (FIG. 12B) were not affected. This cell death response was specific because a cell-permeable MFF peptide #8-11 containing the double mutation R225D/R236D (DD) did not affect tumor cell viability (FIG. 4D).

Figure 12D:
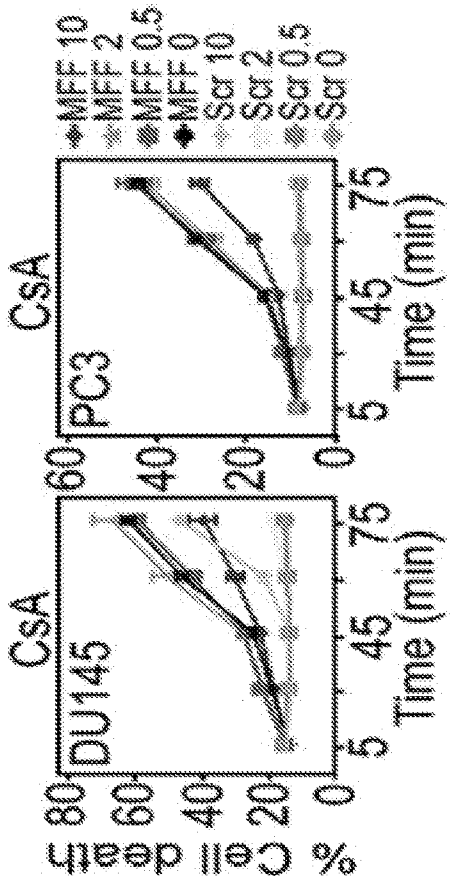
Figure 12C:
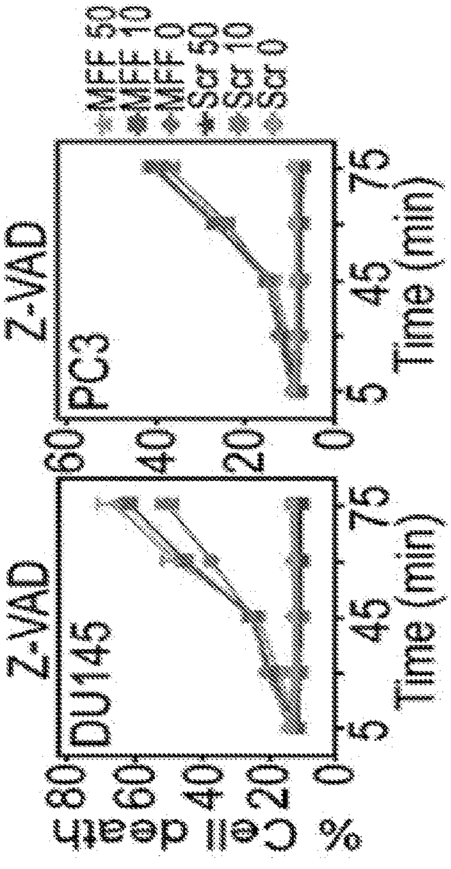
Figure 12E:
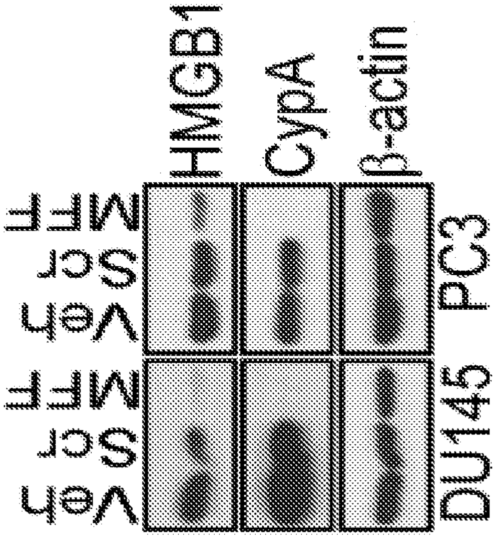
Figure 12F:
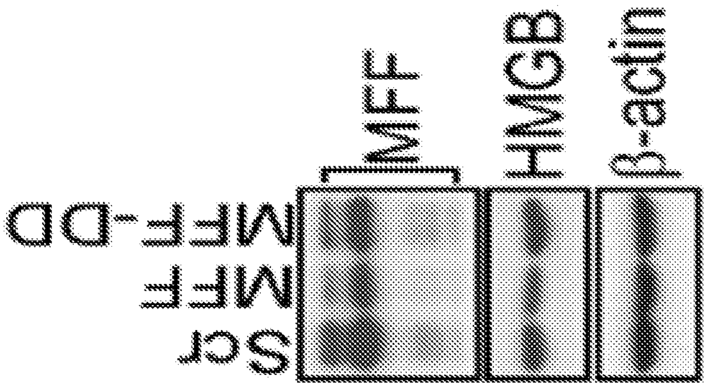
Figure 12G:
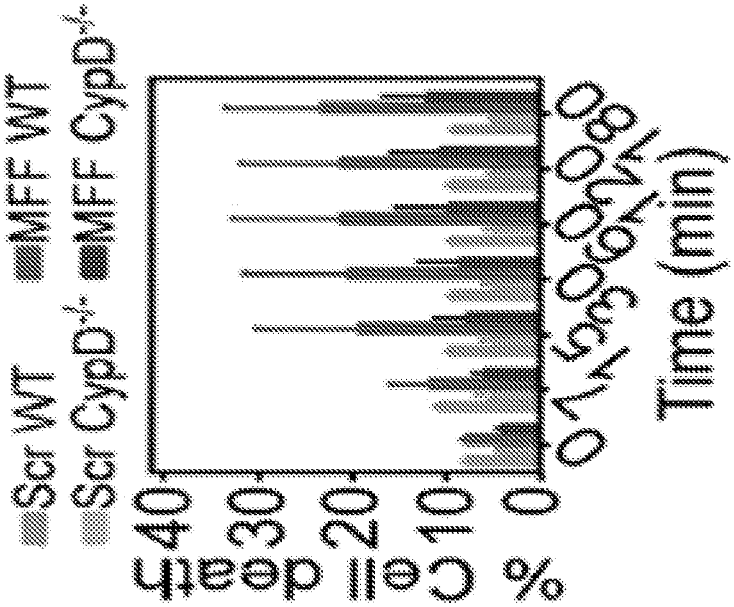

These reagents were used to map more in detail the cell death pathway(s) modulated by the MFF-PTP complex. First, it was found that a pan-caspase inhibitor, Z-VAD-fmk did not significantly reduce tumor cell death induced by the cell-permeable MFF peptide #8-11 (FIG. 12C). Instead, an inhibitor of regulated necrosis, cyclosporine A (CsA) (Conrad, M., Angeli, J. P., Vandenabeele, P. & Stockwell, B. R. Regulated necrosis: disease relevance and therapeutic opportunities. *Nat Rev Drug Discov* 15, 348-366 (2016)), partially reversed tumor cell killing induced by MFF targeting (FIG. 12D). In addition, treatment with the cell-permeable MFF peptide #8-11 induced the release of HMGB1 and cyclophilin A (CypA) from tumor cells, a marker of necrosis (FIG. 12E). A cell-permeable scrambled peptide or MFF peptide #8-11 containing the double mutation R225D/R236D (DD) had no effect on HMGB1 release (FIGS. 12E and 12F). Finally, homozygous deletion of Cyclophilin D (CypD), the only component of the PTP required for regulated necrosis (Baines, C. P., et al. Loss of cyclophilin D reveals a critical role for mitochondrial permeability transition in cell death. Nature 434, 658-662 (2005)), abolished cell death induced by cell-permeable MFF peptide #8-11 (FIG. 12G). Without wishing to be bound by theory, the data indicates that the MFF-VDAC complex controls both apoptosis and necrosis downstream of mitochondrial permeability transition, and that tumor cell death induced by MFF targeting predominantly involves regulated necrosis (Dillon, C. P., Tummers, B., Baran, K. & Green, D. R. Developmental checkpoints guarded by regulated necrosis. *Cell Mot Life Sci* 73, 2125-2136 (2016)).

Figure 13A:
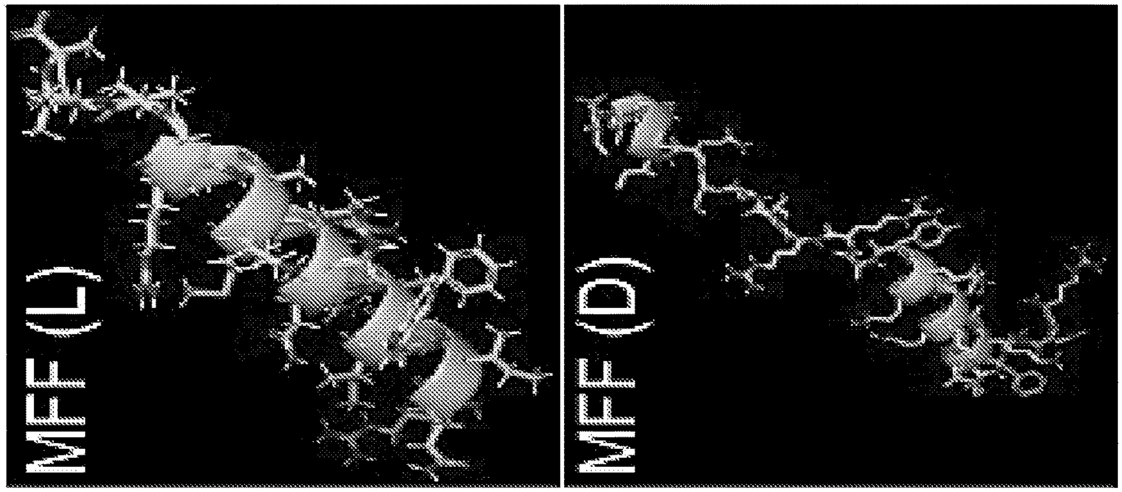
FIGS. 13A-13G illustrate MFF peptidomimetic.
Figure 13B:
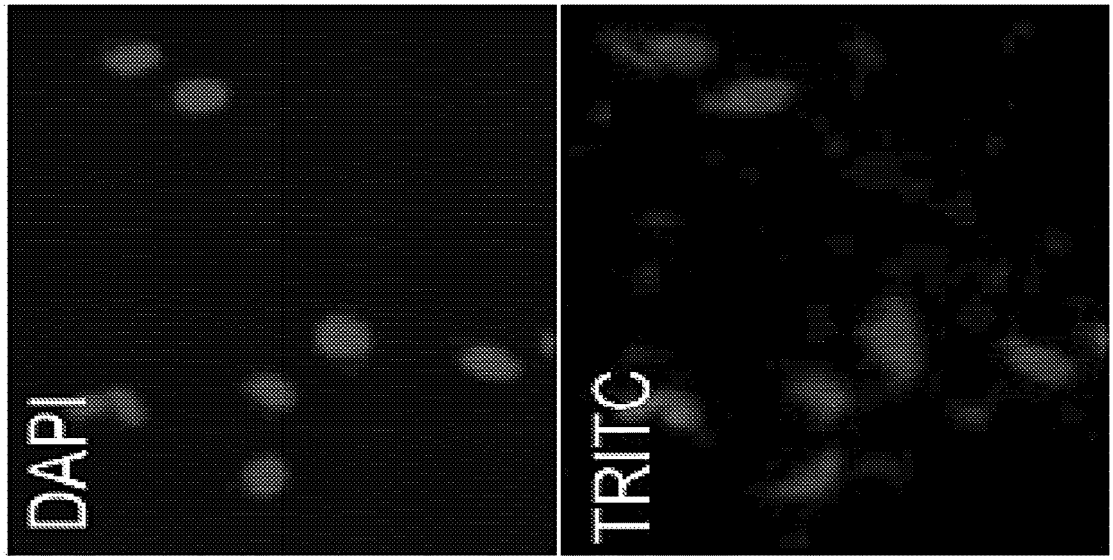
Figure 13D:
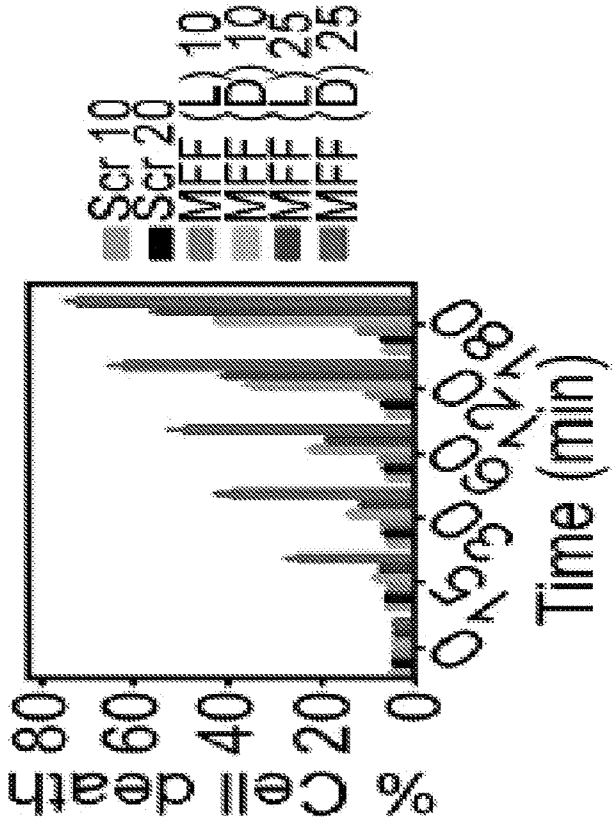
Figure 13C:
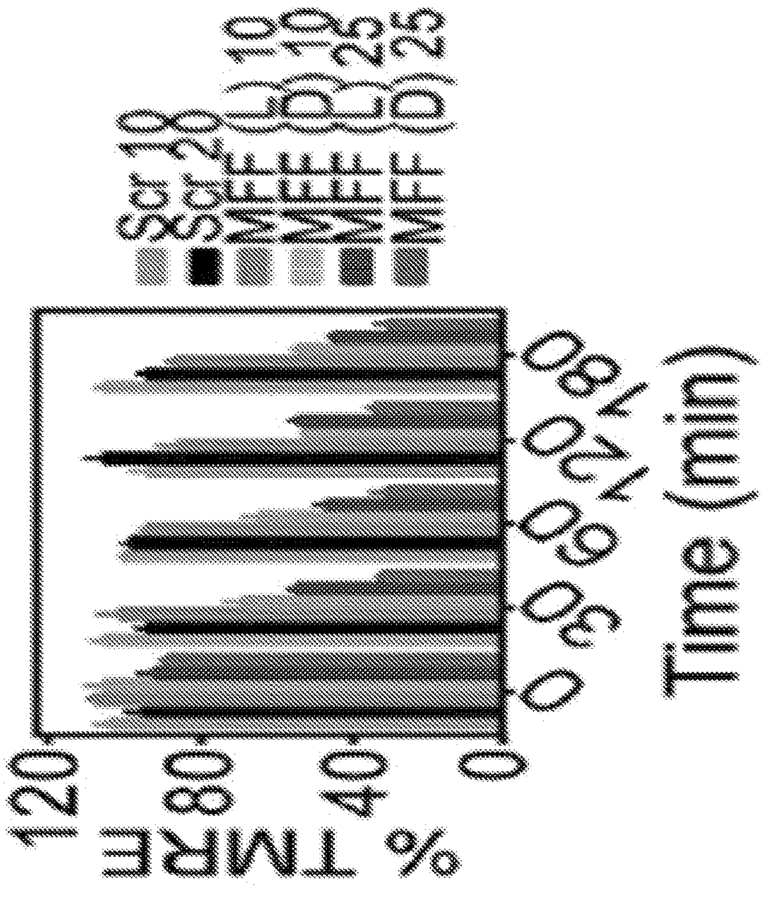

Based on these data, a potential clinical candidate was generated to target the MFF pathway for cancer therapy, in vivo. For these studies, a cell-permeable retro-inverso peptidomimetic of the $Ser^{223}$-$Leu^{243}$MFF sequence was synthesized, containing all D-amino acids in the reverse orientation (FIG. 13A) designed to improve stability during systemic administration (de la Fuente-Nunez, C., et al. D-enantiomeric peptides that eradicate wild-type and multidrug-resistant biofilms and protect against lethal *Pseudomonas aeruginosa* infections. *Chem Biol* 22, 196-205 (2015)). This retro-inverso D-enantiomeric MFF peptidomimetic, designated MFF (D) 8-11 rapidly (<20 min) accumulated intracellularly (FIG. 13B), was more active than the L-enantiomeric (L) MFF peptide #8-11 at depolarizing tumor mitochondria (FIG. 13C) and killed tumor cells in a time- and concentration-dependent manner also more efficiently than the MFF (L) peptide #8-11 (FIG. 13D). By time-lapse videomicroscopy, the MFF (D) peptidomimetic killed tumor cells within 15 min of exposure and with morphologic appearance of necrotic cell death (FIG. 13E). A cell-permeable scrambled peptidomimetic had no effect (FIG. 13E).

Figure 4E:
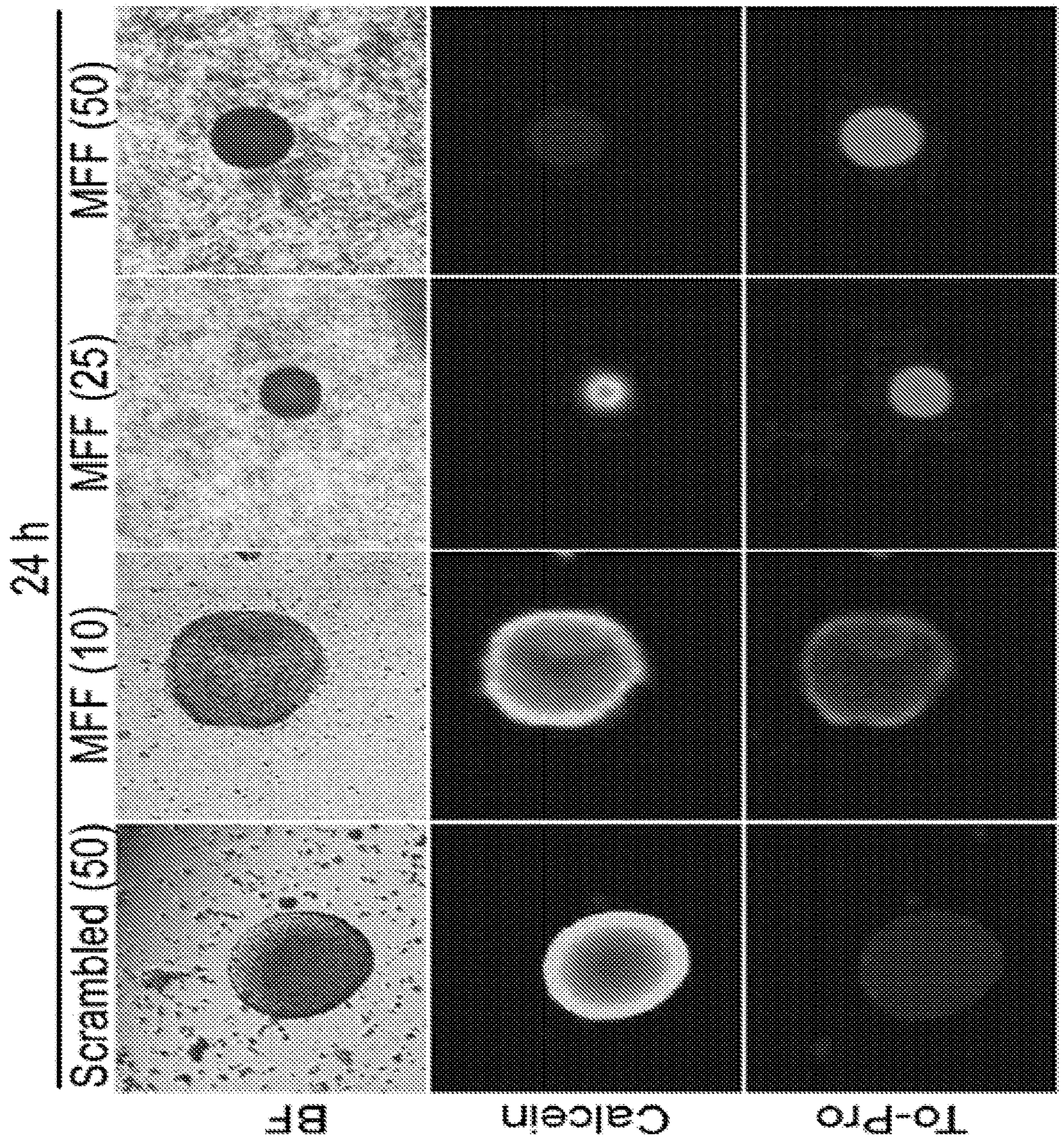
Figure 4F:
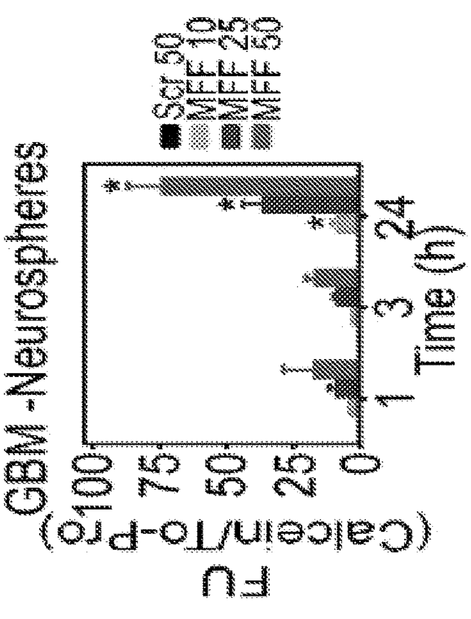
Figure 4G:
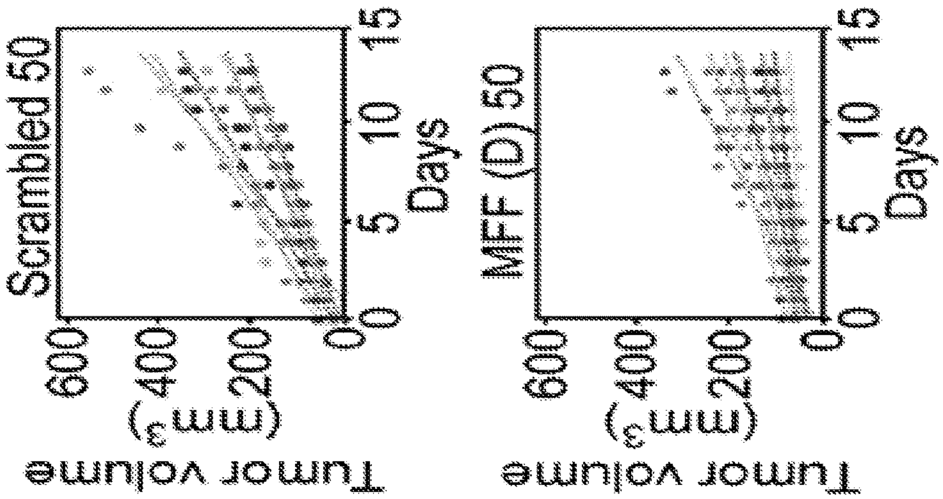
Figure 4H:
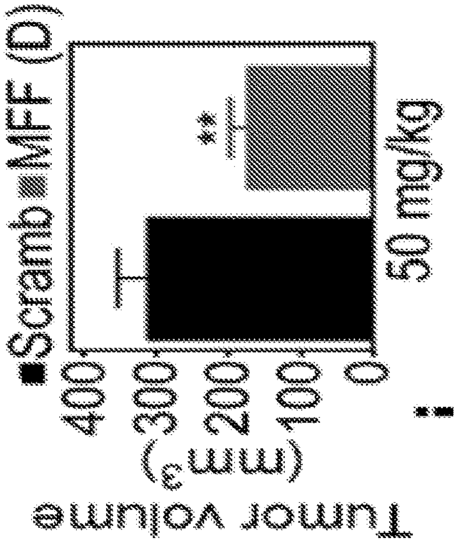
Figure 4I:
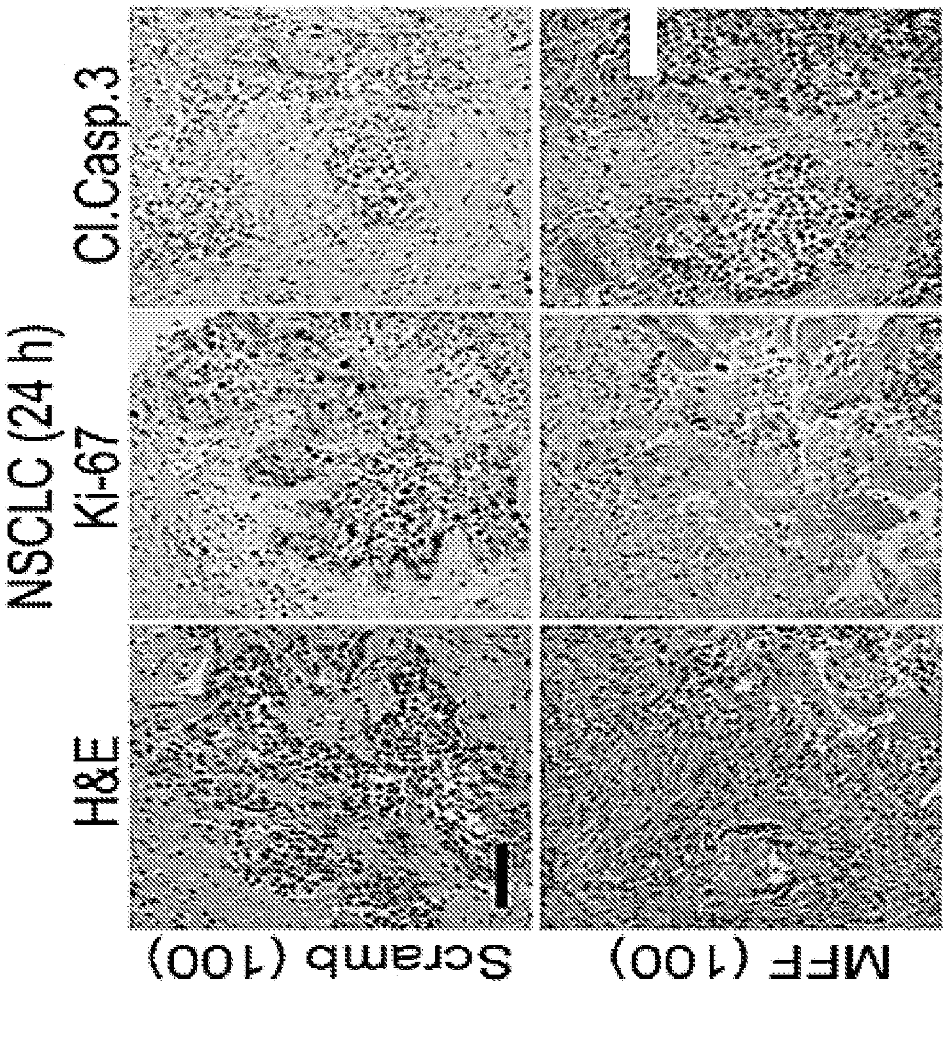
Figure 4J:
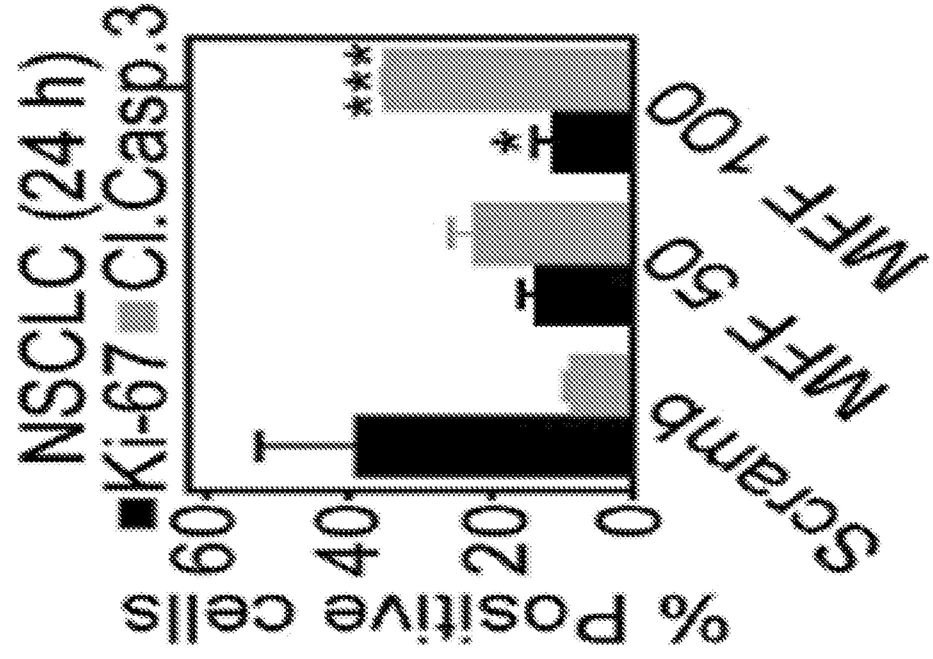
Figure 13F:
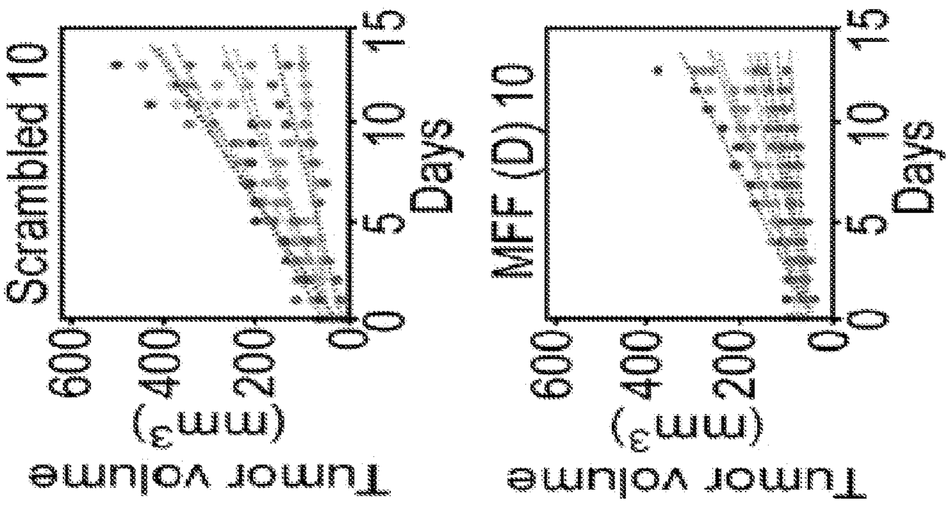
Figure 13E:
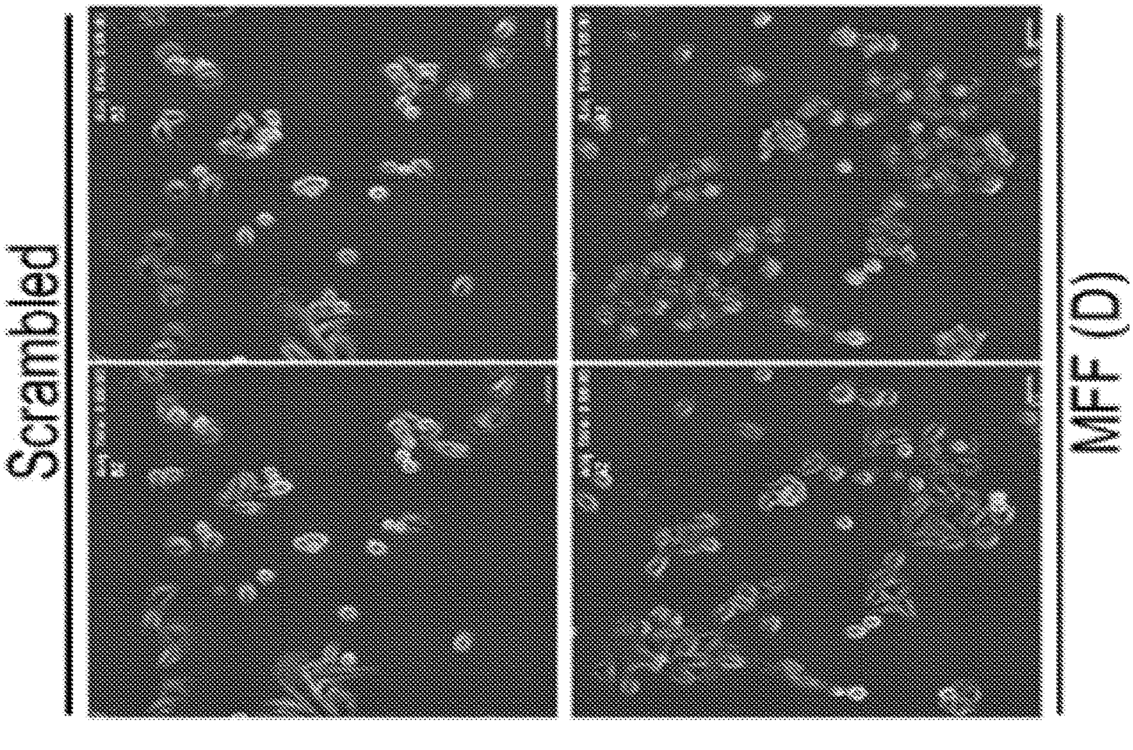
Figure 13G:
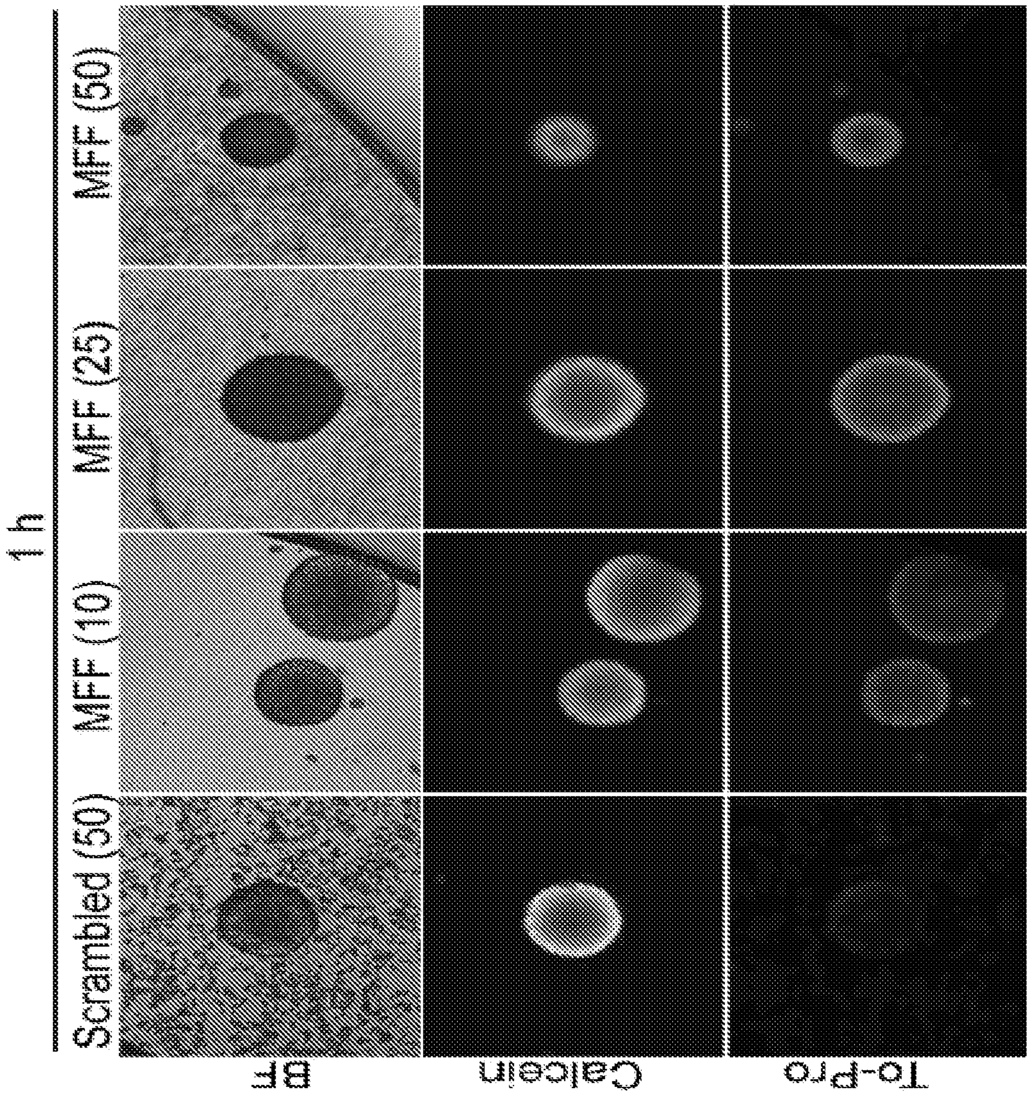
Figure 14B:
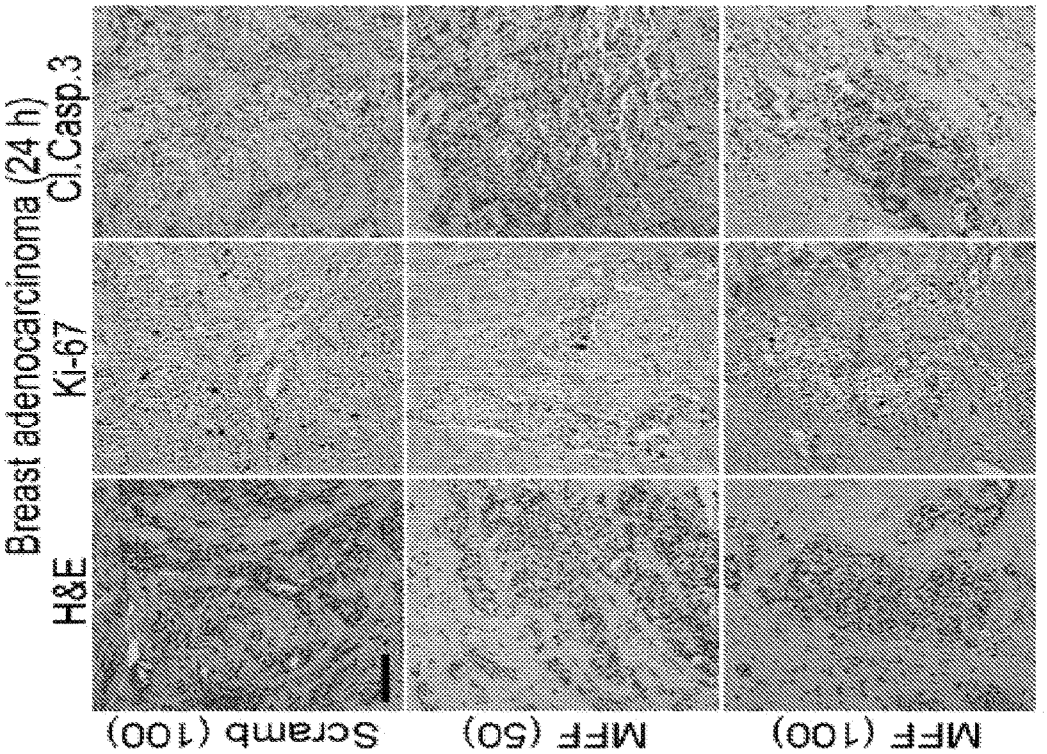
FIGS. 14A-14F illustrate preclinical activity of MFF peptidomimetic.
Figure 14A:
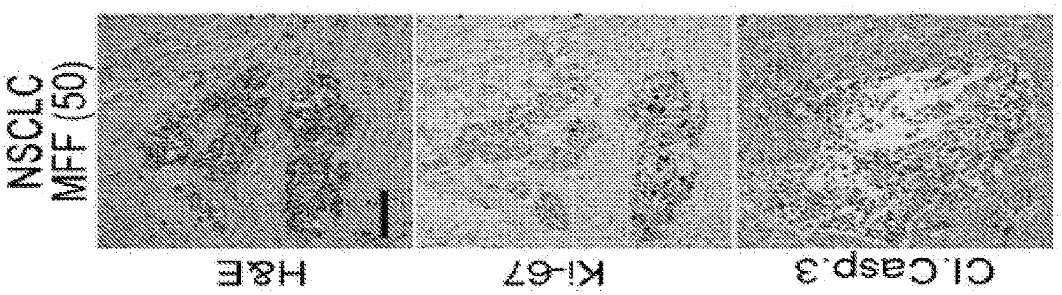
Figure 14D:
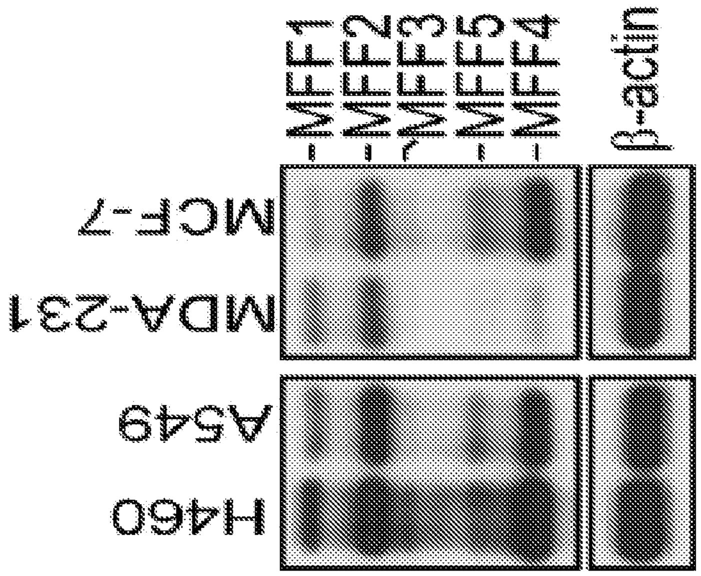
Figure 14C:
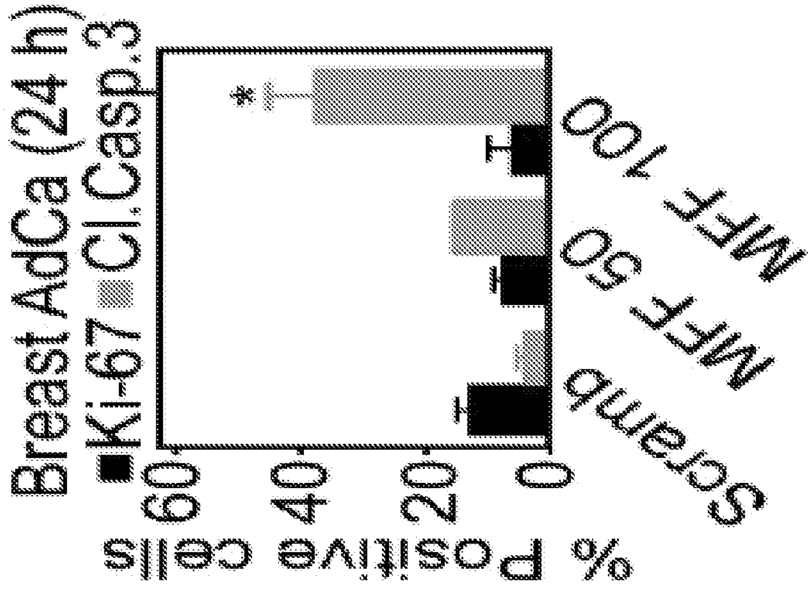
Figure 14E:
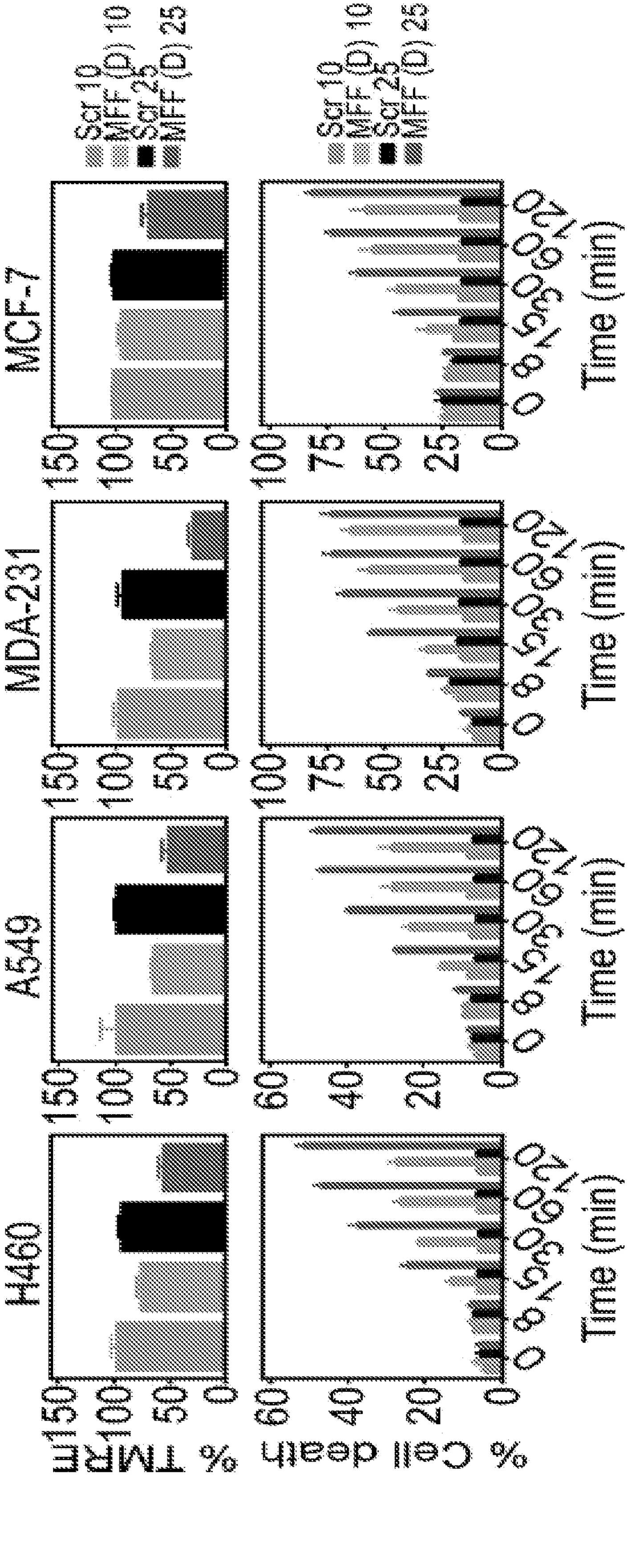
Figure 14F:
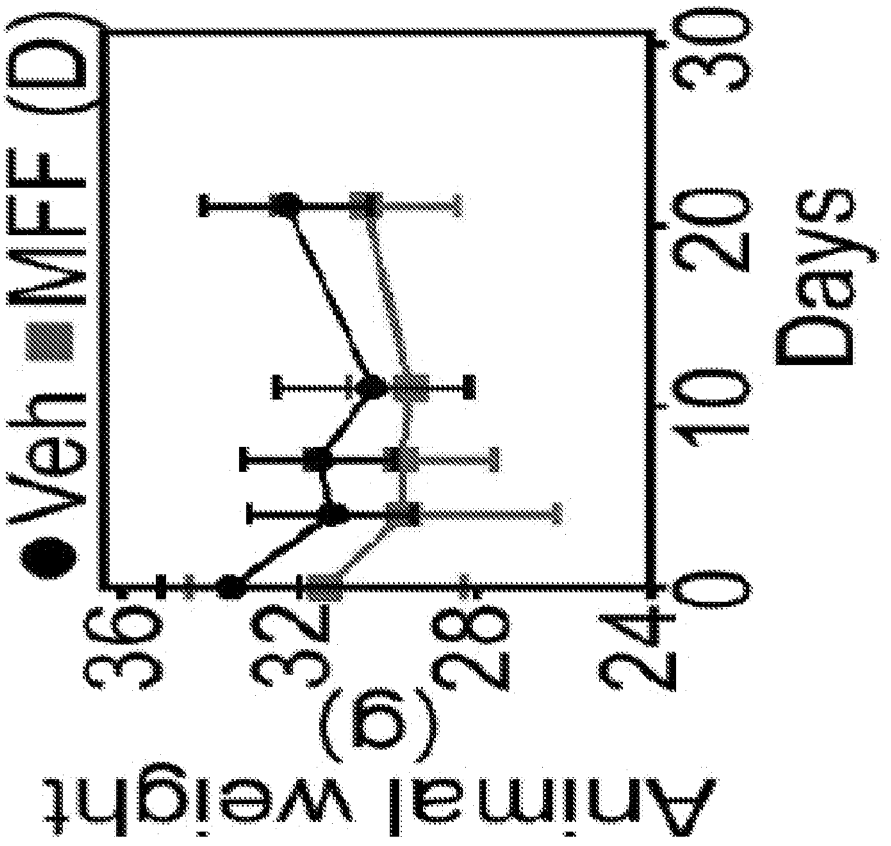

When analyzed for preclinical efficacy, the MFF (D) 8-11 peptidomimetic was cytotoxic for primary, patient-derived glioblastoma (GBM) neurospheres, inducing loss of cell viability (FIGS. 4E and 4F), as early as one hour after exposure (FIG. 13F). By time-lapse videomicroscopy, the MFF (D) 8-11 peptidomimetic killed tumor cells within 15 min of exposure with morphologic features of regulated necrosis. A cell-permeable scrambled peptidomimetic had no effect. In addition, when tested in preclinical models, daily systemic administration of the MFF (D) 8-11 peptidomimetic (10-50 mg/kg i.p.) to tumor (PC3)-bearing immunocompromised mice was feasible and did not cause overt signs of toxicity or animal weight loss (FIG. 14F). Treatment with the MFF (D) 8-11 peptidomimetic inhibited xenograft tumor growth in a concentration-dependent response, compared to cell-permeable scrambled peptide (FIGS. 4G, 4H, and 13G). In a third preclinical model, treatment with the MFF (D) 8-11 peptidomimetic inhibited cell proliferation (loss of Ki-$67^+$ cells) and induced apoptosis (increased cleaved caspase-$3^+$ cells) in primary tumor organoids established from patients with non-small cell lung cancer (NSCLC, FIGS. 4I, 4J and 14A) or breast adenocarcinoma (FIGS. 14B and 14C). A cell-permeable scrambled peptide had no effect (FIGS. 4I, 4J and 14A-14C). Consistent with these results, breast adenocarcinoma MDA-231 or MCF-7 cells as well as NSCLC A549 and H460 cells expressed MFF isoforms, especially MFF1, 2 and 4 (FIG. 14D). Similar to the results in prostate cancer, these cells were also sensitive to the MFF (D) 8-11 peptidomimetic, exhibiting acute loss of mitochondrial membrane potential and tumor cell death, whereas a cell-permeable scrambled peptide had no effect (FIG. 14E).

Figure 27A:
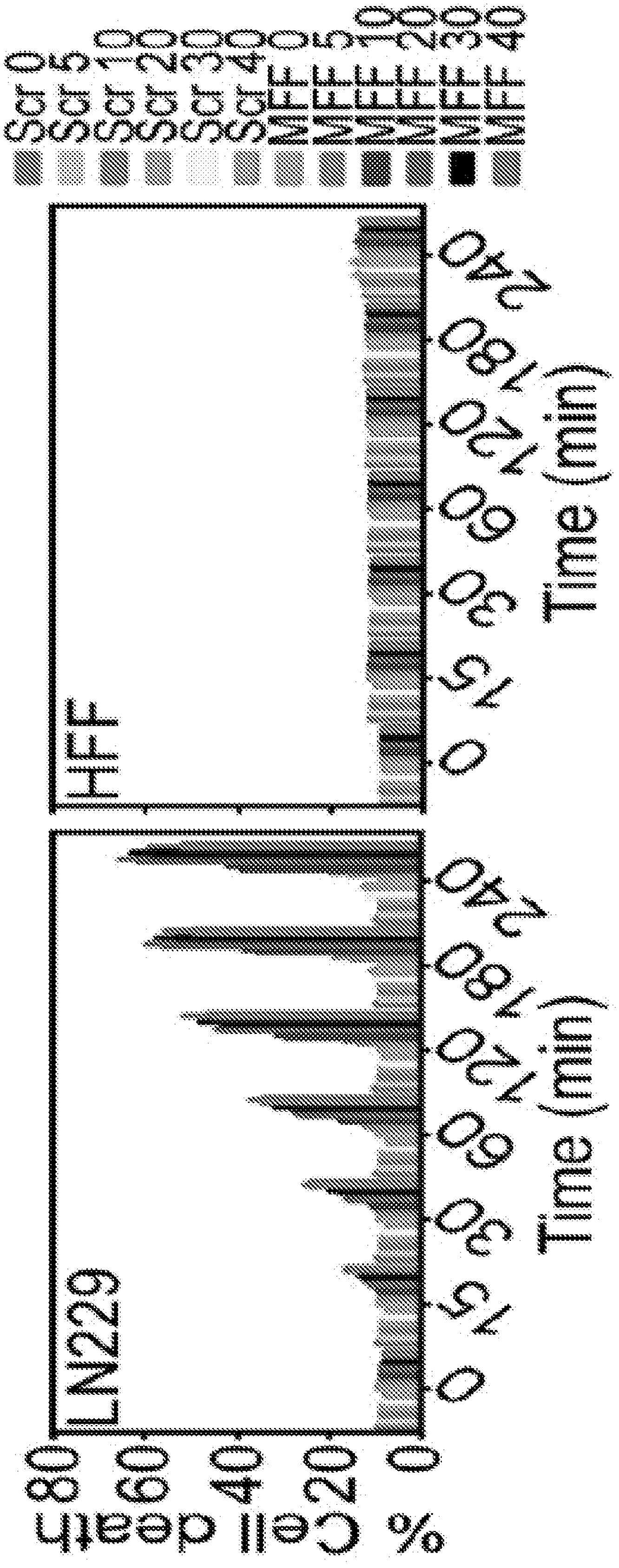
FIGS. 27A-27B illustrate anti-glioma activity of MFF peptidomimetic.
Figure 27B:
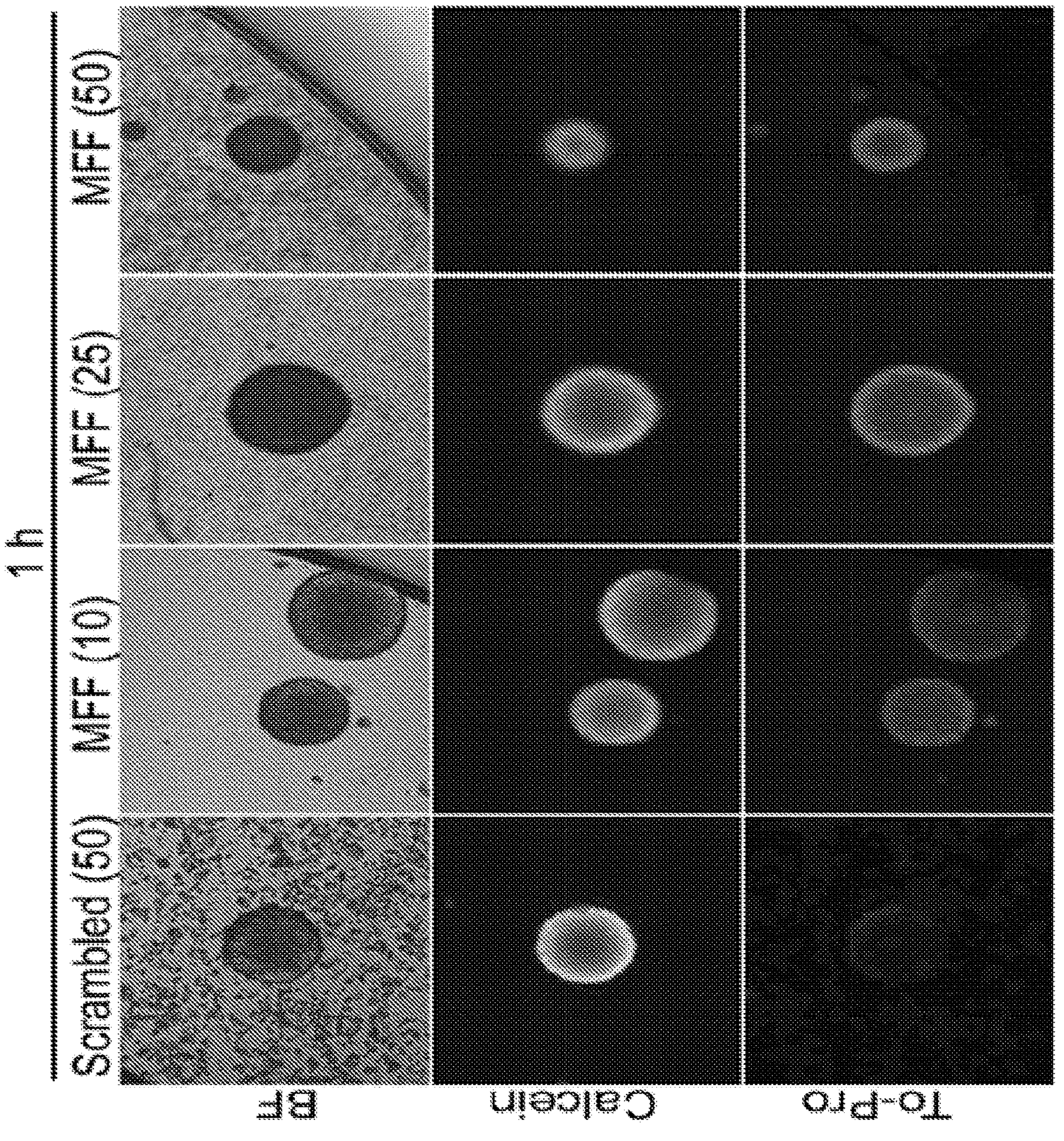

The effect of MFF-VDAC1 targeting was examined in patient-derived xenograft (PDX) models of melanoma resistant to the combination therapy of Dabrafenib (mutant BRAF inhibitor) and Trametinib (MEK inhibitor). When exposed to vehicle or the combination Dabrafenib/Trametinib, these PDX tumors grew exponentially in immunocompromised mice (FIG. 25F). Conversely, treatment with the MFF (D) 8-11 peptidomimetic significantly inhibited the growth of drug-resistant PDX melanoma in these settings (FIG. 25F). In a third preclinical model, treatment with the MFF (D) 8-11 peptidomimetic inhibited cell proliferation (loss of Ki-$67^+$ cells) and induced markers of cell death (increased cleaved caspase-3-positive cells) in patient-derived NSCLC (FIGS. 25G and 25H) or breast adenocarcinoma 3D tissue organoids maintained in short-term culture (FIG. 14B, FIG. 25I). A cell-permeable scrambled peptidomimetic had no effect on 3D tumor organoids (FIG. 25G-25I, FIG. 14B). Consistent with these results, matched tumor cell lines, NSCLC A549 and H460 or breast adenocarcinoma MDA-231 and MCF-7 cells (FIG. 14D) expressed MFF1, MFF2 and MFF4, and exhibited mitochondrial depolarization and nearly complete killing after treatment with the MFF (D) 8-11 peptidomimetic, but not a scrambled sequence (FIG. 14E). Finally, patient-derived glioblastoma (GBM) neurospheres were looked at as a preclinical model enriched in cancer stem cells. In validation experiments, the cell-permeable MFF (D) 8-11 peptidomimetic efficiently killed GBM LN229 cells in a time- and concentration-dependent manner (FIG. 27A). Normal HFF were not affected and a control scrambled sequence did not cause LN229 cell killing (FIG. 27A). Consistent with these data, treatment with the MFF (D) 8-11 peptidomimetic, but not a scrambled peptide, was highly cytotoxic for patient-derived GBM neurospheres (FIG. 25J, FIG. 27B), resulting in time- and concentration-dependent loss of viability, as early as one hour after drug exposure (FIG. 25K).

In sum, these data identify a novel link between mitochondrial dynamics (Youle, R. J. & van der Bliek, A. M. Mitochondrial fission, fusion, and stress. *Science* 337, 1062-1065 (2012)), in particular MFF-regulated mitochondrial fission (Otera, H., et al. Mff is an essential factor for mitochondrial recruitment of Drp1 during mitochondrial fission in mammalian cells. *J Cell Biol* 191, 1141-1158 (2010)) and the control of the PTP (Izzo, V., Bravo-San Pedro, J. M., Sica, V., Kroemer, G. & Galluzzi, L. Mitochondrial Permeability Transition: New Findings and Persisting Uncertainties. *Trends Cell Biol* 26, 655-667 (2016)) in cancer. Without wishing to be bound by theory it seems that the regulation of mitochondrial permeability transition (Fuchs, Y. & Steller, H. Live to die another way: modes of programmed cell death and the signals emanating from dying cells. *Nat Rev Mol Cell Biol* 16, 329-344 (2015); Izzo, V., Bravo-San Pedro, J. M., Sica, V., Kroemer, G. & Galluzzi, L. Mitochondrial Permeability Transition: New Findings and Persisting Uncertainties. *Trends Cell Biol* 26, 655-667 (2016)), especially in chronically "stressed" cancer cells, may be highly "plastic", and involve the recruitment of diverse molecules, such as MFF homo- and/or heterodimers (Otera, H., et al. Mff is an essential factor for mitochondrial recruitment of Drp1 during mitochondrial fission in mammalian cells. *J Cell Biol* 191, 1141-1158 (2010)) to gate the PTP in a cell- and context-dependent manner (He, L. & Lemasters, J. J. Regulated and unregulated mitochondrial permeability transition pores: a new paradigm of pore structure and function? *FEBS Lett* 512, 1-7 (2002)). This is consistent with the upregulation of multiple survival pathways in cancer (Hanahan, D. & Weinberg, R. A. Hallmarks of cancer: the next generation. *Cell* 144, 646-674 (2011)), and may anticipate a need for greater mitochondrial protection under conditions of high organelle dynamics (Eisner, V., Picard, M. & Hajnoczky, G. Mitochondrial dynamics in adaptive and maladaptive cellular stress responses. *Nat Cell Biol* 20, 755-765 (2018)). Conversely, and without wishing to be bound by theory, the MFF-VDAC complex is druggable, and a peptidomimetic antagonist of this interaction, i.e. MFF (D) 8-11, delivered proof-of-concept cytotoxic activity in multiple preclinical models, without overt systemic or organ toxicity. Compared to other mitochondrial-directed therapies (Croce, C. M. & Reed, J. C. Finally, An Apoptosis-Targeting Therapeutic for Cancer. Cancer Res 76, 5914-5920 (2016)), disrupting the MFF-VDAC complex may be "tumor agnostic", and therefore broadly indicated for heterogeneous malignancies, while bypassing common drug resistance mechanisms mediated by anti-apoptotic Bcl2 proteins (Adams, J. M. & Cory, S. The BCL-2 arbiters of apoptosis and their growing role as cancer targets. *Cell Death Differ* 25, 27-36 (2018)).

Example 5-A MFF-VDAC Complex is Required for Tumor Cell Survival

Figure 11F:
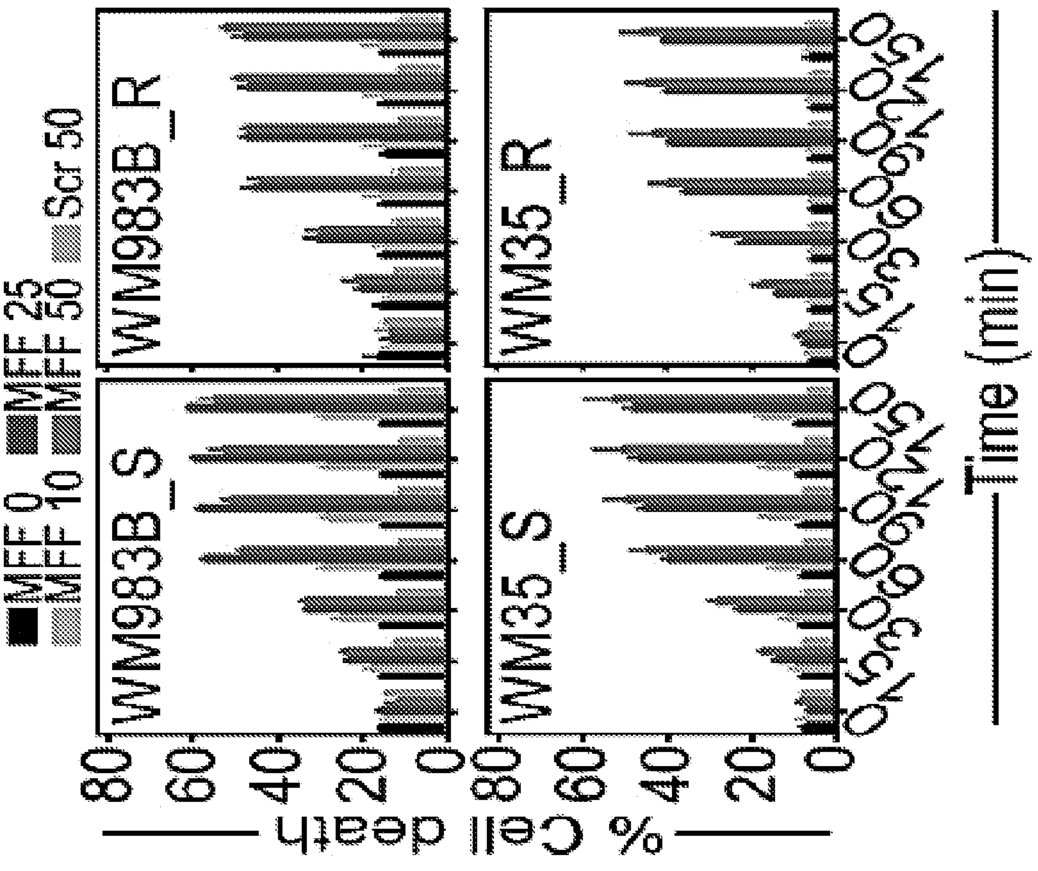
Figure 28A:
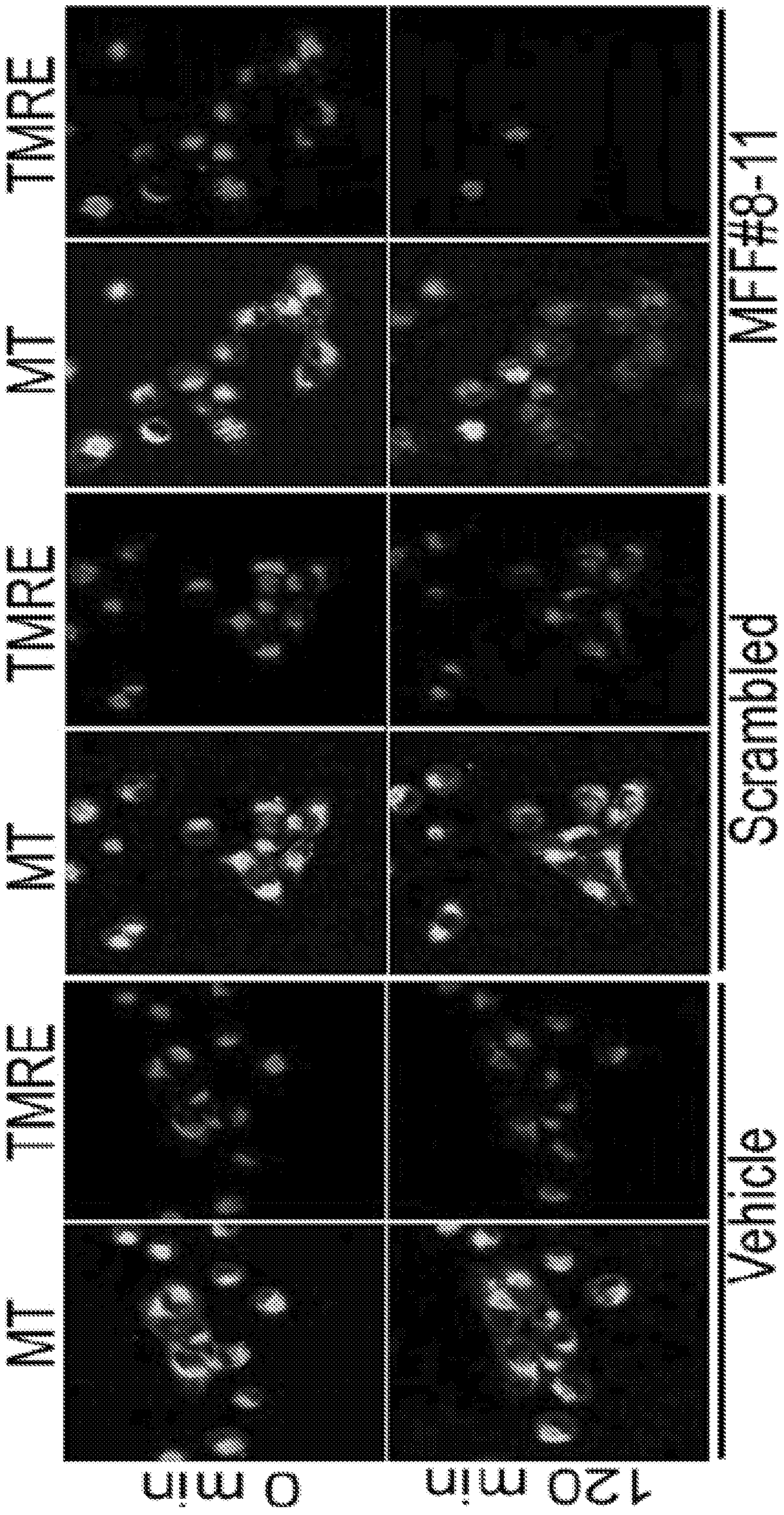
FIGS. 28A-28J illustrate regulation of tumor cell death by MFF-VDAC1 complex.
Figure 28C:
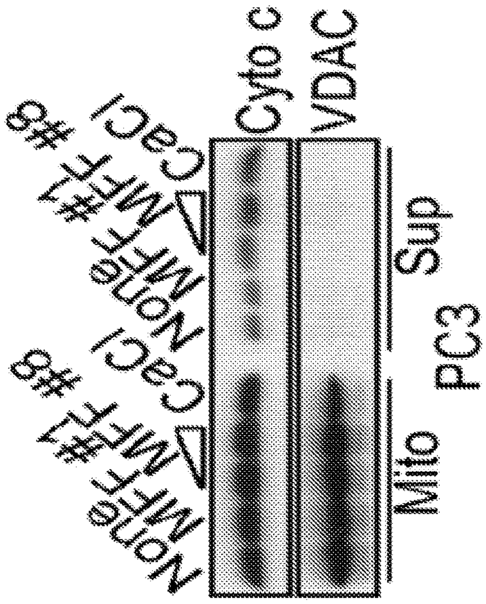
Figure 28D:
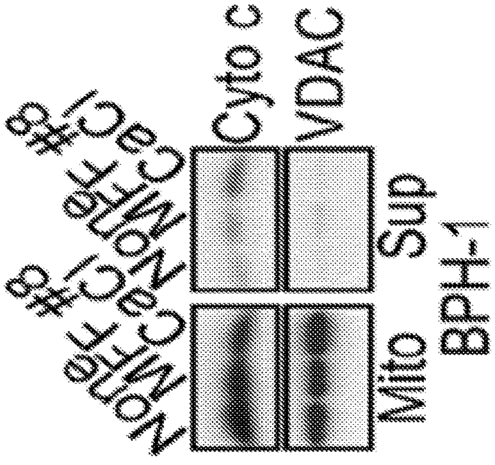
Figure 28B:
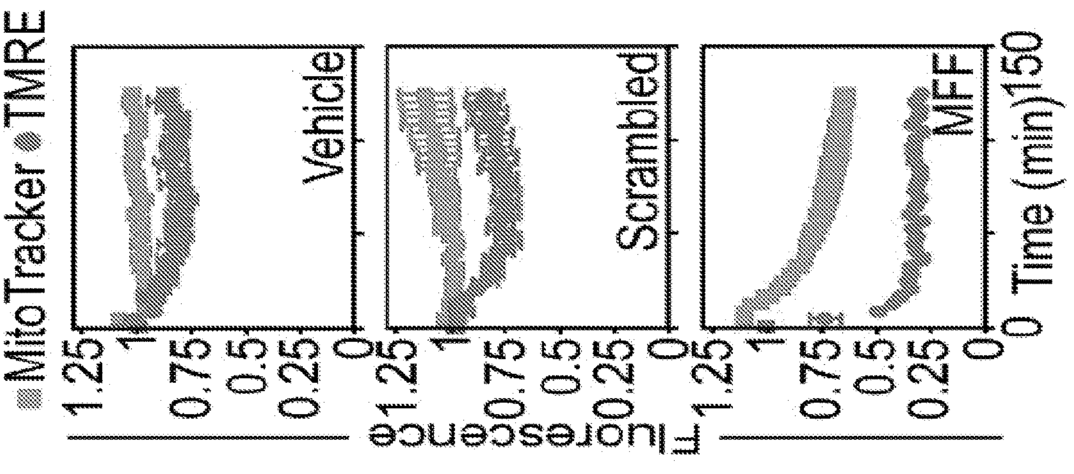
Figure 28G:
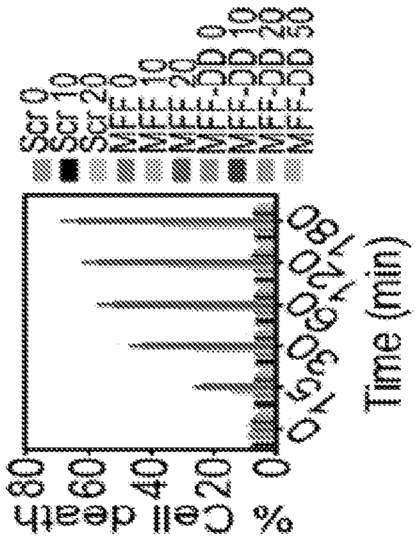
Figure 28F:
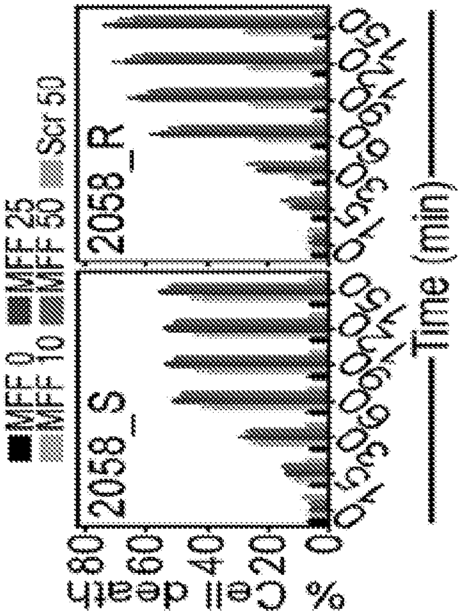
Figure 28E:
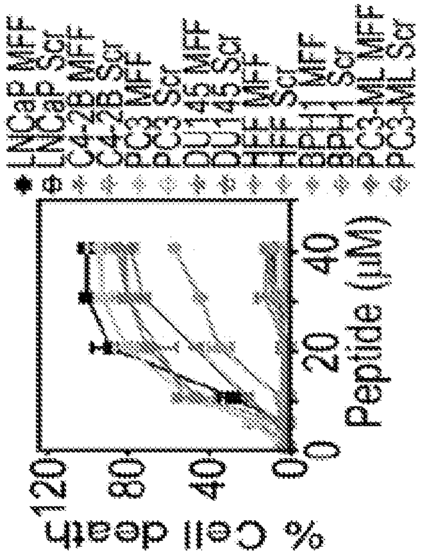

To understand the function of an MFF-VDAC1 complex in tumor cells, the MFF peptide #8-11 was made cell-permeable via the addition of an $NH_2$-terminus RQIKIWFQNRRMK (SEQ ID NO: 24) HIV-Tat cell-penetrating sequence. The cell-permeable MFF peptide, but not a cell-permeable scrambled sequence, induced sudden loss of mitochondrial membrane potential, by single-cell time-lapse videomicroscopy (FIGS. 28A and 28B), as well as analysis of whole tumor cell populations, by flow cytometry (FIGS. 11C and 11D). Consistent with increased mitochondrial outer membrane permeability, treatment with the cell-permeable MFF peptide induced cytochrome c release from tumor (FIG. 28C), but normal BPH-1 (FIG. 28D) cells. An unrelated MFF #1 peptide had no effect (FIG. 28D). Due to loss of mitochondrial integrity, treatment with the cell-permeable MFF peptide #8-11 killed ($IC_{50}$~10 μM) multiple prostate cancer cell types in a concentration- and time-dependent manner (FIG. 28E). Normal prostatic epithelial cells or fibroblasts were not affected, and a cell-permeable scrambled peptide did not kill normal or prostate cancer cells (FIG. 28E). In addition, treatment with the cell-permeable MFF peptide #8-11 comparably killed isogenic pairs of drug-sensitive and drug-resistant melanoma cells (FIG. 28F, FIG. 11F). To validate the specificity of these findings, the Arg225Asp/Arg236Asp double mutation (DD) that prevents VDAC1 binding in the cell-permeable MFF peptide was introduced. This mutant peptide entirely lost the ability to induce tumor (PC3) cell death, whereas WT MFF peptide #8-11 efficiently killed tumor cells in a time- and concentration-dependent manner (FIG. 28G).

Figure 28H:
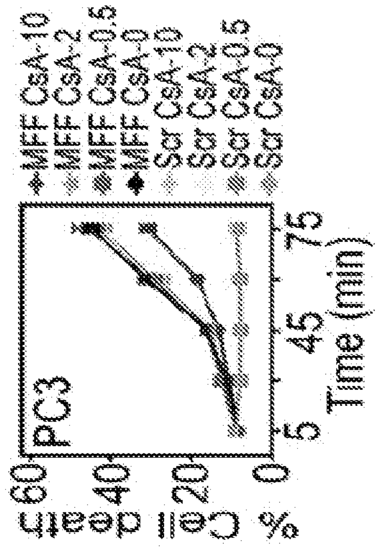
Figure 28I:
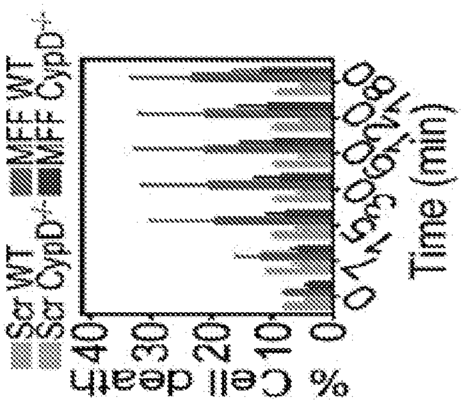
Figure 28J:
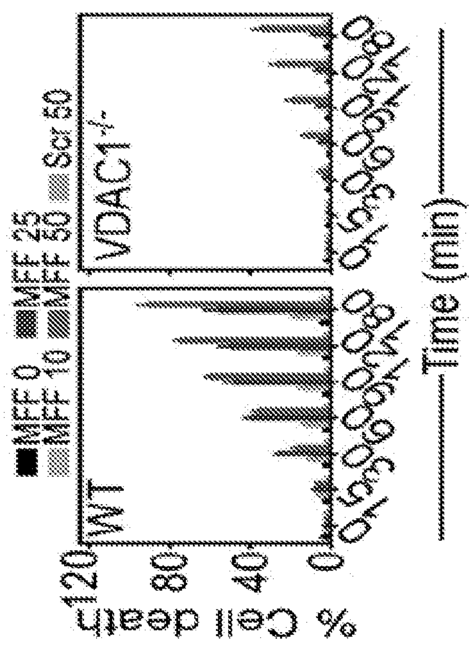

Next, these reagents were used to characterize the type of mitochondrial cell death activated by disrupting the MFF-VDAC1 complex. It was found that a pan-caspase inhibitor, Z-VAD-fmk did not significantly reduce tumor cell death induced by the cell-permeable MFF peptide #8-11 (FIG. 12C). Instead, an inhibitor of regulated necrosis, cyclosporine A (CsA), partially reversed tumor cell killing induced by MFF peptide #8-11 (FIG. 28H, FIG. 12D). Biochemically, tumor cell death in these settings was accompanied by loss of plasma membrane integrity, another marker of regulated necrosis, as determined by release of HMGB1 and cyclophilin A (CypA) from tumor cells (FIG. 12E). Conversely, a cell-permeable scrambled peptide or MFF-DD mutant peptide #8-11 did not induce HMGB1 release (FIGS. 12E and 12F). An essential effector of regulated necrosis is the mitochondrial matrix protein, Cyclophilin D (CypD), and its role in this pathway was next investigated. Treatment with the cell-permeable MFF peptide #8-11 killed immortalized wild type (WT) mouse embryonic fibroblasts (MEF) in a concentration-dependent manner (FIG. 28I). In contrast, $CypD^{-/-}$ MEFs were resistant to cell death induced by the MFF peptide (FIG. 28I). Finally, a requirement of VDAC1 in this pathway of mitochondrial cell death was tested. Consistent with the data above, treatment with MFF peptide #8-11 efficiently killed WT MEF in a time- and concentration-dependent response (FIG. 28J, left). Instead, $VDAC^{-/-}$ MEF were insensitive to cell death in these settings (FIG. 28J, right).

Example 6—Targeting the MFF-VDAC1 Complex for Cancer Therapy

Figure 29A:
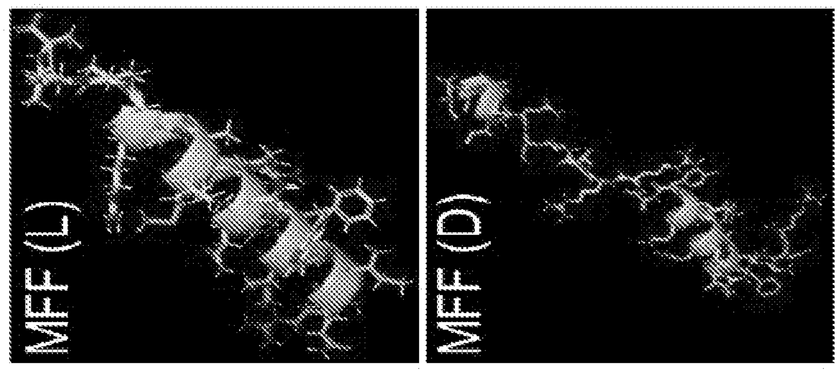
FIGS. 29A-29K illustrate preclinical targeting of MFF-VDAC1 complex for cancer therapy.
Figure 29B:
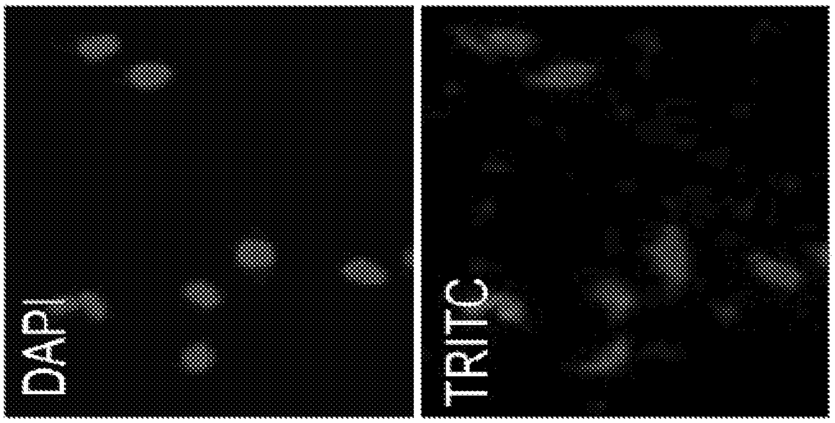
Figure 29C:
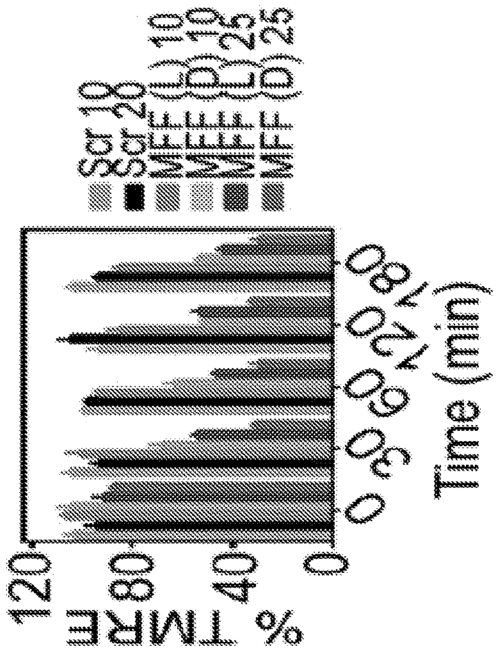
Figure 29E:
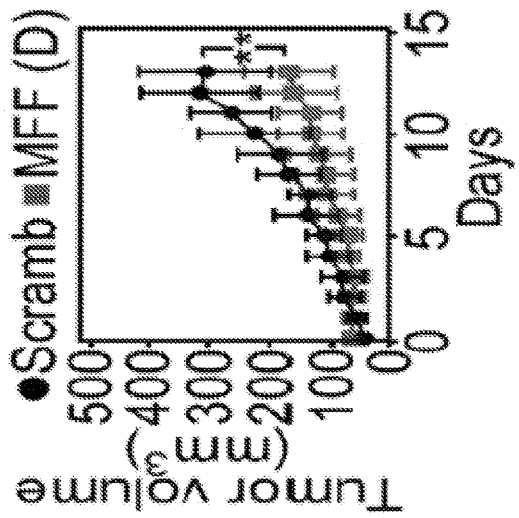
Figure 29D:
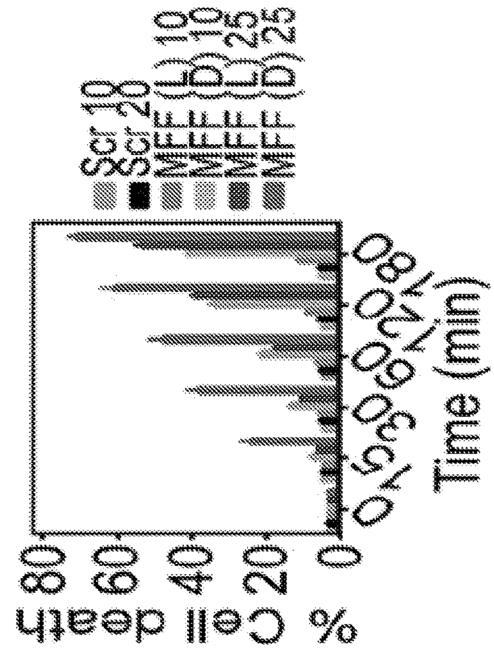

From these proof-of-concept experiments, a clinical candidate was generated to target the MFF-VDAC1 complex for cancer therapy, in vivo. To accomplish this, a cell-permeable retro-inverso peptidomimetic of the Ser223-Leu243 MFF sequence was generated, containing all D-amino acids in the reverse orientation (FIG. 29A) to improve stability during systemic administration. This retro-inverso D-enantiomeric MFF peptidomimetic, designated MFF (D) 8-11 rapidly (<20 min) accumulated intracellularly (FIG. 29B), was more active than the L-enantiomeric (L) MFF peptide #8-11 at depolarizing tumor mitochondria (FIG. 29C) and killed tumor cells in a time- and concentration-dependent manner also more efficiently than the MFF (L) peptide #8-11 (FIG. 29D). By time-lapse videomicroscopy, the MFF (D) 8-11 peptidomimetic killed tumor cells within 15 min of exposure with morphologic features of regulated necrosis. A cell-permeable scrambled peptidomimetic had no effect.

Figure 29F:
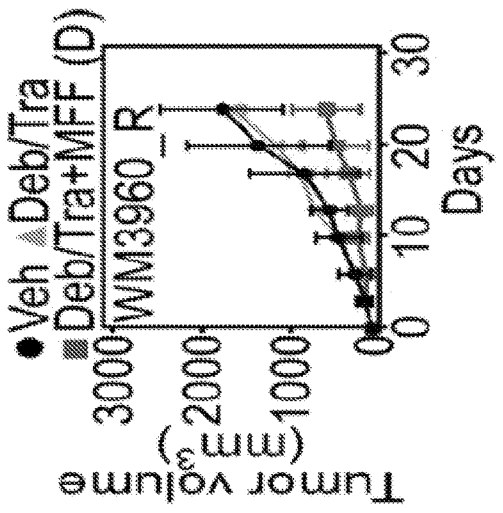

When tested in preclinical models, daily systemic administration of the MFF (D) 8-11 peptidomimetic (50 mg/kg i.p.) inhibited xenograft tumor (PC3) growth in immunocompromised mice (FIG. 29E) without overt signs of toxicity or animal weight loss (FIG. 14F). Systemic administration of a cell-permeable scrambled peptidomimetic had no effect on tumor growth (FIG. 29E). Next, the effect of MFF-VDAC1 targeting was examined in patient-derived xenograft (PDX) models of melanoma resistant to the combination therapy of Dabrafenib (mutant BRAF inhibitor) and Trametinib (MEK inhibitor). When exposed to vehicle or the combination Dabrafenib/Trametinib, these PDX tumors grew exponentially in immunocompromised mice (FIG. 29F). Conversely, treatment with the MFF (D) 8-11 peptidomimetic significantly inhibited the growth of drug-resistant PDX melanoma in these settings (FIG. 29F).

Figure 29I:
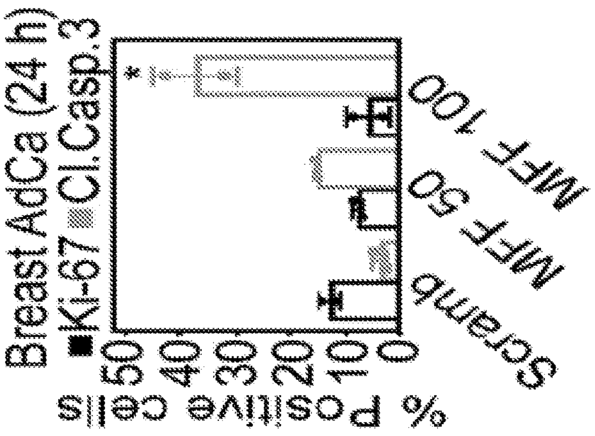
Figure 29H:
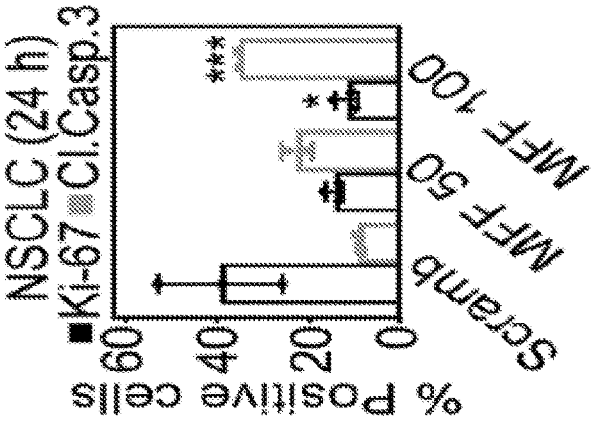
Figure 29G:
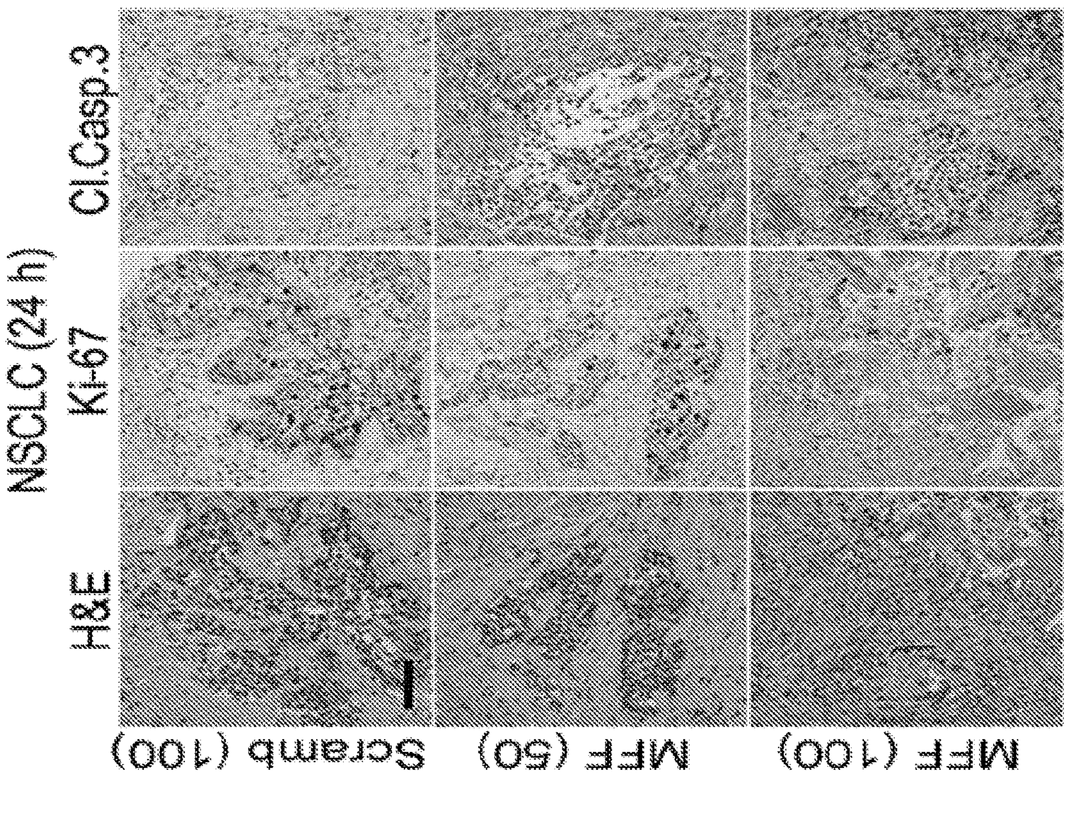
Figure 29K:
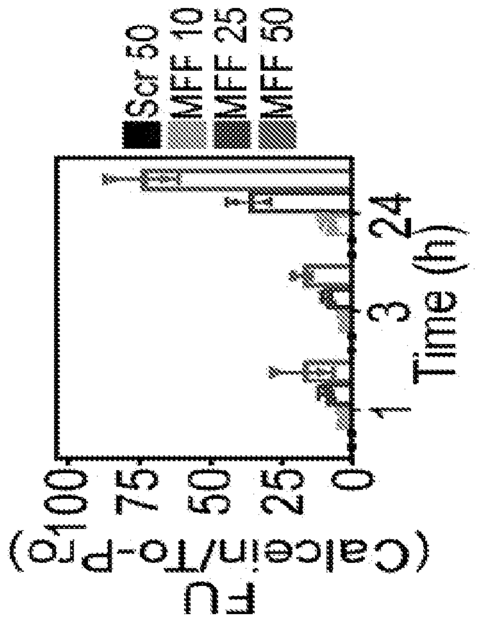
Figure 29J:
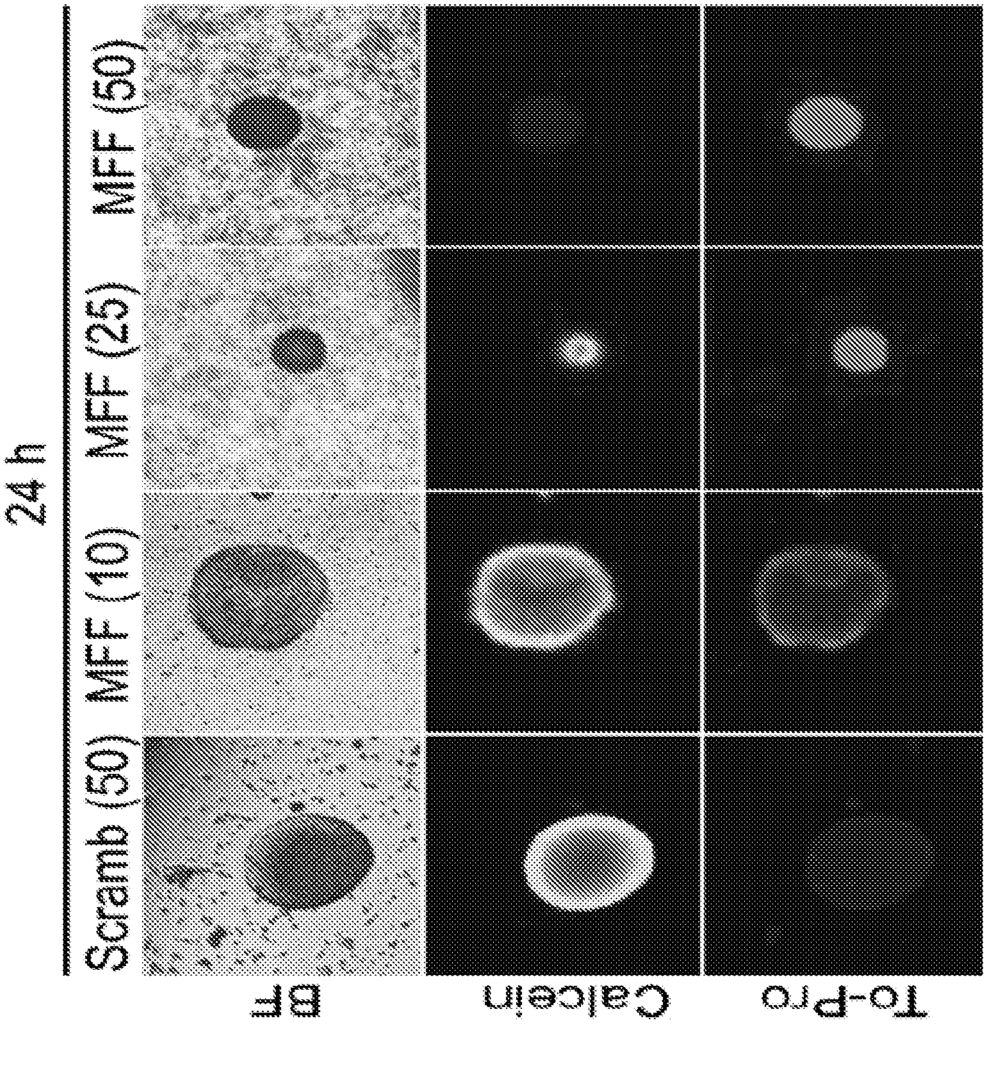

In a third preclinical model, treatment with the MFF (D) 8-11 peptidomimetic inhibited cell proliferation (loss of $Ki\text{-}67^{+}$ cells) and induced markers of cell death (increased cleaved caspase-3-positive cells) in patient-derived NSCLC (FIGS. 29G and 29H) or breast adenocarcinoma 3D tissue organoids maintained in short-term culture (FIG. 4B, FIG. 29I). A cell-permeable scrambled peptidomimetic had no effect on 3D tumor organoids (FIGS. 29G-29I, FIG. 4B). Consistent with these results, matched tumor cell lines, NSCLC A549 and H460 or breast adenocarcinoma MDA-231 and MCF-7 cells (FIG. 14D) expressed MFF1, MFF2 and MFF4, and exhibited mitochondrial depolarization and nearly complete killing after treatment with the MFF (D) 8-11 peptidomimetic, but not a scrambled sequence (FIG. 14E). Finally, patient-derived glioblastoma (GBM) neurospheres were looked at as a preclinical model enriched in cancer stem cells. In validation experiments, the cell-permeable MFF (D) 8-11 peptidomimetic efficiently killed GBM LN229 cells in a time- and concentration-dependent manner (FIG. 27A). Normal HFF were not affected and a control scrambled sequence did not cause LN229 cell killing (FIG. 27A). Consistent with these data, treatment with the MFF (D) 8-11 peptidomimetic, but not a scrambled peptide, was highly cytotoxic for patient-derived GBM neurospheres (FIG. 29J, FIG. 27B), resulting in time- and concentration-dependent loss of viability, as early as one hour after drug exposure (FIG. 29K).

Example 7—Discussion

In this study, it was shown that a regulator of mitochondrial fission, MFF is overexpressed in NSCLC and assembles in isoform-specific (MFF1 and MFF2) homo- and heterodimeric complexes with VDAC1 at the mitochondrial outer membrane. Peptidyl mimicry of the MFF-VDAC1 interaction is feasible and a cell-permeable MFF Ser223-Leu243 D-enantiomeric peptidomimetic disrupted MFF-VDAC1 complex(es), in vivo, triggered mitochondrial outer membrane permeability and killed genetically disparate tumor types, including drug-resistant melanoma, predominantly by regulated necrosis. Treatment with the MFF peptidomimetic was well tolerated and delivered potent anti-cancer activity in multiple preclinical, patient-derived tumor models.

The molecular details of how MFF functions as a novel regulator of VDAC1-directed mitochondrial outer membrane permeability remain to be fully elucidated. Although only MFF1 and MFF2 contain the sequence that directly binds VDAC1, structure-function studies demonstrated that other MFF isoforms are recruited in a multimeric complex with VDAC1, in vivo. NMR and reconstitution studies with isolated mitochondria have shown that also VDAC1 forms oligomers that assemble in "open" or "closed" configurations to regulate channel conductance. In this context, the predicted insertion of MFF multimers in the interior hole of the VDAC1 ring appears ideally suited to shut off oligomeric channel conductance and oppose cell death initiation in tumors. Without wishing to be bound by theory, a similar scenario of "channel closure" has been proposed for other VDAC binding-proteins with pro-survival functions, including HK-I and HK-II, which are also recruited in MFF-VDAC1 complex(es).

Example 8-Differential MFF Overexpression in Cancer

Figure 20B:
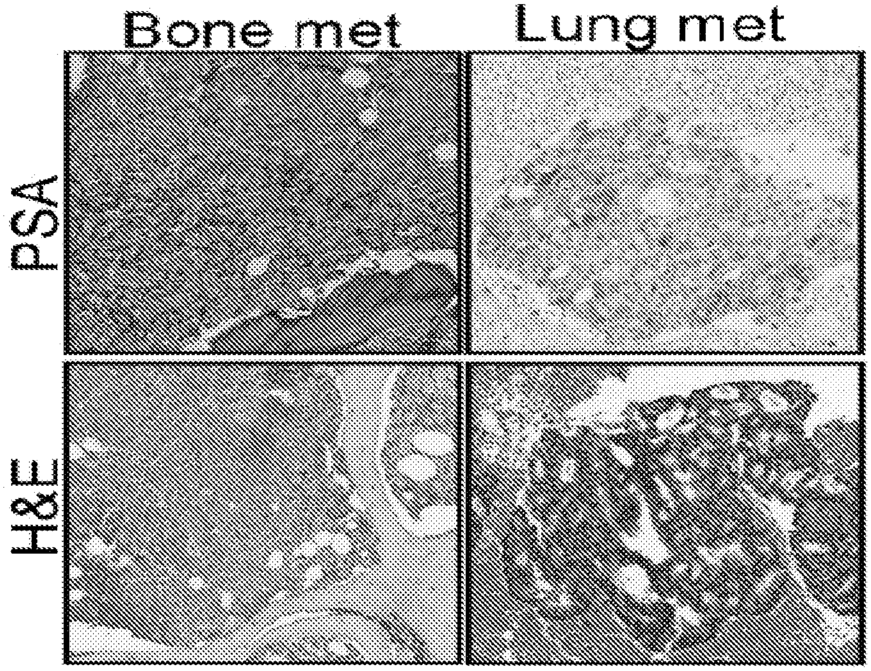
FIGS. 20A-20D illustrate MFF expression in prostate cancer.
Figure 20A:
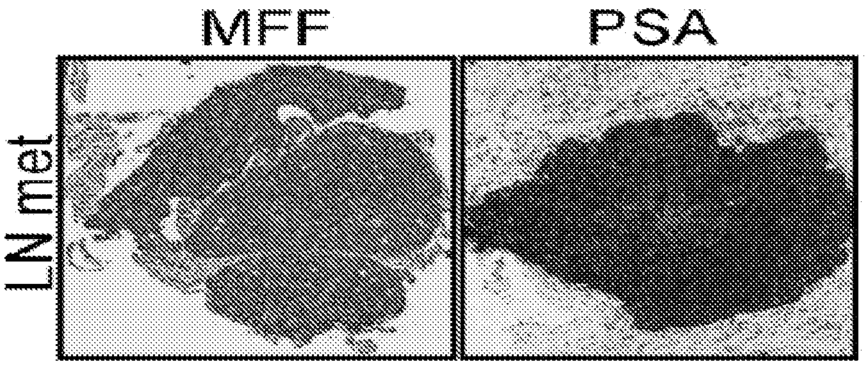
Figure 20D:
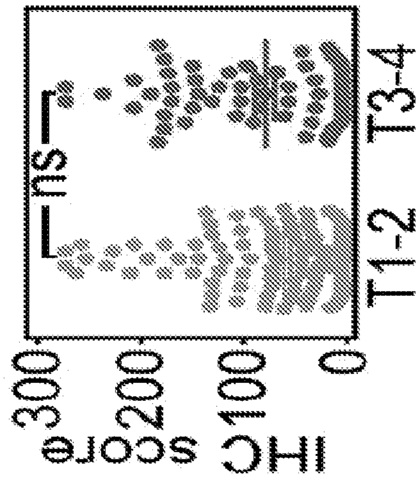
Figure 20C:
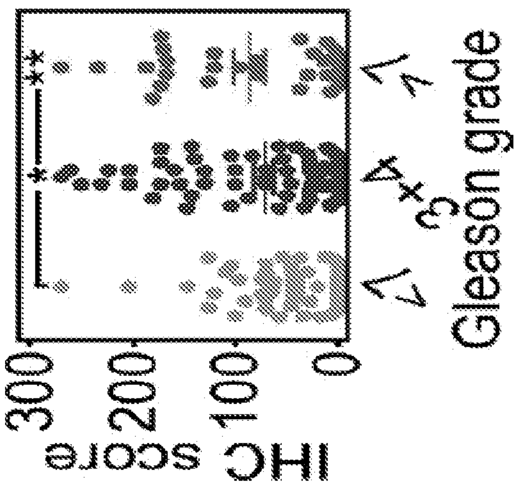

The expression of mitochondrial fission effectors, Drp1 and its outer mitochondrial membrane receptor MFF, was examined in prostate cancer. Analysis of public databases showed that MFF and Drp1 were amplified in castration-resistant and neuroendocrine prostate cancer (FIG. 1I), correlating with prostate cancer relapse (FIG. 1J) and abbreviated patient survival (FIG. 1K). In a cohort of 192 patients with localized and metastatic prostate cancer (Table 3), MFF levels were found to be increased from normal prostate to prostatic intraepithelial neoplasia (PIN) and were the highest in localized (FIGS. 1A and 1B) and metastatic prostate cancer to lymph nodes, bones and visceral sites (FIGS. 1A and 1C), by immunohistochemistry. These metastatic sites stained positive for prostate-specific antigen (PSA), confirming their prostatic origin (FIGS. 20A and 20B). In this patient series, increased MFF expression correlated with high Gleason grade (FIG. 20C), but not tumor size (FIG. 20D).

TABLE 3 clinico-pathological characteristics of patient-derived tissue samples used in this study.

| Group | ID | Site | Notes[2] |
|---|---|---|---|
| PCa metastasis | Met 3 | Brain | PSA positive; NE differentiation |
| | Met 5 | Bone | PSA positive |
| | Met 1 | Lung | PSA positive |
| | Met 2 | Lung | PSA positive |
| | Met 6 | Bone | PSA positive |
| | Met 7 | Bone | PSA positive |
| | Met 8 | Liver | PSA positive |
| | Met 9 | Axillary lymph nodes | PSA positive |
| | Met 10 | Bone | PSA positive |
| | Met 11 | Bone | PSA positive |
| | Met 12 | Brain | PSA positive |
| | Met 13 | Bone | PSA positive |
| | Met 14 | Inguinal lymph nodes | PSA positive |
| | Met 15 | Bone | PSA positive |
| | Met 16 | Bone | PSA positive |
| | Met 17 | Bone | PSA positive |
| | Met 20 | Lung | PSA positive |

TABLE 3-continued clinico-pathological characteristics of patient-derived tissue samples used in this study.

| Group | ID | Site | Notes[2] |
|---|---|---|---|
| Organ cultures | OC1 | Lung | NSCLC-SCC (pT2aN1) |
| | OC2 | Lung | NSCLC-SCC (pT1cN0) |
| | OC3 | Breast | DIC; Grade: G2 |
| GBM | NS91 | Brain | IDH1-WT; MGMT-UM |
| | NS92 | Brain | IDH1-WT; MGMT-M |

Figure 21B:
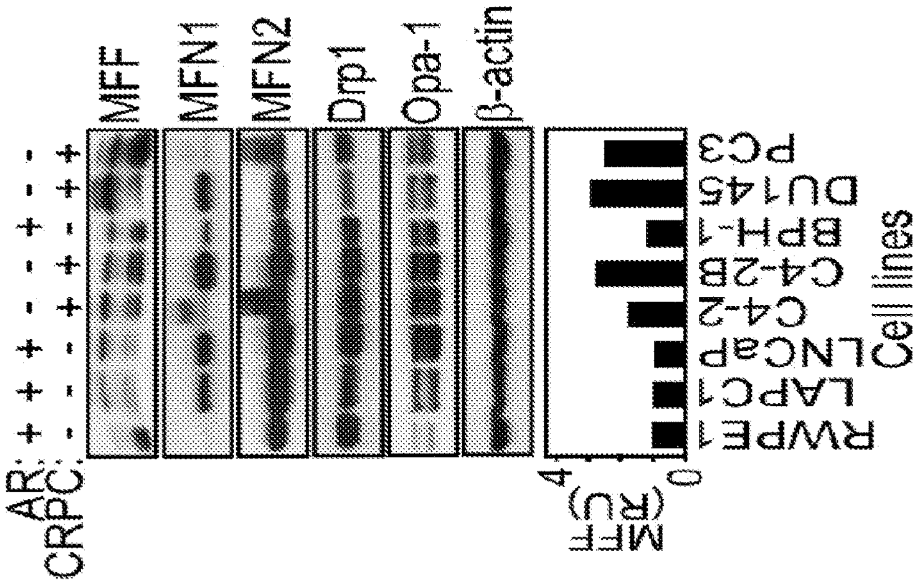
FIGS. 21A-21B illustrate MFF expression in TRAMP mice.
Figure 21A:
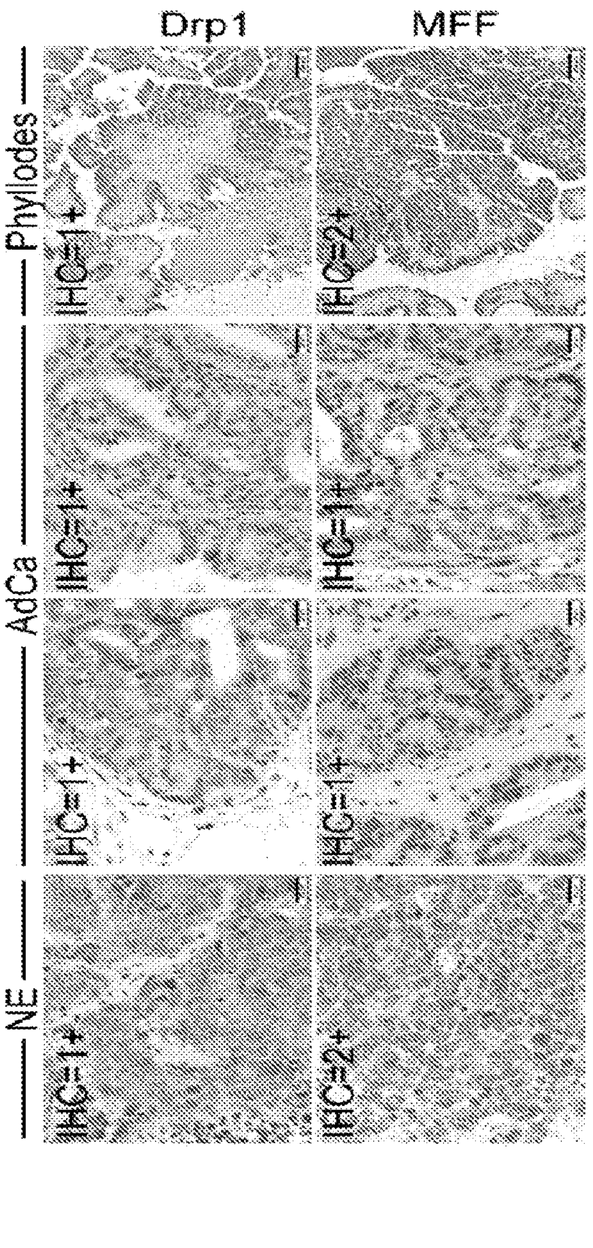

[2]PSA, prostate specific antigen;
NSCLC, Non-Small Cell Lung Cancer;
SCC, squamous cell carcinoma;
DIC, Ductal Infiltrating Carcinoma;
IDH1-WT, IDH1 wild-type;
MGMT-UM/M, MGMT methylated/unmethylated As an independent approach, a genetic model of prostate cancer, i.e. Transgenic Adenocarcinoma of the Mouse Prostate (TRAMP) was looked at. Prostatic tumors formed in TRAMP mice, including neuroendocrine (NE) prostate cancer, well-differentiated adenocarcinoma (AdCa) and phyllodes-type tumors all expressed high levels of MFF, by immunohistochemistry (FIG. 21A). In contrast, Drp1 was present at low levels in these tumors from TRAMP mice (FIG. 21A). Consistent with these observations, most prostate cancer cell lines expressed MFF, with the highest levels observed in castration-resistant as opposed to androgen receptor (AR)-positive cell types (FIG. 21B). Other regulators of mitochondrial fusion (MFN1, MFN2, Opal) or fission (Drp1) showed more variable expression in prostate cancer cell lines (FIG. 21B).

Next, whether MFF was overexpressed in other tumor types was investigated. MFF was found to be highly expressed in patients with non-small cell lung cancer (NSCLC) including cases of adenocarcinoma (AdCa) and squamous cell carcinoma (SCC), compared to normal bronchus, by immunohistochemistry. In addition, MFF was strongly expressed in cases of multiple myeloma (MM), compared to patients with monoclonal gammopathy of uncertain significance (MGUS), by immunohistochemistry (FIGS. 1L and 1M).

Example 9-MFF is a Novel Myc Transcriptional Target

Figure 15B:
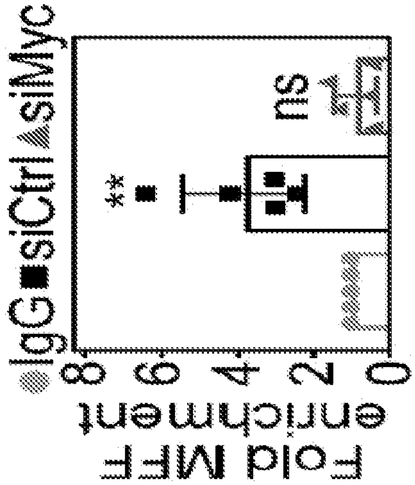
FIGS. 15A-15I illustrate that MFF is a novel transcriptional target of oncogenic Myc.
Figure 15C:
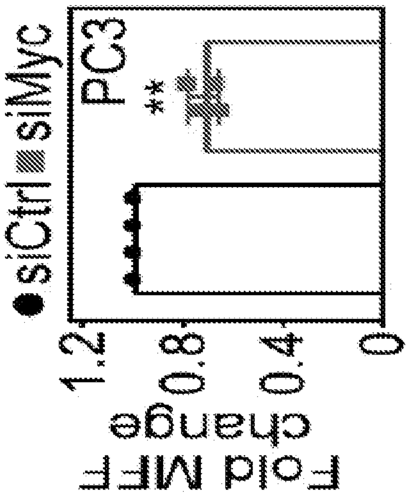
Figure 15A:
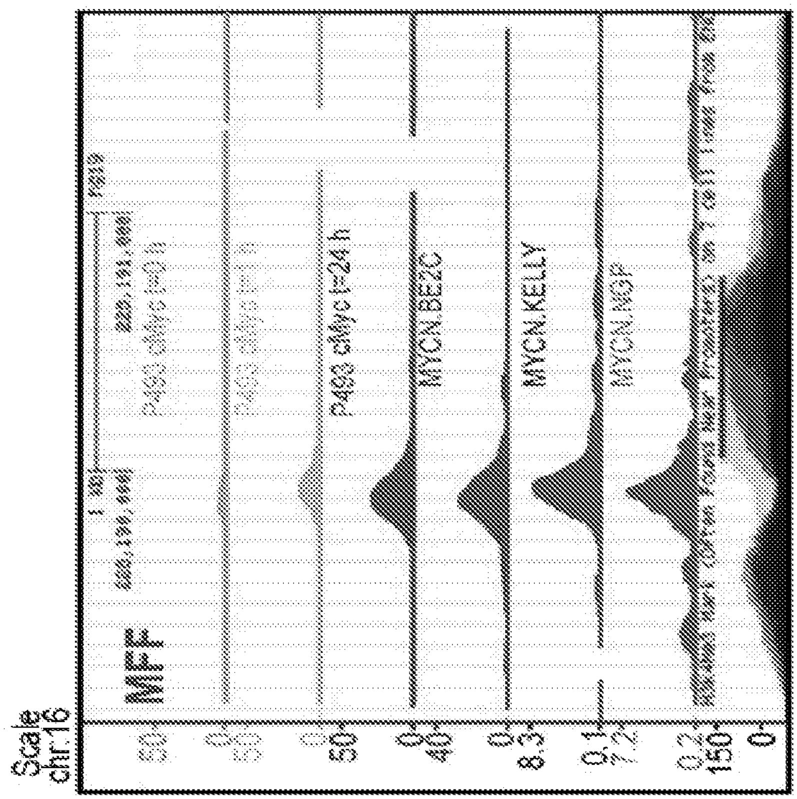
Figure 15D:
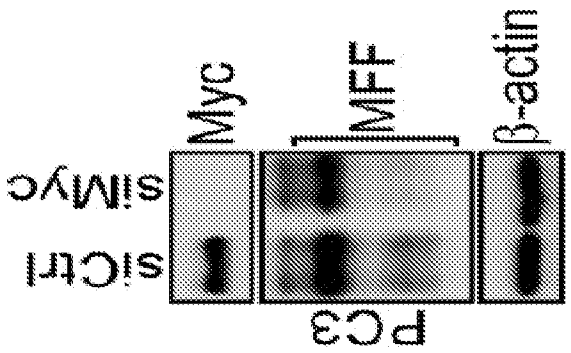

To begin elucidating how MFF becomes overexpressed in cancer, the Myc oncogene was focused on, which is a key disease driver in prostate cancer and MM. Analysis of ChIP-Seq tracks demonstrated time-dependent accumulation of Myc at the MFF promoter in Burkitt lymphoma P493 cells as well as neuroblastoma BE2C, Kelly and NGP cell lines (FIG. 15A). In chromatin immunoprecipitation (ChIP) experiments, Myc readily bound to the promoter of MFF in PC3 cells, in a reaction abolished by siRNA knockdown of Myc (FIG. 15B). Consistent with these data, Myc silencing by siRNA, but not control siRNA, reduced MFF mRNA levels (FIG. 15C) and protein expression (FIG. 15D) in PC3 cells, by quantitative PCR and Western blotting, respectively.

Figure 15E:
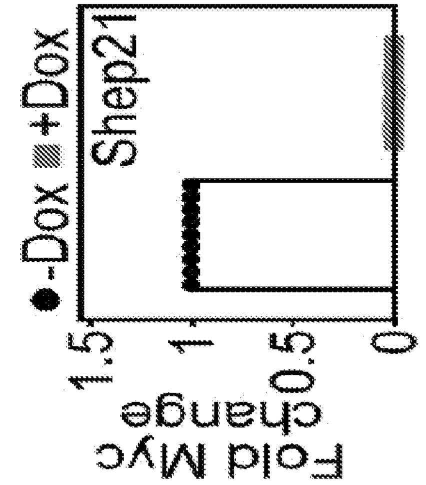
Figure 15F:
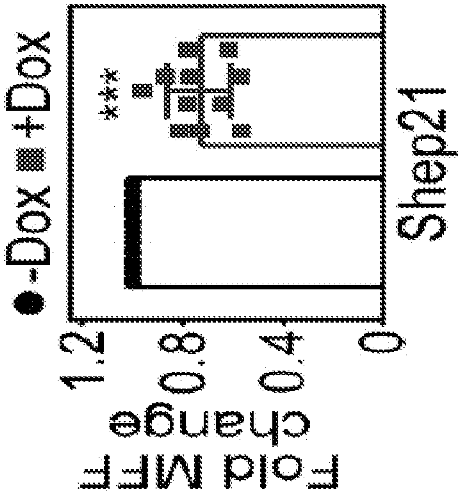
Figure 15G:
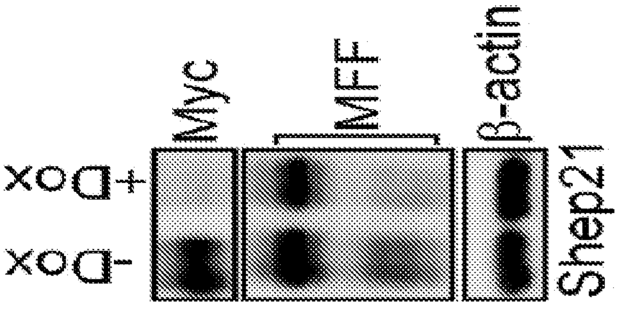

To independently validate these results, the model of Shep21 neuroblastoma cells engineered with doxycycline (Dox)-regulated conditional ablation of Myc, or, alternatively, 4-hydroxy-tamoxifen (4OHT)-dependent Myc induction (Shep21-ER) were used. Addition of Dox abolished Myc mRNA levels in Shep21 cells (FIG. 15E), and this was associated with reduced MFF mRNA (FIG. 15F) and protein (FIG. 15G) expression, compared to control transfectants.

Figure 15H:
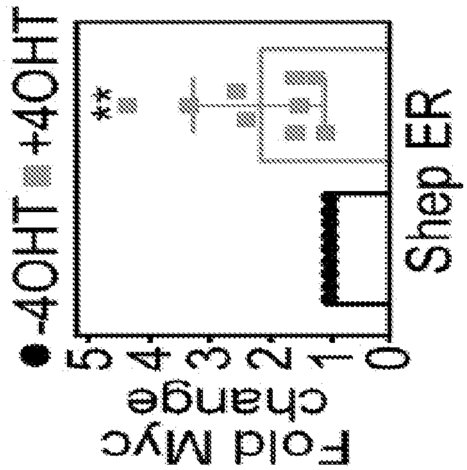
Figure 15I:
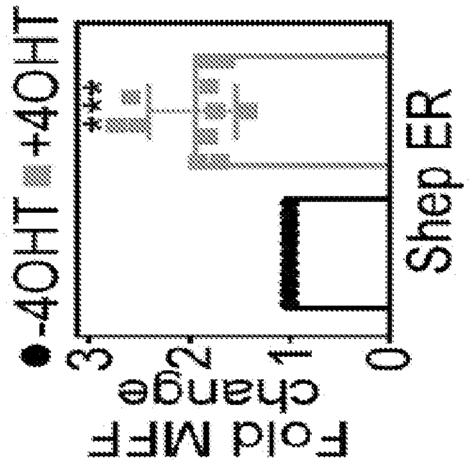

Reciprocally, addition of 4OHT to Shep21-ER cells increased the mRNA levels of Myc (FIG. 15H) as well as MFF (FIG. 15I), compared to cultures in the absence of 4OHT.

Example 10-MFF Controls Mitochondrial Fission in Cancer

Figure 22B:
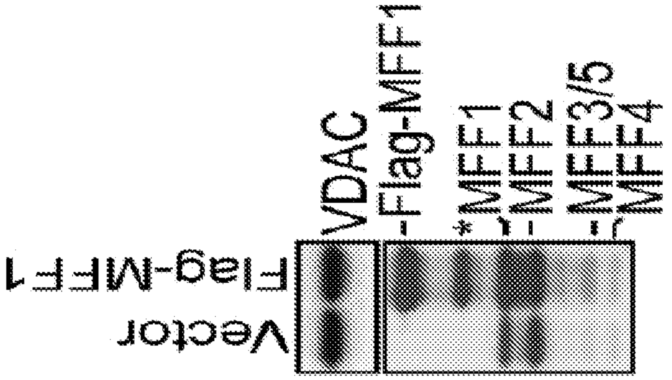
FIGS. 22A-22D illustrate MFF regulation of mitochondrial fission in cancer.
Figure 22A:
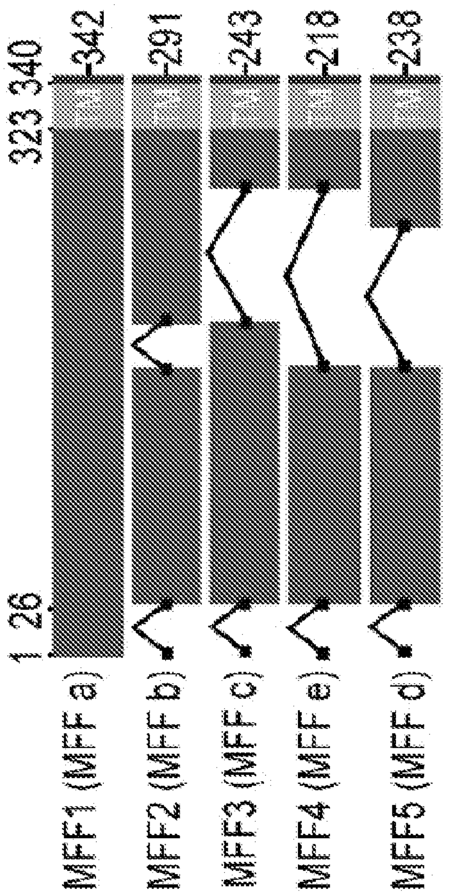
Figure 22C:
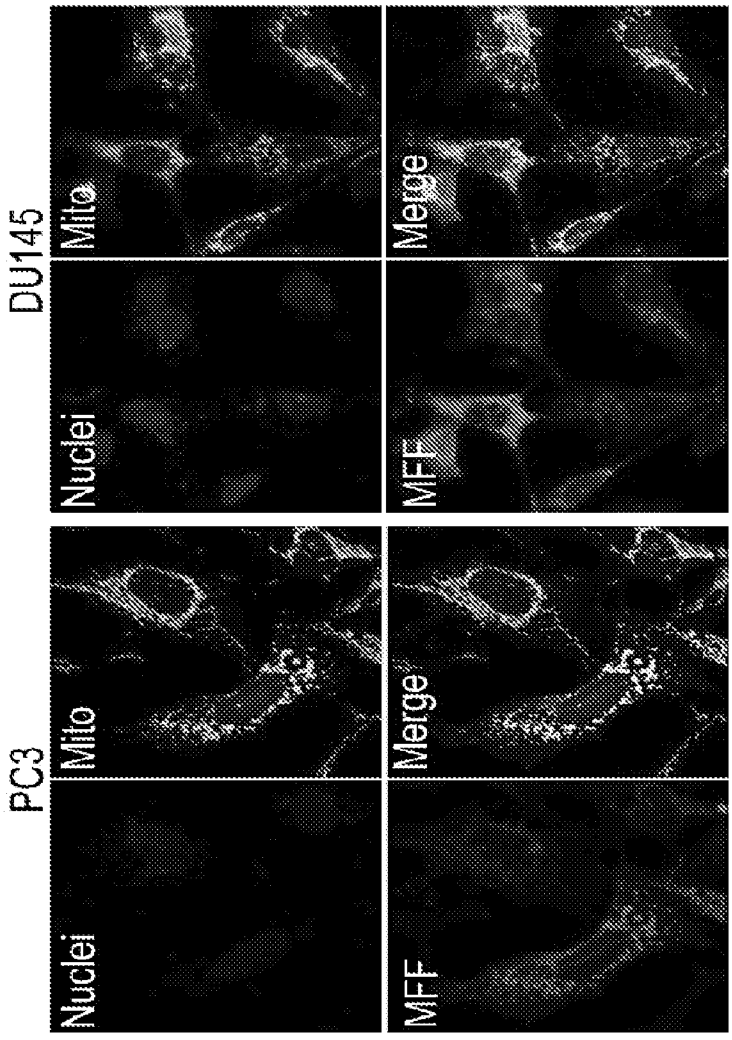
Figure 22D:
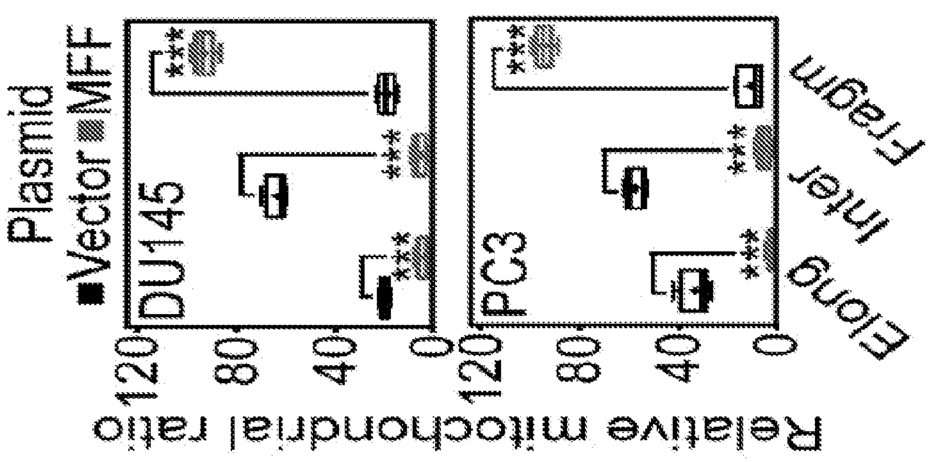

The function of MFF in cancer was examined. Processing of the human MFF locus is predicted to generate at least five protein isoforms by alternative splicing (FIG. 22A). Of these, MFF1 and MFF2 were the most abundantly expressed isoforms in PC3 cells (FIG. 22B). In addition, transfection of Flag-MFF1 in these settings produced levels of recombinant protein comparable to endogenous MFF1 (FIG. 22B). Using this approach, expression of MFF1 in PC3 cells caused extensive mitochondrial fragmentation, i.e. fission, and loss of mitochondrial elongation (FIGS. 22C and 22D), consistent with a role of this pathway in mitochondrial dynamics.

Figure 23A:
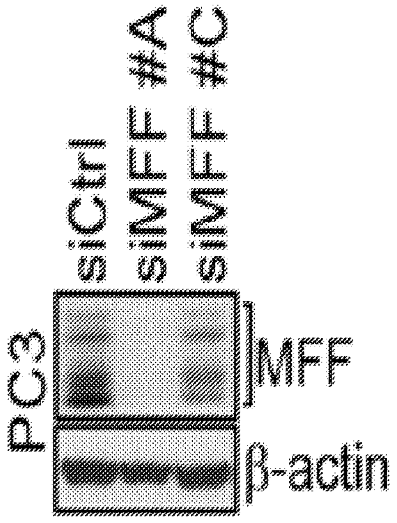
FIGS. 23A-23E illustrate MFF silencing in tumor cells.
Figure 23B:
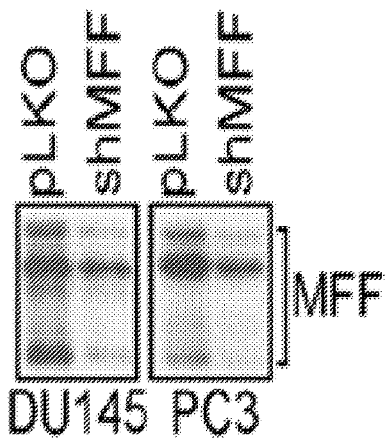
Figure 23C:
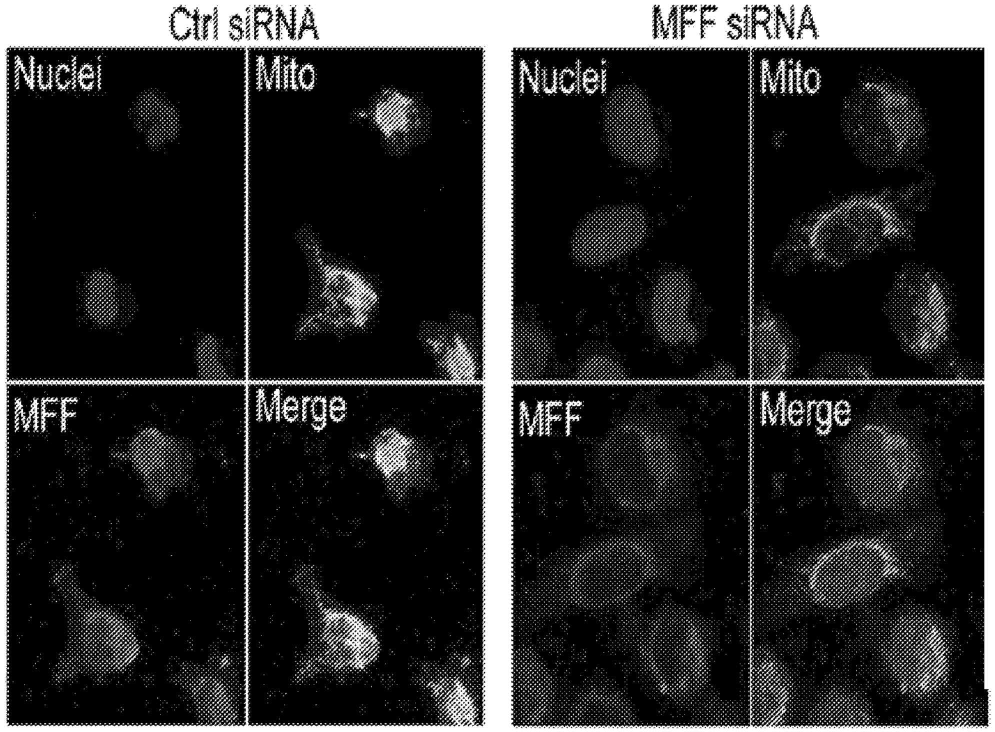
Figure 23E:
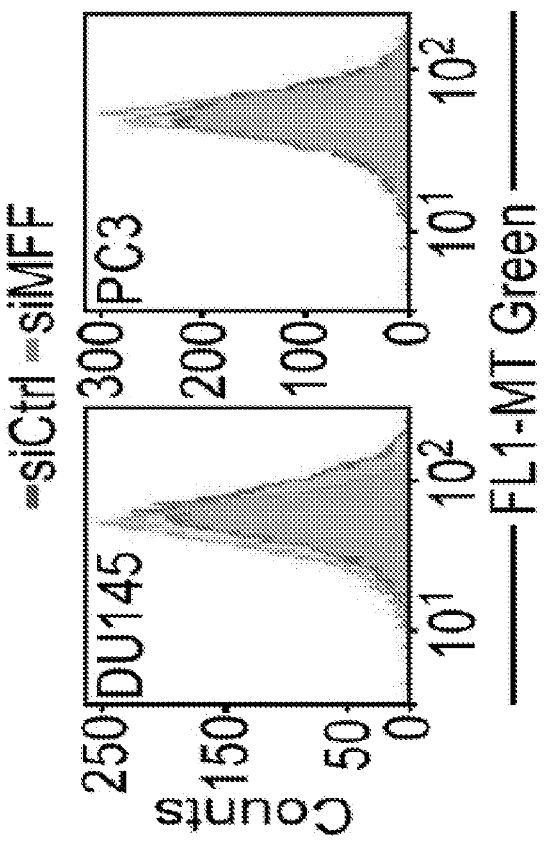
Figure 23D:
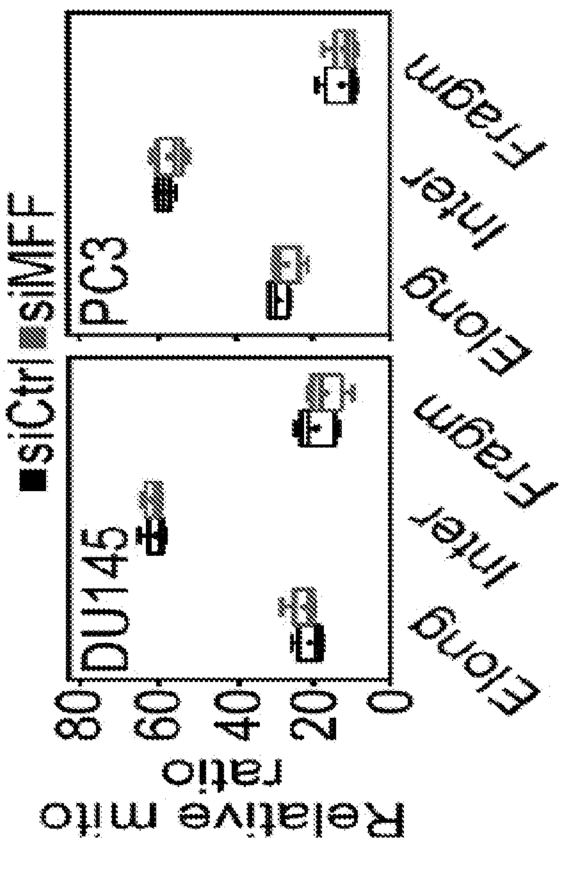

To carry out reciprocal experiments, two independent siRNA sequences were established that reduce expression of all MFF isoforms in PC3 cells (FIG. 23A). In parallel, clones of DU145 and PC3 cells stably transduced with pLKO or MFF-directed shRNA were generated, which also reduced endogenous MFF levels, compared to pLKO cultures (FIG. 23B). Functionally, MFF knockdown did not significantly affect mitochondrial dynamics, as comparable fractions of elongated or fragmented mitochondria were observed in control transfectants and MFF-silenced cells (FIGS. 23C and 23D). Consistent with these data, MFF knockdown did not affect mitochondrial mass in DU145 or PC3 cells (FIG. 23E). These data are consistent with a proposed role for other mitochondrial outer membrane receptor(s) in Drp1 binding and organelle fission.

Example 11—MFF Associates with VDAC1 at the Mitochondrial Outer Membrane

Figure 16C:
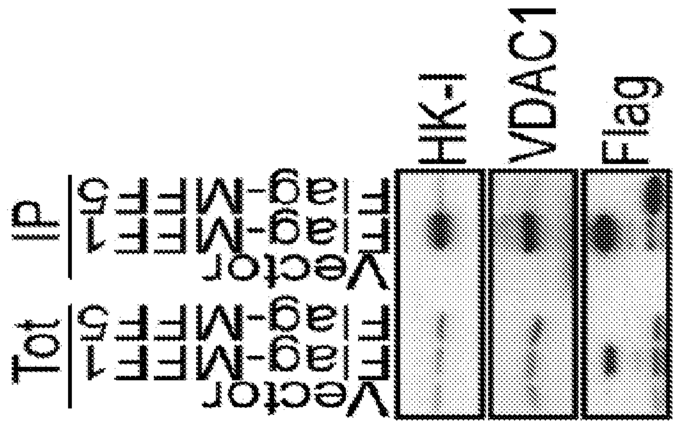
FIGS. 16A-16F illustrate MFF regulation of mitochondrial outer membrane permeability.
Figure 16B:
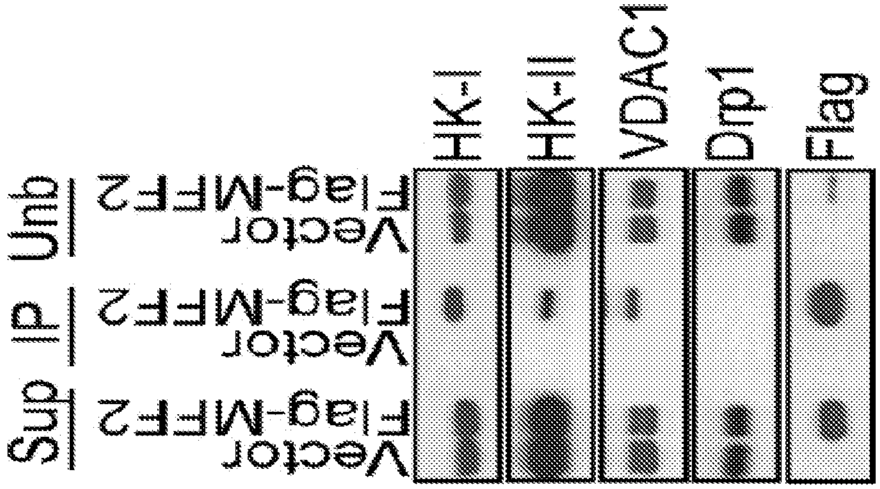
Figure 16A:
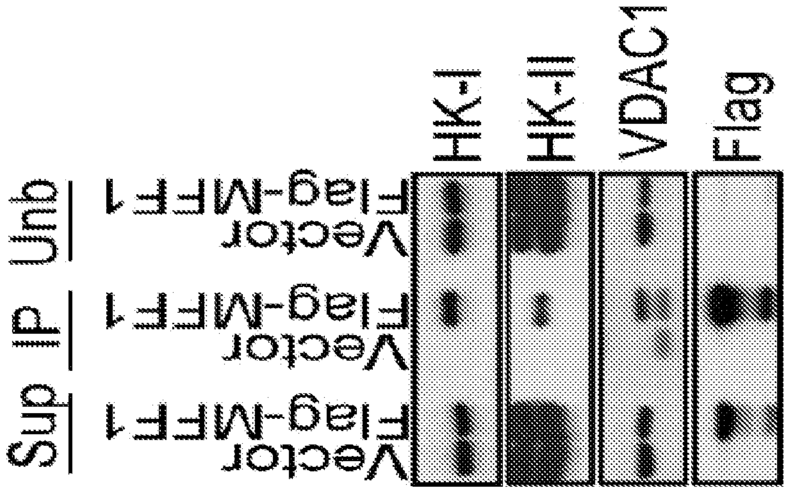

To test whether MFF had other functions in cancer, a proteomics screen for MFF-associated molecules in PC3 cells was conducted. One of the top hits in the screen was VDAC1. Consistent this prediction, it was found that MFF1 (FIG. 16A) and MFF2 (FIG. 16B) co-immunoprecipitated with VDAC1 in PC3 cells. Other mitochondrial outer membrane proteins that bind VDAC1, including hexokinase-I (HK-I) and -II (HK-II) were also present in the MFF-VDAC1 complex in PC3 cells (FIGS. 16A and 16B). In contrast, the MFF ligand Drp1 did not co-immunoprecipitate with the MFF-VDAC1 complex (FIG. 16B). Finally, this interaction was selective as another MFF isoform, MFF5 did not associate with VDAC1 or HK-I, by co-immunoprecipitation in PC3 cells (FIG. 16C).

Figure 16D:
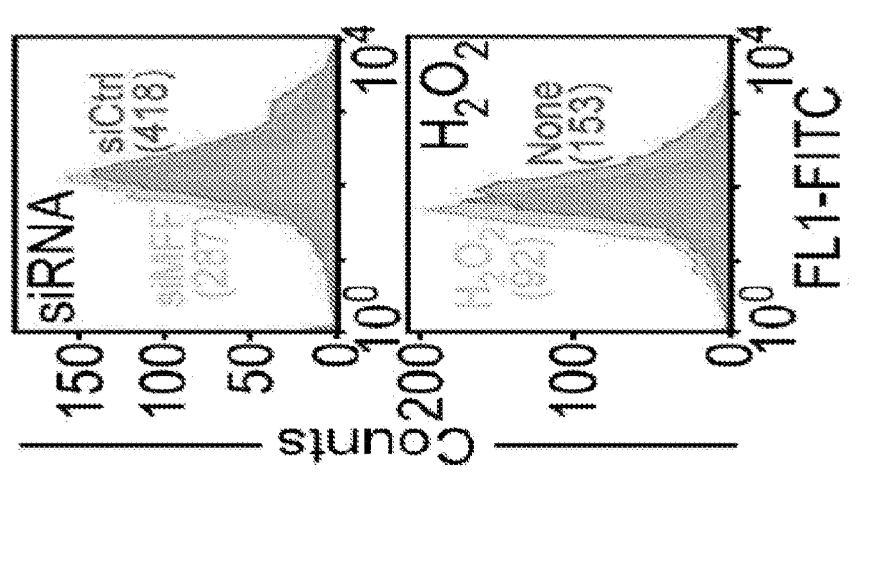
Figure 16E:
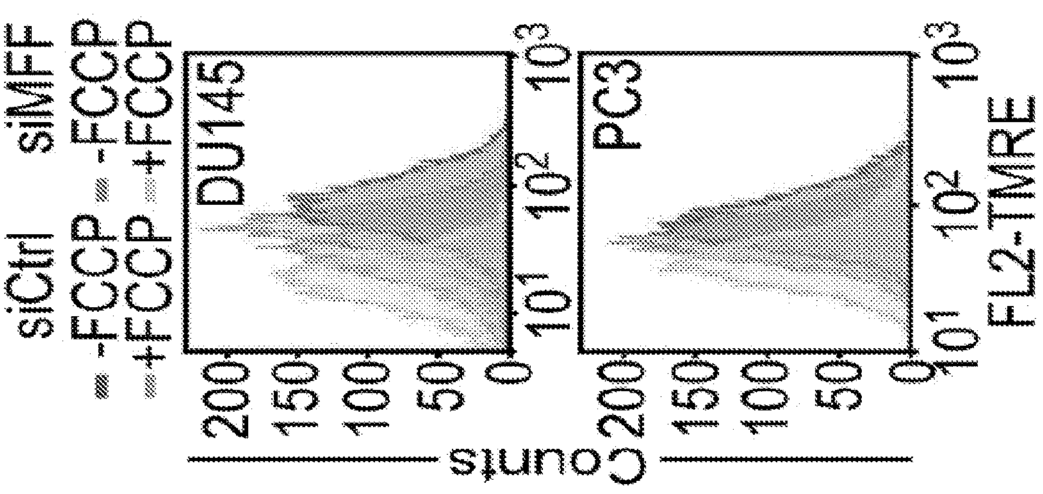
Figure 16F:
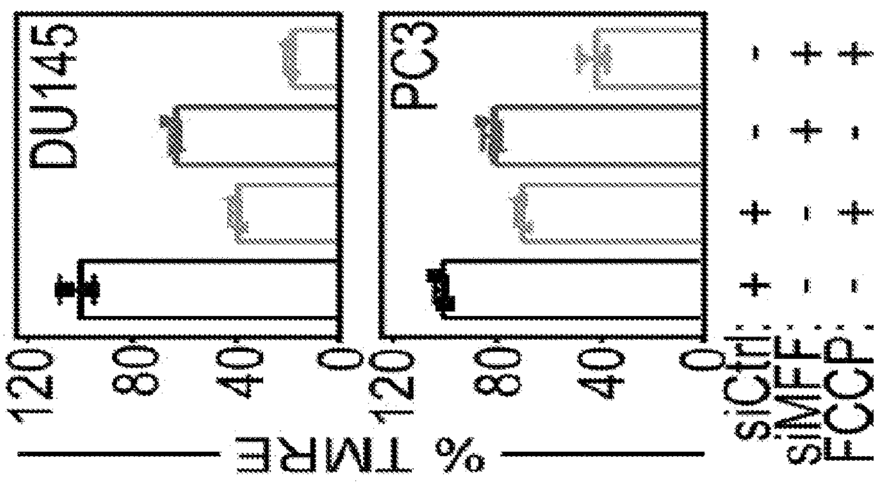
Figure 24B:
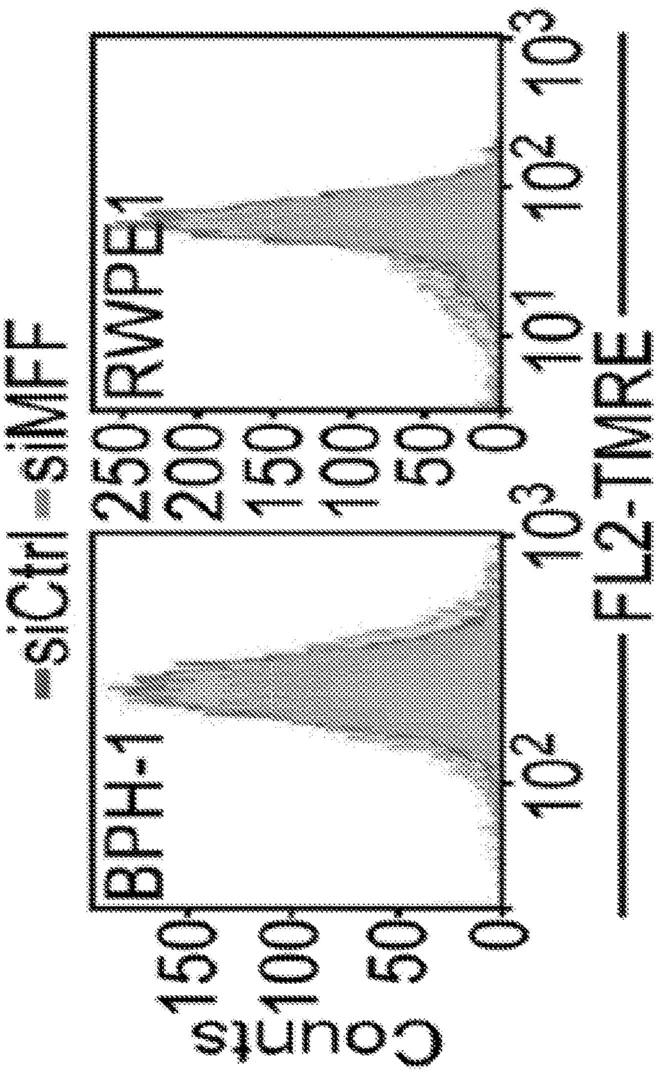
FIGS. 24A-24D illustrate MFF regulation of tumor cell metabolism.
Figure 24A:
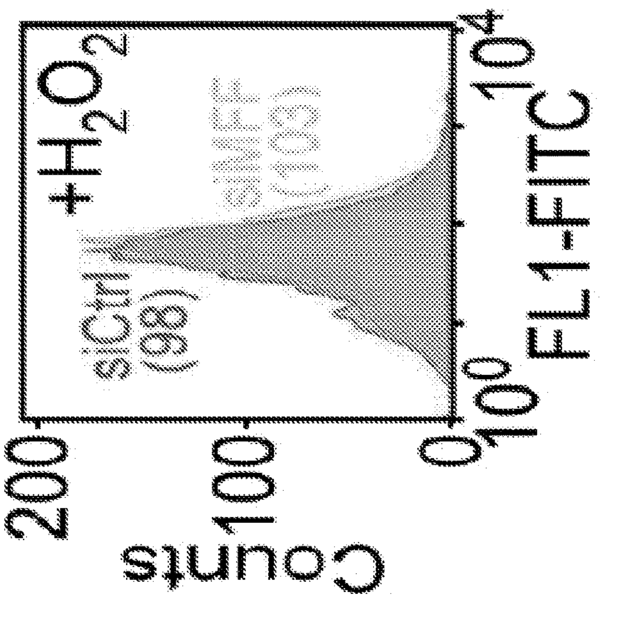

Based on these data, whether MFF regulated VDAC1 function in cancer was investigated. Disruption of the MFF-VDAC1 complex by MFF knockdown resulted in increased permeability of the mitochondrial outer membrane, as measured by quantification of mitochondrial calcein fluorescence and flow cytometry (FIG. 16D). This response was quantitatively comparable to the increase in mitochondrial outer membrane permeability induced by $H_2O_2$ (FIG. 16D) and was not further increased in the combination of $H_2O_2$ plus MFF knockdown (FIG. 24A). In addition, MFF silencing in DU145 or PC3 cells was associated with loss of mitochondrial inner membrane potential, in a reaction further amplified by suboptimal concentrations of the uncoupler, carbonyl cyanide p-trifluoromethoxyphenylhydrazone (FCCP) (FIGS. 16E and 16F). Conversely, MFF silencing did not depolarize mitochondria in normal prostate epithelial BPH-1 or RWPE1 cells (FIG. 24B). In these experiments, normal epithelial cells or prostate cancer cell lines had comparable basal levels of mitochondrial membrane potential (FIG. 16D and FIG. 24B).

Example 12—MFF Control of Tumor Bioenergetics

Figures 17A, 17B, 17C, 17D:
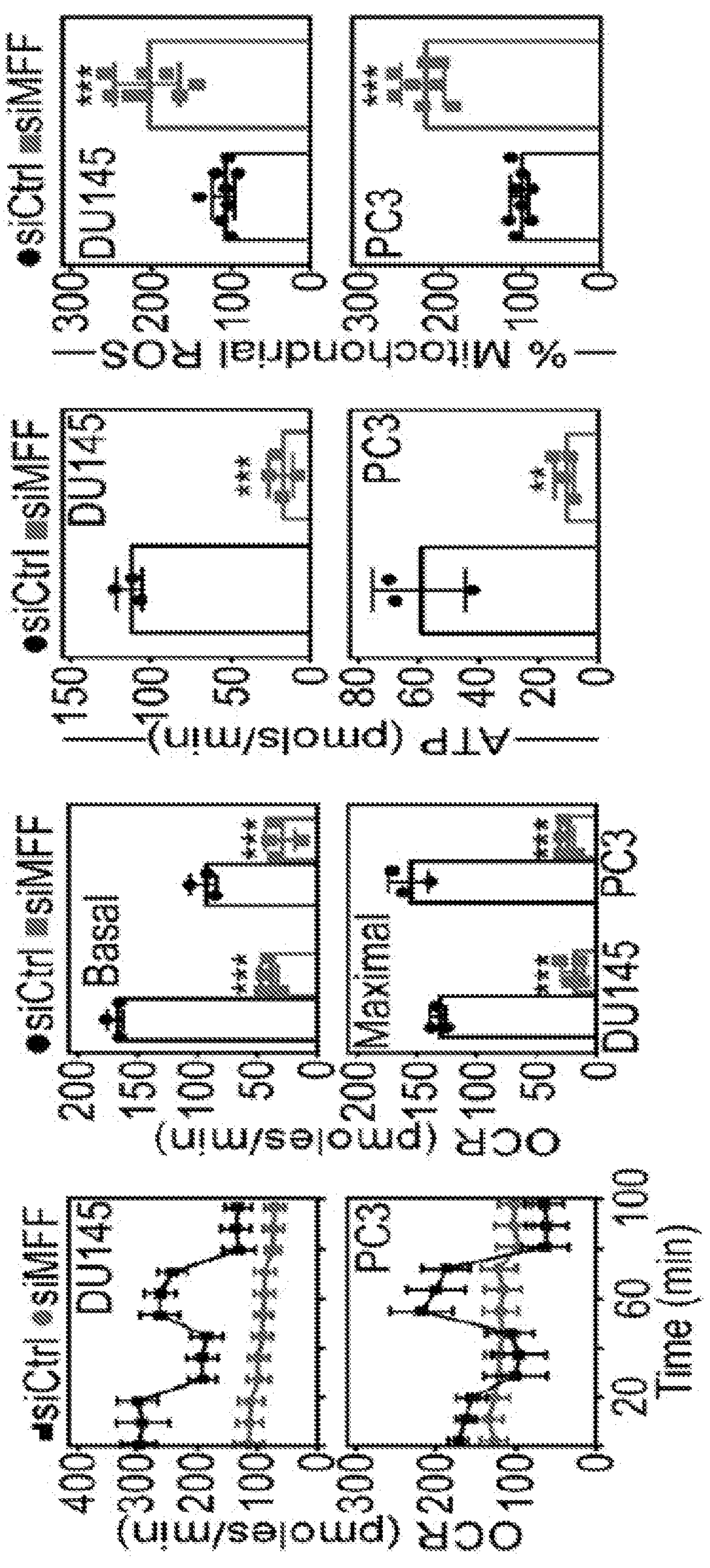
FIGS. 17A-17G illustrate MFF regulation of mitochondrial oxidative metabolism.
Figure 24D:
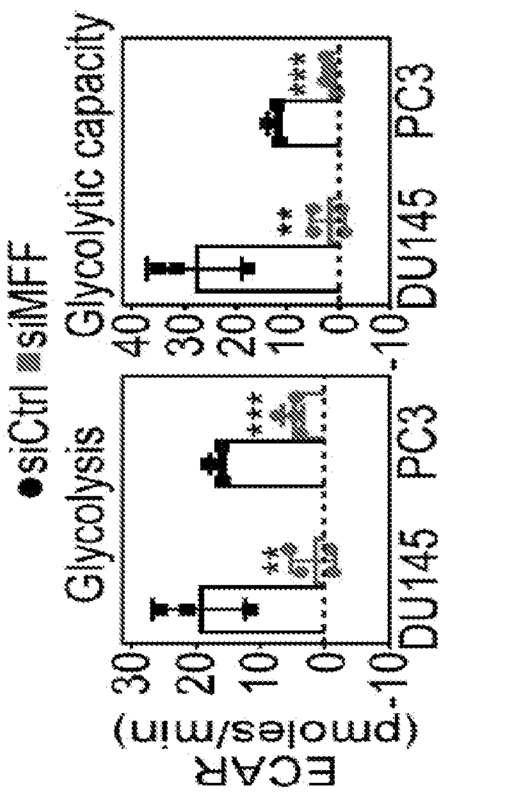
Figure 24C:
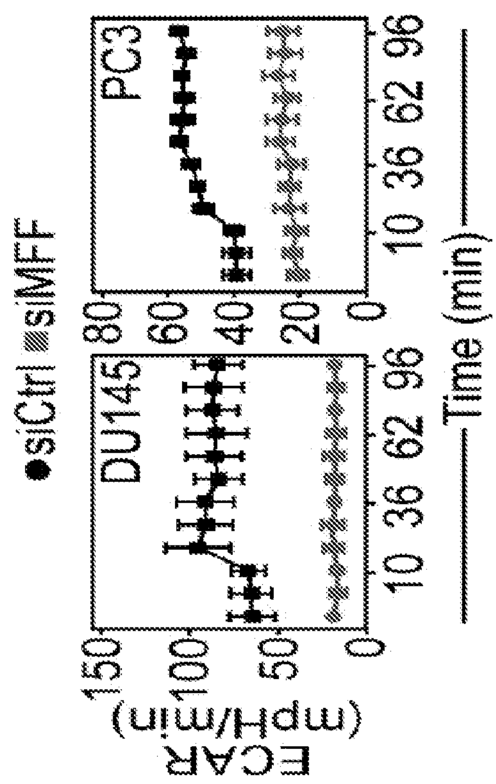

Depolarization of the mitochondrial inner membrane uncouples the TCA cycle, and, accordingly, MFF-targeted cells exhibited extensive bioenergetics defects. This included suppression of Oxygen Consumption Rates (OCR), a marker of oxidative phosphorylation (FIG. 17A), with significant decrease in both basal and maximal respiratory capacity (FIG. 17B). Further, MFF knockdown in DU145 and PC3 cells was accompanied by loss of Extracellular Acidification Rates (ECAR) (FIG. 24C) and decreased glycolysis as well as glycolytic capacity, compared to control transfectants (FIG. 24D).

Figure 17E:
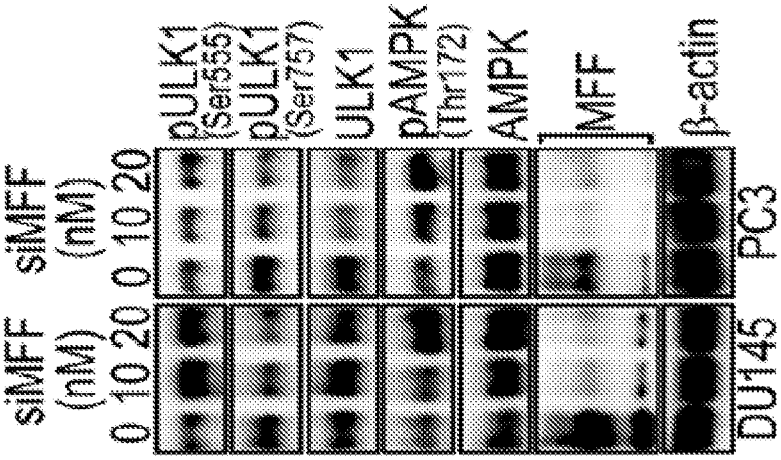
Figure 17F:
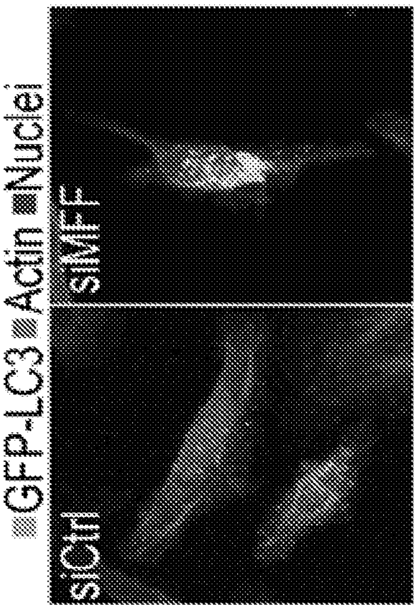
Figure 17G:
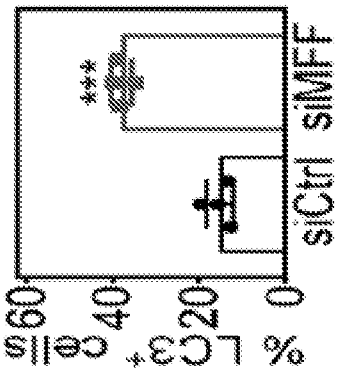

Consistent with impaired bioenergetics, MFF silencing nearly completely abolished ATP production in prostate cancer cells (FIG. 17C). This was associated with oxidative stress and increased production of mitochondrial-derived ROS after MFF knockdown (FIG. 17D). Due to these bioenergetics defects, MFF-targeted DU145 and PC3 cells exhibited hallmarks of nutrient deprivation, with increased phosphorylation ($Thr^{172}$) of the energy sensor, AMPK (FIG. 17E), differential phosphorylation of the autophagy activator, ULK1 with increased phosphorylation on the AMPK ($Ser^{555}$) and decreased phosphorylation on the mTOR ($Ser^{757}$) site (FIG. 17E), and induction of autophagy, with increased punctate LC3 staining, by fluorescence microscopy (FIGS. 17F and 17G).

Example 13—MFF Regulates Mitochondrial Cell Death

Figure 18A:
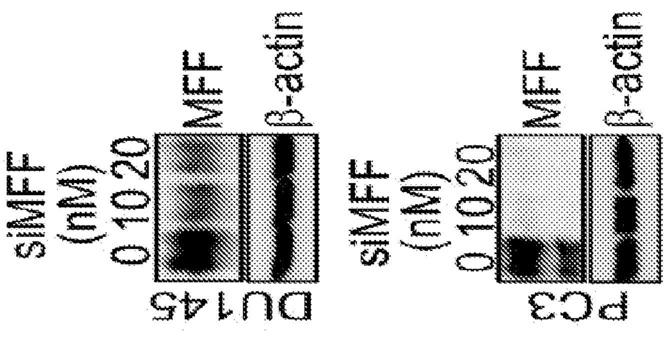
FIGS. 18A-18G illustrate MFF inhibition of mitochondrial cell death.
Figure 18B:
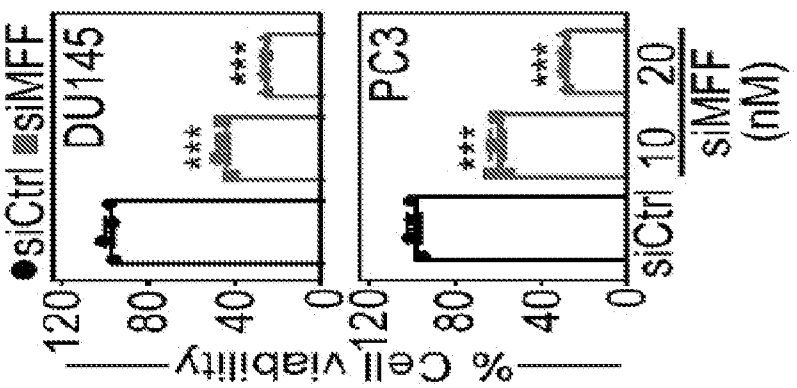
Figure 18C:
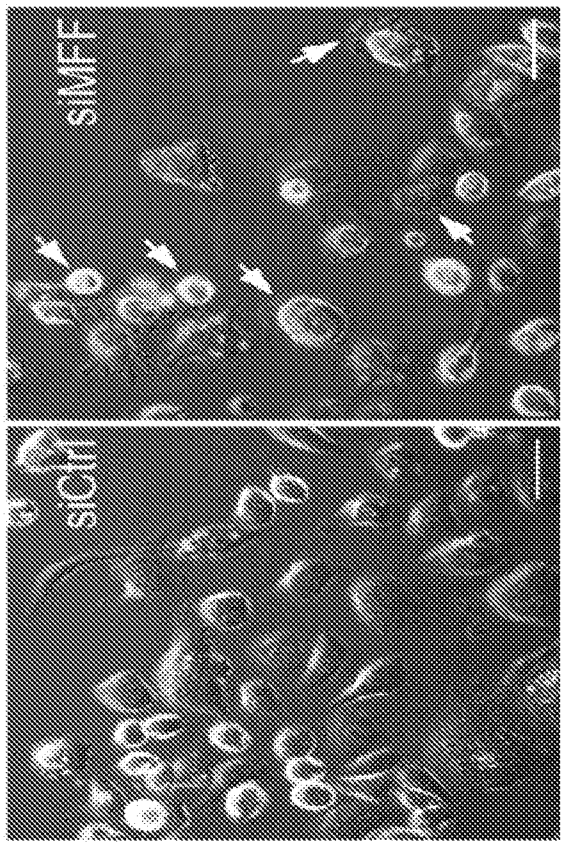
Figure 18E:
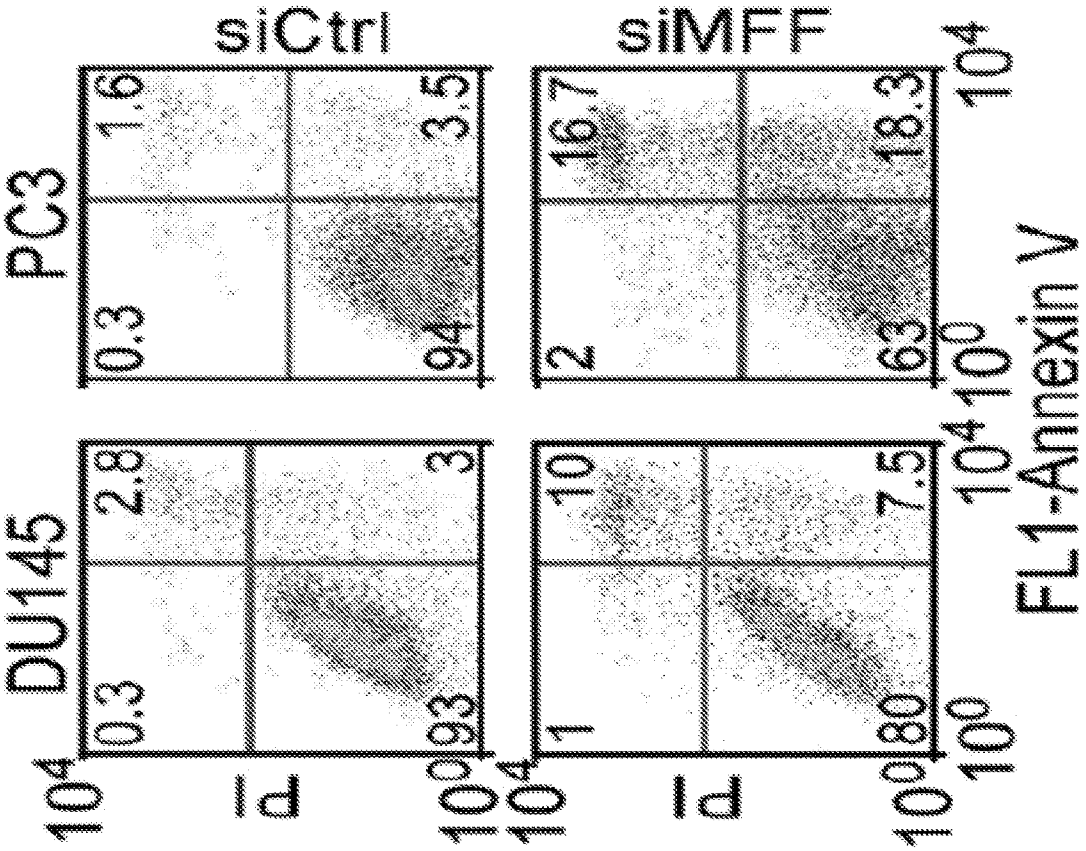
Figure 18D:
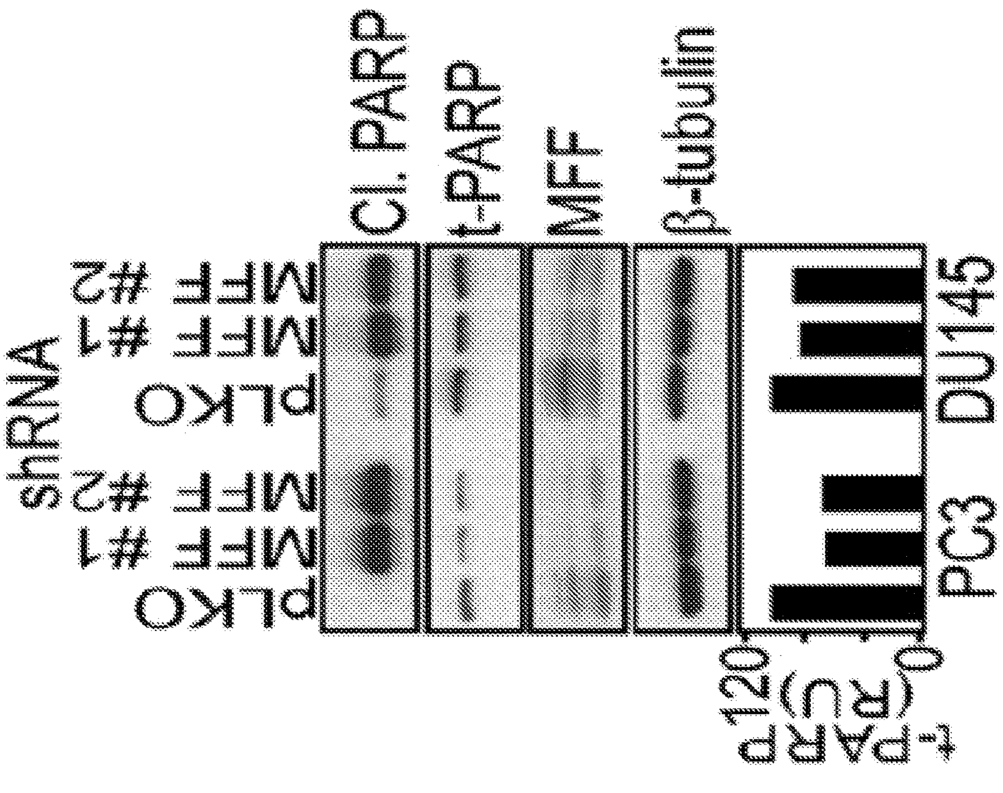

Consistent with a general collapse of mitochondrial integrity, concentration-dependent depletion of MFF by siRNA (FIG. 18A) induced mitochondrial-dependent killing of DU145 and PC3 cells (FIG. 18B). This response was associated with hallmarks of apoptosis, including membrane blebbing and chromatin condensation (FIG. 18C), proteolytic processing of PARP (FIG. 18D) and increased Annexin V labeling (FIG. 18E). When combined with other stress stimuli, including nutrient deprivation, oxidative stress ($H_2O_2$) or chemotherapeutic agents, etoposide or doxorubicin, MFF knockdown further augmented PARP cleavage in prostate cancer cells (FIG. 25A).

Figure 18G:
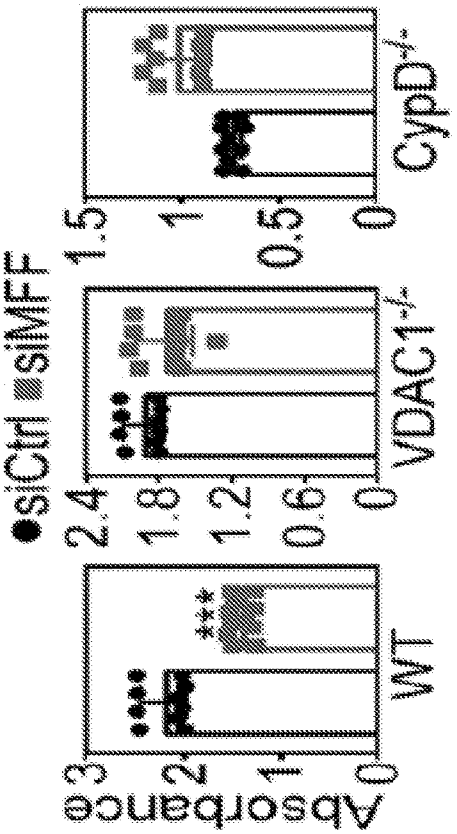
Figure 18F:
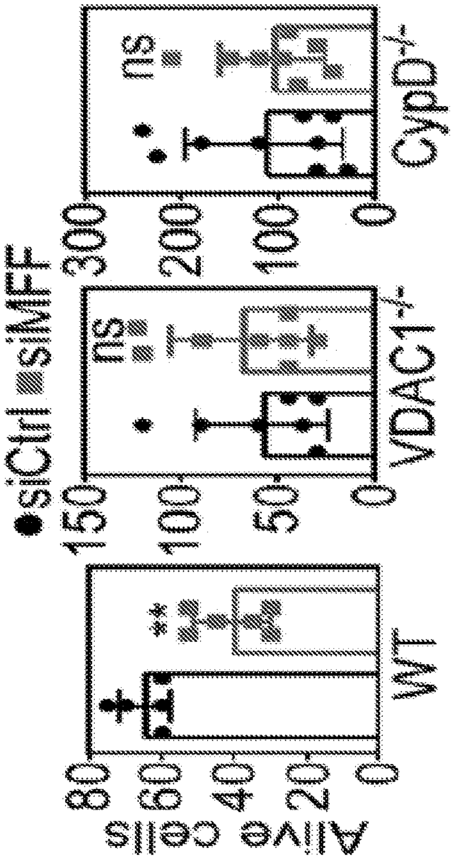
Figure 25B:
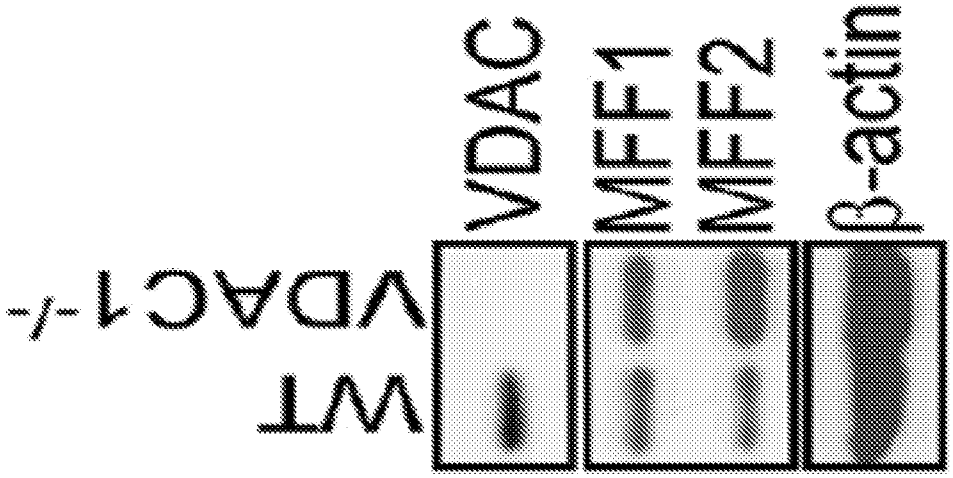
FIGS. 25A-25E illustrate MFF regulation of tumor cell proliferation.
Figure 25A:
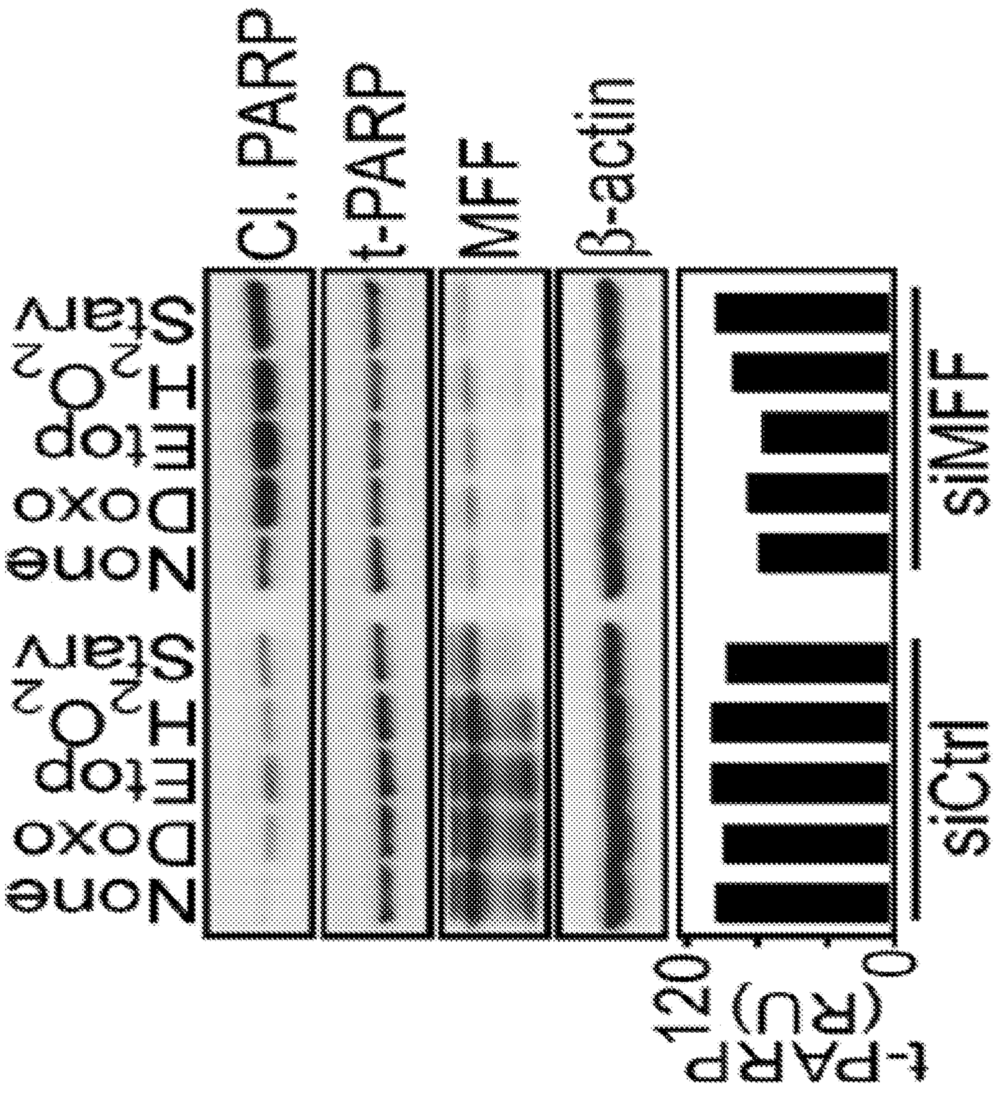

To test the requirements of these cell death pathway(s), genetically-modified mouse embryonic fibroblasts (MEF) that express endogenous levels of MFF1 and MFF2 were used (FIG. 25B). Consistent with the data above, MFF silencing induced cell death in wild type (WT) MEF, as determined by Trypan blue exclusion and light microscopy (FIG. 18F). In contrast, MEF knockout for VDAC1 (FIG. 25B) were entirely resistant to cell death induced by MFF silencing (FIG. 18F). Similarly, MEF with homozygous deletion of Cyclophilin D (CypD), an essential effector of regulated necrosis, were protected from cell death after MFF knockdown (FIG. 18F). Similar studies were carried out by quantifying mitochondrial-associated cell death by an MTT assay. Similar to the data above, MFF silencing induced killing of WT MEF, whereas VDAC1 knockout or CypD knockout MEF were not affected (FIG. 18G).

Example 14—MFF is Required for Tumor Growth

Figure 19B:
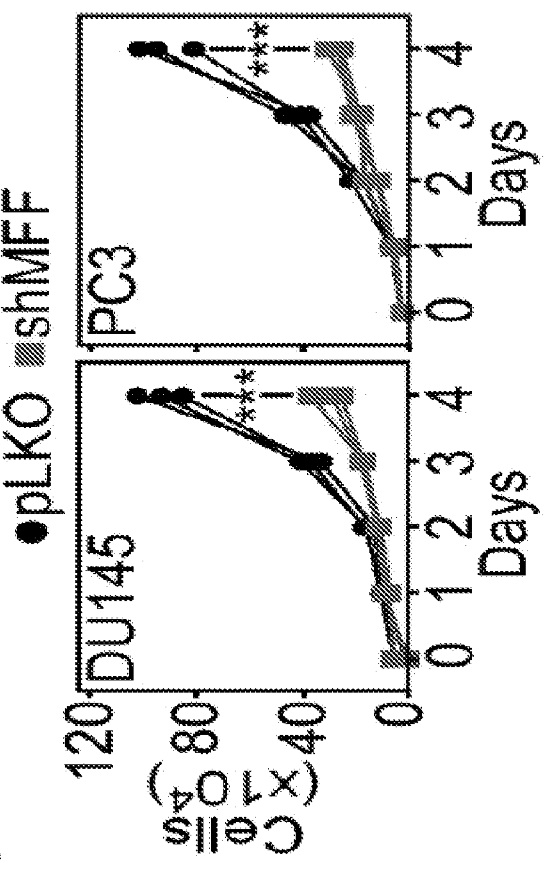
FIGS. 19A-19I illustrate MFF regulation of tumor cell proliferation.
Figure 19A:
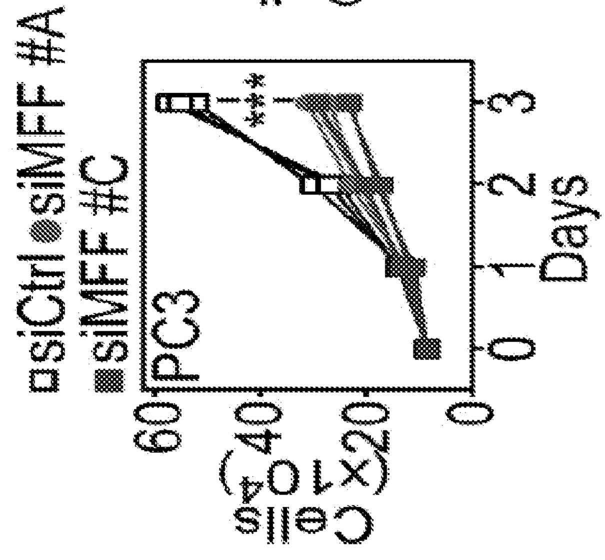
Figure 19C:
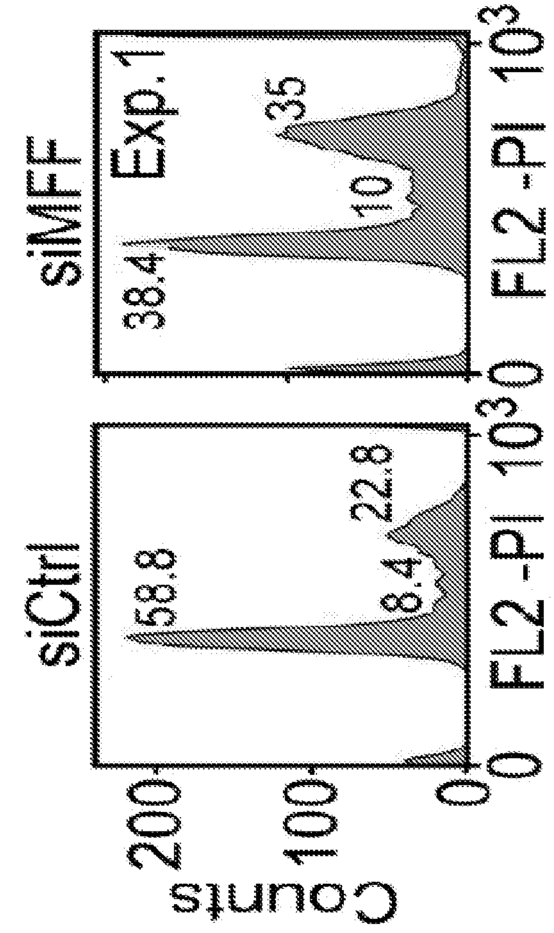
Figure 19D:
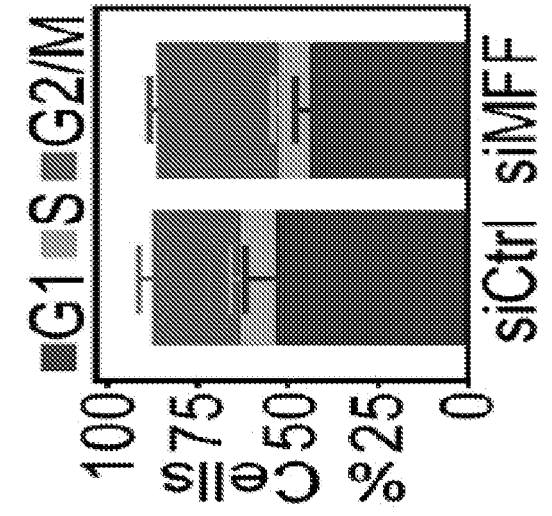
Figure 19F:
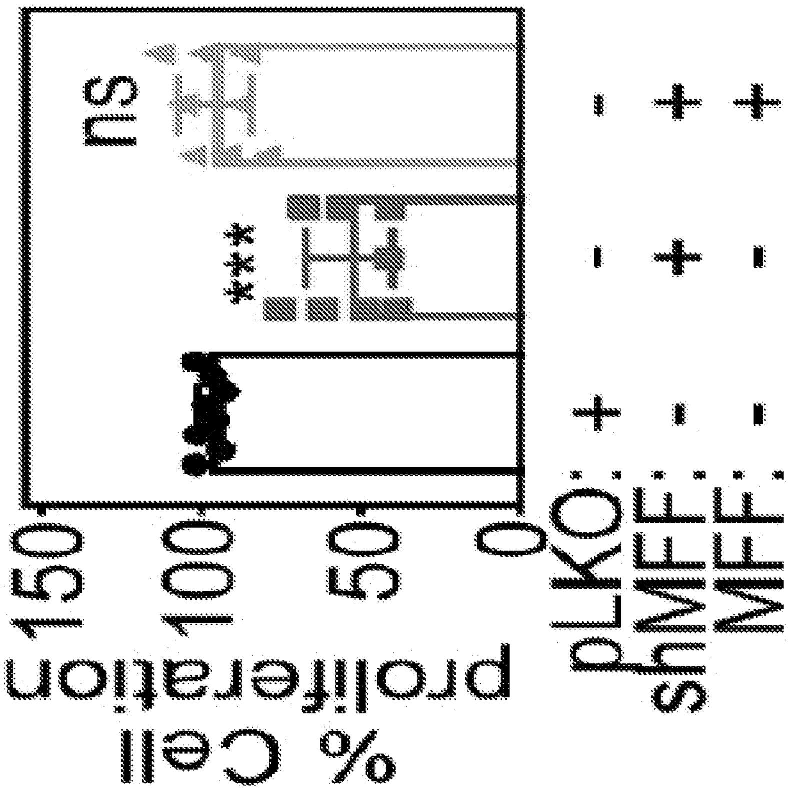
Figure 19E:
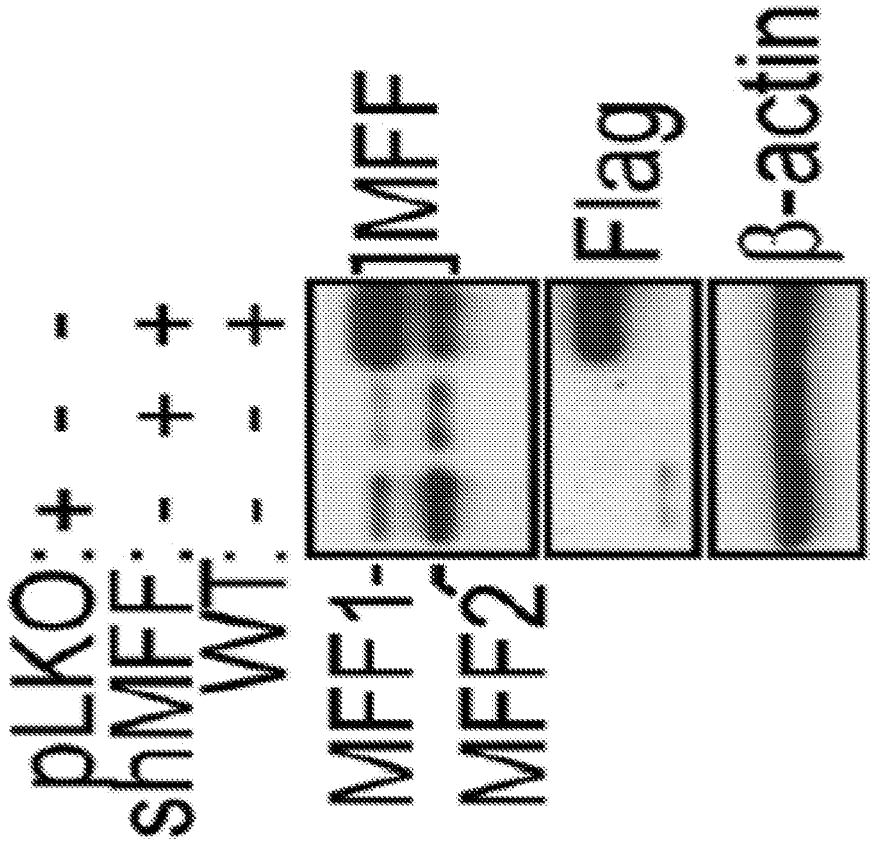
Figure 19G:
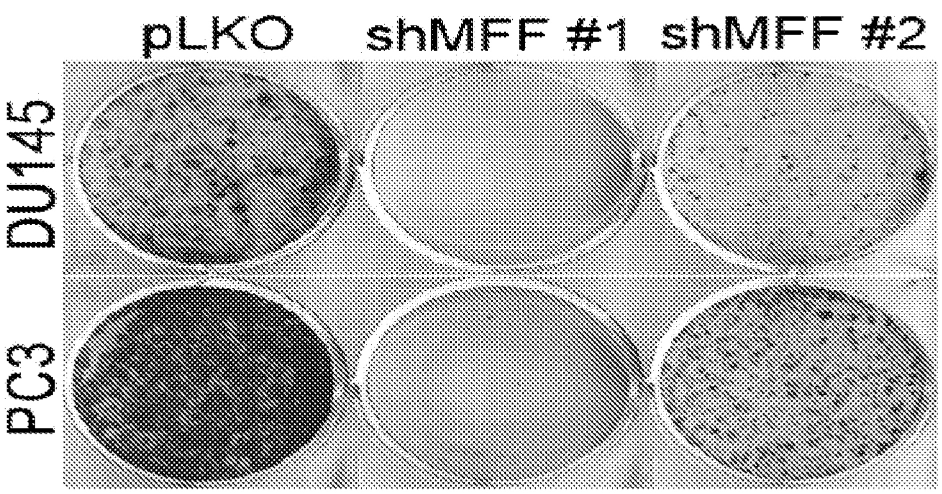
Figure 19H:
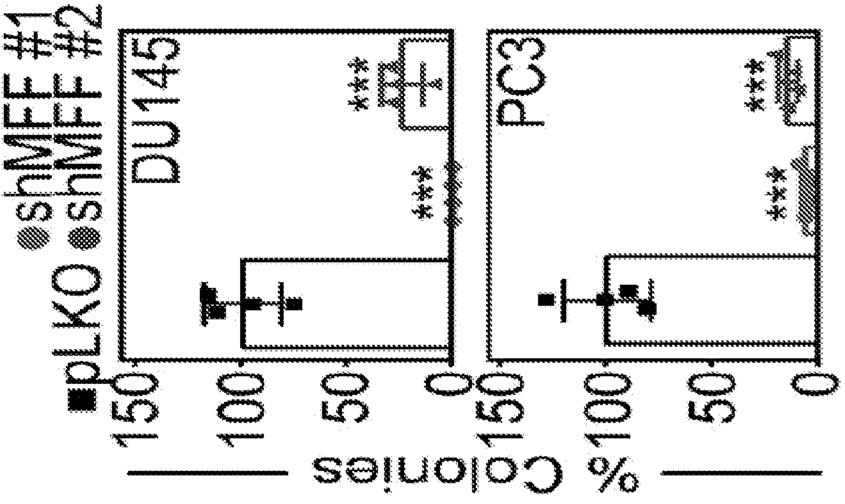
Figure 19I:
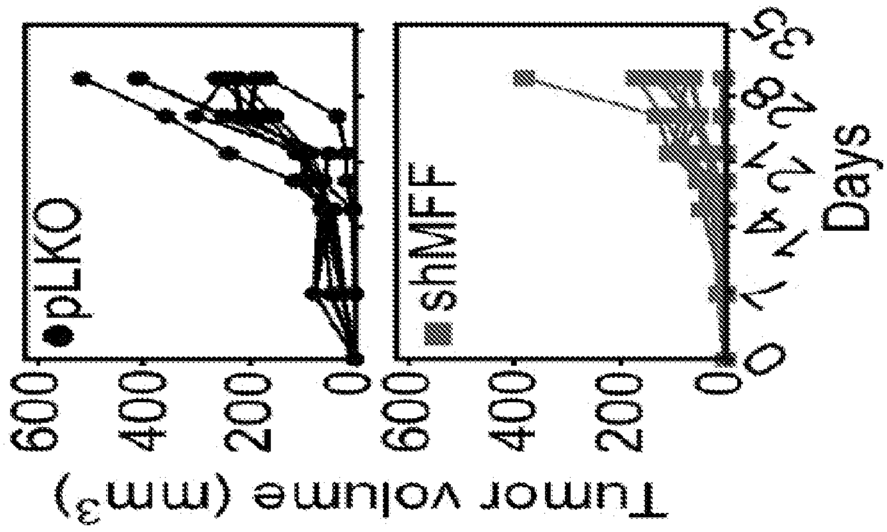
Figure 25E:
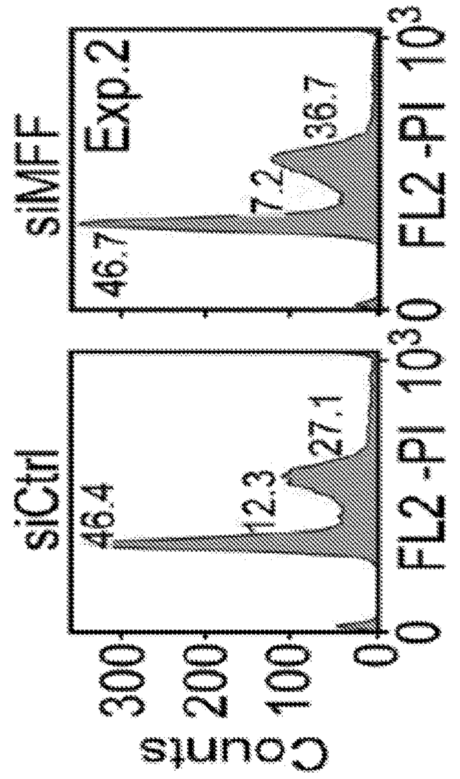
Figure 25C:
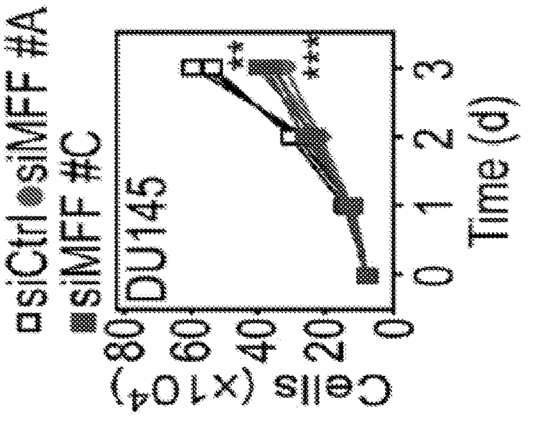
Figure 25D:
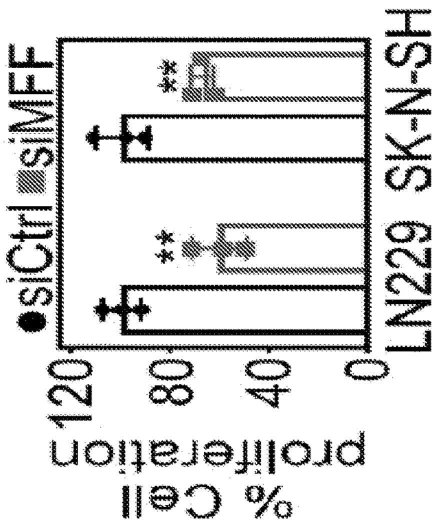

Based on these data, the impact of MFF targeting on tumorigenesis was studied. siRNA silencing of MFF inhibited PC3 (FIG. 19A) or DU145 (FIG. 25C) cell proliferation, compared to control transfectants. Stable knockdown of MFF by shRNA gave similar results, suppressing DU145 or PC3 cell proliferation, compared to pLKO cultures (FIG. 19B). This response was not limited to prostate cancer, as MFF silencing inhibited glioblastoma LN229 or neuroblastoma SK-N-SH cell proliferation (FIG. 25D). When analyzed for DNA content, MFF knockdown caused extensive cell cycle defects (FIG. 19C, FIG. 25E), characterized by accumulation of cells with G2/M DNA content (FIG. 19D). To confirm the specificity of this response, MFF-depleted PC3 cells were reconstituted with shRNA-insensitive MFF2 cDNA (FIG. 19E). Re-expression of MFF2 in these settings restored PC3 cell proliferation to levels of pLKO transfectants (FIG. 19F). Finally, shRNA knockdown of MFF potently suppressed colony formation (FIGS. 19G and 19H), another hallmark of tumorigenicity, and inhibited s.c. xenograft tumor (PC3) growth in immunocompromised mice (FIG. 19I). In contrast, pLKO transfectants exhibited extensive colony formation (FIGS. 19G and 19H) and gave rise to exponentially growing tumors in mice (FIG. 19I).

OTHER EMBODIMENTS

The recitation of a listing of elements in any definition of a variable herein includes definitions of that variable as any single element or combination (or subcombination) of listed elements. The recitation of an embodiment herein includes that embodiment as any single embodiment or in combination with any other embodiment or portions thereof.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A peptide having MFF-VDAC1 disrupting activity, comprising the sequence of:

SEQ ID NO: 8, wherein the peptide is 30 amino acids in length;

SEQ ID NO: 11, wherein the peptide is 27 amino acids in length;

SEQ ID NO: 12, wherein the peptide is 24 amino acids in length;

SEQ ID NO: 16, wherein the peptide is 27 amino acids in length; or

SEQ ID NO: 21, wherein the peptide is 21 amino acids in length.

2. The peptide of claim 1, wherein the peptide is conjugated to a cell-penetrating amino acid sequence.

3. The peptide of claim 2, wherein the cell-penetrating amino acid sequence is selected from the group consisting of an HIV-Tat cell-penetrating sequence, penetratin (also known as antennapedia), cR10 and Pep-1.

4. The peptide of claim 2, wherein the cell-penetrating amino acid sequence comprises SEQ ID NO: 24.

5. A polynucleotide encoding the peptide of claim 1.

6. A pharmaceutical composition comprising the polynucleotide of claim 5 and a pharmaceutically acceptable carrier, diluent or excipient.

7. A pharmaceutical composition comprising at least one of the peptides of claim 1 and a pharmaceutically acceptable carrier, diluent, or excipient.

8. A method of treating VDAC1 expressing cancer in a subject in need thereof, comprising administering to the subject an effective amount of the peptide of claim 1.

9. The method of claim 8, wherein the cancer is prostate cancer, glioblastoma, breast cancer, breast adenocarcinoma, lung cancer, non-small cell lung cancer, melanoma, ovarian cancer, hematological B-cell cancer, hematological T-cell cancer, metastatic cancer, treatment-resistant tumor or myc+ cancer.

10. The method of claim 8, further comprising administering a second agent to the subject.

11. The method of claim 10, wherein the second agent is a molecularly targeted therapy, a vaccine, a chemotherapeutic agent, radiation, or combinations thereof.

12. A method of disrupting the MFF-VDAC1 complex in a subject in need thereof, comprising administering to the subject an effective amount of the peptide of claim 1.

13. A kit comprising the pharmaceutical composition of claim 6 and a delivery agent.

14. The kit of claim 13, wherein the delivery agent is for oral, intranasal, transbuccal, transdermal, intraperitoneal, intramuscular, intravenous, or other injectable form of delivery.

15. A peptide mimetic, wherein the peptide mimetic is a retro-inverso D-enantiomer of the peptide of claim 1.

16. The peptide mimetic of claim 15, wherein the peptide-comprises the sequence of SEQ ID NO: 21.

17. The peptide mimetic of claim 15, wherein the peptide mimetic is conjugated to a cell-penetrating amino acid sequence.

18. The peptide mimetic of claim 17, wherein the cell-penetrating amino acid sequence is an HIV-Tat cell-penetrating sequence, penetratin, cR10 or Pep-1.

19. The peptide mimetic of claim 18, wherein the cell-penetrating amino acid sequence is SEQ ID NO: 24.

20. A pharmaceutical composition comprising the peptide mimetic of claim 15 and a pharmaceutically acceptable carrier, diluent or excipient.

21. A method of treating VDAC1 expressing cancer in a subject in need thereof, comprising administering to the subject an effective amount of the peptide of claim 15.

22. The method of claim 21, wherein the cancer is prostate cancer, glioblastoma, breast cancer, breast adenocarcinoma, lung cancer, non-small cell lung cancer, melanoma, ovarian cancer, hematological B-cell cancer, hematological T-cell cancer, metastatic cancer, treatment-resistant tumor or myc+ cancer.

23. The method of claim 21, further comprising administering a second agent to the subject.

24. The method of claim 23, wherein the second agent is a molecularly targeted therapy, a vaccine, a chemotherapeutic agent, radiation, or combinations thereof.

25. A method of disrupting the MFF-VDAC1 complex in a subject in need thereof, comprising administering to the subject an effective amount of the peptide of claim 15.

26. A kit comprising the pharmaceutical composition of claim 20 and a delivery agent.

27. The kit of claim 26, wherein the delivery agent is for oral, intranasal, transbuccal, transdermal, intraperitoneal, intramuscular, intravenous, or other injectable form of delivery.

28. A peptide comprising a first amino acid sequence and a second amino acid sequence, wherein the first amino acid sequence is an MFF derived peptide of no more than 30 amino acids in length, having the sequence set forth in any one of SEQ ID NOs: 1-23; and wherein the second amino acid sequence is a cell-penetrating amino acid sequence.

29. The peptide of claim 28, wherein the first amino acid sequence is the sequence set forth in any one of SEQ ID NOs: 8, 11, 12, 16, and 21.

30. The peptide of claim 29, wherein the cell-penetrating amino acid sequence is selected from the group consisting of an HIV-Tat cell-penetrating sequence, penetratin (also known as antennapedia), cR10 and Pep-1.

31. The peptide of claim 29, wherein the cell-penetrating amino acid sequence comprises SEQ ID NO: 24.

* * * * *

SEQUENCE LISTING

```
<160> NUMBER OF SEQ ID NOS: 25

<210> SEQ ID NO 1
<211> LENGTH: 26
<212> TYPE: PRT
<213> ORGANISM: Artificial Sequence
<220> FEATURE:
<223> OTHER INFORMATION: MFF-Derived
<220> FEATURE:
<223> OTHER INFORMATION: Peptide #1

<400> SEQUENCE: 1

Ala Glu Met Ala Glu Ile Ser Arg Ile Gln Tyr Glu Met Glu Tyr Thr
1               5                   10                  15

Glu Gly Ile Ser Gln Arg Met Arg Val Pro
            20                  25


<210> SEQ ID NO 2
<211> LENGTH: 30
<212> TYPE: PRT
<213> ORGANISM: Artificial Sequence
<220> FEATURE:
<223> OTHER INFORMATION: MFF-Derived
<220> FEATURE:
<223> OTHER INFORMATION: Peptide #2

<400> SEQUENCE: 2

Val Pro Glu Lys Leu Lys Val Ala Pro Pro Asn Ala Asp Leu Glu Gln
1               5                   10                  15

Gly Phe Gln Glu Gly Val Pro Asn Ala Ser Val Ile Met Gln
            20                  25                  30


<210> SEQ ID NO 3
<211> LENGTH: 30
<212> TYPE: PRT
<213> ORGANISM: Artificial Sequence
<220> FEATURE:
<223> OTHER INFORMATION: MFF-Derived
<220> FEATURE:
<223> OTHER INFORMATION: Peptide #3

<400> SEQUENCE: 3

Met Gln Val Pro Glu Arg Ile Val Val Ala Gly Asn Asn Glu Asp Val
```

```
1               5                   10                  15

Ser Phe Ser Arg Pro Ala Asp Leu Asp Leu Ile Gln Ser Thr
            20                  25                  30


<210> SEQ ID NO 4
<211> LENGTH: 30
<212> TYPE: PRT
<213> ORGANISM: Artificial Sequence
<220> FEATURE:
<223> OTHER INFORMATION: MFF-Derived
<220> FEATURE:
<223> OTHER INFORMATION: Peptide #4

<400> SEQUENCE: 4

Ser Thr Pro Phe Lys Pro Leu Ala Leu Lys Thr Pro Pro Arg Val Leu
1               5                   10                  15

Thr Leu Ser Glu Arg Pro Leu Asp Phe Leu Asp Leu Glu Arg
            20                  25                  30


<210> SEQ ID NO 5
<211> LENGTH: 30
<212> TYPE: PRT
<213> ORGANISM: Artificial Sequence
<220> FEATURE:
<223> OTHER INFORMATION: MFF-Derived
<220> FEATURE:
<223> OTHER INFORMATION: Peptide #5

<400> SEQUENCE: 5

Glu Arg Pro Pro Thr Thr Pro Gln Asn Glu Glu Ile Arg Ala Val Gly
1               5                   10                  15

Arg Leu Lys Arg Glu Arg Ser Met Ser Glu Asn Ala Val Arg
            20                  25                  30


<210> SEQ ID NO 6
<211> LENGTH: 30
<212> TYPE: PRT
<213> ORGANISM: Artificial Sequence
<220> FEATURE:
<223> OTHER INFORMATION: MFF-Derived
<220> FEATURE:
<223> OTHER INFORMATION: Peptide #6

<400> SEQUENCE: 6

Val Arg Gln Asn Gly Gln Leu Val Arg Asn Asp Ser Leu Trp His Arg
1               5                   10                  15

Ser Asp Ser Ala Pro Arg Asn Lys Ile Ser Arg Phe Gln Ala
            20                  25                  30


<210> SEQ ID NO 7
<211> LENGTH: 30
<212> TYPE: PRT
<213> ORGANISM: Artificial Sequence
<220> FEATURE:
<223> OTHER INFORMATION: MFF-Derived
<220> FEATURE:
<223> OTHER INFORMATION: Peptide #7

<400> SEQUENCE: 7

Gln Ala Pro Ile Ser Ala Pro Glu Tyr Thr Val Thr Pro Ser Pro Gln
1               5                   10                  15

Gln Ala Arg Val Cys Pro Pro His Met Leu Pro Glu Asp Gly
            20                  25                  30


<210> SEQ ID NO 8
```

```
<211> LENGTH: 30
<212> TYPE: PRT
<213> ORGANISM: Artificial Sequence
<220> FEATURE:
<223> OTHER INFORMATION: MFF-Derived
<220> FEATURE:
<223> OTHER INFORMATION: Peptide #8

<400> SEQUENCE: 8

Asp Gly Ala Asn Leu Ser Ser Ala Arg Gly Ile Leu Ser Leu Ile Gln
1               5                   10                  15

Ser Ser Thr Arg Arg Ala Tyr Gln Gln Ile Leu Asp Val Leu
            20                  25                  30


<210> SEQ ID NO 9
<211> LENGTH: 30
<212> TYPE: PRT
<213> ORGANISM: Artificial Sequence
<220> FEATURE:
<223> OTHER INFORMATION: MFF-Derived
<220> FEATURE:
<223> OTHER INFORMATION: Peptide #9

<400> SEQUENCE: 9

Val Leu Asp Glu Asn Arg Arg Pro Val Leu Arg Gly Gly Ser Ala Ala
1               5                   10                  15

Ala Thr Ser Asn Pro His His Asp Asn Val Arg Tyr Gly Ile
            20                  25                  30


<210> SEQ ID NO 10
<211> LENGTH: 18
<212> TYPE: PRT
<213> ORGANISM: Artificial Sequence
<220> FEATURE:
<223> OTHER INFORMATION: MFF-Derived
<220> FEATURE:
<223> OTHER INFORMATION: Peptide #10

<400> SEQUENCE: 10

Gly Ile Ser Asn Ile Asp Thr Thr Ile Glu Gly Thr Ser Asp Asp Leu
1               5                   10                  15

Thr Val


<210> SEQ ID NO 11
<211> LENGTH: 27
<212> TYPE: PRT
<213> ORGANISM: Artificial Sequence
<220> FEATURE:
<223> OTHER INFORMATION: MFF Deletion
<220> FEATURE:
<223> OTHER INFORMATION: Peptide 8 #1

<400> SEQUENCE: 11

Asn Leu Ser Ser Ala Arg Gly Ile Leu Ser Leu Ile Gln Ser Ser Thr
1               5                   10                  15

Arg Arg Ala Tyr Gln Gln Ile Leu Asp Val Leu
            20                  25


<210> SEQ ID NO 12
<211> LENGTH: 24
<212> TYPE: PRT
<213> ORGANISM: Artificial Sequence
<220> FEATURE:
<223> OTHER INFORMATION: MFF Deletion
<220> FEATURE:
<223> OTHER INFORMATION: Peptide 8 #2
```

-continued

<400> SEQUENCE: 12

Ser Ala Arg Gly Ile Leu Ser Leu Ile Gln Ser Ser Thr Arg Arg Ala
1 5 10 15

Tyr Gln Gln Ile Leu Asp Val Leu
20

<210> SEQ ID NO 13
<211> LENGTH: 21
<212> TYPE: PRT
<213> ORGANISM: Artificial Sequence
<220> FEATURE:
<223> OTHER INFORMATION: MFF Deletion
<220> FEATURE:
<223> OTHER INFORMATION: Peptide 8 #3

<400> SEQUENCE: 13

Gly Ile Leu Ser Leu Ile Gln Ser Ser Thr Arg Arg Ala Tyr Gln Gln
1 5 10 15

Ile Leu Asp Val Leu
20

<210> SEQ ID NO 14
<211> LENGTH: 18
<212> TYPE: PRT
<213> ORGANISM: Artificial Sequence
<220> FEATURE:
<223> OTHER INFORMATION: MFF Deletion
<220> FEATURE:
<223> OTHER INFORMATION: Peptide 8 #4

<400> SEQUENCE: 14

Ser Leu Ile Gln Ser Ser Thr Arg Arg Ala Tyr Gln Gln Ile Leu Asp
1 5 10 15

Val Leu

<210> SEQ ID NO 15
<211> LENGTH: 15
<212> TYPE: PRT
<213> ORGANISM: Artificial Sequence
<220> FEATURE:
<223> OTHER INFORMATION: MFF Deletion
<220> FEATURE:
<223> OTHER INFORMATION: Peptide 8 #5

<400> SEQUENCE: 15

Gln Ser Ser Thr Arg Arg Ala Tyr Gln Gln Ile Leu Asp Val Leu
1 5 10 15

<210> SEQ ID NO 16
<211> LENGTH: 27
<212> TYPE: PRT
<213> ORGANISM: Artificial Sequence
<220> FEATURE:
<223> OTHER INFORMATION: MFF Deletion
<220> FEATURE:
<223> OTHER INFORMATION: Peptide 8 #6

<400> SEQUENCE: 16

Asp Gly Ala Asn Leu Ser Ser Ala Arg Gly Ile Leu Ser Leu Ile Gln
1 5 10 15

Ser Ser Thr Arg Arg Ala Tyr Gln Gln Ile Leu
20 25

<210> SEQ ID NO 17
<211> LENGTH: 24

```
<212> TYPE: PRT
<213> ORGANISM: Artificial Sequence
<220> FEATURE:
<223> OTHER INFORMATION: MFF Deletion
<220> FEATURE:
<223> OTHER INFORMATION: Peptide 8 #7

<400> SEQUENCE: 17

Asp Gly Ala Asn Leu Ser Ser Ala Arg Gly Ile Leu Ser Leu Ile Gln
1               5                   10                  15

Ser Ser Thr Arg Arg Ala Tyr Gln
            20


<210> SEQ ID NO 18
<211> LENGTH: 21
<212> TYPE: PRT
<213> ORGANISM: Artificial Sequence
<220> FEATURE:
<223> OTHER INFORMATION: MFF Deletion
<220> FEATURE:
<223> OTHER INFORMATION: Peptide 8 #8

<400> SEQUENCE: 18

Asp Gly Ala Asn Leu Ser Ser Ala Arg Gly Ile Leu Ser Leu Ile Gln
1               5                   10                  15

Ser Ser Thr Arg Arg
            20


<210> SEQ ID NO 19
<211> LENGTH: 18
<212> TYPE: PRT
<213> ORGANISM: Artificial Sequence
<220> FEATURE:
<223> OTHER INFORMATION: MFF Deletion
<220> FEATURE:
<223> OTHER INFORMATION: Peptide 8 #9

<400> SEQUENCE: 19

Asp Gly Ala Asn Leu Ser Ser Ala Arg Gly Ile Leu Ser Leu Ile Gln
1               5                   10                  15

Ser Ser


<210> SEQ ID NO 20
<211> LENGTH: 15
<212> TYPE: PRT
<213> ORGANISM: Artificial Sequence
<220> FEATURE:
<223> OTHER INFORMATION: MFF Deletion
<220> FEATURE:
<223> OTHER INFORMATION: Peptide 8 #10

<400> SEQUENCE: 20

Asp Gly Ala Asn Leu Ser Ser Ala Arg Gly Ile Leu Ser Leu Ile
1               5                   10                  15


<210> SEQ ID NO 21
<211> LENGTH: 21
<212> TYPE: PRT
<213> ORGANISM: Artificial Sequence
<220> FEATURE:
<223> OTHER INFORMATION: MFF Deletion
<220> FEATURE:
<223> OTHER INFORMATION: Peptide 8 #11

<400> SEQUENCE: 21

Ser Ala Arg Gly Ile Leu Ser Leu Ile Gln Ser Ser Thr Arg Arg Ala
1               5                   10                  15
```

-continued

```
Tyr Gln Gln Ile Leu
            20


<210> SEQ ID NO 22
<211> LENGTH: 21
<212> TYPE: PRT
<213> ORGANISM: Artificial Sequence
<220> FEATURE:
<223> OTHER INFORMATION: MFF Scramble
<220> FEATURE:
<223> OTHER INFORMATION: Peptide 8 #11

<400> SEQUENCE: 22

Ser Ser Gln Leu Arg Tyr Leu Ala Arg Ser Gln Arg Ile Thr Ile Gln
1               5                   10                  15

Leu Ile Ala Gly Ser
            20


<210> SEQ ID NO 23
<211> LENGTH: 33
<212> TYPE: PRT
<213> ORGANISM: Artificial Sequence
<220> FEATURE:
<223> OTHER INFORMATION: MFF-Derived
<220> FEATURE:
<223> OTHER INFORMATION: Peptide #11

<400> SEQUENCE: 23

Val Val Asp Ala Ala Ser Leu Arg Arg Gln Ile Ile Lys Leu Asn Arg
1               5                   10                  15

Arg Leu Gln Leu Leu Glu Glu Glu Asn Lys Glu Arg Ala Lys Arg Glu
            20                  25                  30

Met


<210> SEQ ID NO 24
<211> LENGTH: 13
<212> TYPE: PRT
<213> ORGANISM: Artificial Sequence
<220> FEATURE:
<223> OTHER INFORMATION: Cell Penetrating
<220> FEATURE:
<223> OTHER INFORMATION: Peptide

<400> SEQUENCE: 24

Arg Gln Ile Lys Ile Trp Phe Gln Asn Arg Arg Met Lys
1               5                   10


<210> SEQ ID NO 25
<211> LENGTH: 23
<212> TYPE: RNA
<213> ORGANISM: Artificial Sequence
<220> FEATURE:
<223> OTHER INFORMATION: MFF
<220> FEATURE:
<223> OTHER INFORMATION: siRNA

<400> SEQUENCE: 25

gaacaaagaa cgugcuaaau uuu                                            23
```